(12) United States Patent
Fuchs et al.

(10) Patent No.: US 8,921,102 B2
(45) Date of Patent: Dec. 30, 2014

(54) DEVICES AND METHODS FOR ENRICHMENT AND ALTERATION OF CIRCULATING TUMOR CELLS AND OTHER PARTICLES

(75) Inventors: Martin Fuchs, Uxbridge, MA (US);
Ying-Xin Wang, Newtonville, MA (US);
Yi-Shuian Huang, Roslindale, MA (US); Neil X. Krueger, Jamaica Plain, MA (US)

(73) Assignee: GPB Scientific, LLC, Richmond, VA (US)

( * ) Notice: Subject to any disclaimer, the term of this patent is extended or adjusted under 35 U.S.C. 154(b) by 1350 days.

(21) Appl. No.: 11/322,791

(22) Filed: Dec. 29, 2005

(65) Prior Publication Data
US 2007/0026469 A1 Feb. 1, 2007

Related U.S. Application Data

(60) Provisional application No. 60/703,833, filed on Jul. 29, 2005.

(51) Int. Cl.
| C12N 5/00 | (2006.01) |
| C12N 5/02 | (2006.01) |
| C12N 13/00 | (2006.01) |
| A01N 1/02 | (2006.01) |
| B01L 3/00 | (2006.01) |
| G01N 33/569 | (2006.01) |
| G01N 33/543 | (2006.01) |
| G01N 33/574 | (2006.01) |
| B82Y 10/00 | (2011.01) |
| B82Y 5/00 | (2011.01) |

(52) U.S. Cl.
CPC .... G01N 33/54366 (2013.01); B01L 3/502761 (2013.01); B01L 2400/0406 (2013.01); B01L 2400/0409 (2013.01); G01N 33/56966 (2013.01); B01L 2400/0415 (2013.01); G01N 2800/52 (2013.01); B01L 2400/086 (2013.01); B01L 2200/0668 (2013.01); B01L 2400/0487 (2013.01); G01N 33/57492 (2013.01); B82Y 10/00 (2013.01); B01L 3/502707 (2013.01); B01L 3/502746 (2013.01); B82Y 5/00 (2013.01)
USPC ............... 435/325; 435/173.9; 435/2

(58) Field of Classification Search
None
See application file for complete search history.

(56) References Cited

U.S. PATENT DOCUMENTS

| 3,560,754 A | 2/1971 | Kamentsky |
| 3,799,742 A | 3/1974 | Coleman |
| 3,906,929 A | 9/1975 | Augspurger |
| 3,924,947 A | 12/1975 | Hogg |
| 3,984,307 A | 10/1976 | Kamentsky |
| 4,009,435 A | 2/1977 | Hogg |
| 4,055,799 A | 10/1977 | Coster et al. |
| 4,115,534 A | 9/1978 | Ithakissios |
| 4,190,535 A | 2/1980 | Luderer et al. |
| 4,233,029 A | 11/1980 | Columbus |
| 4,302,313 A | 11/1981 | Columbus |
| 4,350,768 A | 9/1982 | Tihon et al. |
| 4,415,405 A | 11/1983 | Ruddle et al. |
| 4,434,156 A | 2/1984 | Trowbridge |
| 4,508,625 A | 4/1985 | Graham |
| 4,562,157 A | 12/1985 | Lowe et al. |
| 4,584,268 A | 4/1986 | Ceriani et al. |
| 4,618,476 A | 10/1986 | Columbus |
| 4,664,796 A | 5/1987 | Graham et al. |
| 4,675,286 A | 6/1987 | Calenoff |
| 4,676,274 A | 6/1987 | Brown |
| 4,729,949 A | 3/1988 | Weinreb et al. |
| 4,755,460 A | 7/1988 | Bostwick et al. |
| 4,789,628 A | 12/1988 | Nayak |
| 4,790,640 A | 12/1988 | Nason |
| 4,800,159 A | 1/1989 | Mullis et al. |
| 4,814,098 A | 3/1989 | Inada et al. |
| 4,886,761 A | 12/1989 | Gustafson et al. |
| 4,894,343 A | 1/1990 | Tanaka et al. |
| 4,895,805 A | 1/1990 | Sato et al. |
| 4,906,439 A | 3/1990 | Grenner |
| 4,908,112 A | 3/1990 | Pace |
| 4,911,782 A | 3/1990 | Brown |
| 4,925,788 A | 5/1990 | Liberti |
| 4,936,465 A | 6/1990 | Zoeld |
| 4,963,498 A | 10/1990 | Hillman et al. |
| 4,968,600 A | 11/1990 | Haraguchi et al. |
| 4,971,904 A | 11/1990 | Luddy |
| 4,977,078 A | 12/1990 | Niimura et al. |

(Continued)

FOREIGN PATENT DOCUMENTS

| CA | 2466896 A1 | 3/2003 |
| DE | 19712309 A1 | 5/1998 |

(Continued)

OTHER PUBLICATIONS

Archer, et al. Cell Reactions to Dielectrophoretic Manipulation. Biochemical and Biophysical Research Communications. 1999;257:687-98.

(Continued)

*Primary Examiner* — Thane Underdahl
(74) *Attorney, Agent, or Firm* — Wilson Sonsini Goodrich & Rosati

(57) ABSTRACT

The invention features devices and methods for detecting, enriching, and analyzing circulating tumor cells and other particles. The invention further features methods of diagnosing a condition, e.g., cancer, in a subject by analyzing a cellular sample from the subject.

21 Claims, 108 Drawing Sheets

(7 of 108 Drawing Sheet(s) Filed in Color)

(56) References Cited

U.S. PATENT DOCUMENTS

| | | |
|---|---|---|
| 4,984,574 A | 1/1991 | Goldberg et al. |
| 4,999,283 A | 3/1991 | Zavos |
| 5,001,225 A | 3/1991 | Taylor |
| 5,039,426 A | 8/1991 | Giddings |
| 5,101,825 A | 4/1992 | Gravenstein et al. |
| 5,114,858 A | 5/1992 | Williams et al. |
| 5,135,627 A | 8/1992 | Soane |
| 5,135,720 A | 8/1992 | Uchida |
| 5,147,606 A | 9/1992 | Charlton et al. |
| 5,153,117 A | 10/1992 | Simons |
| 5,173,158 A | 12/1992 | Schmukler |
| 5,183,744 A | 2/1993 | Kawamura et al. |
| 5,186,827 A | 2/1993 | Liberti et al. |
| 5,215,926 A | 6/1993 | Etchells, III et al. |
| 5,240,856 A | 8/1993 | Goffe et al. |
| 5,275,933 A | 1/1994 | Teng et al. |
| 5,296,375 A | 3/1994 | Kricka et al. |
| 5,300,779 A | 4/1994 | Hillman et al. |
| 5,304,487 A | 4/1994 | Wilding et al. |
| 5,306,420 A | 4/1994 | Bisconte |
| 5,310,674 A | 5/1994 | Weinreb et al. |
| 5,328,843 A | 7/1994 | Fukuda et al. |
| 5,376,252 A | 12/1994 | Ohman et al. |
| 5,427,663 A | 6/1995 | Austin et al. |
| 5,427,946 A | 6/1995 | Kricka et al. |
| 5,432,054 A | 7/1995 | Saunders et al. |
| 5,437,987 A | 8/1995 | Tens et al. |
| 5,447,842 A | 9/1995 | Simons |
| 5,457,024 A | 10/1995 | Goldbard |
| 5,466,574 A | 11/1995 | Liberti et al. |
| 5,472,842 A | 12/1995 | Stokke et al. |
| 5,474,744 A | 12/1995 | Lerch |
| 5,486,335 A | 1/1996 | Wilding et al. |
| 5,489,506 A | 2/1996 | Crane |
| 5,498,392 A | 3/1996 | Wilding et al. |
| 5,506,141 A | 4/1996 | Weinreb |
| 5,529,903 A | 6/1996 | Kübler et al. |
| 5,541,072 A | 7/1996 | Wang et al. |
| 5,549,796 A | 8/1996 | Chu et al. |
| 5,556,773 A | 9/1996 | Youmo |
| 5,587,070 A | 12/1996 | Pall et al. |
| 5,622,831 A | 4/1997 | Liberti et al. |
| 5,629,147 A | 5/1997 | Asgari et al. |
| 5,635,358 A | 6/1997 | Wilding et al. |
| 5,637,458 A | 6/1997 | Frankel et al. |
| 5,637,469 A | 6/1997 | Wilding et al. |
| 5,639,669 A | 6/1997 | Ledley |
| 5,641,628 A | 6/1997 | Bianchi |
| 5,646,001 A | 7/1997 | Terstappen et al. |
| 5,648,220 A | 7/1997 | Bianchi et al. |
| 5,662,813 A | 9/1997 | Sammons et al. |
| 5,665,540 A | 9/1997 | Lebo |
| 5,672,481 A | 9/1997 | Minshall et al. |
| 5,676,849 A | 10/1997 | Sammons et al. |
| 5,707,799 A | 1/1998 | Hansmann et al. |
| 5,707,801 A | 1/1998 | Bresser et al. |
| 5,709,943 A | 1/1998 | Coleman et al. |
| 5,714,325 A | 2/1998 | Bianchi |
| 5,715,946 A | 2/1998 | Reichenbach |
| 5,716,776 A | 2/1998 | Bogart |
| 5,726,026 A | 3/1998 | Wilding et al. |
| 5,731,156 A | 3/1998 | Golbus |
| 5,750,015 A | 5/1998 | Soane et al. |
| 5,750,339 A | 5/1998 | Smith |
| 5,753,014 A | 5/1998 | Van Rijn |
| 5,766,843 A | 6/1998 | Asgari et al. |
| 5,770,029 A | 6/1998 | Nelson et al. |
| 5,798,042 A | 8/1998 | Chu et al. |
| 5,830,679 A | 11/1998 | Bianchi |
| 5,837,115 A | 11/1998 | Austin et al. |
| 5,840,502 A | 11/1998 | Van Vlasselaer |
| 5,842,787 A | 12/1998 | Kopf-Sill et al. |
| 5,843,767 A | 12/1998 | Beattie |
| 5,846,708 A | 12/1998 | Hollis et al. |
| 5,856,174 A | 1/1999 | Lipshutz et al. |
| 5,858,187 A | 1/1999 | Ramsey et al. |
| 5,858,188 A | 1/1999 | Soane et al. |
| 5,858,195 A | 1/1999 | Ramsey |
| 5,858,649 A | 1/1999 | Asgari et al. |
| 5,861,253 A | 1/1999 | Asgari et al. |
| 5,863,502 A | 1/1999 | Southgate et al. |
| 5,866,345 A * | 2/1999 | Wilding et al. ............. 435/7.21 |
| 5,869,004 A | 2/1999 | Parce et al. |
| 5,876,942 A | 3/1999 | Cheng et al. |
| 5,879,624 A | 3/1999 | Boehringer et al. |
| 5,882,465 A | 3/1999 | McReynolds |
| 5,891,651 A | 4/1999 | Roche et al. |
| 5,906,724 A | 5/1999 | Sammons et al. |
| 5,928,880 A | 7/1999 | Wilding et al. |
| 5,935,822 A | 8/1999 | Staehelin et al. |
| 5,944,971 A | 8/1999 | Foote |
| 5,948,278 A | 9/1999 | Sammons et al. |
| 5,952,173 A | 9/1999 | Hansmann et al. |
| 5,957,579 A | 9/1999 | Koph-Sill et al. |
| 5,962,234 A | 10/1999 | Golbus |
| 5,972,721 A | 10/1999 | Bruno et al. |
| 5,993,665 A | 11/1999 | Terstappen et al. |
| 5,994,057 A | 11/1999 | Mansfield |
| 5,994,517 A | 11/1999 | Ts'o et al. |
| 6,001,229 A | 12/1999 | Ramsey |
| 6,004,762 A | 12/1999 | Tse et al. |
| 6,007,690 A | 12/1999 | Nelson et al. |
| 6,008,007 A | 12/1999 | Fruehauf et al. |
| 6,008,010 A | 12/1999 | Greenberger et al. |
| 6,027,623 A | 2/2000 | Ohkawa |
| 6,033,546 A | 3/2000 | Ramsey |
| 6,054,034 A | 4/2000 | Soane et al. |
| 6,056,859 A | 5/2000 | Ramsey et al. |
| 6,074,827 A | 6/2000 | Nelson et al. |
| 6,120,666 A | 9/2000 | Jacobson et al. |
| 6,120,856 A | 9/2000 | Liberti et al. |
| 6,129,848 A | 10/2000 | Chen et al. |
| 6,130,098 A | 10/2000 | Handique et al. |
| 6,143,576 A | 11/2000 | Buechler |
| 6,150,119 A | 11/2000 | Kopf-sill et al. |
| 6,156,270 A | 12/2000 | Buechler |
| 6,169,816 B1 | 1/2001 | Ravkin |
| 6,176,962 B1 | 1/2001 | Soane et al. |
| 6,186,660 B1 | 2/2001 | Koph-Sill et al. |
| 6,197,523 B1 | 3/2001 | Rimm et al. |
| 6,200,765 B1 | 3/2001 | Murphy et al. |
| 6,210,889 B1 | 4/2001 | Drouin et al. |
| 6,210,910 B1 | 4/2001 | Walt et al. |
| 6,213,151 B1 | 4/2001 | Jacobson et al. |
| 6,214,558 B1 | 4/2001 | Shuber et al. |
| 6,216,538 B1 | 4/2001 | Yasuda et al. |
| 6,235,474 B1 | 5/2001 | Feinberg |
| 6,241,894 B1 | 6/2001 | Briggs et al. |
| 6,242,209 B1 | 6/2001 | Ransom et al. |
| 6,251,343 B1 | 6/2001 | Dubrow et al. |
| 6,251,691 B1 | 6/2001 | Seul |
| 6,258,540 B1 | 7/2001 | Lo et al. |
| 6,265,229 B1 | 7/2001 | Fodstad et al. |
| 6,274,337 B1 | 8/2001 | Parce et al. |
| 6,274,339 B1 | 8/2001 | Moore et al. |
| 6,277,489 B1 | 8/2001 | Abbott et al. |
| 6,277,569 B1 | 8/2001 | Bittner et al. |
| 6,280,967 B1 | 8/2001 | Ransom et al. |
| 6,291,249 B1 | 9/2001 | Mahant et al. |
| 6,296,752 B1 | 10/2001 | McBride et al. |
| 6,306,578 B1 | 10/2001 | Schellenberger et al. |
| 6,309,889 B1 | 10/2001 | Cutler et al. |
| 6,315,940 B1 | 11/2001 | Nisch et al. |
| 6,315,953 B1 | 11/2001 | Ackley et al. |
| 6,319,468 B1 | 11/2001 | Sheppard, Jr. et al. |
| 6,331,274 B1 | 12/2001 | Ackley et al. |
| 6,337,472 B1 | 1/2002 | Garner et al. |
| 6,344,326 B1 | 2/2002 | Nelson et al. |
| 6,355,491 B1 | 3/2002 | Zhou et al. |
| 6,361,958 B1 | 3/2002 | Shieh et al. |
| 6,365,362 B1 | 4/2002 | Terstappen et al. |
| 6,368,562 B1 | 4/2002 | Yao |
| 6,368,871 B1 | 4/2002 | Christel et al. |
| 6,372,432 B1 | 4/2002 | Tocque et al. |

(56) References Cited

U.S. PATENT DOCUMENTS

| | | |
|---|---|---|
| 6,372,542 B1 | 4/2002 | Martin et al. |
| 6,376,181 B2 | 4/2002 | Ramsey et al. |
| 6,377,721 B1 | 4/2002 | Walt et al. |
| 6,379,884 B2 | 4/2002 | Wada et al. |
| 6,383,759 B1 | 5/2002 | Murphy et al. |
| 6,387,290 B1 | 5/2002 | Brody et al. |
| 6,387,707 B1 | 5/2002 | Seul et al. |
| 6,394,942 B2 | 5/2002 | Moon et al. |
| 6,395,232 B1 | 5/2002 | McBride |
| 6,399,023 B1 | 6/2002 | Chow |
| 6,432,630 B1 | 8/2002 | Blankenstein |
| 6,432,720 B2 | 8/2002 | Chow |
| 6,444,461 B1 | 9/2002 | Knapp et al. |
| 6,453,928 B1 | 9/2002 | Kaplan et al. |
| 6,454,938 B2 | 9/2002 | Moon et al. |
| 6,454,945 B1 | 9/2002 | Weigl et al. |
| 6,455,260 B1 | 9/2002 | Muller et al. |
| 6,465,225 B1 | 10/2002 | Fuhr et al. |
| 6,479,299 B1 | 11/2002 | Parce et al. |
| 6,488,895 B1 | 12/2002 | Kennedy |
| 6,495,340 B2 | 12/2002 | Huberman et al. |
| 6,500,612 B1 | 12/2002 | Gray et al. |
| 6,511,967 B1 | 1/2003 | Weissleder et al. |
| 6,517,234 B1 | 2/2003 | Koph-Sill et al. |
| 6,521,188 B1 | 2/2003 | Webster |
| 6,524,456 B1 | 2/2003 | Ramsey et al. |
| 6,529,835 B1 | 3/2003 | Wada et al. |
| 6,537,505 B1 | 3/2003 | LaBudde et al. |
| 6,540,895 B1 | 4/2003 | Spence et al. |
| 6,551,841 B1 | 4/2003 | Wilding et al. |
| 6,569,626 B2 | 5/2003 | Bittner et al. |
| 6,570,196 B1 | 5/2003 | Fromherz et al. |
| 6,576,478 B1 | 6/2003 | Wagner et al. |
| 6,582,904 B2 | 6/2003 | Dahm |
| 6,582,969 B1 | 6/2003 | Wagner et al. |
| 6,589,791 B1 | 7/2003 | LaBudde et al. |
| 6,591,852 B1 | 7/2003 | McNeely et al. |
| 6,596,144 B1 | 7/2003 | Regnier et al. |
| 6,596,545 B1 | 7/2003 | Wagner et al. |
| 6,605,453 B2 | 8/2003 | Ozkan et al. |
| 6,605,454 B2 | 8/2003 | Barenburg et al. |
| 6,613,525 B2 | 9/2003 | Nelson et al. |
| 6,618,679 B2 | 9/2003 | Loehriein et al. |
| 6,632,619 B1 | 10/2003 | Harrison et al. |
| 6,632,652 B1 | 10/2003 | Austin et al. |
| 6,632,655 B1 | 10/2003 | Mehta et al. |
| 6,635,163 B1 | 10/2003 | Han et al. |
| 6,637,463 B1 | 10/2003 | Lei et al. |
| 6,645,731 B2 | 11/2003 | Terstappen et al. |
| 6,664,104 B2 | 12/2003 | Pourahmadi et al. |
| 6,673,541 B1 | 1/2004 | Klein et al. |
| 6,674,525 B2 | 1/2004 | Bardell et al. |
| 6,685,841 B2 | 2/2004 | Lopez et al. |
| 6,689,615 B1 | 2/2004 | Murto et al. |
| 6,692,952 B1 | 2/2004 | Braff et al. |
| 6,743,636 B2 | 6/2004 | Chung et al. |
| 6,746,503 B1 | 6/2004 | Benett et al. |
| 6,762,059 B2 | 7/2004 | Chan et al. |
| 6,770,434 B2 | 8/2004 | Shvets et al. |
| 6,770,441 B2 | 8/2004 | Dickinson et al. |
| 6,783,647 B2 | 8/2004 | Culbertson et al. |
| 6,783,928 B2 | 8/2004 | Hvichia et al. |
| 6,805,841 B2 | 10/2004 | Shvets et al. |
| 6,815,664 B2 | 11/2004 | Wang et al. |
| 6,818,184 B2 | 11/2004 | Fulwyler et al. |
| 6,830,936 B2 | 12/2004 | Anderson et al. |
| 6,849,423 B2 | 2/2005 | Mutz et al. |
| 6,858,439 B1 | 2/2005 | Xu et al. |
| 6,875,619 B2 | 4/2005 | Blackburn |
| 6,878,271 B2 | 4/2005 | Gilbert et al. |
| 6,881,315 B2 | 4/2005 | Iida et al. |
| 6,893,836 B2 | 5/2005 | Mutz et al. |
| 6,893,881 B1 | 5/2005 | Fodstad et al. |
| 6,911,345 B2 | 6/2005 | Quake et al. |
| 6,913,605 B2 | 7/2005 | Fletcher et al. |
| 6,913,697 B2 | 7/2005 | Lopez et al. |
| 6,942,771 B1 | 9/2005 | Kayyem |
| 6,942,978 B1 | 9/2005 | O'Brien |
| 6,949,355 B2 | 9/2005 | Yamanishi et al. |
| 6,953,668 B1 | 10/2005 | Israeli et al. |
| 6,958,245 B2 | 10/2005 | Seul et al. |
| 6,960,449 B2 | 11/2005 | Wang et al. |
| 6,974,667 B2 | 12/2005 | Horne et al. |
| 6,991,917 B2 | 1/2006 | Mutz et al. |
| 7,067,306 B2 | 6/2006 | Singhvi et al. |
| 7,081,192 B1 | 7/2006 | Wang et al. |
| 7,115,709 B1 | 10/2006 | Gray et al. |
| 7,150,812 B2 | 12/2006 | Huang et al. |
| 7,160,687 B1 | 1/2007 | Kapur et al. |
| 7,190,818 B2 | 3/2007 | Ellis et al. |
| 7,192,698 B1 | 3/2007 | Kinch et al. |
| 7,198,787 B2 | 4/2007 | Fodstad et al. |
| 7,208,275 B2 | 4/2007 | Gocke et al. |
| 7,212,660 B2 | 5/2007 | Wetzel et al. |
| 7,220,594 B2 | 5/2007 | Foster et al. |
| 7,227,002 B1 | 6/2007 | Kufer et al. |
| 7,229,838 B2 | 6/2007 | Foster et al. |
| 7,250,256 B2 | 7/2007 | Reinhard et al. |
| 7,252,976 B2 | 8/2007 | Lin et al. |
| 7,258,774 B2 | 8/2007 | Chou et al. |
| 7,258,987 B2 | 8/2007 | Lamorte et al. |
| 7,262,177 B2 | 8/2007 | Ts'O et al. |
| 7,262,269 B2 | 8/2007 | Lam et al. |
| 7,264,972 B2 | 9/2007 | Foster |
| 7,272,252 B2 | 9/2007 | De La Torre-Bueno et al. |
| 7,276,170 B2 | 10/2007 | Oakey et al. |
| 7,312,085 B2 | 12/2007 | Chou et al. |
| 7,318,902 B2 | 1/2008 | Oakey et al. |
| 7,428,325 B2 | 9/2008 | Douglass et al. |
| 7,431,889 B2 | 10/2008 | Engstrom et al. |
| 7,597,791 B2 | 10/2009 | Huang et al. |
| 7,783,098 B2 | 8/2010 | Douglass et al. |
| 7,785,810 B2 | 8/2010 | Chen |
| 2001/0007749 A1 | 7/2001 | Feinberg |
| 2001/0018192 A1 | 8/2001 | Terstappen et al. |
| 2001/0036672 A1 | 11/2001 | Anderson et al. |
| 2001/0053958 A1 | 12/2001 | Ried et al. |
| 2002/0005354 A1 | 1/2002 | Spence et al. |
| 2002/0006621 A1 | 1/2002 | Bianchi |
| 2002/0009738 A1 | 1/2002 | Houghton et al. |
| 2002/0012931 A1 | 1/2002 | Waldman et al. |
| 2002/0016450 A1 | 2/2002 | Laugharn et al. |
| 2002/0019001 A1 | 2/2002 | Light |
| 2002/0028431 A1 | 3/2002 | Julien |
| 2002/0042079 A1 | 4/2002 | Simon et al. |
| 2002/0058332 A1 | 5/2002 | Quake et al. |
| 2002/0076825 A1 | 6/2002 | Cheng et al. |
| 2002/0086329 A1 | 7/2002 | Shvets et al. |
| 2002/0090741 A1 | 7/2002 | Jurgensen et al. |
| 2002/0106715 A1 | 8/2002 | Huberman et al. |
| 2002/0108859 A1 | 8/2002 | Wang et al. |
| 2002/0110835 A1 | 8/2002 | Kumar |
| 2002/0115163 A1 | 8/2002 | Wang et al. |
| 2002/0115164 A1 | 8/2002 | Wang et al. |
| 2002/0115201 A1 | 8/2002 | Barenburg et al. |
| 2002/0119482 A1 | 8/2002 | Nelson et al. |
| 2002/0123078 A1 | 9/2002 | Seul et al. |
| 2002/0123112 A1 | 9/2002 | Wang et al. |
| 2002/0127616 A1 | 9/2002 | Burchell et al. |
| 2002/0132315 A1 | 9/2002 | Wang et al. |
| 2002/0132316 A1 | 9/2002 | Wang et al. |
| 2002/0137088 A1 | 9/2002 | Bianchi |
| 2002/0142471 A1 | 10/2002 | Handique et al. |
| 2002/0160363 A1 | 10/2002 | McDevitt et al. |
| 2002/0164825 A1 | 11/2002 | Chen |
| 2002/0166760 A1 | 11/2002 | Prentiss et al. |
| 2002/0172987 A1 | 11/2002 | Terstappen et al. |
| 2002/0173043 A1 | 11/2002 | Merabet et al. |
| 2003/0004402 A1 | 1/2003 | Hitt et al. |
| 2003/0017514 A1 | 1/2003 | Pachmann et al. |
| 2003/0033091 A1 | 2/2003 | Opalsky et al. |
| 2003/0036054 A1 | 2/2003 | Ladisch et al. |
| 2003/0036100 A1 | 2/2003 | Fisk et al. |
| 2003/0044832 A1 | 3/2003 | Blankenstein |

(56) References Cited

U.S. PATENT DOCUMENTS

| | | |
|---|---|---|
| 2003/0049563 A1 | 3/2003 | Iida et al. |
| 2003/0068642 A1 | 4/2003 | Urnovitz |
| 2003/0072682 A1 | 4/2003 | Kikinis |
| 2003/0077292 A1 | 4/2003 | Hanash et al. |
| 2003/0082148 A1 | 5/2003 | Ludwig et al. |
| 2003/0104461 A1 | 6/2003 | Muehlbauer et al. |
| 2003/0113528 A1 | 6/2003 | Moya |
| 2003/0119077 A1 | 6/2003 | Ts'o et al. |
| 2003/0119724 A1 | 6/2003 | Ts'o et al. |
| 2003/0129676 A1 | 7/2003 | Terstappen et al. |
| 2003/0134416 A1 | 7/2003 | Yamanishi et al. |
| 2003/0153085 A1 | 8/2003 | Leary et al. |
| 2003/0159999 A1 | 8/2003 | Oakey et al. |
| 2003/0165852 A1 | 9/2003 | Schueler et al. |
| 2003/0165927 A1 | 9/2003 | Hulten |
| 2003/0170609 A1 | 9/2003 | Rigler |
| 2003/0170631 A1 | 9/2003 | Houghton et al. |
| 2003/0170703 A1 | 9/2003 | Piper et al. |
| 2003/0175990 A1 | 9/2003 | Hayenga |
| 2003/0178641 A1 | 9/2003 | Blair et al. |
| 2003/0180754 A1 | 9/2003 | Bergholtz et al. |
| 2003/0180762 A1 | 9/2003 | Tuma et al. |
| 2003/0186889 A1 | 10/2003 | Forssmann et al. |
| 2003/0190602 A1 | 10/2003 | Pressman et al. |
| 2003/0199685 A1 | 10/2003 | Pressman et al. |
| 2003/0206901 A1 | 11/2003 | Chen |
| 2003/0232350 A1 | 12/2003 | Afar et al. |
| 2003/0234210 A1 | 12/2003 | Deshpande et al. |
| 2004/0005582 A1* | 1/2004 | Shipwash ................... 435/6 |
| 2004/0009471 A1 | 1/2004 | Cao |
| 2004/0018116 A1 | 1/2004 | Desmond et al. |
| 2004/0018509 A1 | 1/2004 | Bianchi |
| 2004/0018611 A1 | 1/2004 | Ward et al. |
| 2004/0019300 A1 | 1/2004 | Leonard |
| 2004/0023222 A1 | 2/2004 | Russell et al. |
| 2004/0043506 A1 | 3/2004 | Haussecker et al. |
| 2004/0048360 A1 | 3/2004 | Wada et al. |
| 2004/0053352 A1 | 3/2004 | Ouyang et al. |
| 2004/0063162 A1 | 4/2004 | Dunlay et al. |
| 2004/0063163 A1 | 4/2004 | Buffiere et al. |
| 2004/0072278 A1 | 4/2004 | Chou et al. |
| 2004/0077105 A1 | 4/2004 | Wu et al. |
| 2004/0101444 A1 | 5/2004 | Sommers et al. |
| 2004/0121343 A1 | 6/2004 | Buechler et al. |
| 2004/0142463 A1 | 7/2004 | Walker et al. |
| 2004/0144651 A1 | 7/2004 | Huang et al. |
| 2004/0166555 A1 | 8/2004 | Braff et al. |
| 2004/0171091 A1 | 9/2004 | Lesko et al. |
| 2004/0185495 A1 | 9/2004 | Schueler et al. |
| 2004/0214240 A1 | 10/2004 | Cao |
| 2004/0232074 A1 | 11/2004 | Peters et al. |
| 2004/0241653 A1 | 12/2004 | Feinstein et al. |
| 2004/0241707 A1 | 12/2004 | Gao et al. |
| 2004/0245102 A1 | 12/2004 | Gilbert et al. |
| 2005/0003351 A1 | 1/2005 | Fejgin et al. |
| 2005/0014208 A1 | 1/2005 | Krehan et al. |
| 2005/0026167 A1 | 2/2005 | Birch-Machin et al. |
| 2005/0042623 A1 | 2/2005 | Ault-Riche et al. |
| 2005/0042685 A1 | 2/2005 | Albert et al. |
| 2005/0042766 A1 | 2/2005 | Ohman et al. |
| 2005/0049793 A1 | 3/2005 | Paterlini-Brechot |
| 2005/0061962 A1 | 3/2005 | Mueth et al. |
| 2005/0069528 A1 | 3/2005 | Teicher |
| 2005/0069886 A1 | 3/2005 | Sun et al. |
| 2005/0092662 A1 | 5/2005 | Gilbert et al. |
| 2005/0100951 A1 | 5/2005 | Pircher |
| 2005/0118591 A1 | 6/2005 | Tamak et al. |
| 2005/0123454 A1 | 6/2005 | Cox |
| 2005/0124009 A1 | 6/2005 | van Weeghel et al. |
| 2005/0129582 A1 | 6/2005 | Breidford et al. |
| 2005/0136551 A1 | 6/2005 | Mpock |
| 2005/0142663 A1 | 6/2005 | Parthasarathy et al. |
| 2005/0145497 A1 | 7/2005 | Gilbert et al. |
| 2005/0147977 A1 | 7/2005 | Koo et al. |
| 2005/0153329 A1 | 7/2005 | Hakansson et al. |
| 2005/0153342 A1 | 7/2005 | Chen |
| 2005/0158754 A1 | 7/2005 | Puffenberger et al. |
| 2005/0164158 A1 | 7/2005 | Wang et al. |
| 2005/0170373 A1 | 8/2005 | Monforte |
| 2005/0170418 A1 | 8/2005 | Moreland et al. |
| 2005/0175505 A1 | 8/2005 | Cantor et al. |
| 2005/0175981 A1 | 8/2005 | Voldman et al. |
| 2005/0175996 A1 | 8/2005 | Chen |
| 2005/0181353 A1 | 8/2005 | Rao et al. |
| 2005/0181463 A1 | 8/2005 | Rao et al. |
| 2005/0191636 A1 | 9/2005 | Hahn |
| 2005/0207940 A1 | 9/2005 | Butler et al. |
| 2005/0211556 A1 | 9/2005 | Childers et al. |
| 2005/0214855 A1 | 9/2005 | Wagner et al. |
| 2005/0236314 A1 | 10/2005 | Neyer et al. |
| 2005/0239101 A1 | 10/2005 | Sukumar et al. |
| 2005/0244843 A1 | 11/2005 | Chen et al. |
| 2005/0249635 A1 | 11/2005 | Okun et al. |
| 2005/0250111 A1 | 11/2005 | Xie et al. |
| 2005/0250155 A1 | 11/2005 | Lesko et al. |
| 2005/0250199 A1 | 11/2005 | Anderson et al. |
| 2005/0252840 A1 | 11/2005 | Arnold et al. |
| 2005/0255001 A1 | 11/2005 | Padmanabhan et al. |
| 2005/0262577 A1 | 11/2005 | Guelly et al. |
| 2005/0266433 A1 | 12/2005 | Kapur et al. |
| 2005/0272049 A1 | 12/2005 | Banerjee et al. |
| 2005/0272103 A1 | 12/2005 | Chen |
| 2005/0282196 A1 | 12/2005 | Costa |
| 2005/0282220 A1 | 12/2005 | Prober et al. |
| 2005/0282293 A1 | 12/2005 | Cosmen et al. |
| 2006/0000772 A1 | 1/2006 | Sano et al. |
| 2006/0008807 A1 | 1/2006 | O'Hara et al. |
| 2006/0008824 A1 | 1/2006 | Ronaghi et al. |
| 2006/0019235 A1 | 1/2006 | Soen et al. |
| 2006/0024756 A1 | 2/2006 | Tibbe et al. |
| 2006/0051265 A1* | 3/2006 | Mohamed et al. ............ 422/243 |
| 2006/0051775 A1 | 3/2006 | Bianchi et al. |
| 2006/0060767 A1 | 3/2006 | Wang et al. |
| 2006/0073125 A1 | 4/2006 | Clarke et al. |
| 2006/0094109 A1 | 5/2006 | Trainer |
| 2006/0121452 A1 | 6/2006 | Dhallan |
| 2006/0121624 A1 | 6/2006 | Huang et al. |
| 2006/0128006 A1 | 6/2006 | Gerhardt et al. |
| 2006/0134599 A1* | 6/2006 | Toner et al. ................. 435/4 |
| 2006/0160105 A1 | 7/2006 | Dhallan |
| 2006/0160243 A1 | 7/2006 | Tang et al. |
| 2006/0194192 A1 | 8/2006 | Rao et al. |
| 2006/0223178 A1 | 10/2006 | Barber et al. |
| 2006/0252054 A1 | 11/2006 | Lin et al. |
| 2006/0252061 A1 | 11/2006 | Zabeau et al. |
| 2006/0252071 A1 | 11/2006 | Lo et al. |
| 2006/0252087 A1 | 11/2006 | Tang et al. |
| 2006/0266692 A1 | 11/2006 | Foster et al. |
| 2006/0285996 A1 | 12/2006 | Ohman et al. |
| 2007/0017633 A1 | 1/2007 | Tonkovich et al. |
| 2007/0020772 A1 | 1/2007 | Cao et al. |
| 2007/0026381 A1 | 2/2007 | Huang et al. |
| 2007/0026413 A1 | 2/2007 | Fuchs et al. |
| 2007/0026414 A1 | 2/2007 | Fuchs et al. |
| 2007/0026415 A1 | 2/2007 | Fuchs et al. |
| 2007/0026416 A1 | 2/2007 | Fuchs |
| 2007/0026417 A1 | 2/2007 | Fuchs et al. |
| 2007/0026418 A1 | 2/2007 | Fuchs et al. |
| 2007/0026419 A1 | 2/2007 | Fuchs et al. |
| 2007/0026469 A1 | 2/2007 | Fuchs et al. |
| 2007/0037172 A1 | 2/2007 | Chiu et al. |
| 2007/0037173 A1 | 2/2007 | Allard et al. |
| 2007/0037273 A1 | 2/2007 | Shuler et al. |
| 2007/0037275 A1 | 2/2007 | Shuler et al. |
| 2007/0042238 A1 | 2/2007 | Kim et al. |
| 2007/0042339 A1 | 2/2007 | Toner et al. |
| 2007/0042360 A1 | 2/2007 | Afar et al. |
| 2007/0042368 A1 | 2/2007 | Zehentner-Wilkinson et al. |
| 2007/0048750 A1 | 3/2007 | Peck et al. |
| 2007/0054268 A1 | 3/2007 | Sutherland et al. |
| 2007/0054287 A1 | 3/2007 | Bloch |
| 2007/0059216 A1 | 3/2007 | Larsson et al. |
| 2007/0059680 A1 | 3/2007 | Kapur et al. |
| 2007/0059683 A1 | 3/2007 | Barber et al. |

(56) References Cited

U.S. PATENT DOCUMENTS

| | | |
|---|---|---|
| 2007/0059716 A1 | 3/2007 | Balis et al. |
| 2007/0059718 A1 | 3/2007 | Toner et al. |
| 2007/0059719 A1 | 3/2007 | Grisham et al. |
| 2007/0059737 A1 | 3/2007 | Baker et al. |
| 2007/0059774 A1 | 3/2007 | Grisham et al. |
| 2007/0059781 A1 | 3/2007 | Kapur et al. |
| 2007/0059785 A1 | 3/2007 | Bacus et al. |
| 2007/0065845 A1 | 3/2007 | Baker et al. |
| 2007/0065858 A1 | 3/2007 | Haley |
| 2007/0071762 A1 | 3/2007 | Ts'o et al. |
| 2007/0072228 A1 | 3/2007 | Brauch |
| 2007/0072290 A1 | 3/2007 | Hvichia |
| 2007/0077578 A1 | 4/2007 | Penning et al. |
| 2007/0092444 A1 | 4/2007 | Benos et al. |
| 2007/0092881 A1 | 4/2007 | Ohnishi et al. |
| 2007/0092917 A1 | 4/2007 | Guyon |
| 2007/0099219 A1 | 5/2007 | Teverovskiy et al. |
| 2007/0099289 A1 | 5/2007 | Irimia et al. |
| 2007/0105105 A1 | 5/2007 | Clelland et al. |
| 2007/0105133 A1 | 5/2007 | Clark et al. |
| 2007/0110773 A1 | 5/2007 | Asina et al. |
| 2007/0117158 A1 | 5/2007 | Coumans et al. |
| 2007/0122856 A1 | 5/2007 | Georges et al. |
| 2007/0122896 A1 | 5/2007 | Shuler et al. |
| 2007/0128655 A1 | 6/2007 | Obata |
| 2007/0131622 A1 | 6/2007 | Oakey et al. |
| 2007/0134713 A1 | 6/2007 | Cao |
| 2007/0135621 A1 | 6/2007 | Bourel et al. |
| 2007/0141587 A1 | 6/2007 | Baker et al. |
| 2007/0141588 A1 | 6/2007 | Baker et al. |
| 2007/0141717 A1 | 6/2007 | Carpenter et al. |
| 2007/0154928 A1 | 7/2007 | Mack et al. |
| 2007/0154960 A1 | 7/2007 | Connelly et al. |
| 2007/0160503 A1 | 7/2007 | Sethu et al. |
| 2007/0160974 A1 | 7/2007 | Sidhu et al. |
| 2007/0160984 A1 | 7/2007 | Huang et al. |
| 2007/0161064 A1 | 7/2007 | Kinch et al. |
| 2007/0166770 A1 | 7/2007 | Hsieh et al. |
| 2007/0170811 A1 | 7/2007 | Rubel |
| 2007/0172903 A1 | 7/2007 | Toner et al. |
| 2007/0178067 A1 | 8/2007 | Maier et al. |
| 2007/0178458 A1 | 8/2007 | O'Brien et al. |
| 2007/0187250 A1 | 8/2007 | Huang et al. |
| 2007/0196663 A1 | 8/2007 | Schwartz et al. |
| 2007/0196840 A1 | 8/2007 | Roca et al. |
| 2007/0196869 A1 | 8/2007 | Perez et al. |
| 2007/0202106 A1 | 8/2007 | Palucka et al. |
| 2007/0202109 A1 | 8/2007 | Nakamura et al. |
| 2007/0202525 A1 | 8/2007 | Quake et al. |
| 2007/0207351 A1 | 9/2007 | Christensen et al. |
| 2007/0212698 A1 | 9/2007 | Bendele et al. |
| 2007/0212737 A1 | 9/2007 | Clarke et al. |
| 2007/0212738 A1 | 9/2007 | Haley et al. |
| 2007/0231851 A1 | 10/2007 | Toner et al. |
| 2007/0259424 A1 | 11/2007 | Toner et al. |
| 2007/0264675 A1 | 11/2007 | Toner et al. |
| 2007/0266777 A1 | 11/2007 | Bergman et al. |
| 2008/0023399 A1 | 1/2008 | Inglis et al. |
| 2008/0026390 A1 | 1/2008 | Stoughton et al. |
| 2008/0038733 A1 | 2/2008 | Bischoff et al. |
| 2008/0050739 A1 | 2/2008 | Stoughton et al. |
| 2008/0070792 A1 | 3/2008 | Stoughton et al. |
| 2008/0090239 A1 | 4/2008 | Shoemaker et al. |
| 2008/0093306 A1 | 4/2008 | Oakey et al. |
| 2008/0113350 A1 | 5/2008 | Terstappen |
| 2008/0113358 A1 | 5/2008 | Kapur et al. |
| 2008/0124721 A1 | 5/2008 | Fuchs |
| 2008/0138809 A1 | 6/2008 | Kapur et al. |
| 2008/0220422 A1 | 9/2008 | Shoemaker et al. |
| 2008/0248499 A1 | 10/2008 | Chiu et al. |
| 2009/0061456 A1 | 3/2009 | Allard et al. |
| 2009/0136982 A1 | 5/2009 | Tang et al. |
| 2009/0317836 A1 | 12/2009 | Kuhn et al. |
| 2010/0059414 A1 | 3/2010 | Sturm et al. |
| 2010/0167337 A1 | 7/2010 | Tsinberg et al. |
| 2010/0233693 A1 | 9/2010 | Kopf-Sill et al. |
| 2010/0233694 A1 | 9/2010 | Kopf-Sill et al. |
| 2010/0248358 A1 | 9/2010 | Yoshioka |

FOREIGN PATENT DOCUMENTS

| | | |
|---|---|---|
| EP | 0057907 | 8/1982 |
| EP | 0094193 | 11/1983 |
| EP | 0094193 A3 | 10/1984 |
| EP | 0689051 B1 | 12/1995 |
| EP | 0444115 B2 | 8/1996 |
| EP | 0745682 A | 12/1996 |
| EP | 0549709 B1 | 1/1997 |
| EP | 0637996 B1 | 7/1997 |
| EP | 783694 | 7/1997 |
| EP | 0791659 A2 | 8/1997 |
| EP | 0791659 A3 | 9/1997 |
| EP | 0500727 B1 | 1/1998 |
| EP | 0430402 B1 | 1/1999 |
| EP | 0405972 B1 | 5/1999 |
| EP | 0950665 A1 | 10/1999 |
| EP | 1325331 | 4/2002 |
| EP | 1221342 A2 | 7/2002 |
| EP | 1262776 A2 | 12/2002 |
| EP | 1221342 A3 | 5/2003 |
| EP | 1338894 A2 | 8/2003 |
| EP | 0970365 B1 | 10/2003 |
| EP | 1198595 B1 | 11/2003 |
| EP | 1262776 A3 | 1/2004 |
| EP | 1388013 B1 | 2/2004 |
| EP | 1542802 A1 | 3/2004 |
| EP | 1412729 A2 | 4/2004 |
| EP | 1413346 A1 | 4/2004 |
| EP | 0920627 B1 | 5/2004 |
| EP | 1418003 A1 | 5/2004 |
| EP | 0739240 B1 | 6/2004 |
| EP | 1438398 A2 | 7/2004 |
| EP | 1338894 A3 | 8/2004 |
| EP | 1462800 A1 | 9/2004 |
| EP | 0919812 B1 | 10/2004 |
| EP | 1499706 A2 | 1/2005 |
| EP | 1706720 | 5/2005 |
| EP | 1539350 A1 | 6/2005 |
| EP | 1561507 A1 | 8/2005 |
| EP | 1328803 B1 | 9/2005 |
| EP | 1765503 | 9/2005 |
| EP | 1409727 B1 | 11/2005 |
| EP | 1781986 | 3/2006 |
| EP | 1272668 B1 | 2/2007 |
| EP | 1754788 A2 | 2/2007 |
| EP | 1757694 A2 | 2/2007 |
| EP | 1409745 B1 | 4/2007 |
| EP | 1754788 A3 | 4/2007 |
| EP | 1770171 A1 | 4/2007 |
| EP | 1313882 B1 | 5/2007 |
| EP | 1803822 A1 | 7/2007 |
| EP | 951645 B1 | 8/2007 |
| EP | 1813681 A2 | 8/2007 |
| EP | 1832661 A1 | 9/2007 |
| EP | 1757694 A3 | 2/2008 |
| EP | 1597353 B1 | 11/2010 |
| FR | 2659347 | 9/1991 |
| GB | 2238619 | 6/1991 |
| GB | 2238619 A | 6/1991 |
| GB | 2239311 | 6/1991 |
| GB | 2239311 A | 6/1991 |
| JP | 4152885 | 5/1992 |
| JP | 2004-351309 | 12/2004 |
| WO | WO 83/01906 A | 6/1983 |
| WO | WO 85/02201 A1 | 5/1985 |
| WO | WO 86/06170 A1 | 10/1986 |
| WO | WO 90/06509 A1 | 6/1990 |
| WO | WO 91/07660 A1 | 5/1991 |
| WO | WO 91/07661 A1 | 5/1991 |
| WO | WO 91/13338 A2 | 5/1991 |
| WO | WO 91/08304 A1 | 6/1991 |
| WO | WO 91/11262 A1 | 8/1991 |
| WO | WO 91/13338 A3 | 10/1991 |
| WO | WO 91/15750 A | 10/1991 |

(56) References Cited

FOREIGN PATENT DOCUMENTS

| | | |
|---|---|---|
| WO | WO 91/16452 A1 | 10/1991 |
| WO | WO 92/05185 A1 | 4/1992 |
| WO | WO 93/22053 A1 | 11/1993 |
| WO | WO 93/22055 A2 | 11/1993 |
| WO | WO 1993/022055 A3 | 3/1994 |
| WO | WO 94/29707 | 12/1994 |
| WO | WO 95/09245 A1 | 4/1995 |
| WO | WO 96/32467 A1 | 10/1996 |
| WO | WO 97/45644 A | 12/1997 |
| WO | WO 97/46882 A1 | 12/1997 |
| WO | WO 98/00231 A | 1/1998 |
| WO | WO 98/02528 A1 | 1/1998 |
| WO | WO 98/08931 A1 | 3/1998 |
| WO | WO 98/10267 A1 | 3/1998 |
| WO | WO 98/10869 A | 3/1998 |
| WO | WO 98/12539 A1 | 3/1998 |
| WO | WO 98/22819 A1 | 5/1998 |
| WO | WO 98/31839 A2 | 7/1998 |
| WO | WO 98/31839 A3 | 9/1998 |
| WO | WO 98/40746 A1 | 9/1998 |
| WO | WO 98/57159 A1 | 12/1998 |
| WO | WO 99/31503 A1 | 6/1999 |
| WO | WO 99/38612 A | 8/1999 |
| WO | WO 99/44064 A1 | 9/1999 |
| WO | WO 99/61888 A2 | 12/1999 |
| WO | WO 00/00816 A1 | 1/2000 |
| WO | WO 00/04978 A1 | 2/2000 |
| WO | WO 00/37163 A1 | 6/2000 |
| WO | WO 00/47322 A2 | 8/2000 |
| WO | WO 00/62931 | 10/2000 |
| WO | WO 01/35071 A2 | 5/2001 |
| WO | WO 01/37958 A2 | 5/2001 |
| WO | WO 01/51668 A1 | 7/2001 |
| WO | WO 01/70381 A2 | 9/2001 |
| WO | WO 01/71026 A2 | 9/2001 |
| WO | WO 01/81621 A2 | 11/2001 |
| WO | WO 99/61888 A3 | 12/2001 |
| WO | WO 02/07302 A1 | 1/2002 |
| WO | WO 02/08751 A2 | 1/2002 |
| WO | WO 2001/37958 A3 | 1/2002 |
| WO | WO 02/12896 A1 | 2/2002 |
| WO | WO 2001/35071 A3 | 2/2002 |
| WO | WO 02/28523 A2 | 4/2002 |
| WO | WO 02/30562 A1 | 4/2002 |
| WO | WO 02/31506 A1 | 4/2002 |
| WO | WO 02/43771 A2 | 6/2002 |
| WO | WO 02/44318 A1 | 6/2002 |
| WO | WO 02/44319 A2 | 6/2002 |
| WO | WO 02/44689 A2 | 6/2002 |
| WO | WO 02/08751 A3 | 8/2002 |
| WO | WO 02/073204 A2 | 9/2002 |
| WO | WO 02/090386 A2 | 11/2002 |
| WO | WO 2001/81621 A3 | 11/2002 |
| WO | WO 2001/71026 A3 | 12/2002 |
| WO | WO 03/000418 A2 | 1/2003 |
| WO | WO 03/000418 A3 | 3/2003 |
| WO | WO 03/018198 A1 | 3/2003 |
| WO | WO 03/018757 A2 | 3/2003 |
| WO | WO 03/019141 A2 | 3/2003 |
| WO | WO 03/023057 A2 | 3/2003 |
| WO | WO 03/031938 | 4/2003 |
| WO | WO 2002/44689 A3 | 4/2003 |
| WO | WO 03/035894 | 5/2003 |
| WO | WO 03/035895 A2 | 5/2003 |
| WO | WO 03/044224 A1 | 5/2003 |
| WO | WO 03/066191 A | 8/2003 |
| WO | WO 03/069421 A2 | 8/2003 |
| WO | WO 03/071277 A1 | 8/2003 |
| WO | WO 03/071278 A1 | 8/2003 |
| WO | WO 2002/43771 A3 | 8/2003 |
| WO | WO 03/018757 A3 | 9/2003 |
| WO | WO 03/078972 A | 9/2003 |
| WO | WO 03/079006 A1 | 9/2003 |
| WO | WO 03/085379 | 10/2003 |
| WO | WO 2002/073204 A3 | 10/2003 |
| WO | WO 03/031938 A3 | 11/2003 |
| WO | WO 03/093795 A2 | 11/2003 |
| WO | WO 03/023057 A3 | 12/2003 |
| WO | WO 03/035894 A3 | 12/2003 |
| WO | WO 03/069421 A3 | 12/2003 |
| WO | WO 03/085379 A3 | 12/2003 |
| WO | WO 03/099440 A | 12/2003 |
| WO | WO 03/102595 A1 | 12/2003 |
| WO | WO 2002/090386 A3 | 12/2003 |
| WO | WO 2003/035895 A3 | 1/2004 |
| WO | WO 2004/004906 | 1/2004 |
| WO | WO 2004/015411 | 2/2004 |
| WO | WO 2004/024327 A1 | 3/2004 |
| WO | WO 2004/025251 A2 | 3/2004 |
| WO | WO 2002/43771 A3 | 4/2004 |
| WO | WO 2002/44319 A3 | 4/2004 |
| WO | WO 2003/019141 A3 | 4/2004 |
| WO | WO 2004/029221 | 4/2004 |
| WO | WO 2004/029221 A3 | 5/2004 |
| WO | WO 2004/037374 | 5/2004 |
| WO | WO 2004/044236 A1 | 5/2004 |
| WO | WO 2003/035894 A3 | 6/2004 |
| WO | WO 2004/056978 A1 | 7/2004 |
| WO | WO 2004/076643 A2 | 9/2004 |
| WO | WO 2003/093795 A3 | 10/2004 |
| WO | WO 2004/037374 A3 | 10/2004 |
| WO | WO 2004/088310 A1 | 10/2004 |
| WO | WO 2004/025251 A3 | 11/2004 |
| WO | WO 2004/101762 A2 | 11/2004 |
| WO | WO 2004/113877 | 12/2004 |
| WO | WO 2004/101762 A3 | 2/2005 |
| WO | WO 2005/023091 A2 | 3/2005 |
| WO | WO 2005/028663 A2 | 3/2005 |
| WO | WO 2005/042713 A2 | 5/2005 |
| WO | WO 2005/043121 A2 | 5/2005 |
| WO | WO 2005/047529 A1 | 5/2005 |
| WO | WO 2005/023091 A3 | 6/2005 |
| WO | WO 2005/049168 A2 | 6/2005 |
| WO | WO 2005/058937 A2 | 6/2005 |
| WO | WO 2005/061075 A1 | 7/2005 |
| WO | WO 2005/068503 A2 | 7/2005 |
| WO | WO 2005/049168 A3 | 9/2005 |
| WO | WO 2005/084374 | 9/2005 |
| WO | WO 2005/084380 A2 | 9/2005 |
| WO | WO 2005/085861 A1 | 9/2005 |
| WO | WO 2005/089253 A2 | 9/2005 |
| WO | WO 2005/091756 A2 | 10/2005 |
| WO | WO 2005/098046 A2 | 10/2005 |
| WO | WO 2005/068503 A3 | 11/2005 |
| WO | WO 2005/108621 A1 | 11/2005 |
| WO | WO 2005/108963 A1 | 11/2005 |
| WO | WO 2005/109238 A2 | 11/2005 |
| WO | WO 2005/028663 A3 | 12/2005 |
| WO | WO 2005/098046 A3 | 12/2005 |
| WO | WO 2005/116264 A2 | 12/2005 |
| WO | WO 2005/121362 A2 | 12/2005 |
| WO | WO 2005/085861 A3 | 2/2006 |
| WO | WO 2006/012820 A1 | 2/2006 |
| WO | WO 2005/121362 A3 | 4/2006 |
| WO | WO 2006/035846 A1 | 4/2006 |
| WO | WO 2006/037561 A1 | 4/2006 |
| WO | WO 2006/041453 | 4/2006 |
| WO | WO 2005/109238 A3 | 6/2006 |
| WO | WO 2006/076567 A2 | 7/2006 |
| WO | WO 2006/078470 A2 | 7/2006 |
| WO | WO 2005/043121 A3 | 8/2006 |
| WO | WO 2006/076567 A3 | 9/2006 |
| WO | WO 2006/078470 A3 | 9/2006 |
| WO | WO 2006/100366 A2 | 9/2006 |
| WO | WO 2006/108087 A2 | 10/2006 |
| WO | WO 2006/108101 A2 | 10/2006 |
| WO | WO 2005/042713 A3 | 11/2006 |
| WO | WO 2006/023563 A3 | 11/2006 |
| WO | WO 2005/084380 A3 | 12/2006 |
| WO | WO 2006/133208 A2 | 12/2006 |
| WO | WO 2005/116264 A3 | 2/2007 |
| WO | WO 2007/020081 A1 | 2/2007 |
| WO | WO 2004/076643 A3 | 3/2007 |
| WO | WO 2005/089253 A3 | 3/2007 |

(56) References Cited

FOREIGN PATENT DOCUMENTS

| | | |
|---|---|---|
| WO | WO 2007/024264 A2 | 3/2007 |
| WO | WO 2007/028146 A2 | 3/2007 |
| WO | WO 2007/030949 A2 | 3/2007 |
| WO | WO 2007/033167 A2 | 3/2007 |
| WO | WO 2007/034221 A2 | 3/2007 |
| WO | WO 2007/035414 A2 | 3/2007 |
| WO | WO 2007/035498 A2 | 3/2007 |
| WO | WO 2005/091756 A3 | 4/2007 |
| WO | WO 2007/024264 A3 | 4/2007 |
| WO | WO 2007/036025 A1 | 4/2007 |
| WO | WO 2007/038264 A2 | 4/2007 |
| WO | WO 2007/041610 A2 | 4/2007 |
| WO | WO 2007/044690 A2 | 4/2007 |
| WO | WO 2007/048076 A2 | 4/2007 |
| WO | WO 2004/037374 * | 5/2007 |
| WO | WO 2007/030949 A3 | 5/2007 |
| WO | WO 2007/034221 A3 | 5/2007 |
| WO | WO 2007/050495 A2 | 5/2007 |
| WO | WO 2007/053142 A1 | 5/2007 |
| WO | WO 2007/053648 A2 | 5/2007 |
| WO | WO 2007/053785 A2 | 5/2007 |
| WO | WO 2007/059430 A2 | 5/2007 |
| WO | WO 2007/062222 A2 | 5/2007 |
| WO | WO 2005/058937 A3 | 6/2007 |
| WO | WO 2007/067734 A2 | 6/2007 |
| WO | WO 2007/048076 A3 | 7/2007 |
| WO | WO 2007/053648 A3 | 7/2007 |
| WO | WO 2007/075879 A2 | 7/2007 |
| WO | WO 2007/076989 A1 | 7/2007 |
| WO | WO 2007/079229 A2 | 7/2007 |
| WO | WO 2007/079250 A2 | 7/2007 |
| WO | WO 2007/082144 A2 | 7/2007 |
| WO | WO 2007/082154 A2 | 7/2007 |
| WO | WO 2007/082379 A2 | 7/2007 |
| WO | WO 2007/050495 A3 | 8/2007 |
| WO | WO 2007/075879 A3 | 8/2007 |
| WO | WO 2007/087612 A2 | 8/2007 |
| WO | WO 2007/089880 A2 | 8/2007 |
| WO | WO 2007/089911 A2 | 8/2007 |
| WO | WO 2007/090670 A1 | 8/2007 |
| WO | WO 2007/092713 A2 | 8/2007 |
| WO | WO 2007/098484 A2 | 8/2007 |
| WO | WO 2006/100366 A3 | 9/2007 |
| WO | WO 2007/100684 A2 | 9/2007 |
| WO | WO 2007/101609 A1 | 9/2007 |
| WO | WO 2007/033167 A3 | 10/2007 |
| WO | WO 2007/038264 A3 | 10/2007 |
| WO | WO 2007/044690 A3 | 10/2007 |
| WO | WO 2007/053785 A3 | 10/2007 |
| WO | WO 2007/059430 A3 | 10/2007 |
| WO | WO 2007/087612 A3 | 10/2007 |
| WO | WO 2005/084374 A3 | 11/2007 |
| WO | WO 2006/0133208 A3 | 11/2007 |
| WO | WO 2007/035414 A3 | 11/2007 |
| WO | WO 2007/035498 A3 | 11/2007 |
| WO | WO 2007/089880 A3 | 11/2007 |
| WO | WO 2007/126938 A2 | 11/2007 |
| WO | WO 2007/082379 A3 | 12/2007 |
| WO | WO 2007/098484 A3 | 12/2007 |
| WO | WO 2007/062222 A3 | 1/2008 |
| WO | WO 2007/100684 A3 | 1/2008 |
| WO | WO 2008/017871 A1 | 2/2008 |
| WO | WO 2007/089911 A3 | 5/2008 |
| WO | WO 2007/028146 A3 | 6/2008 |
| WO | WO 2007/075879 A3 | 7/2008 |
| WO | WO 2007/067734 A3 | 8/2008 |
| WO | WO 2007/082379 A3 | 9/2008 |
| WO | WO 2007/126938 A3 | 10/2008 |
| WO | WO 2007/082154 A3 | 11/2008 |
| WO | WO 2007/087612 | 11/2008 |
| WO | WO 2007/082144 A3 | 12/2008 |
| WO | WO 2007/092713 A3 | 12/2008 |
| WO | WO 2007/098484 A3 | 12/2008 |
| WO | WO 2007/079229 A3 | 1/2009 |
| WO | WO 2007/079250 A3 | 3/2009 |
| WO | WO 2006/108101 A3 | 4/2009 |
| WO | WO 2007/041610 A3 | 4/2009 |
| WO | WO 2006/108087 A3 | 6/2009 |

OTHER PUBLICATIONS

Ashcroft, et al. Solid State Physics. Saunders College Publishing. Orlando, Fl. 1976. (Table of Contents only.).

Bauer, J. Advances in cell separation: recent developments in counterflow centrifugal elutriation and continuous flow cell separation. Journal of Chromatography. 1999;722:55-69.

Becker, et al. Fabrication of Microstructures With High Aspect Ratios and Great Structural Heights by Synchrotron Radiation Lithography, Galvanoforming, and Plastic Moulding (LIGA Process). Microelectronic Engineering. 1986;4:35-56.

Becker, et al. Planar quartz chips with submicron channels for two-dimensional capillary electrophoresis applications. J. Micromech Microeng.1998;9:24-28.

Beebe et al. Functional Hydrogel Structures for Autonomous Flow Control Inside Microfluidic Channels. Nature. 2000; 404:588-590.

Benincasa, et al. Cell Sorting by One Gravity SPLITT Fractionation. Analytical Chemistry. 2005; 77(16):5294-5301.

Berg, H. C. Random Walks. In Biology, Ch. 4. Princeton University Press. Princeton, NJ. 1993. pp. 48-64.

Chiu, et al. Patterned Deposition of Cells and Proteins Onto Surfaces by Using Three-Dimensional Microfluidic Systems. Proceedings of the National Academy of Sciences of the United States of America. 2000; pp. 2408-2413.

Chou, et al. A Microfabricated Device for Sizing and Sorting DNA Molecules. Proceedings of the National Academy of Sciences of the United States of America. 1999; pp. 11-13.

Chou, et al. Sorting by diffusion: An asymmetric obstacle course for continuous molecular separation. PNAS. 1999; 96(24):13762-13765.

Das, et al. Dielectrophoretic segregation of different human cell types on microscope slides. Anal. Chem. 2005; 77:2708-2719.

De Kretser, et al. The Separation of Cell Populations using Monoclonal Antibodies attached to Sepharose. Tissue Antigens. 1980;16:317-325.

Delamarche, et al. Microfluidic Networks for Chemical Patterning of Substrates: Design and Application to Bioassays. Journal of the American Chemical Society. 1998; 120:500-508.

Delamarche, et al. Patterned Delivery of Immunoglobulins to Surfaces Using Microfluidic Networks. Science. 1997; 276:779-781.

Deshmukh, et al. Continuous Micromixer With Pulsatile Micropumps. Solid-State Sensor and Actuator Workshop. Hilton Head Island, South Carolina; Jun. 4-8, 2000:73-76.

Eigen, et al. Sorting Single Molecules: Application to Diagnostics and Evolutionary Biotechnology. Proceedings of the National Academy of Sciences of the United States of America. 1994; 91:5740-5747.

Evans, et al. The Bubble Spring and Channel (BSAC) Valve: An Actuated, Bi-Stable Mechanical Valve for In-Plane Fluid Control. Transducers '99. Sendai, Japan; Jun. 7-10, 1999.

Farooqui, et al. Microfabrication of Submicron Nozzles in Silicon Nitride. Journal of Microelectromechanical Systems. 1992; 1(2):86-88.

Fiedler, et al. Dielectrophoretic Sorting of Particles and Cells in a Microsystem. Analytical Chemistry. 1998; pp. 1909-1915.

Freemantle, M. Downsizing Chemistry. Chemical analysis and synthesis on microchips promise a variety of potential benefits. Chemical & Engineering News. 1999; pp. 27-36.

Fu, et al. An integrated microfabricated cell sorter. Anal Chem. 2002;74:2451-2457.

Fu, et al. A Microfabricated Fluorescence-Activated Cell Sorter. Nature Biotechnology.1999; 17:1109-1111.

Fuhr, et al. Biological Application of Microstructures. Topic sin Current Chemistry. 1997; 194:83-116.

Giddings, J.C. Unified Separation Science. John Wiley & Sons, Inc. 1991; Cover Page & Table of Contents only.

Giddings, J. C. Chemistry 'Eddy' Diffusion in Chromatography. Nature. 1959;184:357-358.

(56) References Cited

OTHER PUBLICATIONS

Giddings, J. C. Field-Flow Fractionation: Analysis of Macromolecular, Colloidal, and Particulate Materials. Science. 1993;260:1456-1465.
Han, et al. Separation of Long DNA Molecules in a Microfabricated Entropic Trap Array. Science. 2000;288:1026-1029.
Huang, et al. A DNA prism for high-speed continuous fractionation of large DNA molecules. Nature Biotechnology. 2002;20:1048-1051.
Huang, et al. Electric Manipulation of Bioparticles and Macromoledules on Microfabricated Electrodes. Analytical Chemistry. 2001; pp. 1549-1559.
Huang, et al. Role of Molecular Size in Ratchet Fractionation. 2002; 89(17):178301-1-178301-4.
Huh, et al. Gravity-driven microhydrodynamics-based cell sorter (microHYCS) for rapid, inexpensive, and efficient cell separation and size-profiling. 2nd Annual International IEEE-EMBS Special Topic Conference on Microtechnology in Medicine and Biology. Madison, Wisconsin USA; May 2-4, 2002:466-469.
Jeon, et al. Generation of Solution and surface Gradients Using Microfluidic Systems. Langmuir. 2000, pp. 8311-8316.
Kamholz, et al. Quantitative Analysis of Molecular Interaction in a Microfluidic Channel: the T-Sensor. Analytical Chemistry. 1999; pp. 5340-5347.
Kenis, et al. Microfabrication Inside Capillaries Using Multiphase Laminar Flow Patterning. Science. 1999; 285:83-85.
Kim, et al. Polymer microstructures formed by moulding in capillaries. Nature. 1995;376:581-584.
Kumar, et al. Cell Separation: A Review. Pathology. 1984;16:53-62.
Li ,et al. Transport, Manipulation, and Reaction of Biological Cells On-Chip Using Electrokinetic Effects. Analytical Chemistry., 1997; pp. 1564-1568.
Mehrishi , et al. Electrophoresis of cells and the biological relevance of surface charge. Electrophoresis.2002;23:1984-1994.
Mohamed, et al. Development of a rare cell fractionation device: application for cancer detection. IEEE Trans Nanobioscience. 2004; 3(4): 251-6.
Moore, et al. Lymphocyte fractionation using immunomagnetic colloid and a dipole magnet flow cell sorter. J Biochem Biophys Methods. 1998;37:11-33.
Oakey et al. Laminar Flow-Based Separations at the Microscale. Biotechnology Progress. 2002; pp. 1439-1442.
Olson, et al. An in Situ Flow Cytometer for the Optical Analysis of Individual Particles in Seawater. Available at http://www.whoi.edu/science/B/Olsonlab/insitu2001.htm. Accessed Apr. 24, 2006.
Product literature for GEM, a system for blood testing: GEM Premier 3000. Avaiable at http://www.ilus.com/premier_gem3000_iqm.asp. Accessed Apr. 24, 2006.
Raymond, et al. Continuous Separation of High Molecular Weight Compounds Using a Microliter Volume Free-Flow Electrophoresis Microstructure. 1996;68:2515-2522.
Takayama, et al. Patterning Cells and Their Environments Using Multiple Laminar Fluid Flows in Capillary Networks. Proceedings of the National Academy of Sciences of the United States of America. 1999:5545-5548.
Takayama, et al. Subcellular Position of Small Molecules. Nature. 2001; 411:1016.
Tong, et al. Low Temperature Wafer Direct Bonding. Journal of Microelectromechanical Systems. 1994;3:29-35.
Turner, et al. Confinement-Induced Entropic Recoil of Single DNA Molecules in a Nanofluidic Structure. Physical Review Letters. 2002;88:128103.1-128103.4.
Voldman, et al. Holding Forces of Single-Particle Dielectrophoretic Traps. Biophysical Journal.2001;80:531-541.
Volkmuth, et al. DNA electrophoresis in microlithographic arrays. Nature. 1992; 358:600-602.
Weigl, et al. Microfluidic Diffusion-Based Separation and Detection. Science. 1999; pp. 346-347.
Xu, et al. Dielectrophoresis of human red cells in microchips. Electrophoresis.1999;20:1829-1831.
Zhang, et al. High-speed free-flow electrophoresis on chip. Anal Chem. 2003;75:5759-5766.
Fuchs, et al., U.S. Appl. No. 11/449,161, entitled "Devices and Methods for Enrichment and Alteration of Circulating Tumor Cells and Other Particles," filed Jun. 8, 2006.
Kapuri et al., U.S. Appl. No. 11/227,904, entitled "Devices and Methods for Enrichment and Alteration of Cells and Other Particles," filed Sep. 15, 2005.
"Micromechanics Imitate Blood Vessels" Design News 15 (Mar. 22, 1993).
Carlson, et al. Self-Sorting of White Blood Cells in a Lattice. Phys. Rev. Lett. 79:2149-2152 (1997).
Doyle, et al. Self-Assembled Magnetic Matrices for DNA Separation Chips. Science 295:2237 (2002).
Huang, et al. Continuous Particle Separation Through Deterministic Lateral Displacement. Science 304:987-90 (2004).
Ivker, M. Direct Observation of Reptation in Artificial Gel Environments. Bachelor of Arts thesis, Princeton University. Spring 1991.
Petersen, et al. The Promise of Miniaturized Clinical Diagnostic Systems. IVD Technol. 4:43-49 (1998).
Sethu, et al. Continuous Flow Microfluidic Device for Rapid Erythrocyte Lysis. Anal. Chem. 76:6247-6253 (2004).
Toner, et al. Blood-on-a-Chip. Annu. Rev. Biomed. Eng. 7:77-103, C1-C3 (2005).
Volkmuth, et al. Observation of Electrophoresis of Single DNA Molecules in Nanofabricated Arrays. Presentation at joint annual meeting of Biophysical Society and the American Society for Biochemistry and Molecular Biology. Feb. 9-13, 1992.
Zuska, P. Microtechnology Opens Doors To the Universe of Small Space. MD&DI Jan. 1997, p. 131.
Adinolfi, et al. Gene Amplification to Detect Fetal Nucleated Cells in Pregnant Women. The Lancet. Aug. 5, 1989:328-329.
Adinolfi, M. On a Non-Invasive Approach to Prenatel Diagnosis based on the detection of Fetal Nucleated Cells in Maternal Blood Samples. Prenatal Diagnosis. 1991;11:799-804.
Al Saadi, A. Cystic Hygroma Cells as Source for Prenatal Diagnosis. The American Journal of Human Genetics. Oct. 1989. Supplemental to vol. 45, No. 4:A252-0990.
Al-Mufti, et al. Distribution of Fetal and Embryonic Hemoglobins in Fetal Erythroblasts Enriched from Maternal Blood. Haematologica. 2001; 86:357-362.
Alvarez, H. Morphology and Physiopathology of the Human Placenta. Obstetrics and Gynecology.1964. 23:813-817;819-825.
Anderson, et al. Simutaneous fluorescence-activated cell sorter analysis of two distinct transcriptional elements within a single cell using engineered green fluorescent proteins. Genetics. 1996;93:8508-8511.
Associated Press, "Blood Test May Erase Risk of Amniocentesis," The Worcester Telegram & Gazette Oct. 9, 1991: A7.
Bartley, et al. Adrenal Hypoplasia, Mental Retardation, Microcephaly, Short Stature, and Small Testes in a Male with a Xp21 Deletion of LOCI DXS28 (C7), DXS68 (L1.4) and DXS67 (B24). Pediatric Research. Apr. 1989: 139A-816.
Ben-Yoseph, et al. Diagnosis and Carrier Detection of Farber Disease (Ceramidase Deficiency) in Plasma and Leukocytes. Pediatric Research. Apr. 1989: 139A-817.
Berenson, et al. Antigen CD34 Marrow Cells Engraft Lethally irradiated Baboons. J Clin Invest.1988;81:951-955.
Bertero, et al. Circulating "trophoblast" cells in pregnancy have maternal genetic markers. Prenatal Diagnosis. 1988;8:585-590.
Bianchi, et al. Isolation of fetal DNA from nucleated erythrocytes in maternal blood. Medical Sciences. 1990;87:3279-3283.
Bianchi, et al. Demonstration of fetal gene sequences in nucleated erythrocytes isolated from maternal blood. American Journal of Human Genetics. 1989;45:A252.
Bianchi, et al. Direct Hybridization to DNA From Small Numbers of Flow-Sorted Nucleated Newborn Cells. Cytometry. 1987; 8:197-202.
Bianchi, et al. Fetal nucleated erythrocytes (FNRBC) in maternal blood: erythroid-specific antibodies improve detection. The American Journal of Human Genetics. Oct. 1992. Supplemental to vol. 51, No. 4: 996.

(56) References Cited

OTHER PUBLICATIONS

Bianchi, et al. Isolation of Male Fetal DNA from Nucleated Erythrocytes (NRBC) in Maternal Blood. The American Pediatric Society and Society for Pediatric Research, (1989) Mar. 1989; 818:139A.

Bianchi, et al. Possible Effects of Gestational Age on the Detection of Fetal Nucleated Erythrocytes in Maternal Blood. Prenatal Diagnosis. 1991;11:523-528.

Bick, et al. Prenatal diagnosis and investigation of a fetus with chondrodysplasia punctata, ichthyosis and Kallmann syndrome due to an Xp deletion: Evidence for a neuronal migration defect in Kallmann syndrome. Prenatal Diagnosis. Jan. 1992. vol. 12: 19-29.

Bickers, et al; Fetomaternal Transfusion Following Trauma. Obstetrics & Gynecology.1983;61:258-259.

Bigbee, et al. Monoclonal Antibodies Specific for the M- and N-Forms of Human Glycophorin A. Molecular Immunolgy. 1983;20:1353-1362.

Black, , et al. Complex mosaicism on chorionic sampling confirmed postnatally. The American Journal of Human Genetics. Oct. 1989. Supplemental to vol. 45, No. 4:A252-0993.

Blake, et al. Assessment of multiplex fluorescent PCR for screening single cells for trisomy 21 and single gene defects. Mol. Hum. Reprod. 1999; 5(12):1166-75.

Bode, et.al. Mutations in the tyrosine kinase domain of the EGFR gene are rare in synovial sarcoma. Mod Pathol. Apr. 2006;19(4):541-7.

Bodurtha, et al. Genetic Analysis of Fat Deposition in 11-Year Old Twins. Pediatric Research. Apr. 1989: 139A-819.

Boehm, et al. Analysis of Defective Dystrophin Genes with cDNA Probes: Rearrangement Polymorphism, Detection of Deletions in Carrier Females, and Lower Than Expected Frequency of Carrier Mothers in Isolated Cases of Defections. Pediatric Research. Apr. 1989: 139A-820.

Bohmer, et al. Differential Development of Fetal and Adult Haemoglobin Profiles in Colony Culture: Isolation of Fetal Nucleated Red Cells by Two-Colour Fluorescence Labelling. Br. J. Haematol. 1998; 103:351-60.

Boyer, et al. Enrichment of Erythrocytes of Fetal Origin From Adult-Fetal Blood Mixtures via Selective Hemolysis of Adult Blood Cells: An Aid to Antenatal Diagnosis of Hemoglobinopathies. Blood: The Journal of the American Society of Hemotology. 1976;47:883-97.

Brizot, et al. Maternal serum hCG and fetal nuchal translucency thickness for the prediction of fetal trisomies in the first trimester of pregnancy. Br J Obstet Gynaecol. 1995;102(2):127-32.

Brizot, et al. Maternal serum pregnancy-associated plasma protein a and fetal nuchal translucency thickness for the prediction of fetal trisomies in early pregnancy. Obstet Gynecol. 1994; 84(6):918-22.

Bulmer, et al. Antigen Expression by Trophoblast Populations in the Human Placenta and Their Possible Immunobiological Relevance. Placenta. 1985;6:127-140.

Caggana, M. Microfabricated devices for sparse cell isolation. CNF Project #905-00. Cornell NanoScale Facility. 2003; pp. 38-39.

Caggana, M. Microfabricated devices for sparse cell isolation. CNF Project #905-00. Cornell NanoScale Facility. 2004-2005; pp. 32-33.

Cai, et al. A New TATA Box Mutation Detected at Prenatal Diagnosis for b-Thalassemia. Am J Hum Genet. 1989;45:112-114.

Cai, et al. Rapid Prenatal Diagnosis of b Thalassemia Using DNA Amplification and Nonrradioactive Probes. Blood. 1989;73:372-374.

Chamberlain, et al. Deletion screening of the Duchenne muscular dystrophy locus via multiplex DNA amplification. Nucleic Acids Research. 1988;16:11141-11156.

Charnas, et al. Prader Willi Syndrome in a Patient with Septo-Optic Dysplasia. Pediatric Research. Apr. 1989: 139A-821.

Cheung, et al. Prenatal diagnosis of sickle cell anaemia and thalassaemia by analysis of fetal cells in maternal blood. Nat Genet. 1996; 14(3):264-8.

Choesmel, et al. Enrichment methods to detect bone marrow micrometastases in breast carcinoma patients: clinical relevance. Breast Cancer Res. 2004;6(5):R556-569.

Choolani, et al. Characterization of First Trimester Fetal Erythroblasts for Non-Invasive Prenatal Diagnosis. Mol. Hum. Reprod. 2003; 9:227-35.

Christensen, et al. Fetal Cells in Maternal Blood: A Comparison of Methods for Cell Isolation and Identification. Fetal Diagn. Ther. 2005; 20:106-12.

Chueh, et al. Prenatal Diagnosis Using Fetal Cells from the Maternal Circulation. West J. Med. 159:308-311 (1993).

Chueh, et al. Prenatal Diagnosis Using Fetal Cells in the Maternal Circulation. Seminars in Perinatology. 1990;14:471-482.

Chueh, et al. The search for fetal cells in the maternal circulation. J Perinat Med. 1991;19:411-420.

Clayton, et al. Fetal Erythrocytes in the Maternal Circulation of Pregnant Women. Obstetrics and Gynecology. 1964;23:915-919.

Cohen, et al. Mechanisms of Isoimmunization II. Transplacental Passage and Postnatal Survival of Fetal Erythrocytes in Heterospecific Pregnancies. Blood. 1967;30:796-804.

Covone, et al. Analysis of Peripheral Maternal Blood Samples for the Presence of Placenta-Derived Cells Using Y-Specific Probes and McAb H315. Prenatal Diagnosis.1988;8:591-607.

Cremer; et al. Detection of chromosome aberrations in human interphase nucleus by visualization of specific target DNAs with radioactive and non-radioactive in situ hybridization techniques: diagnosis of trisomy 18 with probe L1.84. Human Genetics. 1986;74:346-352.

Cristofanilli, et al. Circulating tumor cells revisited. JAMA. Mar. 17, 2010;303(11):1092-3.

Deng, et al., Manipulation of magnetic microbeads in suspension using micromagnetic systems fabricated with soft lithography, Applied Physics Letters. (Mar. 2001). vol. 78, No. 12: 1175-1777.

Di Naro, et al. Prenatal diagnosis of beta-thalassaemia using fetal erythroblasts enriched from maternal blood by a novel gradient. Mol Hum Reprod. 2000; 6(6):571-4.

Dilella, et al. Screening for Phenylketonuria Mutations by DNA Amplification with the Polymerase Chain Reaction. The Lancet. Mar. 5, 1988:497-499.

Douglas , et al. Trophoblast in the Circulating Blood During Pregnancy. Am J Obst & Gynec. 1959;78:960-973.

Dragovich, et al. Anti-EGFR-Targeted Therapy for Esophageal and Gastric Cancers: An Evolving Concept. J Oncol. 2009;2009:804108. Epub Jul. 14, 2009.

Elias, S. Prenatal blood test can signal genetic disorders. The Associated Press, The Boston Globe. Oct. 8, 1991:4.

Ergin, et al. Nucleated Red Blood Cell Count in Infants of Women with Well-controlled Gestational Diabetes Mellitus. Artemis. 2003; 4(1): 33-36.

Farber, et al. Demonstration of spontaneous XX/XY chimerism by DNA fingerprinting. Human Genetics. 1989;82:197-198.

Fernandes, B. Identification and Enumeration of Nucleated Red Blood Cells in Peripheral Blood. Sysmex Journal International. 2002; 12(2): 56-62.

Fibach , et al. Proliferation and Maturation of Human Erythroid Progenitors in Liquid Culture. Blood. 1989;73:100-103.

Forestier, et al. Hematological Values of 163 Normal Fetuses between 18 and 30 weeks of Gestation. Pediatric Research. 1986;20:342-346.

Galbraith, et al. Demonstration of Transferrin Receptors on Human Placental Trophoblast. Blood. 1980;5:240-242.

Ganshirt-Ahlert, et al. Magnetic cell sorting and the transferrin receptor as potential means of prenatal diagnosis from maternal blood. Am J Obstet Gynecol. 1992;166:1350-1355.

Ganshirt-Ahlert, et al. Noninvasive prenatal diagnosis: Triple density gradient, magnetic activated cell sorting and FISH prove to be an efficient and reproducible method for detection of fetal aneuploidies from maternal blood. The American Journal of Human Genetics. Oct. 1992. Supplemental to vol. 51, No. 4: 182.

Gasparini , et al. First-Trimester Prenatal Diagnosis of Cystic Fibrosis Using the Polymerase Chain Reaction: Report of Eight Cases. Prenatal Diagnosis. 1989;9:349-355.

Guerin, et al. A New TaqI BO Variant Detected With the p49 Probe on the Human Y Chromosome. Nucleic Acids Research.1988;16:7759.

(56) References Cited

OTHER PUBLICATIONS

Guetta, et al. Analysis of fetal blood cells in the maternal circulation: challenges, ongoing efforts, and potential solutions. Stem Cells Dev. 2004;13(1):93-9.
Hall, et al. Isolation and Purification of CD34+ Etal Cells From Maternal Blood. The American Journal of Human Genetics. Oct. 1992. Supplemental to vol. 51, No. 4: 1013.
Hames, et al. Nucleic acid hybridisation: a practical approach. Oxford: IRL Press Limited. 1985:190-193.
Hamsberger, et al. Imaging tumors of the central nervous system and extracranial head and neck. CA Cancer J Clin. Jul.-Aug. 1987;37(4):225-38.
Handyside, et al. Biopsy of Human Preimplantation Embryos and Sexing by DNA Amplification. The Lancet. Feb. 18, 1989:347-349.
Harnsberger, et al. Imaging tumors of the central nervous system and extracranial head and neck. CA Cancer J Clin. Jul.-Aug. 1987;37(4):225-38.
Hennerbichler, et al. Detection and Relocation of Cord Blood Nucleated Red Blood Cells by Laser Scanning Cytometry. Cytometry. 2002; 48:87-92.
Herzenberg, et al. Fetal cells in the blood of pregnant women: Detection and enrichment by flourescence-activated cell sorting. Proc. Natl. Acad. Sci. 1979;76:1453-1455.
Holzgreve, et al. Fetal Cells in the Maternal Circulation. Journal of Reproductive Medicine. 1992;37:410-418.
Huang, et al. Possible association of beta2- and beta3-adrenergic receptor gene polymorphisms with susceptibility to breast cancer. Breast Cancer Res. 2001;3(4):264-9.
Huie, et al. Antibodies to human fetal erythroid cells from a nonimmune phage antibody library. PNAS. 2001; 98(5): 2682-7.
Hviid T. In-Cell PCT method for specific genotyping of genomic DNA from one individual in a micture of cells from two individuals: a model study with specific relevance to prenatal diagnosis based on fetal cells in maternal blood. Molecular Diagnostics and Genetics. 2002; 48:2115-2123.
Iverson, et al. Detection and Isolation of Fetal Cells From Maternal Blood Using the Flourescence-Activated Cell Sorter (FACS). Prenatal Diagnosis 1981;1:61-73.
Jan, et al. Fetal Erythrocytes Detected and Separated from Maternal Blood by Electronic Fluorescent Cell Sorter. Texas Rep Biol Med. 1973;31:575.
Kan, et al. Concentration of Fetal Red Blood Cells From a Mixture of Maternal and Fetal Blood by Anti-i Serum—An Aid to Prenatal Diagnosis of Hemoglobinopathies. Blood. 1974; 43:411-415.
Kawata, et al. Transcriptional Control of HLA-A,B,C, Antigen in Human Placental Cytotrophoblast Isolated Using Trophoblast- and HLA-Specific Monoclonal Antibodies and the Fluorescence-Activated Cell Sorter. J Exp Med.1984;160:633-651.
Kelly, D. A simpler, safer blood test for birth defects. USA Today. Nov. 14, 1989;1D.
Klinger, et al. Rapid Detection of Chromosome Aneuploidies in Uncultured Amniocytes by Using Flourescence in Situ Hybridization (FISH). Am J Hum Genet. 1992; 51:55-65.
Kogan, et al. An Improved Method for Prenatal Diagnosis of Genetic Diseases by Analysis of Amplified DNA Sequences, Application to Hemophilia A. The New England Journal of Medicine. 1987;317:985-990.
Kohn, et al. Elevated maternal serum human chorionic gonadotropin associated with a chromosomal deletion. Prenat. Diagn. 1992; 12:853-854.
Krabchi, et al. Quantification of all fetal nucleated cells in maternal blood between the 18th and 22nd weeks of pregnancy using molecular cytogenic techniques. Clin. Genet. 2001; 60:145-150.
Kulch, et al. Racial Differences in Mate al Serum Human Chorionic Gonadotropin and Unconjugated Oestriol Levels. Prenatal Diagnosis.1993 vol. 13: 191-195.
Kulozik, et al. Fetal Cell in the Maternal Circulation: Detection by Direct AFP-Immunoflourescence. Human Genetics. 1982;62:221-224.

Kwok, et al. Avoiding false positives with PCR. Nature. 1989;339:237-238.
Lanier, et al. Subpopulations of Human Natural Killer Cells Defined by Expression of the LEU-7 (HNK-1) and LEU-11 (NK-15) Antigens. The Journal of Immunology.1983;131:1789-1796.
Latt, S. A. Prenatal Genetic Diagnosis. In: Schaffer's Diseases of the Newborn.1984:24-36.
Lau, et al. A Rapid Screening Test for Antenatal Sex Determination. The Lancet. Jan. 7, 1984:14-16.
Li, et al. Amplification and analysis of DNA sequences in single human sperm and diploid cells. Nature. 1988;335:414-417.
Lin, et al. Microbubble Powered Actuator. Transducers '91. 1991:1041-1044. IEEE Catalog No. 91CH2817-5.
Lipinski, et al. Human trophoblast cell-surface antigens defined by monoclonal antibodies. Medical Sciences. 1981;78:5147-5150.
Lloyd, et al. Intrapartum Fetomaternal Bleeding in Rh-Negative Women. Obstetrics & Gynecology.1980;56:285-287.
Lo, et al. False-Positive Results and the Polymerase Chain Reaction. The Lancet. Sep. 17, 1988:679.
Lo, et al. Prenatal sex determination by DNA amplification from material peripheral blood. The Lancet.Dec. 9, 1989:1363-1365.
Lubetzky, et al. Nucleated Red Blood Cells in Preterm Infants with Retinopathy of Prematurity. Pediatrics. 2005; 116: e619-e622.
Macadam, et al. Standardization of Ultrasound Measurements in pregnancy dating for the purposes of triple marker screening. The American Journal of Human Genetics. Oct. 1992. Supplemental to vol. 51, No. 4: 1620.
Mahr, et al. Fluorescence in situ hybridization of fetal nucleated red blood cells. The American Journal of Human Genetics. Oct. 1992. Supplemental to vol. 51, No. 4: 1621.
Marks, et al. Epidermal growth factor receptor (EGFR) expression in prostatic adenocarcinoma after hormonal therapy: a fluorescence in situ hybridization and immunohistochemical analysis. Prostate. Jun. 15, 2008;68(9):919-23.
Mavrou, et al. Identification of nucleated red blood cells in maternal circulation: A second step in screening for fetal aneuploidies and pregnancy complications. Prenat Diagn. 2007; 247:150-153.
McCabe, et al. DNA microextraction from dried blood spots on filter paper blotters: potential applications to newborn screening. Hum Genet.1987;75:213-216.
McCarley, et al. Royal Society of Chemistry Special Publications. Ed. Kutter et al. Royal Soc Chemistry, thomas Graham House. 2005; 130-132. Abstract. 8th International Conference on Miniaturized systems for Chemistry and Life Sciences, Malmo, Sweden, Sep. 26-30, 2004.
Millar, et al. Normal Blood Cell Values in the Early Mid-Trimester Fetus. Prenatal Diagnosis. 1985;5:367-373.
Mohamed, et al. A Micromachined Sparse Cell Isolation Device: Application in Prenatal Diagnostics. Nanotech 2006 vol. 2; 641-644. (Abstract only).
Mohamed, et al. Biochip for separating fetal cells from maternal circulation. J Chromatogr A. Aug. 31, 2007;1162(2):187-92.
Muller, et al. Moderately repeated DNA sequences specific for the short arm of the human Y chromosome are present in XX makes and reduced in copy number in an XY female. 1986;14:1325-1340.
Mullis, et al. Specific Enzymatic Amplification of DNA in Vitro: The Polymerase Chain Reaction. Cold Spring Harbor Symposia on Quantitative Biolgy 1986;51:263-273.
Newman, et al. The Transferrin Receptor. Trends Biochem Sci. 1982;1:397-400.
Oberle, et al. Genetic Screening for Hemophilia A (Classic Hemophilia) With a Polymorphic DNA Probe. New Engl J Med. 1985;312:682-686.
Ockenhouse, et al. Activation of Monocytes and Platelets by Monoclonal Antibodies or Malaria-infected Erythrocytes Binding to the CD36 Surface Receptor in vitro. J Clin Invest. 1989;84:468-475.
Oosterwijk, et al. Prenatal diagnosis of trisomy 13 on fetal cells obtained from maternal blood after minor enrichment. Prenat Diagn. 1998;18(10):1082-5.
Owen, et al. High gradient magnetic separation of erythrocytes. Biophys. J. 1978; 22:171-178.

(56) References Cited

OTHER PUBLICATIONS

Pallavicini, et al. Analysis of fetal cells sorted from maternal blood using fluorescence in situ hybridization. The American Journal of Human Genetics. Oct. 1992. Supplemental to vol. 51, No. 4: 1031.
Papavasiliou, et al. Electrolysis-Bubble Actuated Gate Valve. Solid-State Sensor and Actuator Workshop, Hilton Head Island, SC. Jun. 4-8, 2000; 48-51.
Parano, et al. Noninvasive Prenatal Diagnosis of Chromosomal Aneuploidies by Isolation and Analysis of Fetal Cells from Maternal Blood. Am. J. Med. Genet. 101:262-7 (2001).
Payne R. The Development and Persistence of Leukoagglutinins in Parous Women. Blood.1962;19:411-424.
Pembrey, et al. Maternal Synthesis of Hemoglobin F in Pregnancy. The Lancet. Jun. 16, 1973:1350-1354.
Pertl, et al. First trimester prenatal diagnosis: fetal cells in the maternal circulation. Semin Perinatol. Oct. 1999;23(5):393-402.
Pinkel, et al. Fluorescence in situ Hybridization with Human Chromosome-specific Libraries: Detection of Trisomy 21 and Translocations of Chromosome 4. Genetics.1988;85:9138-9142.
Price, et al. Prenatal Diagnosis with Fetal Cells Isolated from Maternal Blood by Multiparameter Flow Cytometry. Am. J. Obstet. Gynecol. 1991; 165:1731-7.
Prieto, et al. Isolation of fetal nucleated red blood cells from maternal blood in normal and aneuploid pregnancies. Clin Chem Lab Med. Jul. 2002;40(7):667-72.
Purwosunu, et al. Clinical potential for noninvasive prenatal diagnosis through detection of fetal cells in maternal blood. Taiwan J Obstet Gynecol. Mar. 2006;45(1):10-20.
Ried, et al. Multicolor Fluorescence in situ Hybridization for the Simultaneous Detection of Probe Sets for Chromosomes 13, 18, 21, X and Y in Uncultured Amniotic Fluid Cells. Human Molecular Genetics. 1992;1:307-313.
Saiki, et al. Diagnosis of Sickle Cell Anemia andβ—Thalassemia with Enzymatically Amplified DNA and Nonradioactive Allele-Specific Oligonucleotide Probes. New Engl J Med. 1988;319:537-541.
Saltus, R. New Test Speeds Detection of Birth Defects. The Boston Globe. Oct. 8, 1991:4.
Saltus, R. Noninvasive Way is Cited to Detect Down Syndrome in Fetuses. The Boston Globe. Nov. 12, 1992:8.
Samura, et al. Diagnosis of trisomy 21 in fetal nucleated erythrocytes from maternal blood by use of short tandem repeat sequences. Clin. Chem. 2001; 47(9):1622-6.
Samura, et al. Female fetal cells in maternal blood: use of DNA polymorphisms to prove origin. Hum. Genet. 2000;107(1):28-32.
Schaefer, et al. The Clinical Relevance of Nucleated Red Blood Cells counts. Sysmex Journal International. 2000; 10(2):59-63.
Schröder, et al. Fetal Lymphocytes in the Maternal Blood. The Journal of Hematolog:Blood. 1972;39:153-162.
Schröder, J. Transplacental Passage of Blood Cells. Journal of Medical Genetics. 1975;12:230-242.
Simpson, et al. Elevated second trimester maternal serum alpha fetoprotein (MSAFP) is more predictive of certain pregnancy complications than elevated third trimester MSAFP: A cohort study. The American Journal of Human Genetics. Oct. 1992. Supplemental to vol. 51, No. 4: A19-65.
Simpson, et al. Prenatal Genetic Diagnosis. Genetics in Obstetrics and Gynecology. New York: Grune & Stratton; 1982; 101-120.
Sitar, et al. The Use of Non-Physiological Conditions to Isolate Fetal Cells from Maternal Blood. Exp. Cell. Res. 2005; 302:153-61.
Slunga-Tallberg, et al. Maternal Origin of nucleated erythrocytes in peripheral venous blood of pregnant women. Hum Genet. 1995; 96:53-57.
Snider, M. Birth Defects Detected with Simple Blood Test. USA Today. Oct. 9, 1991. page 1D.
Sohda, et al. The Proportion of Fetal Nucleated Red Blood Cells in Maternal Blood: Estimation by FACS Analysis. Prenat. Diagn. 1997; 17:743-52.
Stipp, D. IG Labs Licenses New Technology for Fetal Testing. The Wall Street Journal. Aug. 10, 1990:B5.

Takayasu, et al. Continuous Magnetic Separation of Blood Components from Whole Blood. IEEE Trans. on Applied Superconductivity 10:927-930 (2000).
Theophilus, et al. Gaucher Disease: Molecular Heterogeneity and Phenotype-Genotype Correlations. Am J Hum Genet.1989;45:212-225.
Trask, et al. Detection of DNA Sequences and Nuclei in Suspension by in Situ Hybridization and Dual Beam Flow Cytometry. Science. 1985;230:1401-1403.
Troeger, et al. Approximately half of the erythroblasts in maternal blood are of fetal origin. Mol Hum Reprod. 1999; 5(12):1162-5.
Trowbridge, et al. Human Cell Surface Glycoprotein Related to Cell Proliferation is the Receptor for Transferrin. Cell Biology. 1981;78:3039-3043.
Uitto, et al. Probing the fetal genome: progress in non-invasive prenatal diagnosis. Trends Mol Med. Aug. 2003;9(8):339-43.
UPI (United Press International). Researchers find safer prenatal tests. The Boston Herald. Nov. 14, 1989:25.
Voldborg, et al. Epidermal growth factor receptor (EGFR) and EGFR mutations, function and possible role in clinical trials. Arm Oncol. Dec. 1997;8(12):1197-206.
Voldman, et al. A microfabrication-based dynamic array cytometer. Anal. Chem. 2002; 74:3984-3990.
Vona, et al. Enrichment, immunomorphological, and genetic characterization of fetal cells circulating in maternal blood. Am J Pathol. Jan. 2002;160(1):51-8.
Vrettou, et al. Real-time PCR for single-cell genotyping in sickle cell and thalassemia syndromes as a rapid, accurate, reliable, and widely applicable protocol for preimplantation genetic diagnosis. Human Mutation. 2004; 23(5):513-21.
Wachtel, et al. Fetal Cells in the Maternal Circulation: Isolation by Multiparameter Flow Cytometry and Confirmation by Polymerase Chain Reaction. Human Reproduction. 1991;6:1466-1469.
Walknowska, et al. Practical and Theoretical Implications of Fetal/Maternal Lymphocyte Transfer. The Lancet. Jun. 7, 1969:1119-1122.
Williams, et al. Comparison of cell separation methods to entrich the proportion of fetal cells in material blood samples. The American Journal of Human Genetics. Oct. 1992. Supplemental to vol. 51, No. 4: 1049.
Williams, et al. Prenatal Diagnosis of 46, XX Males: Confirmation of X-Y interchange by fluorescence in Situ hybridization (FISH). Am. J. Hum. Gent. Supplement to 51(4):A266 (1049) (1992).
Wirtschafter, et al. Micrometastatic tumor detection in patients with head and neck cancer: a preliminary report. Arch Otolaryngol Head Neck Surg. Jan. 2002;128(1):40-43.
Yu, et al. Molecular basis of the adult I phenotype and the gene responsible for the expression of the human blood group I antigen. Blood. 2001; 98:3840-3845.
Yuan, et al. The Pumping Effect of Growing and Collapsing Bubbles in a Tube. J Micromech Microeng.1999;9:402-413.
Zborowski, et al. Red Blood Cell Magnetophoresis. Biophys. J. 84:2638-45 (2003).
Zhen, et al. Poly-FISH: a technique of repeated hybridizations that improves cytogenetic analysis of fetal cells in maternal blood. Prenat Diagn. 1998; 18(11):1181-5.
Adinolfi, et al. Rapid detection of aneuploidies by microsatellite and the quantitative fluorescent polymerase chain reaction. Prenat. Diagn. 1997; 17(13):1299-311.
Ahn, et al. A fully integrated micromachined magnetic particle separator. Journal of Microelectromechanical Systems. 1996; 5(3):151-158.
Andre, et al. (2000). "Lectin-Mediated Drug Targeting: Selection of Valency, Sugar Type (Gal/Lac), and Spacer Length for Cluster Glycoides as Parameters to Distinguish Ligand Binding to C-Type Asialoglycoprotein Receptors and Galectins" Pharmaceutical Research 2000 United States, vol. 17, No. 8, 2000, pp. 985-990.
Andre, et al. (2001). "Wedgelike Glycodendrimers as Inhibitors of Binding of Mammalian Galectins to Glycoproteins, Lactose Maxiclusters, and Cell Surface Glycoconjugates" Chembiochem : A European Journal of Chemical Biology vol. 2 pp. 822-830.
Armani, et al. Re-configurable Fluid Circuits by PDMS Elastomer Micromachining. Proc. 12th International Conference on MEMS (MEMS '99) 17-21:222-227 (1999).

(56) References Cited

OTHER PUBLICATIONS

Arnould, et al. Agreement between chromogenic in situ hybridisation (CISH) and FISH in the determination of HER2 status in breast cancer. Br J Cancer. 2003; 88(10):1587-91. (Abstract only).
Balko, et al. Gene expression patterns that predict sensitivity to epidermal growth factor receptor tyrosine kinase inhibitors in lung cancer cell lines and human lung tumors. BMC Genomics. Nov. 10, 2006;7:289 (14 pages).
Barrett, et al. Comparative genomic hybridization using oligonucleotide microarrays and total genomic DNA. Proc Natl Acad Sci U S A. 2004; 101(51):17765-70.
Basch, et al. Cell separation using positive immunoselective techniques. Journal of Immunological Methods. 1983;56:269-280.
Bennett, et al. Toward the 1,000 dollars human genome. Pharmacogenomics. 2005; 6(4):373-82.
Berenson, et al. Cellular Immunoabsorption Using Monoclonal Antibodies. Transplantation.1984;38:136-143.
Berenson, et al. Positive selection of viable cell populations using avidin-biotin immunoadsorption. Journal of Immunological Methods. 1986;91:11-19.
Berger, et al. Design of a microfabricated magnetic cell separator. Electrophoresis. Oct. 2001;22(18):3883-92.
Beroud, et al. Prenatal diagnosis of spinal muscular atrophy by genetic analysis of circulating fetal cells. Lancet. 2003; 361:1013-1014.
Bignell, et al. High-resolution analysis of DNA copy number using oligonucleotide microarrays. Genome Research. 2004; 14(2):287-295.
Birner, et al. Evaluation of the United States Food and Drug Administration-approved scoring and test system of HER-2 protein expression in breast cancer. Clin Cancer Res. Jun. 2001;7(6):1669-75.
Blankenstein, G., et al. Modular Concept of a Laboratory on a Chip for Chemical and Bichemical Analysis. Biosensors and Bioelectronics. 1998;13(3-4):427-438.
Bousse, et al. Micromachined Multichannel Systems for the Measurement of Cellular Metabolism. Sensors and Actuators. 1994; 20:145-150.
Brison, et al. General Method for Cloning Amplified DNA by Differential Screening with Genomic Probes. Molecular and Cellular Biology. 1982;2:578-587.
Brody, et al. Deformation and Flow of Red Blood Cells in a Synthetic Lattice: Evidence for an Active Cytoskeleton. Biophys. J. 68:2224-2232 (1995).
Brody, et al. Biotechnology at Low Reynolds Numbers. Biophys J. 1996; 71:3430-3441.
Butterworth, et al. Human Cytotrophoblast Populations Studied by Monoclonal Antibodies Using Single and Double Biotin-Avidin-Peroxidase Immunocytochemistry. The Journal of Histochemistry and Cytochemistry. 1985;33:977-983.
Calin, et al. A microRNA signature Associated with prognosis and progression in chronic lymphocytic leukemia. New England Journal of Medicine. 2005; 353:1793-1801.
Cancer Genetics. Am J Hum Genet. 1998; 43(3):A35, 2pgs.
Chang, et al. Biomimetic technique for adhesion-based collection and separation of cells in a microfluidic channel. Lab Chip. 2005; 5:64-73.
Cheung, et al. Development and validation of a CGH microarray for clinical cytogenetic diagnosis. Genet Med. 2005; 7(6):422-32.
Chinn, et al. Reactive Ion Etching for Submicron Structures. J. Vac. Sci. Technol. 1981; 19:1418-1422.
Christel, et al. High aspect ratio silicon microstructures for nucleic acid extraction Solid-state Sensor and actuator workshop. Hilton Head, SC. Jun. 8-11, 1998; 363-366.
Covone , et al. Trophoblast Cells in Peripheral Blood from Pregnant Women. The Lancet. Oct. 13, 1984:841-843.
Cremer, et al. Detection of chromosome aberaations in metaphase and interphase tumor cells by in situ hybridization using chromosome-specific library probes. Human Genetics.1988;80:235-246.
De Alba, et al. Prenatal diagnosis on fetal cells obtained from maternal peripheral blood: report of 66 cases. Prenat Diagn. Oct. 1999;19(10):934-40.
Duff, et al. (1998). "Intrabody Tissue-Specific Delivery of Antisense Conjugates in Animals: Ligand-Linker-Antisense Oligomer Conjugates", Methods in Enzymology, Academic Press Inc, San Diego, CA, US vol. 313, No. A pp. 297-321.
Duke, et al. Microfabricated sieve for the continuous sorting of macromolecules. Physical Review Letters. 1998; 80:1552-1555.
Dutta, et al. Electroosmotic Flow Control in Complex Microgeometries. Journal of Microelectromechanical Systems. 2002; 11:36-44.
Fan, et al. Highly parallel SNP genotyping. Cold Spring Harb. Symp. Quant. Biol. 2003; 68:69-78.
Findlay, et al. Using MF-PCR to diagnose multiple defects from single cells: implications for PGD. Mol Cell Endocrinol. 2001; 183 Suppl 1:S5-12.
Galbraith, et al. Imaging cytometry by multiparameter fluorescence. Cytometry. 1991;12(7):579-96.
Genome Web. Immunicon inks biomarker assay, lab services deal with merck serona. Available at C:\Documents and Settings\fc3 \Local Settings\Temporary Internet Files \ OLK35E\141896-1.htm. Accessed on Sep. 11, 2007.
Gingrich, et al. Metastatic prostate cancer in a transgenic mouse. Cancer Res. Sep. 15, 1996;56(18):4096-102.
Goldberg, C. Test reveals gender early in pregnancy ethicists fear use in sex selection. Boston Globe. Jun. 27, 2005.
Gonzalez, et al. Multiple displacement amplification as a pre-polymerase chain reaction (pre-PCR) to process difficult to amplify samples and low copy number sequences from natural environments. Environ Microbiol. 2005; 7(7):1024-8.
Graham. Efficiency comparison of two preparative mechanisms for magnetic separation of erthrocytes from whole blood. J. Appl. Phys. 1981; 52:2578-2580.
Greaves, et al. Expression of the OKT Monoclonat Antibody Defined Antigenic Determinants in Malignancy. Int. J. Immunopharmac. 1981;3:283-299.
Gunderson, et al. A genome-wide scalable Snp genotyping assay using microarray technology. Nat Genet. 2005; 37(5):549-54.
Hahn, et al. Current applications of single-cell Pcr. Cell. Mol. Life Sci. 2000; 57(1):96-105. Review.
Hardenbol, et al. Highly multiplexed molecular inversion probe genotyping: over 10,000 targeted SNPs genotyped in a single tube assay. Genome Res. 2005;15(2):269-75.
Hardenbol, et al. Multiplexed genotyping with sequence-tagged molecular inversion probes. Nat. Biotechnol. 2003; 21(6):673-8.
Hartmann, et al. Gene expression profiling of single cells on large-scale oligonucleotide arrays. Nucleic Acids Research. 2006; 34(21): e143. (11 pages).
Hatch, et al. A rapid diffusion immunoassay in a T-serisor. Nature Biotechnology. 2001; 19:461-465.
Henning, et al. Microfluidic MEMS. Proc. IEEE Aerospace Conference. 1998; 1:471-486.
Hong, et al. A nanoliter-scale nucleic acid processor with parallel architecture. Nat. Biotechnol. 2004; 22(4):435-9.
PMA Final Decisions Rendered for Sep. 1998, http://www.fda.gov/ cdrh/pma/pmasep98.html, 16 pgs.
International Search Report for PCT/US2004/018373 dated Oct. 20, 2004, 5 pgs.
Jansen, et al. The effect of chorionic villus sampling on the number of fetal cells isolated from material blood and on maternal serum alpha-fetoprotein levels. Prenatal Diagnosis. 1997; 17:953-959.
Jayasena, S. Aptamers: an emerging class of molecule's that rival antibodies in diagnostics. Clin Chem. Sep. 1999;45(9):1628-50.
Jiang, et al. Genome amplification of single sperm using multiple displacement amplification. Nucleic Acids Res. 2005; 33(10):e91. (9 pages).
Klein, C. A. Single cell amplification methods for the study of cancer and cellular ageing. Mech. Ageing Dev. 2005; 126(1):147-51.
Klein, et al. Comparative genomic hybridization, loss of heterozygosity, and DNA sequence analysis of single cells. Proc Natl Acad Sci U S A. 1999; 96(8):4494-9.

(56) References Cited

OTHER PUBLICATIONS

Krivacic, et al. A rare-cell detector for cancer. PNAS. 2004;101:10501-10504.
Kubuschok, et al. Disseminated tumor cells in lymph nodes as a determinant for survival in surgically resected non-small-cell lung cancer. J Clin Oncol. Jan. 1999;17(1):19-24.
Lee, et al. (1990). "Binding characteristics of galactoside-binding lectin (galaptin) from human spleen" J. Biol. Chem., vol. 265, Issue 14, 7864-7871, 05, 1990.
Leyland-Jones, B. Trastuzumab: hopes and realities. Lancet Oncol. Mar. 2002;3(3):137-44.
Lichter, et al. Delineation of individual human chromosomes in metaphase and interphase cells by in situ suppression hyridization using recombinant DNA libraries. Hum Genet. 1988;80:224-234.
Liu, et al. Development and validation of a T7 based linear amplification for genomic DNA. BMC Genomics. 2003;.4(1):19. (11 pages).
Loken, et al. Flow Cytometric Analysis of Human Bone Marrow: I. Normal Erythroid Development. Blood. 1987;69:255-263.
Lynch, et al. Activating mutations in the epidermal growth factor receptor underlying responsiveness of non-small-cell lung cancer to gefitinib. N Engl J Med. May 20, 2004;350(21):2129-39.
Maren, et al. Kinetics of carbonic anhydrase in whole red cells as measured by transfer of carbon dioxide and ammonia. Molecular Pharmocology. 1970; 6:430-440.
Margulies, et al. Genome sequencing in microfabricated high-density picolitre reactors. Nature. 2005; 437:376-80.
Maxwell, et al. A Microbubble-Powered Bioparticle Actuator. Journal of Microelectromechanical Systems. 2003; 12:630-640.
Melville, et al. Direct magnetic separation of red cells from whole blood. Nature. 1975; 255:706.
Miller, et al. Oligothymidylate analogues having stereoregular, alternating methylphosphonate/phosphodiester backbones. Synthesis and physical studies. J Biol Chem. Oct. 25, 1980;255(20):9659-65.
Moorhead, et al. Optimal genotype determination in highly multiplexed SNP data. Eur. J. Hum. Genet. 2006;14(2):207-15. (published online Nov. 23, 2005).
Mueller, et al. Identification of extra-villous trophoblast cells in human decidua using an apparently unique murine monoclonal antibody to trophoblast. Histochemical Journal.1987;19:288-296.
Mueller, et al. Isolation of fetal trophoblast cells from peripheral blood of pregnant women. The Lancet. 1990;336:197-200.
Murthy, et al. Assessment of multiple displacement amplification for polymorphism discovery and haplotype determination at a highly polymorphic locus, MC1R. Hum. Mutat. 2005; 26(2):145-52.
Nagrath, et al. Isolation of rare circulating tumour cells in cancer patients by microchip technology (with Supplementary information). Nature. Dec. 20-27, 2007; 450(20):1235-1239.
Newcombe, R. G. Two-sided confidence intervals for the single proportion: comparison of seven methods. Statistics in Medicine. 1998; 17:857-872.
Paterlini-Brechot, et al. Circulating tumor cells (CTC) detection: Clinical impact and future directions. Cancer Letter. 2007. (in press, 25 pages.) Available at www.sciencedirect.com.
Paul, et al. Single-molecule dilution and multiple displacement amplification for molecular haplotyping. Biotechniques. 2005; 38(4):553-4, 556, 558-9.
Pawlik, et al. Prodrug Bioactivation and Oncolysis of Diffuse Liver Metastases by a Herpes Simplex Virus 1 Mutant that Expresses the CYP2B1 Transgene. Cancer. 2002;95:1171-81.
Peng, et al. Real-time detection of gene expression in cancer cells using molecular beacon imaging: new strategies for cancer research. Cancer Res. 2005; 65(5):1909-17.
Pinkel, et al. Cytogenetic Analysis Using Quantitative, High-sensitivity, Fluorescence Hybridization. Genetics. 1986;83:2934-2938.
Pinkel, et al. Detection of structural chromosome abberations in metaphase in metaphase spreads and interphase nuclei by in situ hybridization high complexity probes which stain entire human chromosomes. The American Journal of Human Genetics. Sep. 1988. Supplemental to vol. 43, No. 3: 0471.
Pinzani, et al. Isolation by size of epithelial tumor cells in peripheral blood of patients with breast cancer: correlation with real-time reverse transcriptase-polymerase chain reaction results and feasibility of molecular analysis by laser microdissection. Hum Pathol. 2006; 37(6):711-8.
Plank, et al. Gene Transfer into Hepatocytes Using Asialoglycoprotein Receptor Mediated Endocytosis of DNA Complexed with an Artificial Tettra-Antennary Galactose Ligands. Bioconjugate Chemistry. 1992; 3(6): 533-539.
Potti, et al. Genomic signatures to guide the use of chemotherapeutics. Nat Med. 2006; 12(11):1294-1300.
Proteins and Biotechnology. Laboratory Adventures in the Biological Sciences. Week Three 2002. Northwestern University.
Ren, et al. Reduced lysyl oxidase messenger RNA levels in experimental and human prostate cancer. Cancer Res. Mar. 15, 1998;58(6):1285-90.
Rolle, et al. Increase in number of circulating disseminated epithelia cells after surgery for non-small cell lung cancer monitored by MAINTRAC is a predictor for relapse: a preliminary report. World Journal of Surgical Oncology. 2005; 9 pages.
Ruan, et al. Identification of clinically significant tumor antigens by selecting phage antibody library on tumor cells in situ using laser capture microdissection. Molecular & Cellular Proteomics. 2006; 5(12): 2364-73.
Sakhnini, et al. Magnetic behavior of human erythrocytes at different hemoglobin states. Eur Biophys J. Oct. 2001;30(6):467-70.
Sato, et al. Individual and Mass Operation of Biological Cells Using Micromechanical Silicon Devices. Sensors and Actuators. 1990;A21-A23:948-953.
Schomburg, et al. Microfluidic Components in LIGA Technique. J. Micromech. Microeng. 1994; 4:186-191.
Scoazec. J. Y. Tissue and cell imaging in situ: potential for applications in pathology and endoscopy. Gut. Jun. 2003; 52(Suppl 4): iv1-iv6.
Seow, et al. (2002). "Expression of a Functional Asialoglycoprotein Receptor in Human Renal Proximal Tubular Epithelial Cells" Nephron 2002;91:431-438.
Shen, et al. High-throughput SNP genotyping on universal bead arrays. Mutat. Res. 2005; 573:70-82.
Shendure, et al. Accurate multiplex polony sequencing of an evolved bacterial genome. Science. 2005; 309:1728-32.
Sherlock, et al. Assessment of diagnostic quantitative fluorescent multiplex polymerase chain reaction assays performed on single cells. Ann. Hum. Genet. 1998; 62:9-23.
Shoji, et al. Microflow Devices and Systems. Journal of Micromechanics and Microengineering. 1994; 4:157-171.
Stoecklein, et al. SCOMP is superior to degenerated oligonucleotide primed-polymerase chain reaction for global amplification of minute amounts of DNA from microdissected archival tissue samples. Am J Pathol. 2002;.161(1):43-51.
Stoughton, et al. Data-adaptive algorithms for calling alleles in repeat polymorphisms. Electrophoresis. 1997;18(1):1-5.
Sun, et al. Whole-genome amplification: relative efficiencies of the current methods. Leg Med. 2005; 7(5):279-86.
Tepperberg, et al. Prenatal diagnosis using interphase fluorescence in situ. hybridization (FISH): 2-year multi-center retrospective study and review of literature. Prenatal Diagnosis. 2001; 21:293-301.
Thomas, et al. Specific Binding and Release of Cells from Beads Using Cleavable Tetframetric Antibody Complexes. Journal of Immunological Methods 1989;120:221-231.
Tibbe, et al. Statistical considerations for enumeration of circulating tumor cells. Cytometry A. Mar. 2007;71(3):154-62.
Van Raamsdonk, et al. Optimizing the detection of nascent transcripts by RNA fluorescence in situ hybridization. Nucl. Acids. Res. 2001; 29(8):e42.
Vandelli, et al. Development of a MEMS Microvalve Array for Fluid Flow Control. Journal of Microelectromechanical Systems. 1998; 7:395-403.
Vona, et al. Isolation by size of epthielal tumor cells. American Journal of Pathology. 2000; 156:57.
Voullaire, et al. Detection of aneuploidy in single cells using comparative genomic hybridization. Prenat Diagn. 1999; 19(9):846-51.

(56) References Cited

OTHER PUBLICATIONS

Vrasidas, et al. (2003). "Rigidified multivalent lactose molecules and their interactions with mammalian galectins: a route to selective inhibitors" Organic & Biomolecidar Chemistry vol. 1, No. 5 pp. 803-810.

Waguri, et al. Sensitive and specific detection of circulating cancer cells in patients with hepatocellular carcinoma; detection of human telomerase reverse transcriptase messenger RNA after immunomagnetic separation. Clin Cancer Res. Aug. 1, 2003;9(8):3004-11.

Wang, et al. Allele quantification using molecular inversion probes (MIP). Nucleic Acids Research. 2005; 33(21); e183 (14 pages).

Washizu, et al. Handling Biological Cells Utilizing a Fluid Integrated Circuit. IEEE Industry Applications Society Annual Meeting Presentations. Oct. 2-7, 1988;: 1735-40.

Washizu, et al. Handling Biological Cells Utilizing a Fluid Integrated Circuit. IEEE Transactions of Industry Applications. 1990; 26: 352-8.

Washizu, M. Manipulation of Biological Objects in Micromachined Structures. Proceeding of the Workshop on Micro Electro Mechanical Systems, Travemunde, Feb. 4 -7, 1992, no. workshop 5, Feb. 4, 1992, Benecke W.; Petzold H.C., pp. 196-201.

Wong, et al. Targeting malignant glioma survival signalling to improve clinical outcomes. J Clin Neurosci. Apr. 2007;14(4):301-8.

Written Opinion of the International Searching Authority for PCT/US2004/018373 dated Oct. 20, 2004.

Yu, et al. Objective Aneuploidy Detection for Fetal and Neonatal Screening Using Comparative Genomic Hybridization (CGH). Cytometry. 1997; 28(3): 191-197.

Zhau, et al. Biomarkers associated with prostate cancer progression. J Cell Biochem Suppl. 1994;19:208-16.

Zheng, et al. Fetal cell identifiers: results of microscope slide-based immunocytochemical studies as a function of gestational age and abnormality Am J Obstet Gynecol. May 1999;180(5):1234-9.

Fuchs, et al. U.S. Appl. No. 11/762,750, entitled "Analysis of rare cell-enriched samples," filed Jun. 13, 2007.

Lopez, et al. U.S. Appl. No. 11/825,298, entitled "Nanostructured Separation and Analysis Devices for Biological Membranes," filed Jul. 5, 2007.

Lopez, et al. U.S. Appl. No. 11/825,677, entitled "Nanostructured Separation and Analysis Devices for Biological Membranes," filed Jul. 5, 2007.

Kapur, et al. U.S. Appl. No. 11/830,546, entitled "Selection of Cells Using Biomarkers," filed Jul. 30, 2007.

Kapur, et al. U.S. Appl. No. 11/763,245 entitled "Methods for the diagnosis of fetal abnormalities," filed Jun. 14, 2007.

Kapur, R. U.S. Appl. No. 60/949,227, entitled "Diagnosis of Fetal Abnormalities Using Nucleated Red Blood Cells," filed Jul. 11, 2007.

Oakey, et al. . U.S. Appl. No. 11/960,457, entitled "Cell sorting device and method of manufacturing the same," filed Dec. 19, 2007.

Shoemaker, et al. U.S. Appl. No. 11/762,747, entitled "Rare cell analysis using sample splitting and DNA tags," filed Jun. 13, 2007.

Shoemaker, et al. U.S. Appl. No. 11/763,421 entitled "Rare cell analysis using sample splitting and DNA tags," filed Jun. 14, 2007.

Stoughton, et al. U.S. Appl. No. 11/763,133, entitled "Use of Highly Parallel Snp Genotyping for Fetal Diagnosis," filed Jun. 14, 2007.

Stoughton, et al. U.S. Appl. No. 11/763,426, entitled "Diagnosis of Fetal Abnormalities Using Polymorphisms Including Short Tandem Repeats," filed Jun. 14, 2007.

Office Action issued Jan. 13, 1996, in connection with U.S. Appl. No. 08/474,688 (U.S. Patent No. 5,837,115. ), under examination.

Office Action issued Apr. 29, 1996, in connection with U.S. Appl. No. 08/474,688 (U.S. Patent No. 5,837,115 ), under examination.

Office Action issued Feb. 19, 1997, in connection with U.S. Appl. No. 08/474,688 (U.S. Patent No. 5,837,115 ), under examination.

Office Action issued Jun. 1, 2005, in connection with U.S. Appl. No. 10/248,653 (U.S. Publication No. 2003-0159999), under examination.

Office Action issued Dec. 30, 2005, in connection with U.S. Appl. No. 10/248,653 (U.S. Publication No. 2003-0159999), under examination.

Office Action issued Feb. 6, 2006, in connection with U.S. Appl. No. 11/071,679 (U.S. Publication No. 2005/0266433), under examination.

Office Action issued May 18, 2006, in connection with U.S. Appl. No. 10/248,653 (U.S. Publication No. 2003-0159999), under examination.

Office Action issued Oct. 12, 2006, in connection with U.S. Appl. No. 11/071,679 (U.S. Publication No. 2005/0266433), under examination.

Office Action issued Oct. 25, 2006, in connection with U.S. Appl. No. 10/248,653 (U.S. Publication No. 2003-0159999), under examination.

Office Action issued Jan. 5, 2007, in connection with U.S. Appl. No. 10/529,453 (U.S. Publication No. 2006-0134599), under examination.

Office Action issued Jan. 15, 2007, in connection with U.S. Appl. No. 11/228,462 (U.S. Publication No. 2007-0059680), under examination.

Office Action issued Feb. 21, 2007, in connection with U.S. Appl. No. 10/787,585 (U.S. Publication No. 2004-0171091), under examination.

Office Action issued May 31, 2007, in connection with U.S. Appl. No. 11/395,691 (U.S. Publication No. 2006-0169642 Al), under examination.

Office Action issued Jun. 4, 2007, in connection with U.S. Appl. No. 11/228,462 (U.S. Publication No. 2007-0059680), under examination.

Office Action issued Jul. 2, 2007, in connection with U.S. Appl. No. 11/071,679 (U.S. Publication No. 2005/0266433), under examination.

Office Action issued Jul. 7, 2007, in connection with U.S. Appl. No. 11/395,691 (U.S. Publication No. 2006-0169642 Al), under examination.

Office Action issued Jul. 18, 2007, in connection with U.S. Appl. No. 11/182,897 (U.S. Publication No. 2005-0250155), under examination.

Office Action issued Jul. 27, 2007, in connection with U.S. Appl. No. 10/529,453 (U.S. Publication No. 2006-0134599), under examination.

Office Action issued Nov. 5, 2007, in connection with U.S. Appl. No. 11/071,679 (U.S. Publication No. 2005/0266433), under examination.

Office Action issued Nov. 30, 2007, in connection with U.S. Appl. No. 11/449,161 (U.S. Publication No. 2007-0099207), under examination.

Office Action issued Dec. 28, 2007, in connection with U.S. Appl. No. 11/229,359 (U.S. Publication No. 2007-0059683), under examination.

Office Action issued Dec. 31, 2007, in connection with U.S. Appl. No. 10/787,585 (U.S. Publication No. 2004-0171091), under examination.

Office Action issued Jan. 11, 2008, in connection with U.S. Appl. No. 11/229,037 (U.S. Publication No. 2007-0059774), under examination.

Office Action issued Feb. 6, 2008, in connection with U.S. Appl. No. 11/182,897 (U.S. Publication No. 2005-0250155), under examination.

Wallis et al., "Field Assisted Glass-Metal Sealing", 40 J. Applied Physics 3946-49 (Sep. 1969).

European office action dated Sep. 20, 2010 for Application No. 06749394. 7 pages.

European search report dated Oct. 5, 2009 for Application No. 06749394. 7 pages.

European search report dated May 27, 1998 for Application No. 94919332. 3 pages.

European SR dated Mar. 17, 2006 for Application No. 03798803.7. 4 pages.

European SR dated Aug. 2, 2006 for Application No. 03798803.7. 5 pages.

(56) References Cited

OTHER PUBLICATIONS

International preliminary examination report dated Sep. 17, 2004 for PCT Application No. US03/30965. 3 pages.
International search report and written opinion dated Sep. 10, 2008 for PCT Application No. US06-12778. 14 pages.
International search report dated Oct. 14, 2008 for PCT Application No. US2008/060546. 4 pages.
International search report dated Oct. 21, 1994 for PCT Application No. US94/06215. 1 page.
International search report dated Mar. 25, 2004 for PCT Application No. US03/30965. 2 pages.
Office action dated Dec. 18, 2009 for U.S. Appl. No. 11/726,276. 8 pages.
Office Action issued Apr. 21, 2009 in connection with U.S. Appl. No. 10/529,453. 12 pages.
Office Action issued Feb. 3, 2010 in connection with U.S. Appl. No. 11/726,231. 7 pages.
Office Action issued Jul. 12, 2010 in connection with U.S. Appl. No. 11/800,940. 8 pages.
Office Action issued Mar. 8, 2010 in connection with U.S. Appl. No. 10/529,453. 11 pages.
Office Action issued May 30, 2008 in connection with U.S. Appl. No. 10/529,453. 12 pages.
Office Action issued Sep. 1, 2010 in connection with U.S. Appl. No. 11/726,231. 8 pages.
Office Action mailed Jan. 14, 2010 from U.S. Appl. No. 11/726,230. 8 pages.
Raeburn, P. Fetal Cells Isolated in Women's Blood. Associated Press (Jul. 28, 1989) [electronic version]. 6 pages.
UK examination report and search report dated Dec. 16, 2010 Application No. GB1017732.7. 6 pages.

* cited by examiner

Average Flow Direction

| | Version 1 | Version 2 | Version 3 |
|---|---|---|---|
| Inlet channel width (blood) | 50 | 100 | 100 |
| Inlet channel width (buffer) | 55 | 110 | 110 |
| Outlet channel width (product) | 49 | 98 | 98 |
| Outlet channel width (waste) | 50 | 100 | 100 |
| Gap size / Deflect cell size | | | |
| Post section 1 | 18/9 | 36/18 | 44/22 | 50/25 |
| Post section 2 | 12/6 | 24/12 | 30/15 | 36/18 |
| Post section 3 | 8/4 | 16/8 | 20/10 | 24/12 |
| Number of parallel sections | 14 | 14 | 14 | 14 |
| Etch depth | 150 | 150 | 150 | 150 |
| Product cell size (cut off) | 4 | 8 | 10 | 12 |
| Estimated Flow rate, ml/hr | 5 | 10 | 20 | 30 |

Fig. 57B

DEVICES AND METHODS FOR ENRICHMENT AND ALTERATION OF CIRCULATING TUMOR CELLS AND OTHER PARTICLES

CROSS-REFERENCE TO RELATED APPLICATIONS

This application claims the benefit of U.S. Provisional Application No. 60/703,833, filed Jul. 29, 2005, which is hereby incorporated by reference.

BACKGROUND OF THE INVENTION

The invention relates to the fields of medical diagnostics and microfluidics.

Cancer is a disease marked by the uncontrolled proliferation of abnormal cells. In normal tissue, cells divide and organize within the tissue in response to signals from surrounding cells. Cancer cells do not respond in the same way to these signals, causing them to proliferate and, in many organs, form a tumor. As the growth of a tumor continues, genetic alterations may accumulate, manifesting as a more aggressive growth phenotype of the cancer cells. If left untreated, metastasis, the spread of cancer cells to distant areas of the body by way of the lymph system or bloodstream, may ensue. Metastasis results in the formation of secondary tumors at multiple sites, damaging healthy tissue. Most cancer death is caused by such secondary tumors.

Despite decades of advances in cancer diagnosis and therapy, many cancers continue to go undetected until late in their development. As one example, most early-stage lung cancers are asymptomatic and are not detected in time for curative treatment, resulting in an overall five-year survival rate for patients with lung cancer of less than 15%. However, in those instances in which lung cancer is detected and treated at an early stage, the prognosis is much more favorable.

Therefore, there exists a need to develop new methods for detecting cancer at earlier stages in the development of the disease.

SUMMARY OF THE INVENTION

The invention features a device for cell enrichment including:
a) a receptacle;
b) a lid detachably attached to the receptacle, the lid having a functionalized lid surface that includes one or more capture moieties that selectively capture a first cell from a cellular sample, and wherein the lid is configured to fit within the receptacle; and
c) a sample mobilizer coupled to either the receptacle or the lid.

The functionalized lid surface can have a cross section that is square, rectangular, or circular, and both the lid and the receptacle can be composed of glass, silicon, or plastic.

The functionalized lid surface can include a microstructure which can include a micro-obstacle, a micro-corrugation, a micro-groove, or a micro-fin.

The capture moieties can include one or more antibodies that specifically bind the first cell. The antibodies can form an array and can specifically bind leukocytes or epithelial cells, or a cell surface cancer marker, e.g. a marker selected from Table 1, e.g. EpCAM, E-Cadherin, Mucin-1, Cytokeratin 8, EGFR, and leukocyte associated receptor (LAR).

The receptacle can include a functionalized receptacle surface having one or more capture moieties that selectively capture a second cell from the cellular sample. The functionalized receptacle surface can include a microstructure that can include a micro-obstacle, a micro-corrugation, a micro-groove, or a micro-fin.

The capture moieties that selectively capture a second cell can include one or more antibodies that specifically bind the second cell, e.g., antibodies that specifically bind leukocytes or epithelial cells, or that specifically bind a cell surface cancer marker of the second cell. The cell surface cancer marker can be one selected from Table 1, e.g., EpCAM, E-Cadherin, Mucin-1, Cytokeratin 8, EGFR, or leukocyte associated receptor (LAR).

The lid can be configured to fit the receptacle at a nonorthogonal angle with respect to a wall of the receptacle.

The sample mobilizer can include a mechanical rocker and can be adapted to provide centrifugal force to the receptacle and the lid; it can also include an axle that rotates the receptacle. Centrifugal force can drive cells rolling along the lid surface. Centrifugal force can also drive the lid into a nonorthogonal angle with respect to the axle.

The sample mobilizer can include a first chamber fluidically coupled to a second chamber, wherein each chamber has a surface in contact with the internal space of the receptacle, and wherein fluid movement between the chambers results in a change in shape of each chamber.

The receptacle preferably can hold at least 10 mL, and more preferably at least 50 mL of fluid.

The device is used for enriching one or more first cells from a cellular sample by:
a) placing the cellular sample in the device;
b) covering the cellular sample with the lid;
c) mobilizing the sample using the sample mobilizer; and
d) removing the lid from the receptacle.

The first cell can be a cancer cell or an epithelial cell. Step c) can include applying a centrifugal force to the receptacle; the receptacle can be subjected to an average relative centrifugal field of between 1,000 g and 10,000 g.

Alternatively, step c) involves applying:
i) a first force; and
ii) a second force opposite to the first force; the first force and the second force can be applied repeatedly and in alternation, and there can be a waiting period between applications of said forces.

Any of the devices of the invention may be used together with a set of instructions for the device.

By "approximately equal" in the context of length, size, area, or other measurements is meant equal to within 10%, 5%, 4%, 3%, 2%, or even 1%.

By "biological particle" is meant any species of biological origin that is insoluble in aqueous media. Examples include cells, particulate cell components, viruses, and complexes including proteins, lipids, nucleic acids, and carbohydrates.

By "biological sample" is meant any sample of biological origin or containing, or potentially containing, biological particles. Preferred biological samples are cellular samples.

By "blood component" is meant any component of whole blood, including host red blood cells, white blood cells, platelets, or epithelial cells, in particular, CTCs. Blood components also include the components of plasma, e.g., proteins, lipids, nucleic acids, and carbohydrates, and any other cells that may be present in blood, e.g., because of current or past pregnancy, organ transplant, infection, injury, or disease.

By "cellular sample" is meant a sample containing cells or components thereof. Such samples include naturally occurring fluids (e.g., blood, sweat, tears, ear flow, sputum, lymph, bone marrow suspension, urine, saliva, semen, vaginal flow, cerebrospinal fluid, cervical lavage, brain fluid, ascites, milk, secretions of the respiratory, intestinal or genitourinary tract, amniotic fluid, and water samples) and fluids into which cells have been introduced (e.g., culture media and liquefied tissue samples). The term also includes a lysate.

By "channel" is meant a gap through which fluid may flow. A channel may be a capillary, a conduit, or a strip of hydrophilic pattern on an otherwise hydrophobic surface wherein aqueous fluids are confined.

By "circulating tumor cell" (CTC) is meant a cancer cell that is exfoliated from a solid tumor of a subject and is found in the subject's circulating blood.

By "component" of cell is meant any component of a cell that may be at least partially isolated upon lysis of the cell. Cellular components may be organelles (e.g., nuclei, perinuclear compartments, nuclear membranes, mitochondria, chloroplasts, or cell membranes), polymers or molecular complexes (e.g., lipids, polysaccharides, proteins (membrane, trans-membrane, or cytosolic), nucleic acids (native, therapeutic, or pathogenic), viral particles, or ribosomes), or other molecules (e.g., hormones, ions, cofactors, or drugs).

By "component" of a cellular sample is meant a subset of cells, or components thereof, contained within the sample.

By "density" in reference to an array of obstacles is meant the number of obstacles per unit of area, or alternatively the percentage of volume occupied by such obstacles. Array density is increased either by placing obstacles closer together or by increasing the size of obstacles relative to the gaps between obstacles.

By "enriched sample" is meant a sample containing components that has been processed to increase the relative population of components of interest relative to other components typically present in a sample. For example, samples may be enriched by increasing the relative population of cells of interest by at least 10%, 25%, 50%, 75%, 100% or by a factor of at least 1,000, 10,000, 100,000, 1,000,000, 10,000,000, or even 100,000,000.

By "exchange buffer" in the context of a cellular sample is meant a medium distinct from the medium in which the cellular sample is originally suspended, and into which one or more components of the cellular sample are to be exchanged.

By "flow-extracting boundary" is meant a boundary designed to remove fluid from an array.

By "flow-feeding boundary" is meant a boundary designed to add fluid to an array.

By "gap" is meant an opening through which fluids or particles may flow. For example, a gap may be a capillary, a space between two obstacles wherein fluids may flow, or a hydrophilic pattern on an otherwise hydrophobic surface wherein aqueous fluids are confined. In a preferred embodiment of the invention, the network of gaps is defined by an array of obstacles. In this embodiment, the gaps are the spaces between adjacent obstacles. In a preferred embodiment, the network of gaps is constructed with an array of obstacles on the surface of a substrate.

By "hydrodynamic size" is meant the effective size of a particle when interacting with a flow, obstacles, or other particles. It is used as a general term for particle volume, shape, and deformability in the flow.

By "hyperspectral" in reference to an imaging process or method is meant the acquisition of an image at five or more wavelengths or bands of wavelengths.

By "intracellular activation" is meant activation of second messenger pathways leading to transcription factor activation, or activation of kinases or other metabolic pathways. Intracellular activation through modulation of external cell membrane antigens may also lead to changes in receptor trafficking.

By "labeling reagent" is meant a reagent that is capable of binding to an analyte, being internalized or otherwise absorbed, and being detected, e.g., through shape, morphology, color, fluorescence, luminescence, phosphorescence, absorbance, magnetic properties, or radioactive emission.

By "microfluidic" is meant having at least one dimension of less than 1 mm.

By "microstructure" in reference to a surface is meant the microscopic structure of a surface that includes one or more individual features measuring less than 1 mm in at least one dimension. Exemplary microfeatures are micro-obstacles, micro-posts, micro-grooves, micro-fins, and micro-corrugation.

By "obstacle" is meant an impediment to flow in a channel, e.g., a protrusion from one surface. For example, an obstacle may refer to a post outstanding on a base substrate or a hydrophobic barrier for aqueous fluids. In some embodiments, the obstacle may be partially permeable. For example, an obstacle may be a post made of porous material, wherein the pores allow penetration of an aqueous component but are too small for the particles being separated to enter.

By "shrinking reagent" is meant a reagent that decreases the hydrodynamic size of a particle. Shrinking reagents may act by decreasing the volume, increasing the deformability, or changing the shape of a particle.

By "swelling reagent" is meant a reagent that increases the hydrodynamic size of a particle. Swelling reagents may act by increasing the volume, reducing the deformability, or changing the shape of a particle.

Other features and advantages will be apparent from the following description and the claims.

BRIEF DESCRIPTION OF THE DRAWINGS

The patent or application file contains at least one drawing executed in color. Copies of this patent or patent application with color drawing(s) will be provided by the Office upon request and payment of the necessary fee.

In FIG. 43A, a cascade configuration is shown, in which outlet 1 of one device is joined to a sample inlet of a second device. In FIG. 43B, a bandpass configuration is shown, in which outlet 2 of one device is joined to a sample inlet of a second device.

FIG. 57B is a table of design parameters corresponding to FIG. 57A.

Figures are not necessarily to scale.

DETAILED DESCRIPTION OF THE INVENTION

The invention features devices and methods for detecting, enriching, and analyzing circulating tumor cells (CTCs) and other particles. The invention further features methods of diagnosing a condition in a subject, e.g., cancer, by analyzing a cellular sample from the subject. In some embodiments, devices of the invention include arrays of obstacles that allow displacement of CTCs or other fluid components.

While this application focuses primarily on the detection, enrichment, and analysis of CTCs or epithelial cells, the devices and methods of the invention are useful for processing a wide range of other cells and particles, e.g., red blood cells, white blood cells, fetal cells, stem cells (e.g., undifferentiated), bone marrow cells, progenitor cells, foam cells, mesenchymal cells, endothelial cells, endometrial cells, trophoblasts, cancer cells, immune system cells (host or graft), connective tissue cells, bacteria, fungi, cellular pathogens (e.g., bacterial or protozoa), cellular organelles and other cellular components (e.g., mitochondria and nuclei), and viruses.

Exemplary devices and methods of the invention are described in detail below.

Circulating Tumor Cells (CTCs)

Epithelial cells that are exfoliated from solid tumors have been found in very low concentrations in the circulation of patients with advanced cancers of the breast, colon, liver, ovary, prostate, and lung, and the presence or relative number of these cells in blood has been correlated with overall prognosis and response to therapy. These CTCs may be an early indicator of tumor expansion or metastasis before the appearance of clinical symptoms.

CTCs typically have a short half-life of approximately one day, and their presence generally indicates a recent influx from a proliferating tumor. Therefore, CTCs represent a dynamic process that may reflect the current clinical status of patient disease and therapeutic response. Enumeration and characterization of CTCs, using the devices and methods of the invention, is useful in assessing cancer prognosis and in monitoring therapeutic efficacy for early detection of treatment failure that may lead to disease relapse. In addition, CTC analysis according to the invention enables the detection of early relapse in presymptomatic patients who have completed a course of therapy.

Figure 33A:
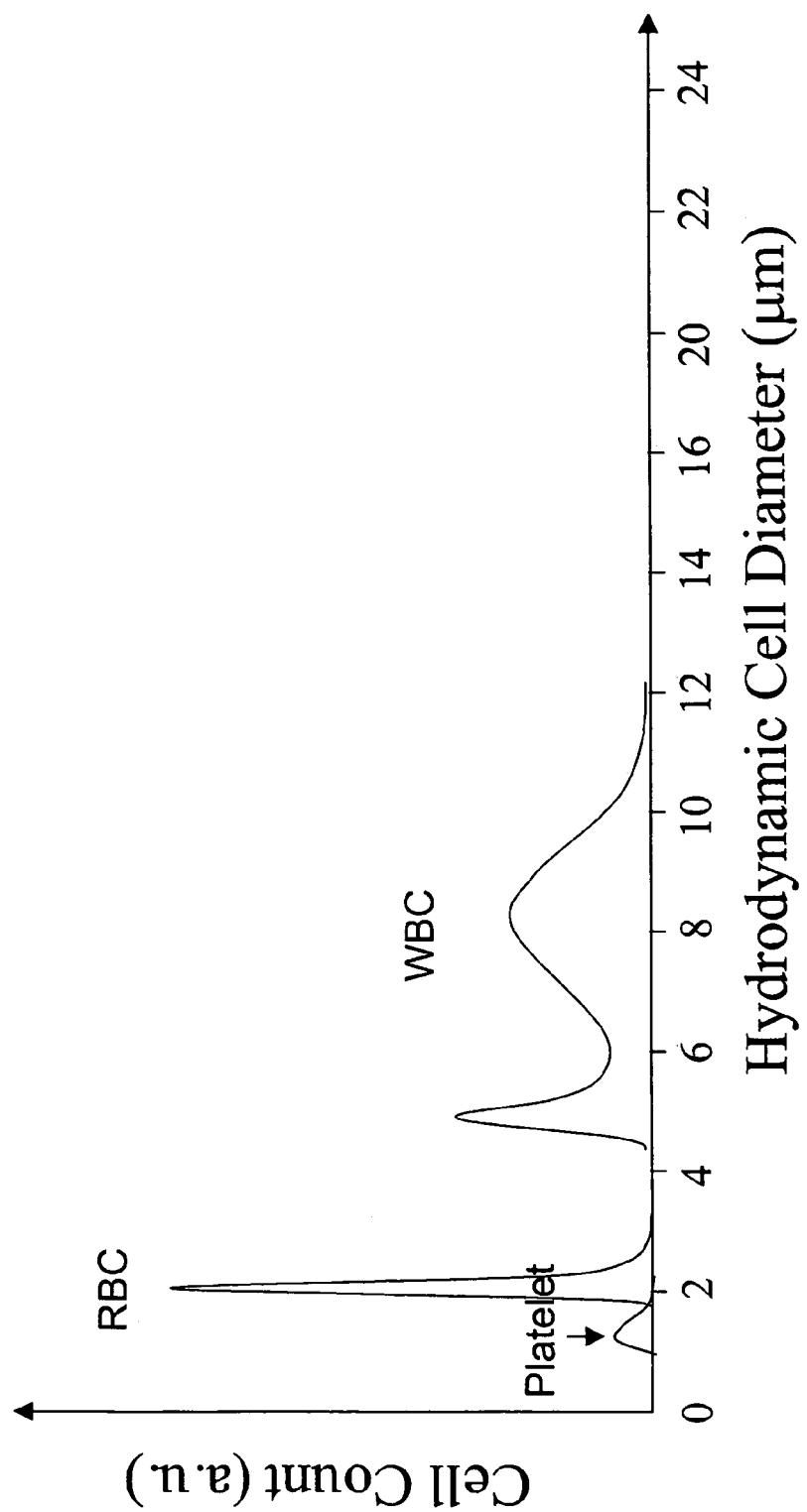
FIG. 33A is a graph of cell count versus hydrodynamic size for a microfluidic separation of normal whole blood.
Figure 33B:
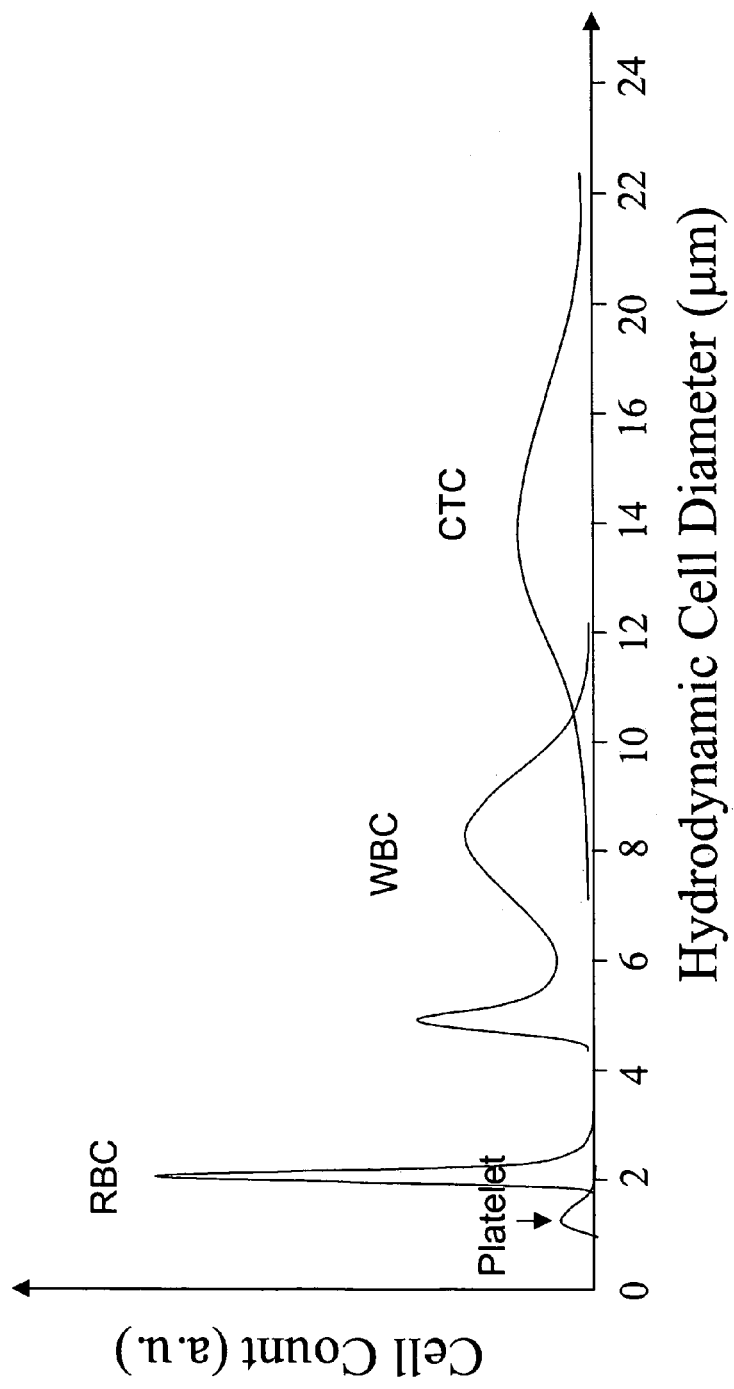
FIG. 33B is a graph of cell count versus hydrodynamic size for a microfluidic separation of whole blood including a population of circulating tumor cells (CTCs).

CTCs are generally larger than most blood cells (see, e.g., FIG. 33B). Therefore, one useful approach for analyzing CTCs in blood is to enrich cells based on size, resulting in a cell population enriched in CTCs. This cell population may then be subjected to further processing or analysis. Other methods of enrichment of CTCs are also possible using the invention. Devices and methods for enriching, enumerating, and analyzing CTCs are described below.

Device

In general, the devices include one or more arrays of obstacles that allow lateral displacement of CTCs and other components of fluids, thereby offering mechanisms of enriching or otherwise processing such components. Prior art devices that differ from those the present invention, but which, like those of the invention, employ obstacles for this purpose, are described, e.g., in Huang et al. *Science* 304, 987-990 (2004) and U.S. Publication No. 20040144651. The devices of the invention for separating particles according to size typically employ an array of a network of gaps, wherein a fluid passing through a gap is divided unequally into subsequent gaps. The array includes a network of gaps arranged such that fluid passing through a gap is divided unequally, even though the gaps may be identical in dimensions. The method uses a flow that carries cells to be separated through the array of gaps. The flow is aligned at a small angle (flow angle) with respect to a line-of-sight of the array. Cells having a hydrodynamic size larger than a critical size migrate along the line-of-sight, i.e., laterally, through the array, whereas those having a hydrodynamic size smaller than the critical size follow the average flow direction. Flow in the device occurs under laminar flow conditions. Devices of the invention are optionally configured as continuous-flow devices.

Figures 1A, 1B, 1C:
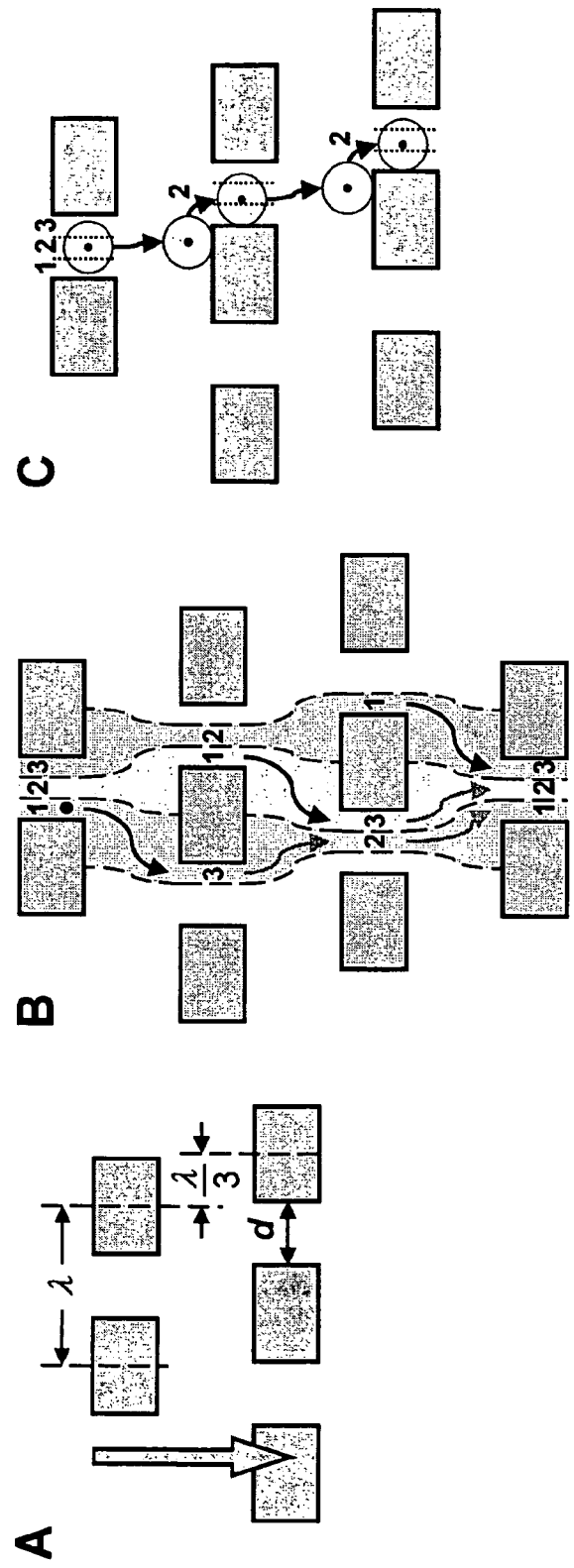
FIGS. 1A-1E are schematic depictions of an array that separates cells based on lateral displacement: (A) illustrates the lateral displacement of subsequent rows; (B) illustrates how fluid flowing through a gap is divided unequally around obstacles in subsequent rows; (C) illustrates how a particle with a hydrodynamic size above the critical size is displaced laterally in the device; (D) illustrates an array of cylindrical obstacles; and (E) illustrates an array of elliptical obstacles.
Figure 2:
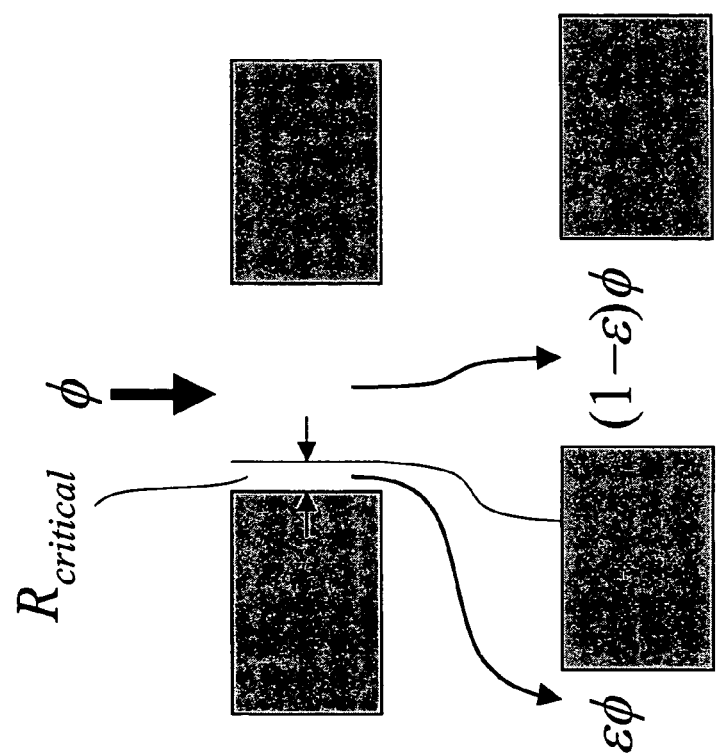
FIG. 2 is a schematic description illustrating the unequal division of the flux through a gap around obstacles in subsequent rows.

The critical size is a function of several design parameters. With reference to the obstacle array in FIGS. 1A-1C, each row of obstacles is shifted horizontally with respect to the previous row by $\Delta\lambda$, where $\lambda$ is the center-to-center distance between the obstacles (FIG. 1A). The parameter $\Delta\lambda/\lambda$ (the "bifurcation ratio," $\epsilon$) determines the ratio of flow bifurcated to the left of the next obstacle. In FIGS. 1A-1C, $\epsilon$ is ⅓, for the convenience of illustration. In general, if the flux through a gap between two obstacles is $\phi$, the minor flux is $\epsilon\phi$, and the major flux is $(1-\epsilon)\phi$ (FIG. 2). In this example, the flux through a gap is divided essentially into thirds (FIG. 1B). While each of the three fluxes through a gap weaves around the array of obstacles, the average direction of each flux is in the overall direction of flow. FIG. 1C illustrates the movement of particles sized above the critical size through the array. Such particles move with the major flux, being transferred sequentially to the major flux passing through each gap.

Figure 3:
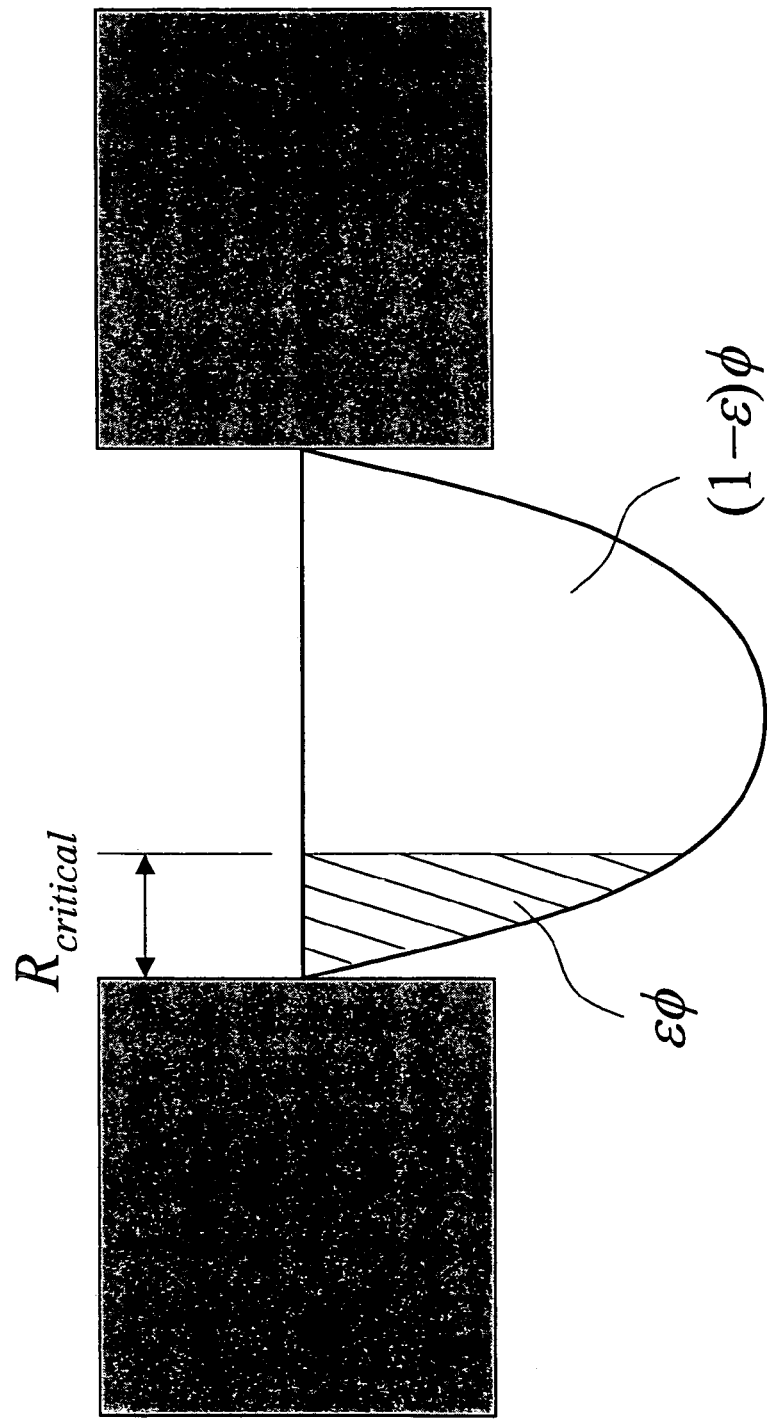
FIG. 3 is a schematic depiction of how the critical size depends on the flow profile, which is parabolic in this example.

Referring to FIG. 2, the critical size is approximately $2R_{critical}$, where $R_{critical}$ is the distance between the stagnant flow line and the obstacle. If the center of mass of a particle, e.g., a cell, falls within $R_{critical}$, the particle would follow the major flux and move laterally through the array. $R_{critical}$ may be determined if the flow profile across the gap is known (FIG. 3); it is the thickness of the layer of fluids that would make up the minor flux. For a given gap size, d, $R_{critical}$ may be tailored based on the bifurcation ratio, $\epsilon$. In general, the smaller $\epsilon$, the smaller $R_{critical}$.

Figure 4:
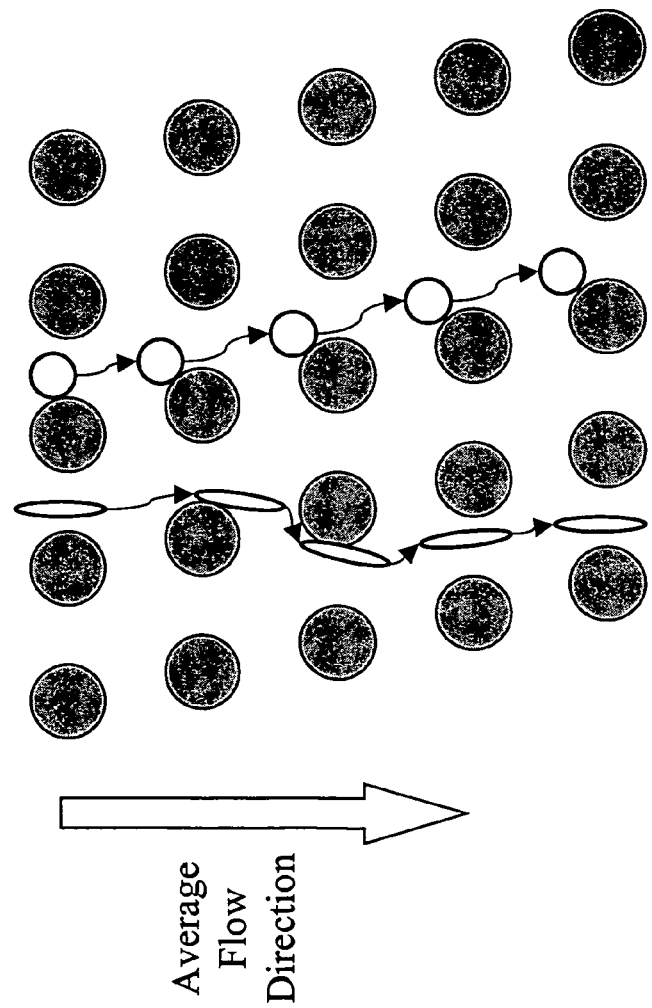
FIG. 4 is an illustration of how shape affects the movement of particles through a device.
Figure 5:
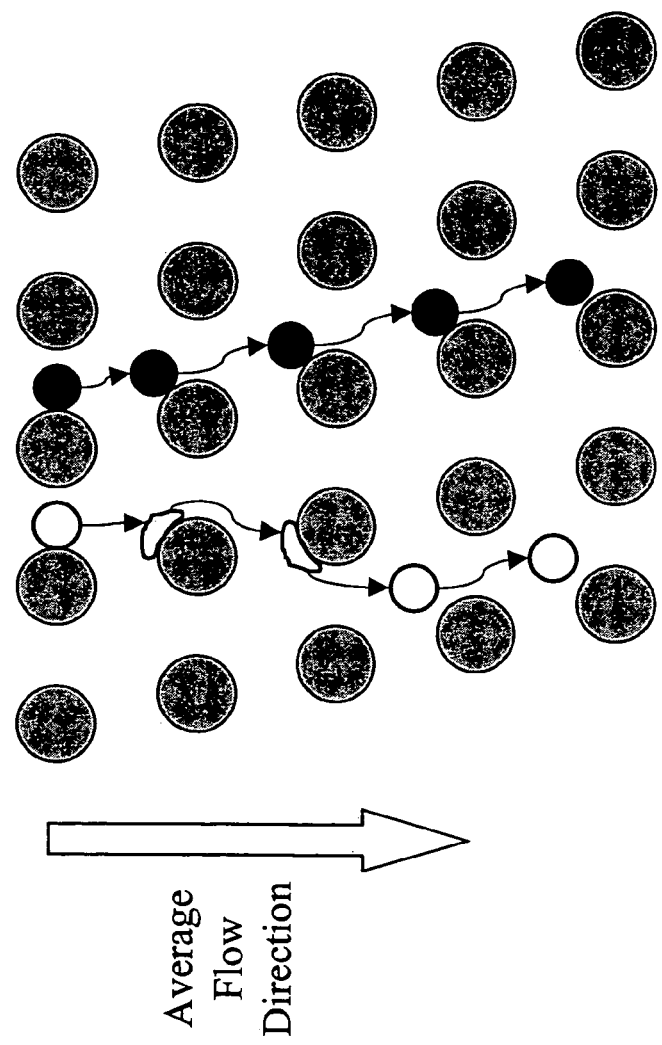
FIG. 5 is an illustration of how deformability affects the movement of particles through a device.

In an array for lateral displacement, particles of different shapes behave as if they have different sizes (FIG. 4). For example, lymphocytes are spheres of ~5 μm diameter, and erythrocytes are biconcave disks of ~7 μm diameter, and ~1.5 μm thick. The long axis of erythrocytes (diameter) is larger than that of the lymphocytes, but the short axis (thickness) is smaller. If erythrocytes align their long axes to a flow when driven through an array of obstacles by the flow, their hydrodynamic size is effectively their thickness (~1.5 μm), which is smaller than lymphocytes. When an erythrocyte is driven through an array of obstacles by a hydrodynamic flow, it tends to align its long axis to the flow and behave like a ~1.5 μm-wide particle, which is effectively "smaller" than lymphocytes. The method and device may therefore separate cells according to their shapes, although the volumes of the cells could be the same. In addition, particles having different deformability behave as if they have different sizes (FIG. 5). For example, two particles having the same undeformed shape may be separated by lateral displacement, as the cell with the greater deformability may deform when it comes into contact with an obstacle in the array and change shape. Thus, separation in the device may be achieved based on any parameter that affects hydrodynamic size including the physical dimensions, the shape, and the deformability of the particle.

Figure 6:
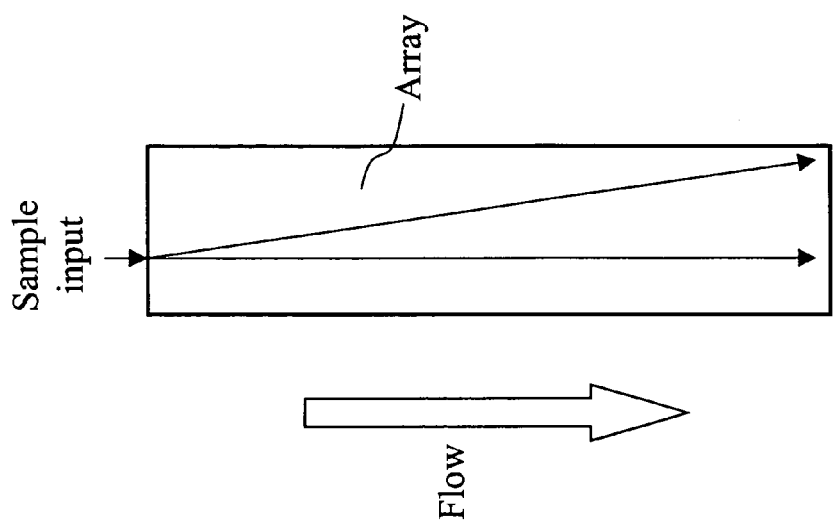
FIG. 6 is a schematic depiction of lateral displacement. Particles having a hydrodynamic size above the critical size move to the edge of the array, while particles having a hydrodynamic size below the critical size pass through the device without lateral displacement.

Referring to FIG. 6, feeding a mixture of particles, e.g., cells, of different hydrodynamic sizes from the top of the array and collecting the particles at the bottom, as shown schematically, produces two outputs, the product containing cells larger than the critical size, $2R_{critical}$, and waste containing cells smaller than the critical size. Although labeled "waste" in FIG. 6, particles below the critical size may be collected while the particles above the critical size are discarded. Both types of outputs may also be desirably collected, e.g., when fractionating a sample into two or more subsamples. Cells larger than the gap size will get trapped inside the array. Therefore, an array has a working size range. Cells have to be larger than a cut-off size ($2R_{critical}$) and smaller than a maximum pass-through size (array gap size) to be directed into the major flux. The "size range" of an array is defined as the ratio of maximum pass-through size to cut-off size.

In some cases, the gaps between obstacles are more than 15 microns, more than 20 microns, or less than 60 microns in size. In other cases, the gaps are between 20 and 100 microns in size.

In certain embodiments, a device of the invention may contain obstacles that include binding moieties, e.g., monoclonal anti-EpCAM antibodies or fragments thereof, that selectively bind to particular cell types, e.g., cells of epithelial origin, e.g., tumor cells. All of the obstacles of the device may include these binding moieties; alternatively, only a subset of the obstacles include them. Devices may also include additional modules that are fluidically coupled, e.g., a cell counting module or a detection module. For example, the detection module may be configured to visualize an output sample of the device. In addition, devices of the invention may be configured to direct cells in a selected size range in one direction, and other cells in a second direction. For example, the device may be configured to enrich cells having a hydrodynamic size greater than 12 microns, 14 microns, 16 microns, 18 microns, or even 20 microns from smaller cells in the sample. Alternatively, the device may enrich cells having a hydrodynamic size greater than or equal to 6 microns and less than or equal to 12 microns, e.g., cells having a hydrodynamic size greater than or equal to 8 microns and less than or equal to 10 microns, from other cells. The device may also enrich cells having a hydrodynamic size greater than or equal to 5 microns and less than or equal to 10 microns from cells having a hydrodynamic size greater than 10 microns; alternatively, it may enrich cells having a hydrodynamic size greater than or equal to 4 microns and less than or equal to 8 microns from cells having a hydrodynamic size greater than 8 microns. In general, the device may be configured to separate two groups of cells, where the first group has a larger average hydrodynamic size than the second group.

In some embodiments, devices of the invention may process more than 20 mL of fluid per hour, or even 50 mL of fluid per hour.

As described above, a device of the invention typically contains an array of obstacles that form a network of gaps. For example, such a device may include a staggered two-dimensional array of obstacles, e.g., such that each successive row is offset by less than half of the period of the previous row. The device may also include a second staggered two-dimensional array of obstacles, which is optionally oriented in a different direction than the first array. In this case, the first array may be situated upstream of the second array, and the second array may have a higher density than the first array. Multiple arrays may be configured in this manner, such that each additional array has an equal or higher density than any array upstream of the additional array.

Devices of the invention may be adapted for implantation in a subject. For example, such a device may be adapted for placement in or near the circulatory system of a subject in order to be able to process blood samples. Such devices may be part of an implantable system of the invention that is fluidically coupled to the circulatory system of a subject, e.g., through tubing or an arteriovenous shunt. In some cases, systems of the invention that include implantable devices, e.g., disposable systems, may remove one or more analytes, components, or materials from the circulatory system. These systems may be adapted for continuous blood flow through the device.

Sample Mobilization Devices

The invention additionally encompasses devices for cell enrichment, e.g., enrichment of CTCs, that employ sample mobilization. A sample mobilization device gives rise to movement of cells, or other components of a fluid sample, relative to features, e.g., obstacles, of the device. For example, one device of the invention includes a receptacle that may hold a cellular sample, a detachably attached lid configured to fit within the receptacle that includes a functionalized lid surface including one or more capture moieties that selectively capture cells of interest, and an sample mobilizer coupled to either the receptacle or the lid. Optionally, the receptacle has a functionalized surface including one or more capture moieties that selectively capture a second cell type. The lid surface may have any shape, e.g., square, rectangular, or circular. The device may be manufactured using any materials known in the art, e.g., glass, silicon, or plastic. In some cases, the lid surface or receptacle surface includes a microstructure, e.g., a micro-obstacle, a micro-corrugation, a micro-groove, or a micro-fin. The capture moieties may include one or more antibodies that specifically bind to a particular cell type, and these antibodies may be configured in an array. As with other devices of the invention, the antibodies may specifically bind to any of a wide variety of cells, e.g., leukocytes or epithelial cells. Preferably, the antibodies are able to bind specifically to CTCs. Furthermore, the antibodies may specifically bind a cell surface cancer marker, e.g., EpCAM, E-Cadherin, Mucin-1, Cytokeratin 8, epidermal growth factor receptor (EGFR), and leukocyte associated receptor (LAR), or a marker selected from Table 1. In some cases, the lid of a sample mobilization device may be designed to fit into the receptacle at a nonorthogonal angle with respect to a wall of the receptacle. The receptacle may be designed to hold any desirable amount of sample, e.g., 10 mL or 50 mL.

TABLE 1

| | | |
|---|---|---|
| 2AR | BETA 5 INTEGRIN SUBUNIT | CD29 |
| A DISINTEGRIN | BETA-2 INTERFERON | CD44 |
| ACTIVATOR OF THYROID | BETA-CATENIN | CD51 |
| AND RETINOIC ACID | BETA-CATENIN | CD54 |
| RECEPTOR (ACTR) | BONE SIALOPROTEIN | CD61 |
| ADAM 11 | (BSP) | CD66e |
| ADIPOGENESIS | BREAST CANCER | CD82 |
| INHIBITORY FACTOR | ESTROGEN-INDUCIBLE | CD87 |
| (ADIF) | SEQUENCE (BCEI) | CD9 |
| ALPHA 6 INTEGRIN | BREAST CANCER | CEA |
| SUBUNIT | RESISTANCE PROTEIN | CELLULAR RETINOL- |
| ALPHA V INTEGRIN | (BCRP) | BINDING PROTEIN 1 |
| SUBUNIT | BREAST CANCER TYPE 1 | (CRBP1) |
| ALPHA-CATENIN | (BRCA1) | c-ERBB-2 |
| AMPLIFIED IN BREAST | BREAST CANCER TYPE 2 | CK7 |
| CANCER 1 (AIB1) | (BRCA2) | CK8 |

TABLE 1-continued

| | | |
|---|---|---|
| AMPLIFIED IN BREAST CANCER 3 (AIB3) | BREAST CARCINOMA AMPLIFIED SEQUENCE 2 (BCAS2) | CK18 |
| AMPLIFIED IN BREAST CANCER 4 (AIB4) | CADHERIN | CK19 |
| AMYLOID PRECURSOR PROTEIN SECRETASE (APPS) | EPITHELIAL CADHERIN-11 | CK20 |
| | CADHERIN-ASSOCIATED PROTEIN | CLAUDIN-7 |
| AP-2 GAMMA | CALCITONIN RECEPTOR (CTR) | c-MET |
| APPS | | COLLAGENASE FIBROBLAST |
| ATP-BINDING CASSETTE TRANSPORTER (ABCT) PLACENTA-SPECIFIC (ABCP) | CALCIUM PLACENTAL PROTEIN (CAPL) | COLLAGENASE INTERSTITIAL |
| | CALCYCLIN | COLLAGENASE-3 |
| | CALLA | COMMON ACUTE LYMPHOCYTIC LEUKEMIA ANTIGEN (CALLA) |
| ATP-BINDING CASSETTE SUBFAMILY C MEMBER (ABCC1) | CAM5 | CONNEXIN 26 (Cx26) |
| | CAPL | CONNEXIN 43 (Cx43) |
| | CARCINOEMBRYONIC ANTIGEN (CEA) | CORTACTIN |
| BAG-1 | | COX-2 |
| BASIGIN (BSG) | CATENIN | CTLA-8 |
| BCEI | ALPHA 1 | CTR |
| B-CELL DIFFERENTIATION FACTOR (BCDF) | CATHEPSIN B | CTSD |
| | CATHEPSIN D | CYCLIN D1 |
| B-CELL LEUKEMIA 2 (BCL-2) | CATHEPSIN K | CYCLOOXYGENASE-2 |
| | CATHEPSIN L2 | CYTOKERATIN 18 |
| B-CELL STIMULATORY FACTOR-2 (BSF-2) | CATHEPSIN O | CYTOKERATIN 19 |
| | CATHEPSIN O1 | CYTOKERATIN 8 |
| BCL-1 | CATHEPSIN V | CYTOTOXIC T-LYMPHOCYTE-ASSOCIATED SERINE ESTERASE 8 (CTLA-8) |
| BCL-2-ASSOCIATED X PROTEIN (BAX) | CD10 | |
| | CD146 | |
| BCRP | CD147 | HUMORAL HYPERCALCEMIA OF MALIGNANCY (HHM) |
| BETA 1 INTEGRIN SUBUNIT | CD24 | |
| BETA 3 INTEGRIN SUBUNIT | GAMMA-CATENIN | |
| DIFFERENTIATION-INHIBITING ACTIVITY (DIA) | GAP JUNCTION PROTEIN (26 kDa) | ICERE-1 |
| DNA AMPLIFIED IN MAMMARY CARCINOMA 1 (DAM1) | GAP JUNCTION PROTEIN (43 kDa) | INT-1 |
| | | INTERCELLULAR ADHESION MOLECULE-1 (ICAM-1) |
| | GAP JUNCTION PROTEIN ALPHA-1 (GJA1) | |
| DNA TOPOISOMERASE II ALPHA | | INTERFERON-GAMMA-INDUCING FACTOR (IGIF) |
| | GAP JUNCTION PROTEIN BETA-2 (GJB2) | |
| DR-NM23 | | INTERLEUKIN-1 ALPHA (IL-1A) |
| E-CADHERIN | GCP1 | |
| EMMPRIN | GELATINASE A | |
| EMS1 | GELATINASE B | INTERLEUKIN-1 BETA (IL-1B) |
| ENDOTHELIAL CELL GROWTH FACTOR (ECGR) PLATELET-DERIVED (PD-ECGF) | GELATINASE (72 kDa) | |
| | GELATINASE (92 kDa) | INTERLEUKIN-11 (IL-11) |
| | GLIOSTATIN | INTERLEUKIN-17 (IL-17) |
| | GLUCOCORTICOID RECEPTOR INTERACTING PROTEIN 1 (GRIP1) | INTERLEUKIN-18 (IL-18) |
| ENKEPHALINASE | | INTERLEUKIN-6 (IL-6) |
| EPIDERMAL GROWTH FACTOR RECEPTOR (EGFR) | | INTERLEUKIN-8 (IL-8) |
| | GLUTATHIONE S-TRANSFERASE p | INVERSELY CORRELATED WITH ESTROGEN RECEPTOR EXPRESSION-1 (ICERE-1) |
| EPISIALIN | | |
| EPITHELIAL MEMBRANE ANTIGEN (EMA) | GM-CSF | |
| | GRANULOCYTE CHEMOTACTIC PROTEIN 1 (GCP1) | KAI1 |
| ER-ALPHA | | KDR |
| ERBB2 | GRANULOCYTE-MACROPHAGE-COLONY STIMULATING FACTOR | KERATIN 8 |
| ERBB4 | | KERATIN 18 |
| ER-BETA | | KERATIN 19 |
| ERF-1 | GROWTH FACTOR RECEPTOR BOUND-7 (GRB-7) | KISS-1 |
| ERYTHROID-POTENTIATING ACTIVITY (EPA) | | LEUKEMIA INHIBITORY FACTOR (LIF) |
| | GSTp | LIF |
| ESR1 | HAP | LOST IN INFLAMMATORY BREAST CANCER (LIBC) |
| ESTROGEN RECEPTOR-ALPHA | HEAT-SHOCK COGNATE PROTEIN 70 (HSC70) | |
| | | LOT ("LOST ON TRANSFORMATION") |
| ESTROGEN RECEPTOR-BETA | HEAT-STABLE ANTIGEN | |
| | HEPATOCYTE GROWTH FACTOR (HGF) | LYMPHOCYTE HOMING RECEPTOR |
| ETS-1 | | |
| EXTRACELLULAR MATRIX METALLOPROTEINASE INDUCER (EMMPRIN) | HEPATOCYTE GROWTH FACTOR RECEPTOR (HGFR) | MACROPHAGE-COLONY STIMULATING FACTOR |
| | | MAGE-3 |
| FIBRONECTIN RECEPTOR BETA POLYPEPTIDE (FNRB) | HEPATOCYTE-STIMULATING FACTOR III (HSF III) | MAMMAGLOBIN |
| | | MASPIN |
| | | MC56 |
| FIBRONECTIN RECEPTOR BETA SUBUNIT (FNRB) | HER-2 | M-CSF |
| | HER2/NEU | MDC |
| FLK-1 | HERMES ANTIGEN | MDNCF |
| GA15.3 | HET | MDR |
| GA733.2 | HHM | P-CADHERIN |
| GALECTIN-3 | NEU | PD-ECGF |
| MELANOMA CELL | NEUTRAL | PDGF-β |

TABLE 1-continued

| | | |
|---|---|---|
| ADHESION MOLECULE (MCAM) | ENDOPEPTIDASE NEUTROPHIL-ACTIVATING | PEANUT-REACTIVE URINARY MUCIN (PUM) |
| MEMBRANE METALLOENDOPEPTIDASE (MME) | PEPTIDE 1 (NAP1) NM23-H1 NM23-H2 | P-GLYCOPROTEIN (P-GP) PGP-1 PHGS-2 |
| MEMBRANE-ASSOCIATED NEUTRAL | NME1 NME2 | PHS-2 PIP |
| ENDOPEPTIDASE (NEP) | NUCLEAR RECEPTOR | PLAKOGLOBIN |
| CYSTEINE-RICH PROTEIN (MDC) | COACTIVATOR-1 (NCoA-1) NUCLEAR RECEPTOR | PLASMINOGEN ACTIVATOR INHIBITOR |
| METASTASIN (MTS-1) | COACTIVATOR-2 (NCoA-2) | (TYPE 1) |
| MLN64 | NUCLEAR RECEPTOR | PLASMINOGEN |
| MMP1 | COACTIVATOR-3 (NCoA-3) | ACTIVATOR INHIBITOR |
| MMP2 | NUCLEOSIDE | (TYPE 2) |
| MMP3 | DIPHOSPHATE KINASE A | PLASMINOGEN |
| MMP7 | (NDPKA) | ACTIVATOR (TISSUE- |
| MMP9 | NUCLEOSIDE | TYPE) |
| MMP11 | DIPHOSPHATE KINASE B | PLASMINOGEN |
| MMP13 | (NDPKB) | ACTIVATOR (UROKINASE- |
| MMP14 | ONCOSTATIN M (OSM) | TYPE) |
| MMP15 | ORNITHINE | PLATELET |
| MMP16 | DECARBOXYLASE (ODC) | GLYCOPROTEIN IIIa |
| MMP17 | OSTEOCLAST | (GP3A) |
| MOESIN | DIFFERENTIATION | PLAU |
| MONOCYTE ARGININE- | FACTOR (ODF) | PLEOMORPHIC ADENOMA |
| SERPIN | OSTEOCLAST | GENE-LIKE 1 (PLAGL1) |
| MONOCYTE-DERIVED | DIFFERENTIATION | POLYMORPHIC |
| NEUTROPHIL | FACTOR RECEPTOR | EPITHELIAL MUCIN (PEM) |
| CHEMOTACTIC FACTOR | (ODFR) | PRAD1 |
| MONOCYTE-DERIVED | OSTEONECTIN (OSN, ON) | PROGESTERONE |
| PLASMINOGEN | OSTEOPONTIN (OPN) | RECEPTOR (PgR) |
| ACTIVATOR INHIBITOR | OXYTOCIN RECEPTOR | PROGESTERONE |
| MTS-1 | (OXTR) | RESISTANCE |
| MUC-1 | p27/kip1 | PROSTAGLANDIN |
| MUC18 | p300/CBP COINTEGRATOR | ENDOPEROXIDE |
| MUCIN LIKE CANCER | ASSOCIATE PROTEIN | SYNTHASE-2 |
| ASSOCIATED ANTIGEN | (p/CIP) | PROSTAGLANDIN G/H |
| (MCA) | p53 | SYNTHASE-2 |
| MUCIN | p9Ka | PROSTAGLANDIN H |
| MUC-1 | PAI-1 | SYNTHASE-2 |
| MULTIDRUG RESISTANCE | PAI-2 | pS2 |
| PROTEIN 1 (MDR, MDR1) | PARATHYROID | PS6K |
| MULTIDRUG RESISTANCE | ADENOMATOSIS 1 (PRAD1) | PSORIASIN |
| RELATED PROTEIN-1 | PARATHYROID HORMONE- | PTHLH |
| (MRP, MRP-1) | LIKE HORMONE (PTHLH) | PTHrP |
| N-CADHERIN | PARATHYROID HORMONE- | RAD51 |
| NEP | RELATED PEPTIDE (PTHrP) | VITRONECTIN RECEPTOR |
| RAD52 | TIMP4 | ALPHA POLYPEPTIDE |
| RAD54 | TISSUE-TYPE | (VNRA) |
| RAP46 | PLASMINOGEN | VITRONECTIN RECEPTOR |
| RECEPTOR-ASSOCIATED | ACTIVATOR | VON WILLEBRAND |
| COACTIVATOR 3 (RAC3) | TN-C | FACTOR |
| REPRESSOR OF | TP53 | VPF |
| ESTROGEN RECEPTOR | tPA | VWF |
| ACTIVITY (REA) | TRANSCRIPTIONAL | WNT-1 |
| S100A4 | INTERMEDIARY FACTOR 2 | ZAC |
| S100A6 | (TIF2) | ZO-1 |
| S100A7 | TREFOIL FACTOR 1 (TFF1) | ZONULA OCCLUDENS-1 |
| S6K | TSG101 | |
| SART-1 | TSP-1 | |
| SCAFFOLD ATTACHMENT | TSP1 | |
| FACTOR B (SAF-B) | TSP-2 | |
| SCATTER FACTOR (SF) | TSP2 | |
| SECRETED | TSP50 | |
| PHOSPHOPROTEIN-1 | TUMOR CELL | |
| (SPP-1) | COLLAGENASE | |
| SECRETED PROTEIN | STIMULATING FACTOR | |
| ACIDIC AND RICH IN | (TCSF) | |
| CYSTEINE (SPARC) | TUMOR-ASSOCIATED | |
| STANNICALCIN | EPITHELIAL MUCIN | |
| STEROID RECEPTOR | uPA | |
| COACTIVATOR-1 (SRC-1) | uPAR | |
| STEROID RECEPTOR | UROKINASE | |
| COACTIVATOR-2 (SRC-2) | UROKINASE-TYPE | |
| STEROID RECEPTOR | PLASMINOGEN | |
| COACTIVATOR-3 (SRC-3) | ACTIVATOR | |
| STEROID RECEPTOR RNA | UROKINASE-TYPE | |
| ACTIVATOR (SRA) | PLASMINOGEN | |
| STROMELYSIN-1 | ACTIVATOR RECEPTOR | |
| STROMELYSIN-3 | (uPAR) | |

TABLE 1-continued

| | |
|---|---|
| TENASCIN-C (TN-C) | UVOMORULIN |
| TESTES-SPECIFIC PROTEASE 50 | VASCULAR ENDOTHELIAL GROWTH FACTOR |
| THROMBOSPONDIN I | VASCULAR ENDOTHELIAL |
| THROMBOSPONDIN II | GROWTH FACTOR |
| THYMIDINE PHOSPHORYLASE (TP) | RECEPTOR-2 (VEGFR2) VASCULAR ENDOTHELIAL |
| THYROID HORMONE RECEPTOR ACTIVATOR | GROWTH FACTOR-A VASCULAR PERMEABILITY |
| MOLECULE 1 (TRAM-1) | FACTOR |
| TIGHT JUNCTION PROTEIN 1 (TJP1) | VEGFR2 VERY LATE T-CELL |
| TIMP1 | ANTIGEN BETA (VLA-BETA) |
| TIMP2 | VIMENTIN |
| TIMP3 | |

Any sample mobilization component may be used in the device. For example, the sample mobilizer may include a mechanical rocker or a sonicator. Alternatively, it may be adapted to provide centrifugal force to the receptacle and lid. A centrifugal sample mobilizer may be used to mobilize sample components, e.g., cells, within a fluid sample, e.g., a fluid sample having a free surface. A centrifugal sample mobilizer may also be used to drive cell rolling along the lid surface. In one example, a centrifugal sample mobilizer may include an axle that rotates the receptacle; in some embodiments, the centrifugal force generated by operating the device is capable of driving the lid into a nonorthogonal angle with respect to the axle.

Another sample mobilization component that may be used in the device utilizes two fluidically coupled chambers, each of which has a surface in contact with the internal space of the receptacle. In such a device, which utilizes pressure-driven flow, each chamber is filled with a fluid, e.g., air, and when one chamber is compressed, a portion of the fluid therein enters the other chamber, increasing its volume. By placing these chambers in contact with a cellular sample in the receptacle and altering their volumes, e.g., squeezing the chambers in alternation, the sample is mobilized.

Uses of Devices of the Invention

The invention features improved devices for the enrichment of CTCs and other particles, including bacteria, viruses, fungi, cells, cellular components, viruses, nucleic acids, proteins, and protein complexes, according to size. The devices may be used to effect various manipulations on particles in a sample. Such manipulations include enrichment or concentration of a particle, including size based fractionation, or alteration of the particle itself or the fluid carrying the particle. Preferably, the devices are employed to enrich CTCs or other rare particles from a heterogeneous mixture or to alter a rare particle, e.g., by exchanging the liquid in the suspension or by contacting a particle with a reagent. Such devices allow for a high degree of enrichment with limited stress on cells, e.g., reduced mechanical lysis or intracellular activation of cells.

Array Design

Figure 1D:
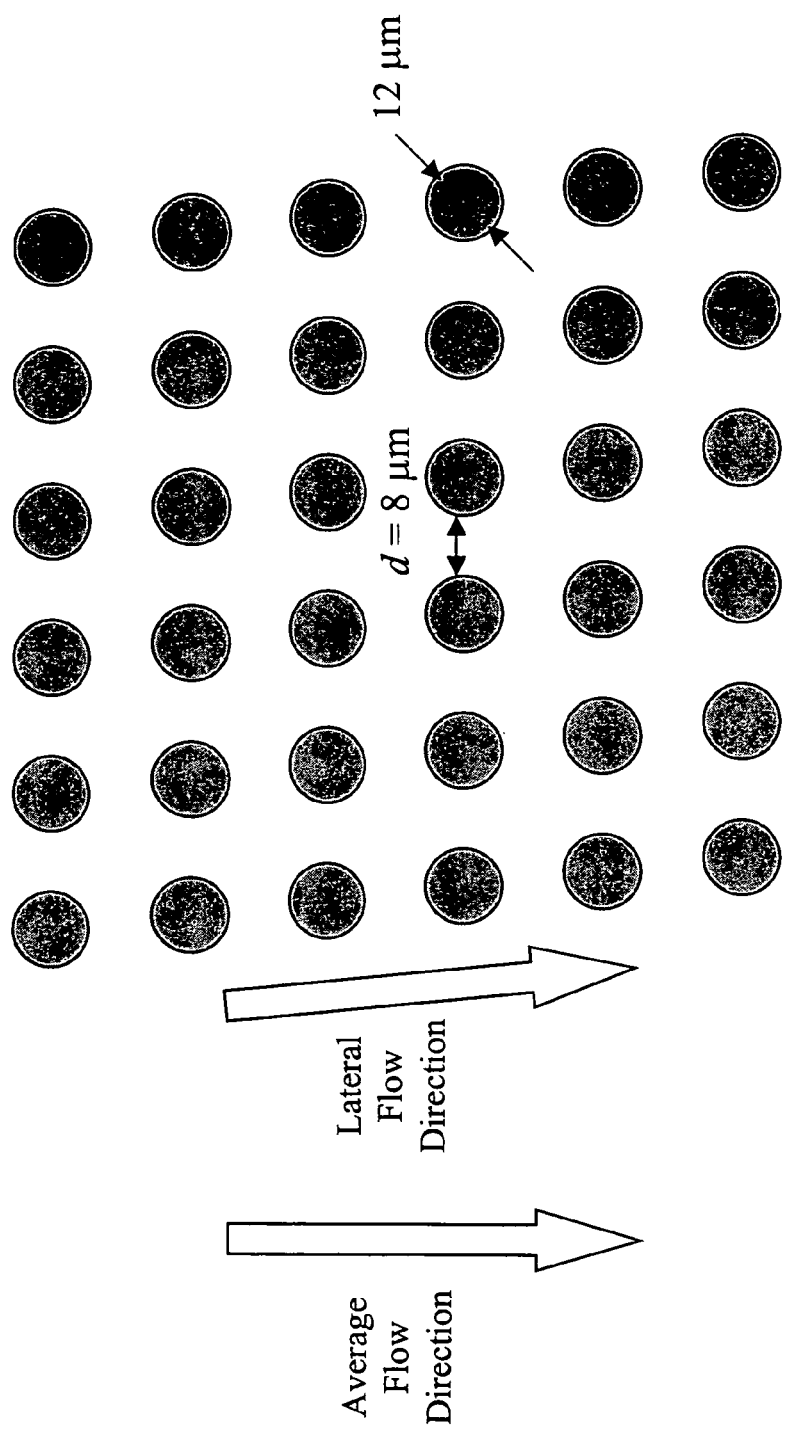
Figure 1E:
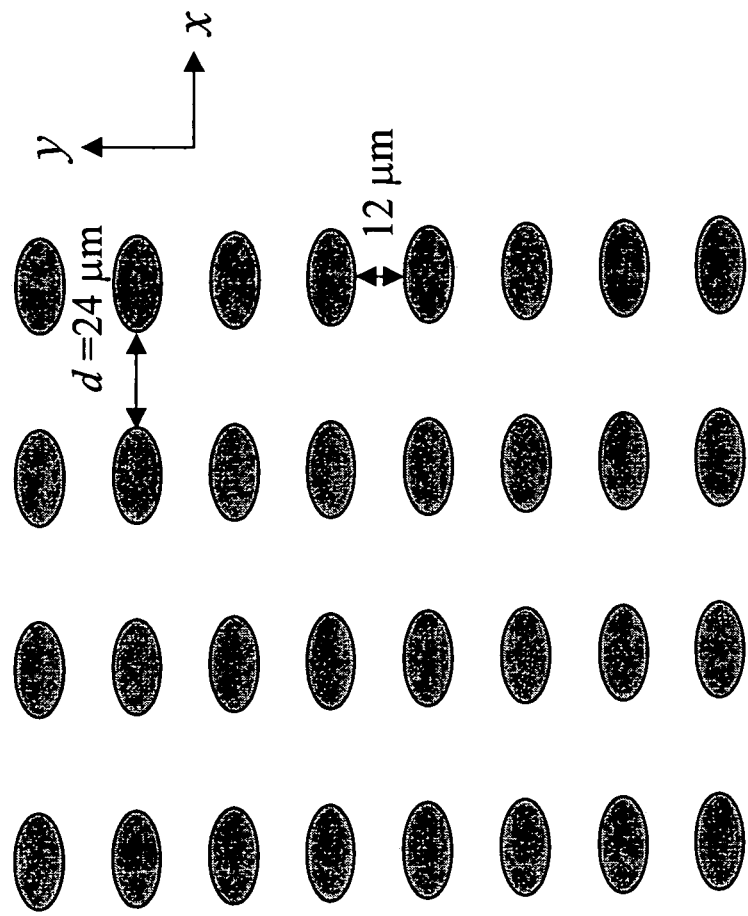

Single-stage array. In one embodiment, a single stage contains an array of obstacles, e.g., cylindrical obstacles (FIG. 1D), forming a network of gaps. In certain embodiments, the array has a maximum pass-through size that is several times larger than the cut-off size, e.g., when enriching CTCs from other cells in a blood sample. This result may be achieved using a combination of a large gap size d and a small bifurcation ratio $\epsilon$. In preferred embodiments, the $\epsilon$ is at most 1/2, e.g., at most 1/3, 1/10, 1/30, 1/100, 1/300, or 1/1000. In such embodiments, the obstacle shape may affect the flow profile in the gap, e.g., such that fluid flowing through the gaps is unevenly distributed around the obstacles; however, the obstacles may be compressed in the flow direction, in order to make the array short (FIG. 1E). Single stage arrays may include bypass channels as described herein.

Figure 7:
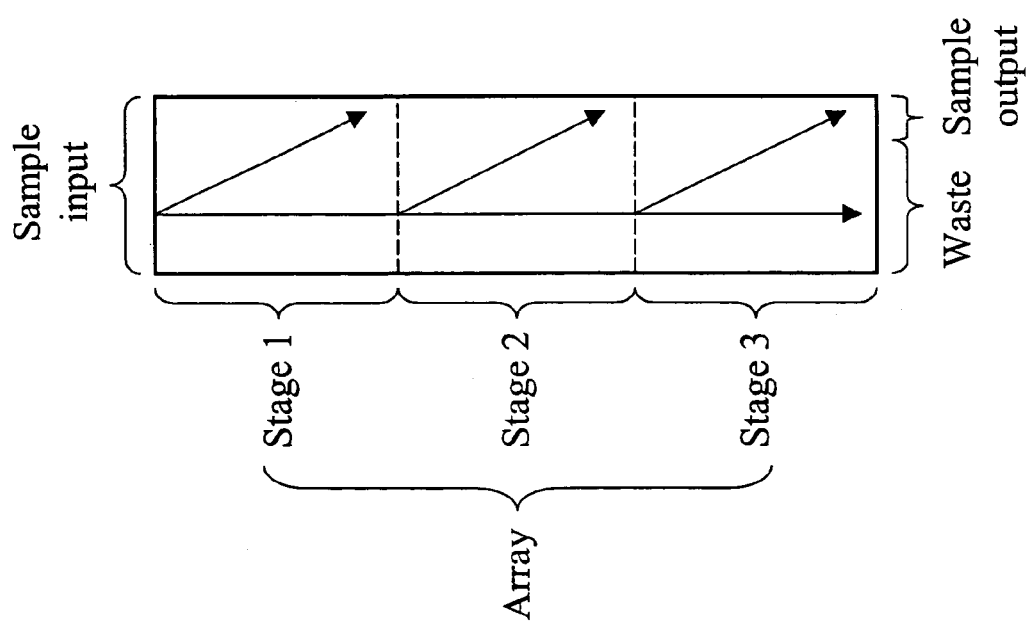
FIG. 7 is a schematic depiction of a three stage device.
Figure 8:
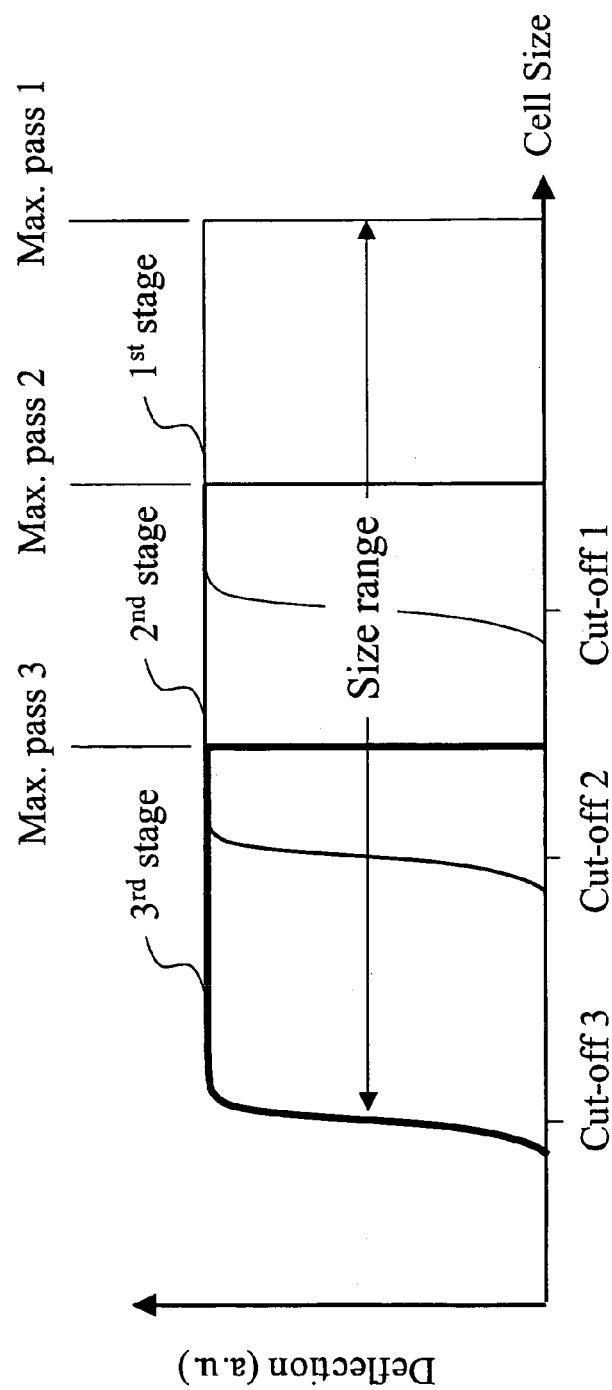
FIG. 8 is a schematic depiction of the maximum size and cut-off size for the device of FIG. 7.

Multiple-stage arrays. In another embodiment, multiple stages are employed to enrich particles over a wide size range. An exemplary device is shown in FIG. 7. The device shown has three stages, but any number of stages may be employed. Typically, the cut-off size in the first stage is larger than the cut-off in the second stage, and the first stage cut-off size is smaller than the maximum pass-through size of the second stage (FIG. 8). The same is true for the following stages. The first stage will deflect (and remove) particles, e.g., that would cause clogging in the second stage, before they reach the second stage. Similarly, the second stage will deflect (and remove) particles that would cause clogging in the third stage, before they reach the third stage. In general, an array may have as many stages as desired, connected either serially or in parallel.

As described, in a multiple-stage array, large particles, e.g., cells, that could cause clogging downstream are deflected first, and these deflected particles need to bypass the downstream stages to avoid clogging. Thus, devices of the invention may include bypass channels that remove output from an array. Although described here in terms of removing particles above the critical size, bypass channels may also be employed to remove output from any portion of the array.

Different designs for bypass channels are as follows.

Figure 9:
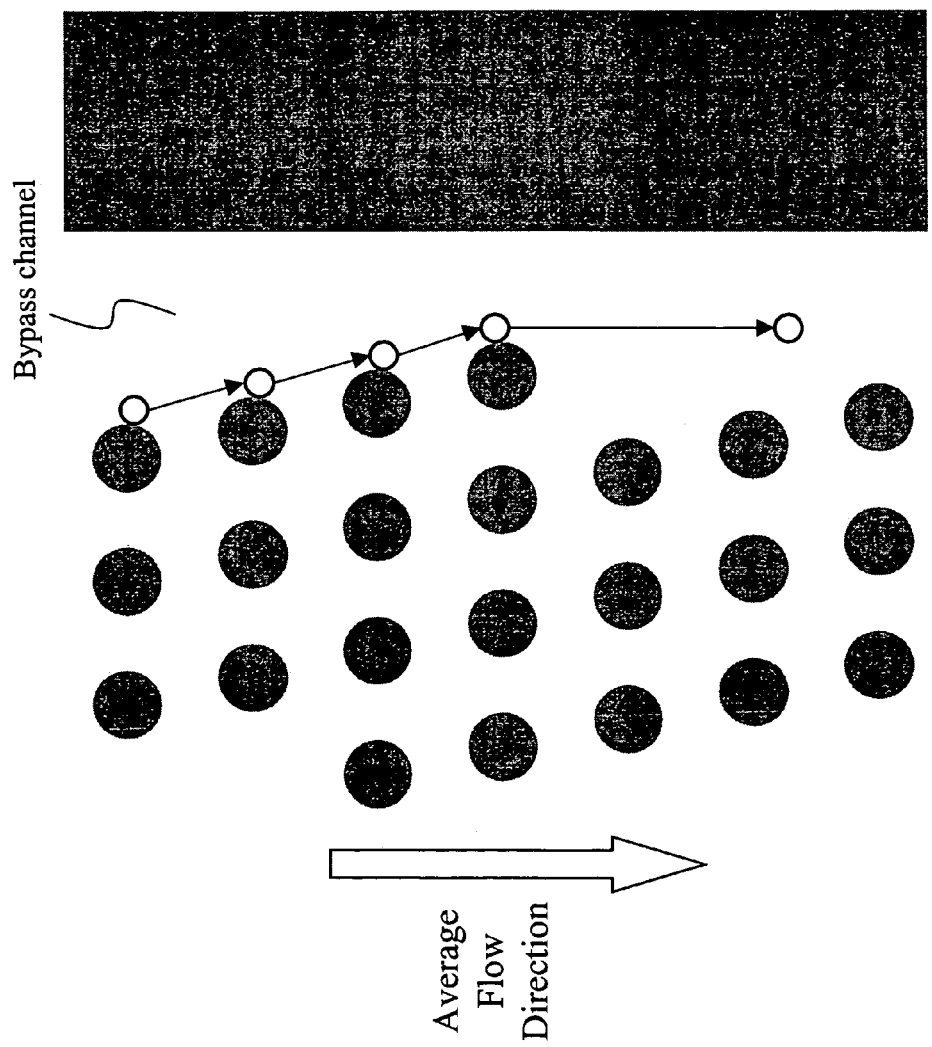
FIG. 9 is a schematic depiction of a bypass channel.
Figure 10:
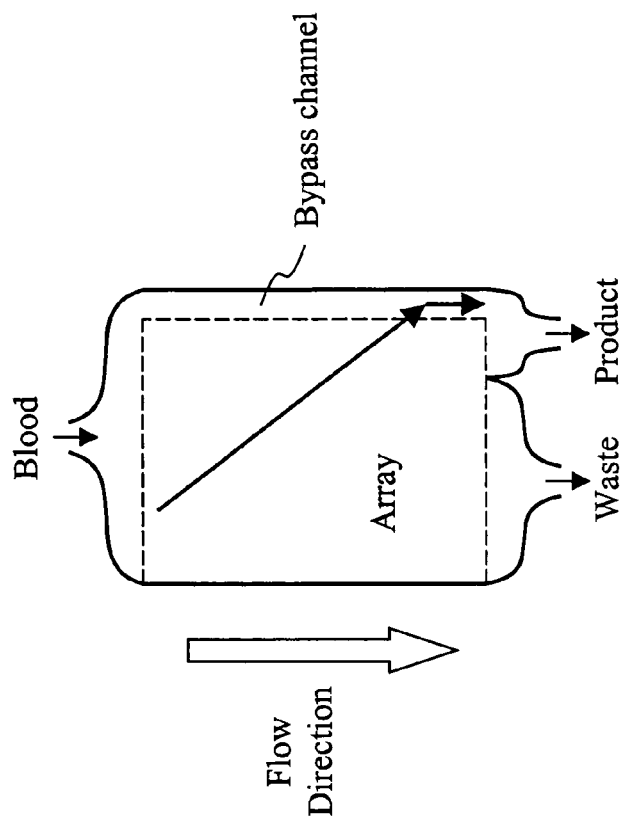
FIG. 10 is a schematic depiction of a bypass channel.
Figure 11:
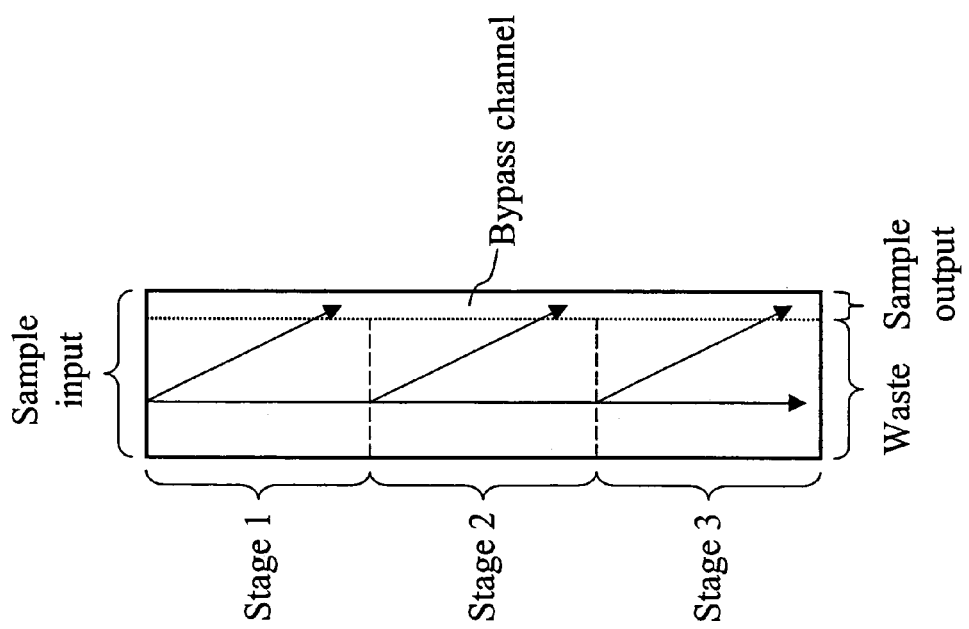
FIG. 11 is a schematic depiction of a three stage device having a common bypass channel.
Figure 12:
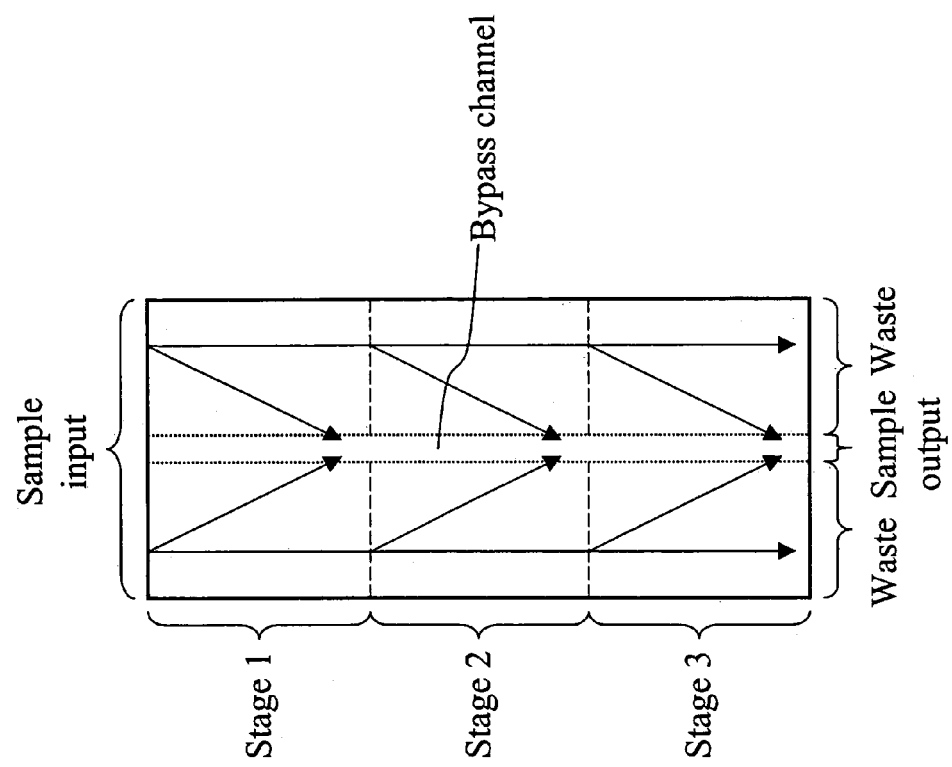
FIG. 12 is a schematic depiction of a three stage, duplex device having a common bypass channel.

Single bypass channels. In this design, all stages share one bypass channel, or there is only one stage. The physical boundary of the bypass channel may be defined by the array boundary on one side and a sidewall on the other (FIGS. 9-11). Single bypass channels may also be employed with duplex arrays (FIG. 12).

Figure 13:
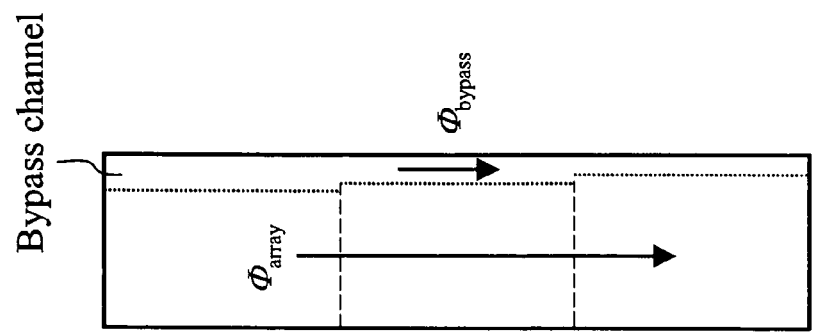
FIG. 13 is a schematic depiction of a three stage device having a common bypass channel, where the flow through the device is substantially constant.
Figure 14:
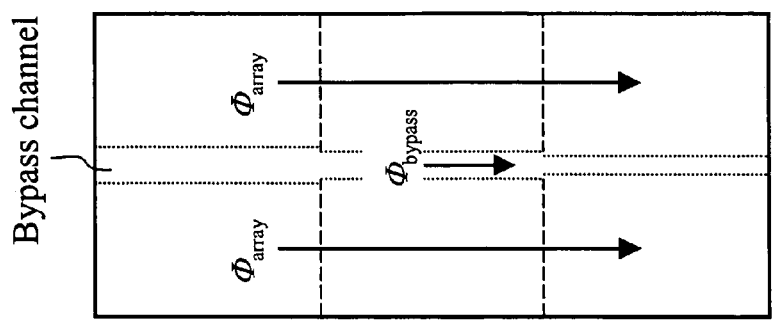
FIG. 14 is a schematic depiction of a three stage, duplex device having a common bypass channel, where the flow through the device is substantially constant.
Figure 15:
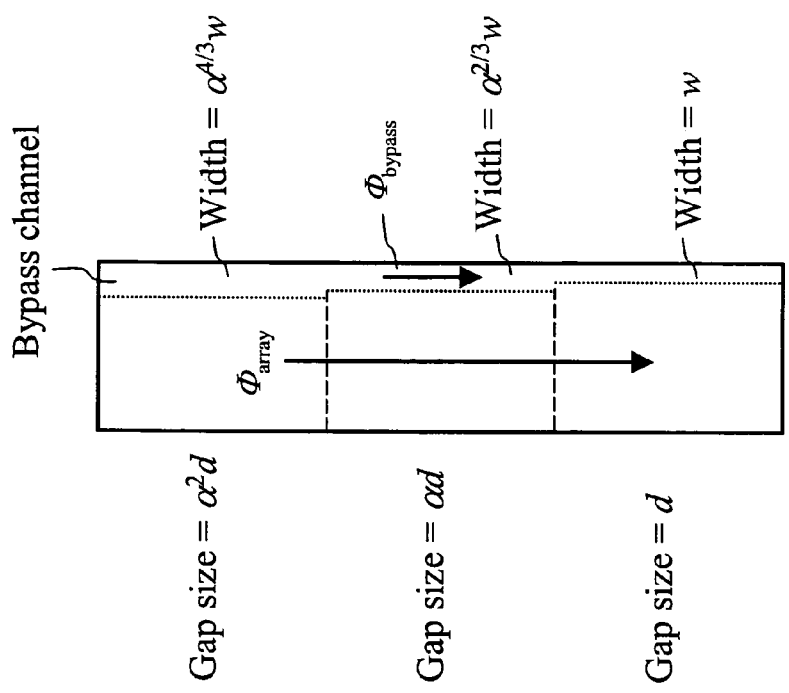
FIG. 15 is a schematic depiction of a three stage device having a common bypass channel, where the fluidic resistance in the bypass channel and the adjacent stage are substantially constant.
Figure 16:
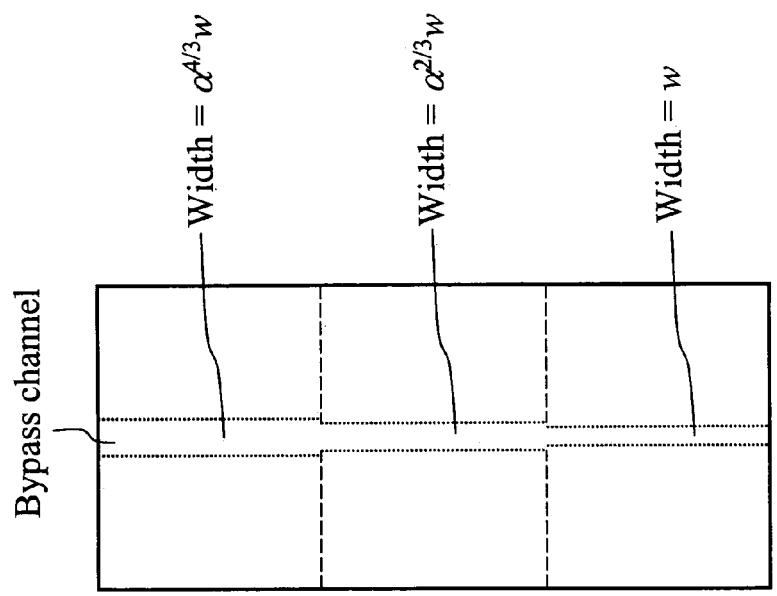
FIG. 16 is a schematic depiction of a three stage, duplex device having a common bypass channel, where the fluidic resistance in the bypass channel and the adjacent stage are substantially constant.

Single bypass channels may also be designed, in conjunction with an array to maintain constant flux through a device (FIG. 13). The bypass channel has varying width designed maintain constant flux through all the stages, so that the flow in the channel does not interfere with the flow in the arrays. Such a design may also be employed with an array duplex (FIG. 14). Single bypass channels may also be designed in conjunction with the array in order to maintain substantially constant fluidic resistance through all stages (FIG. 15). Such a design may also be employed with an array duplex (FIG. 16.)

Figure 17:
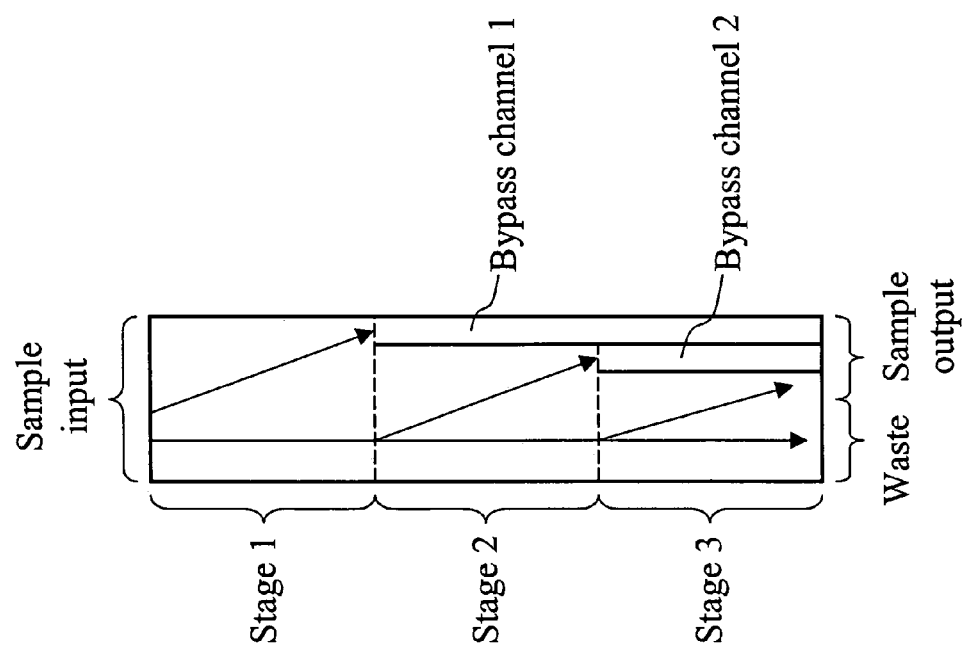
FIG. 17 is a schematic depiction of a three stage device having two, separate bypass channels.
Figure 18:
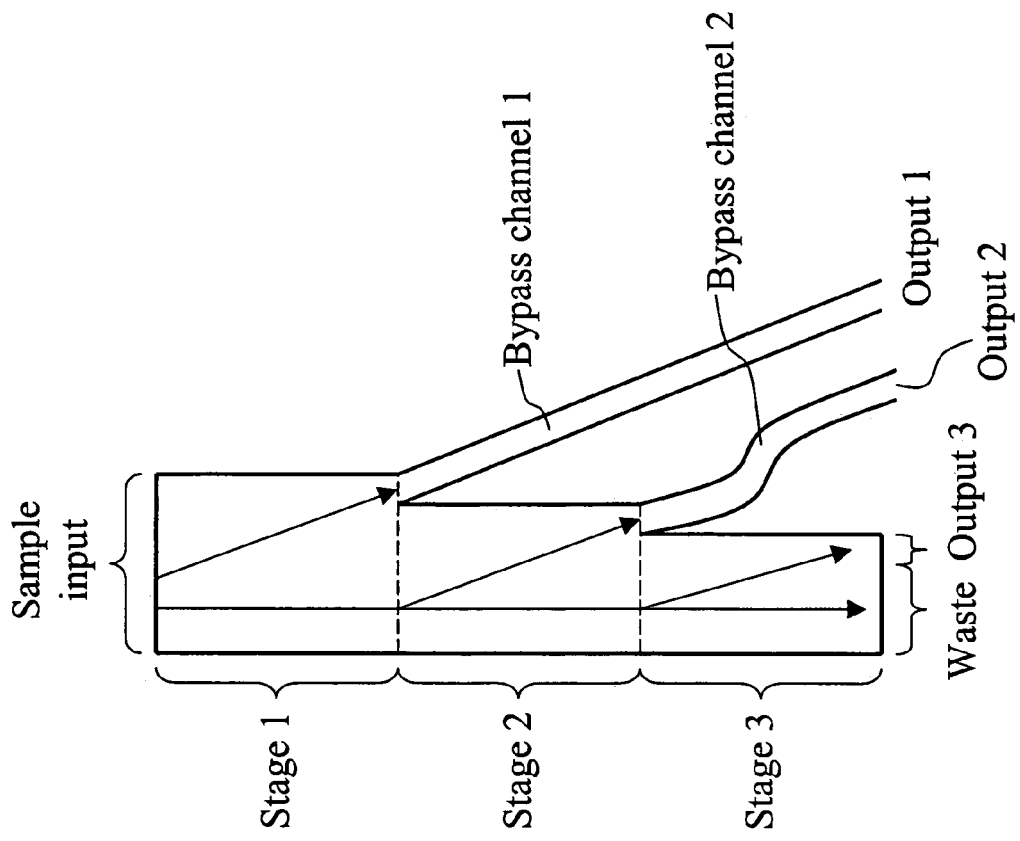
FIG. 18 is a schematic depiction of a three stage device having two, separate bypass channels, which are in arbitrary configuration.
Figure 19:
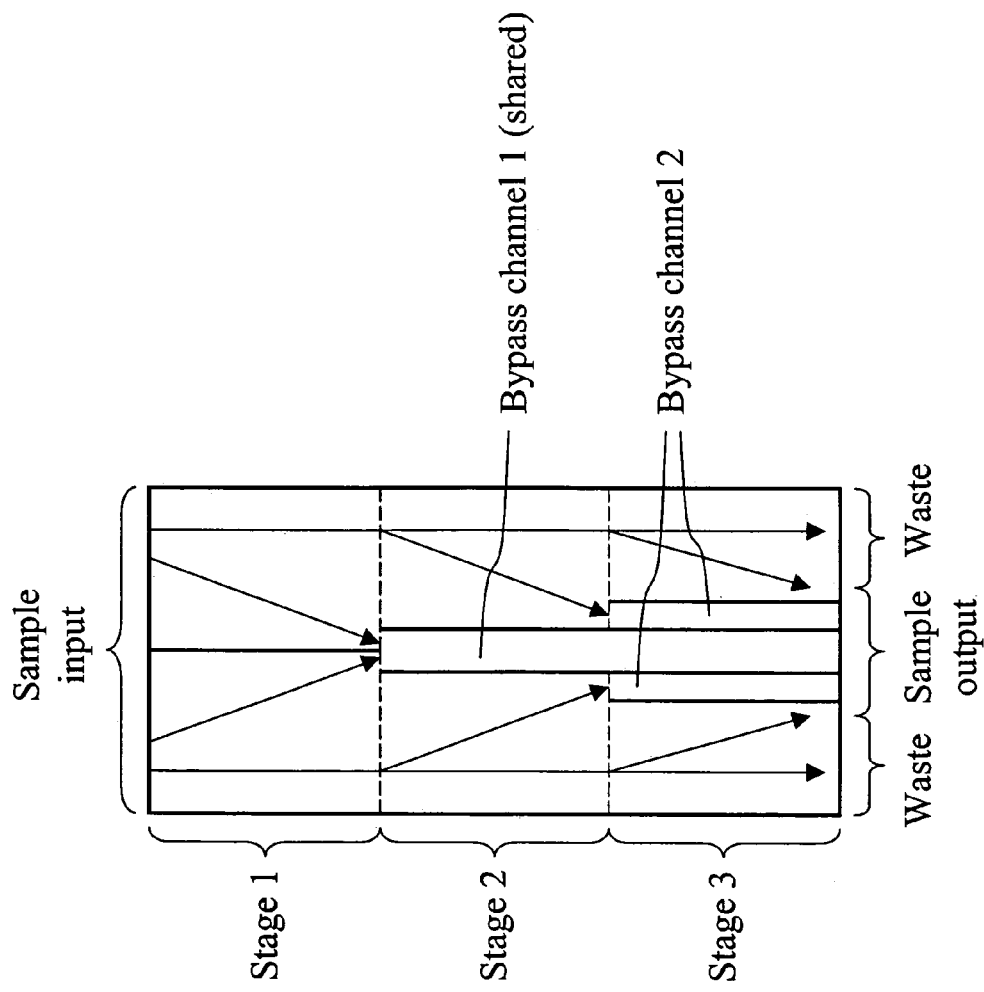
FIG. 19 is a schematic depiction of a three stage, duplex device having three, separate bypass channels.

Multiple bypass channels. In this design (FIG. 17), each stage has its own bypass channel, and the channels are separated from each other by sidewalls. Large particles, e.g., cells are deflected into the major flux to the lower right corner of the first stage and then into in the bypass channel (bypass channel 1 in FIG. 17). Smaller cells that would not cause clogging in the second stage proceed to the second stage, and cells above the critical size of the second stage are deflected to the lower right corner of the second stage and into in another bypass channel (bypass channel 2 in FIG. 17). This design may be repeated for as many stages as desired. In this embodiment, the bypass channels are not fluidically connected, allowing for collection or other manipulation of multiple fractions. The bypass channels do not need to be straight or be physically parallel to each other (FIG. 18). Multiple bypass channels may also be employed with duplex arrays (FIG. 19).

Figure 20:
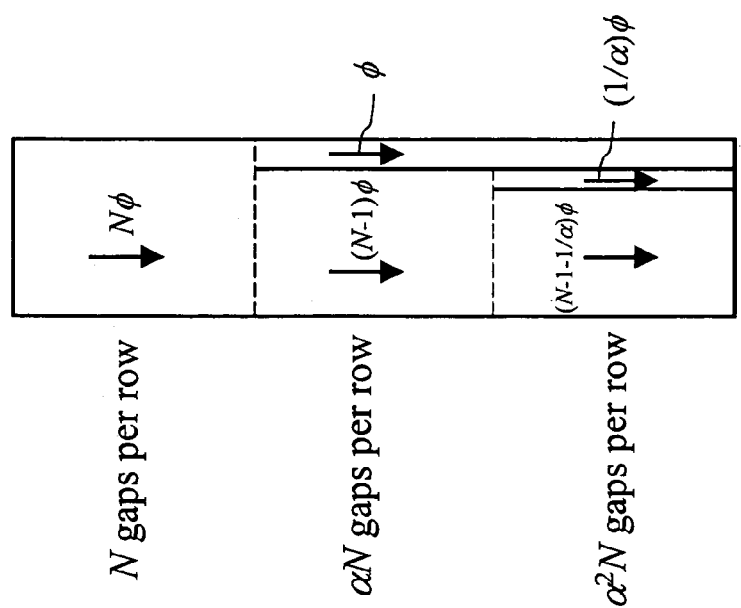
FIG. 20 is a schematic depiction of a three stage device having two, separate bypass channels, wherein the flow through each stage is substantially constant.
Figure 21:
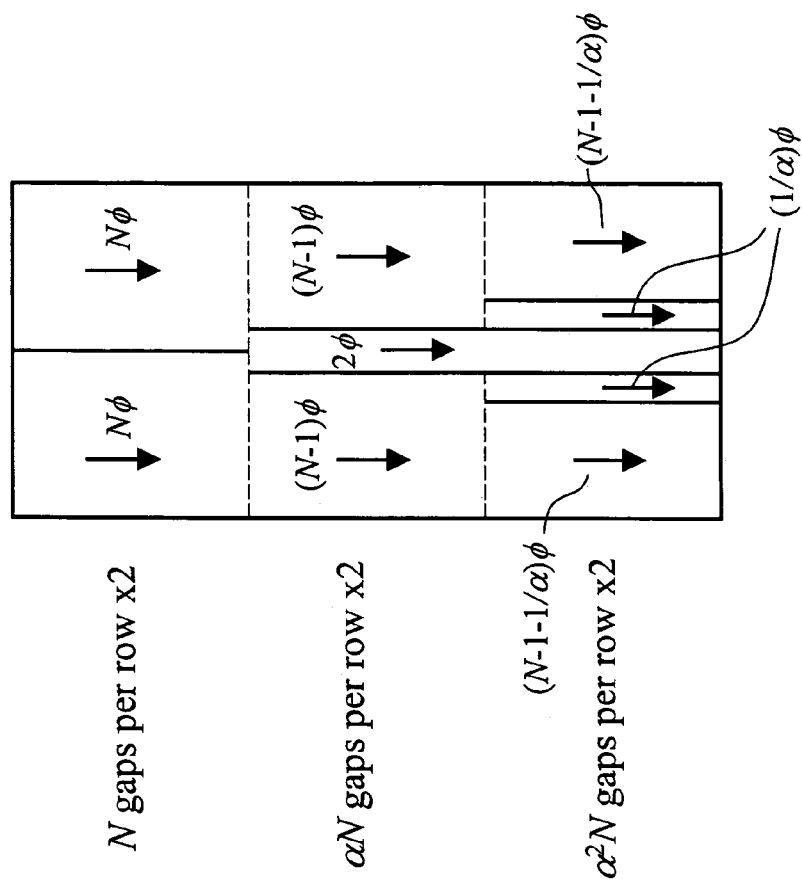
FIG. 21 is a schematic depiction of a three stage, duplex device having three, separate bypass channels, wherein the flow through each stage is substantially constant.

Multiple bypass channels may be designed, in conjunction with an array to maintain constant flux through a device (FIG. 20). In this example, bypass channels are designed to remove an amount of flow so the flow in the array is not perturbed, i.e., substantially constant. Such a design may also be employed with an array duplex (FIG. 21). In this design, the center bypass channel may be shared between the two arrays in the duplex.

Optimal Boundary Design. If the array were infinitely large, the flow distribution would be the same at every gap. The flux $\phi$ going through a gap would be the same, and the minor flux would be $\epsilon\phi$ for every gap. In practice, the boundaries of the array perturb this infinite flow pattern. Portions of the boundaries of arrays may be designed to generate the flow pattern of an infinite array. Boundaries may be flow-feeding, i.e., the boundary injects fluid into the array or flow-extracting, i.e., the boundary extracts fluid from the array.

Figure 22:
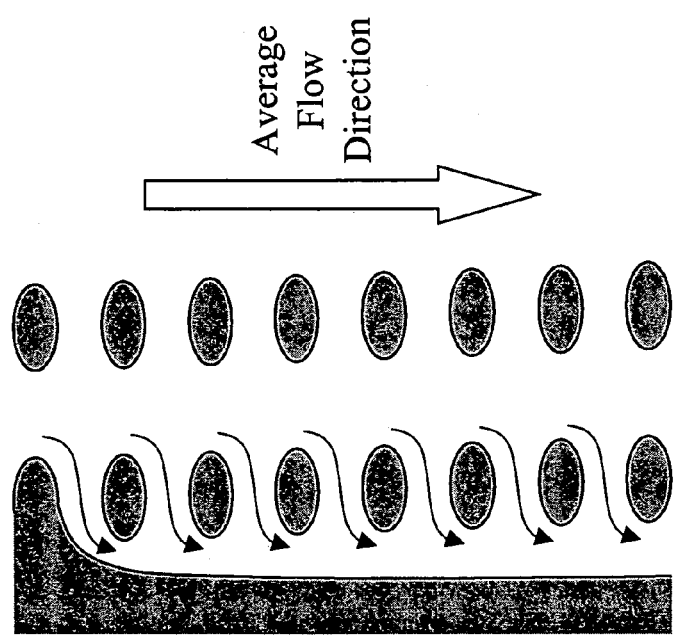
FIG. 22 is a schematic depiction of a flow-extracting boundary.

A preferred flow-extracting boundary widens gradually to extract $\epsilon\phi$ (represented by arrows in FIG. 22) from each gap at the boundary (d=24 µm, $\epsilon$=1/60). For example, the distance between the array and the sidewall gradually increases to allow for the addition of $\epsilon\phi$ from each gap to the boundary. The flow pattern inside this array is not affected by the bypass channel because of the boundary design.

Figure 23:
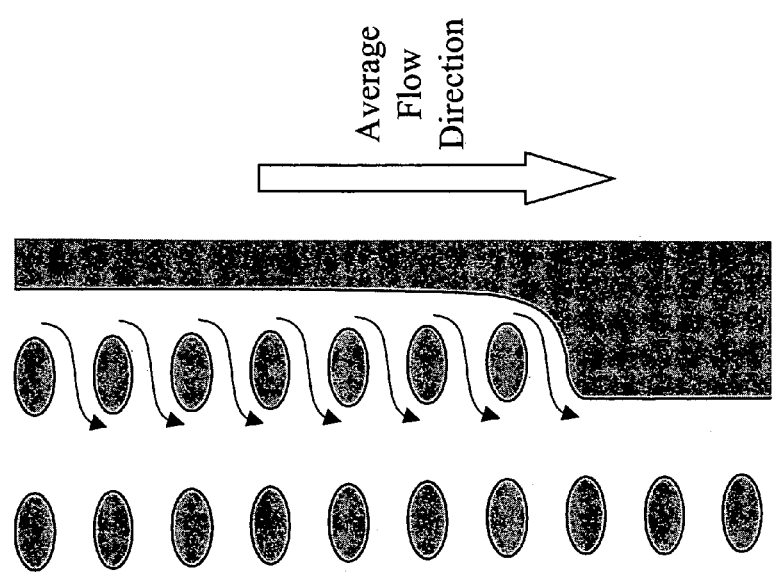
FIG. 23 is a schematic depiction of a flow-feeding boundary.

A preferred flow-feeding boundary narrows gradually to feed exactly $\epsilon\phi$ (represented by arrows in FIG. 23) into each gap at the boundary (d=24 µm, $\epsilon$=1/60). For example, the distance between the array and the sidewall gradually decreases to allow for the removal of $\epsilon\phi$ to each gap from the boundary. Again, the flow pattern inside this array is not affected by the bypass channel because of the boundary design.

Figure 24:
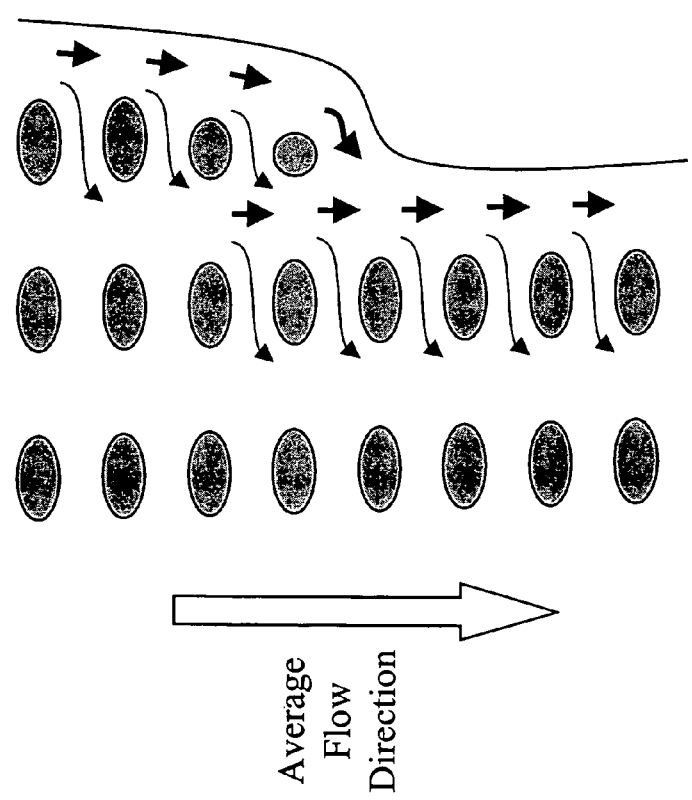
FIG. 24 is a schematic depiction of a flow-feeding boundary, including a bypass channel.

A flow-feeding boundary may also be as wide as or wider than the gaps of an array (FIG. 24) (d=24 µm, $\epsilon$=1/60). A wide boundary may be desired if the boundary serves as a bypass channel, e.g., to allow for collection of particles. A boundary may be employed that uses part of its entire flow to feed the array and feeds $\epsilon\phi$ into each gap at the boundary (represented by arrows in FIG. 24).

Figure 25:
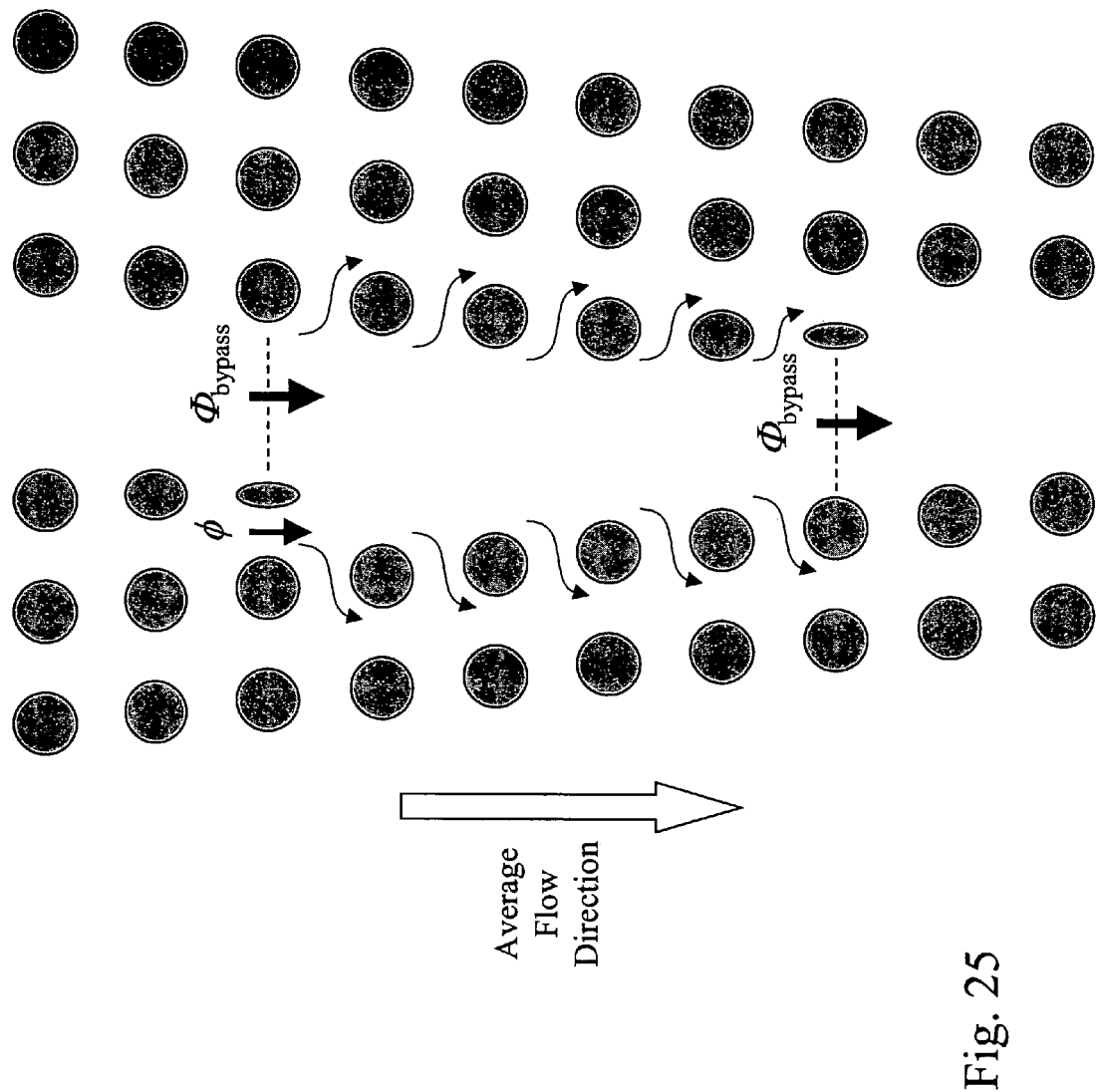
FIG. 25 is a schematic depiction of two flow-feeding boundaries flanking a central bypass channel.

FIG. 25 shows a single bypass channel in a duplex array ($\epsilon$=1/10, d=8 µm). The bypass channel includes two flow-feeding boundaries. The flux across the dashed line 1 in the bypass channel is $\Phi$bypass. A flow $\phi$ joins $\Phi$bypass from a gap to the left of the dashed line. The shapes of the obstacles at the boundaries are adjusted so that the flows going into the arrays are $\epsilon\phi$ at each gap at the boundaries. The flux at dashed line 2 is again $\Phi$bypass In some cases, arrays of the invention may include a plurality of rows of obstacles, each successive row being offset by less than half of the period of the previous row, such that at least 50%, 60%, 70%, 80%, 90%, 95%, or even 99% of gaps between obstacles each has a length approximately equal to a first length parameter, and at most 50%, 40%, 30%, 20%, 10%, 5%, or even 1%, respectively, of gaps between obstacles each has a length approximately equal to a second length parameter shorter than the first length parameter. Gaps having a length approximately equal to the second length parameter may be distributed throughout the array either uniformly or non-uniformly. The second length parameter may be sized to capture a cell of interest larger than a predetermined size from a cellular sample. The first length parameter is longer than the second length parameter, e.g., by a factor of 1.1, 1.5, 2, 3, 5, 10, 20, 50, or even 100. Exemplary distances for the first length parameter are in the range of 30 to 100 microns, and exemplary distances for the second length parameter are in the range of 10 to 50 microns.

Optionally, each obstacle of an array of the invention has approximately the same size; alternatively, at least 50%, 60%, 70%, 80%, 90%, 95%, or even 99% of the obstacles have approximately the same size. In some cases, at least 50%, 60%, 70%, 80%, 90%, 95%, or even 99% of the gaps between obstacles in each row each has a length approximately equal to a first length parameter, and up to 50%, 40%, 30%, 20%, 10%, 5%, or even 1%, respectively, of the gaps between obstacles in each row each has a length approximately equal to a second length parameter, which may be shorter than the first length parameter.

In some arrays, a subset of the obstacles, e.g., 50%, 40%, 30%, 20%, 10%, 5%, or even 1%, are unaligned with the centers of the remaining obstacles in their row. Unaligned obstacles may be distributed throughout the array either uniformly or non-uniformly.

Arrays of the invention may have obstacles with different cross-sections; for example, 50%, 60%, 70%, 80%, 90%, 95%, or even 99% of the obstacles may each have a cross-sectional area approximately equal to a first area parameter, and 50%, 40%, 30%, 20%, 10%, 5%, or even 1%, respectively, of the obstacles may each have a cross-sectional area approximately equal to a second area parameter. Optionally, the second area parameter is larger than the first area parameter. In addition, at least one obstacle having a cross-sectional area approximately equal to the first area parameter or second area parameter may have an asymmetrical cross-section.

Arrays of the invention may also include a first subarray of obstacles and a second subarray of obstacles, such that each of the subarrays includes a gap between two obstacles in that subarray, and, such that the array includes an interface between the first subarray and the second subarray including a restricted gap that is smaller than the gap between two obstacles in either subarray. The subarrays may be arranged in a two-dimensional configuration; furthermore, they may be staggered, either periodically or uniformly. Each subarray may contain any number of obstacles, e.g., between 2 and 200, between 3 and 50, or between 6 and 20. Exemplary diameters for subarray obstacles are, e.g., in the range of 25 to 200 microns. In general, the gap between two obstacles in an array of the invention may be, e.g., at least 20, 40, 60, 80, or 100 microns; in the case of the restricted gap described above, this gap may be, e.g., at most 100, 80, 60, 40, or 20 microns. Other gap lengths are also possible.

Arrays of the invention may be coupled to a substrate, e.g., plastic, and may include a microfluidic gap. Arrays may additionally be coupled to one or more binding moieties, e.g., binding moieties described herein, that selectively bind to cells of interest. Arrays may also be inside a receptacle, e.g., a receptacle coupled to a transparent cover.

In another embodiment, a two-dimensional array of obstacles forms a network of gaps, such that the array of obstacles includes a plurality of rows distributed on a surface to create fluid flow paths through the device, wherein at least 50%, 60%, 70%, 80%, 90%, 95%, or even 99% of the flow paths each has a width approximately equal to a first width parameter, and at most 50%, 40%, 30%, 20%, 10%, 5%, or even 1%, respectively, of the flow paths each has a width approximately equal to a second, smaller width parameter. Such an array may be used, e.g., to enrich an analyte from a fluid sample. Flow paths each having a width approximately equal to the second width parameter may be distributed throughout the device either uniformly or non-uniformly, and the second width parameter may be sized to capture the desired analyte within the flow paths that are approximately of the second width parameter. Optionally, the array includes an inlet and an outlet. Optionally, in arrays that include outlets, a region of obstacles with flow path widths equal to or smaller than the second width surrounds the outlet. Such devices may, e.g., have three two-dimensional arrays fluidically connected in series, such that the percentage of the flow paths of the second width increases in the direction of flow of fluid through the device.

Arrays may be coupled to other elements to form devices of the invention. For example, an array may be fluidically coupled to a sample reservoir, a detector, or other elements or modules disclosed herein. Arrays may also function as devices without the need for additional elements or modules. In addition, arrays of the invention may be two-dimensional arrays, or they may adopt another geometry.

Any of the arrays described herein may be used in conjunction with any of the devices or methods of the invention.

Device Design

On-chip Flow Resistor for Defining and Stabilizing Flow

Figure 26:
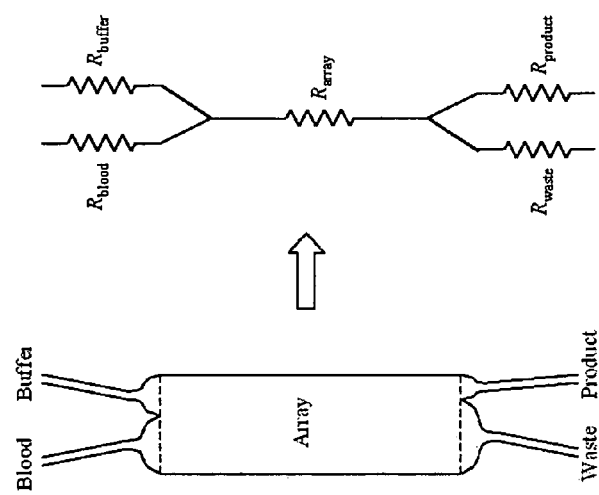
FIG. 26 is a schematic depiction of a device having four channels that act as on-chip flow resistors.

Devices of the invention may also employ fluidic resistors to define and stabilize flows within an array and to also define the flows collected from the array. FIG. 26 shows a schematic of planar device; a sample, e.g., blood containing CTCs, inlet channel, a buffer inlet channel, a waste outlet channel, and a product outlet channel are each connected to an array. The inlets and outlets act as flow resistors. FIG. 26 also shows the corresponding fluidic resistances of these different device components.

Flow Definition Within the Array

Figure 27:
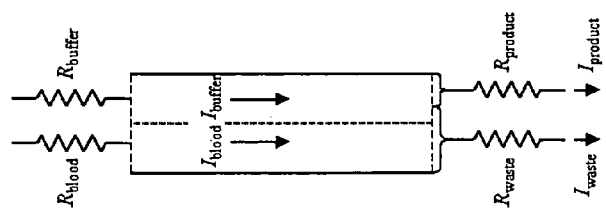
FIGS. 27 and 28 are schematic depictions of the effect of on-chip resistors on the relative width of two fluids flowing in a device.
Figure 28:
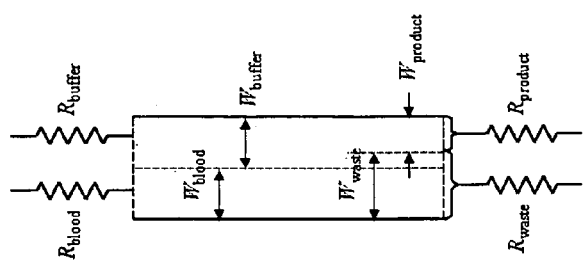

FIGS. 27 and 28 show the currents and corresponding widths of the sample and buffer flows within the array when the device has a constant depth and is operated with a given pressure drop. The flow is determined by the pressure drop divided by the resistance. In this particular device, $I_{blood}$ and $I_{buffer}$ are equivalent, and this determines equivalent widths of the blood and buffer streams in the array.

Definition of Collection Fraction

By controlling the relative resistance of the product and waste outlet channels, one may modulate the collection tolerance for each fraction. For example, in this particular set of schematics, when $R_{product}$ is greater than $R_{waste}$, a more concentrated product fraction will result at the expense of a potentially increased loss to and dilution of waste fraction. Conversely, when $R_{product}$ is less than $R_{waste}$, a more dilute and higher yield product fraction will be collected at the expense of potential contamination from the waste stream.

Multiplexed Arrays

The invention features multiplexed arrays. Putting multiple arrays on one device increases sample-processing throughput of CTCs or other cells of interest and allows for parallel processing of multiple samples or portions of the sample for different fractions or manipulations. Multiplexing is further desirable for preparative devices. The simplest multiplex device includes two devices attached in series, i.e., a cascade. For example, the output from the major flux of one device may be coupled to the input of a second device. Alternatively, the output from the minor flux of one device may be coupled to the input of the second device.

Figure 29:
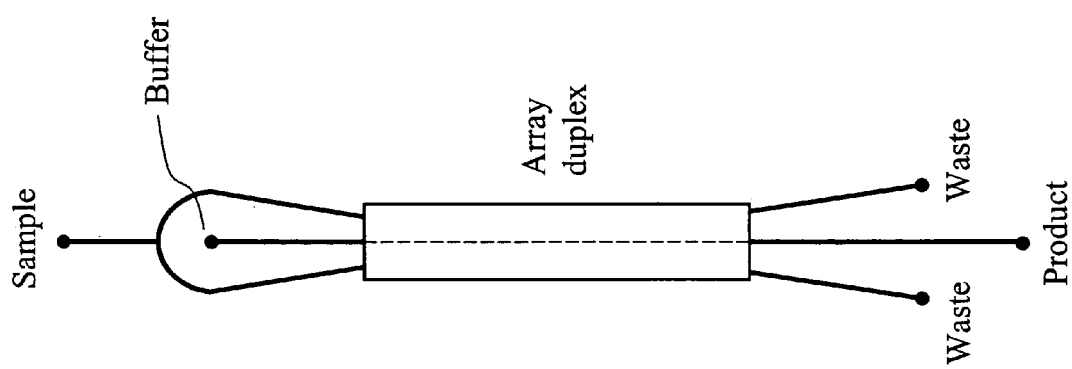
FIG. 29 is a schematic depiction of a duplex device having a common inlet for the two outer regions.

Duplexing. Two arrays may be disposed side-by-side, e.g., as mirror images (FIG. 29). In such an arrangement, the critical size of the two arrays may be the same or different. Moreover, the arrays may be arranged so that the major flux flows to the boundary of the two arrays, to the edge of each array, or a combination thereof. Such a multiplexed array may also contain a central region disposed between the arrays, e.g., to collect particles; above the critical size or to alter the sample, e.g., through buffer exchange, reaction, or labeling.

Figure 30A:
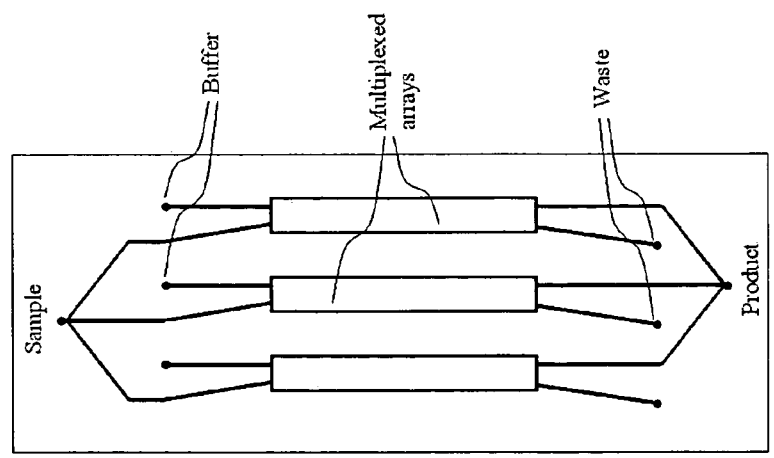
FIG. 30A is a schematic depiction of a multiple arrays on a device.

Multiplexing on a device. In addition to forming a duplex, two or more arrays that have separated inputs may be disposed on the same device (FIG. 30A). Such an arrangement could be employed for multiple samples, or the plurality of arrays may be connected to the same inlet for parallel processing of the same sample. In parallel processing of the same sample, the outlets may or may not be fluidically connected. For example, when the plurality of arrays has the same critical size, the outlets may be connected for high throughput samples processing. In another example, the arrays may not all have the same critical size or the particles in the arrays may not all be treated in the same manner, and the outlets may not be fluidically connected.

Figure 30B:
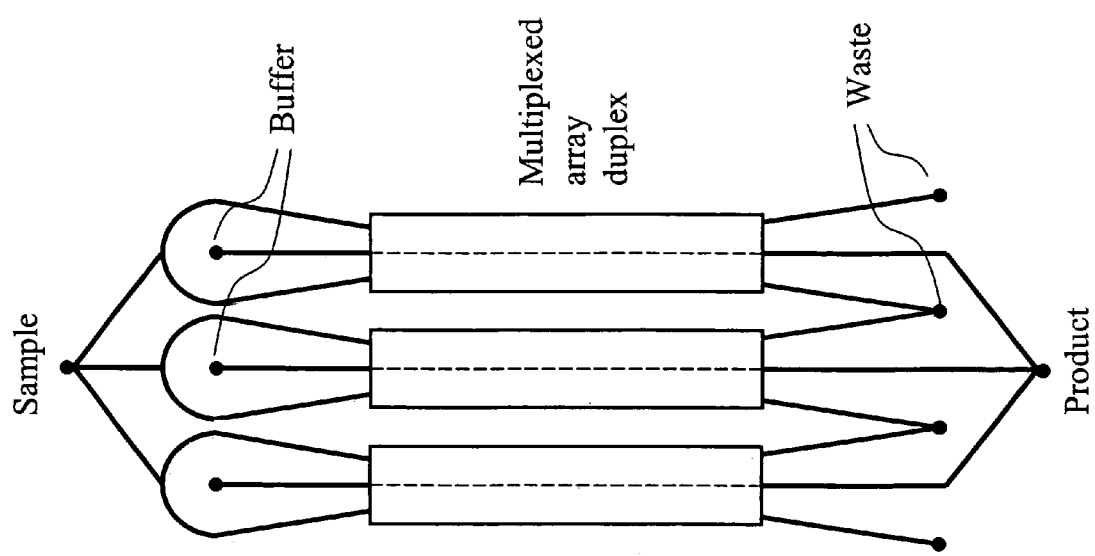
FIG. 30B is a schematic depiction of multiple arrays with common inlets and product outlets on a device.

Multiplexing may also be achieved by placing a plurality of duplex arrays on a single device (FIG. 30B). A plurality of arrays, duplex or single, may be placed in any possible three-dimensional relationship to one another.

Figure 31:
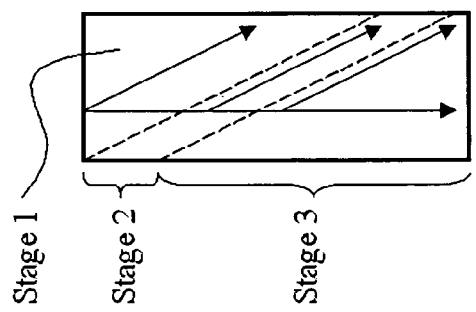
FIG. 31 is a schematic depiction of a multi-stage device with a small footprint.

Devices of the invention also feature a small footprint. Reducing the footprint of an array may lower cost, and reduce the number of collisions with obstacles to eliminate any potential mechanical damage or other effects to particles. The length of a multiple stage array may be reduced if the boundaries between stages are not perpendicular to the direction of flow. The length reduction becomes significant as the number of stages increases. FIG. 31 shows a small-footprint three-stage array.

Additional Components

In addition to an array of gaps, devices of the invention may include additional elements or modules, e.g., for isolation, enrichment, collection, manipulation, or detection, e.g., of CTCs. Such elements are known in the art. For example, devices may include one or more inlets for sample or buffer input, and one or more outlets for sample output. Arrays may also be employed on a device having components for other types of enrichment or other manipulation, including affinity, magnetic, electrophoretic, centrifugal, and dielectrophoretic enrichment. Devices of the invention may also be employed with a component for two-dimensional imaging of the output from the device, e.g., an array of wells or a planar surface. Preferably, arrays of gaps as described herein are employed in conjunction with an affinity enrichment.

In one example, a detection module is fluidically coupled to a separation or enrichment device of the invention. The detection module may operate using any method of detection disclosed herein, or other methods known in the art. For example, the detection module includes a microscope, a cell counter, a magnet, a biocavity laser (see, e.g., Gourley et al., J. Phys. D: Appl. Phys. 36: R228-R239 (2003)), a mass spectrometer, a PCR device, an RT-PCR device, a matrix, a microarray, or a hyperspectral imaging system (see, e.g., Vo-Dinh et al., IEEE Eng. Med. Biol. Mag. 23:40-49 (2004)). In one embodiment, a computer terminal may be connected to the detection module. For instance, the detection module may detect a label that selectively binds to cells of interest.

In another example, a capture module is fluidically coupled to a separation or enrichment device of the invention. For example, a capture module includes one or more binding moieties that selectively bind a particular cell type, e.g., a cancer cell or other rare cell. In capture module embodiments that include an array of obstacles, the obstacles may include such binding moieties.

Additionally, a cell counting module, e.g., a Coulter counter, may be fluidically coupled to a separation or enrichment device of the invention. Other modules, e.g., a programmable heating unit, may alternatively be fluidically coupled.

The methods of the invention may be employed in connection with any enrichment or analytical device, either on the same device or in different devices. Examples include affinity columns, particle sorters, e.g., fluorescent activated cell sorters, capillary electrophoresis, microscopes, spectrophotometers, sample storage devices, and sample preparation devices. Microfluidic devices are of particular interest in connection with the systems described herein.

Exemplary analytical devices include devices useful for size, shape, or deformability based enrichment of particles, including filters, sieves, and enrichment or separation devices, e.g., those described in International Publication Nos. 2004/029221 and 2004/113877, Huang et al. Science 304:987-990 (2004), U.S. Publication No. 2004/0144651, U.S. Pat. Nos. 5,837,115 and 6,692,952, and U.S. Application Nos. 60/703,833, 60/704,067, and 11/227,904; devices useful for affinity capture, e.g., those described in International Publication No. 2004/029221 and U.S. application Ser. No. 11/071,679; devices useful for preferential lysis of cells in a sample, e.g., those described in International Publication No. 2004/029221, U.S. Pat. No. 5,641,628, and U.S. Application No. 60/668,415; devices useful for arraying cells, e.g., those described in International Publication No. 2004/029221, U.S. Pat. No. 6,692,952, and U.S. application Ser. Nos. 10/778,831 and 11/146,581; and devices useful for fluid delivery, e.g., those described in U.S. application Ser. Nos. 11/071,270 and 11/227,469. Two or more devices may be combined in series, e.g., as described in International Publication No. 2004/029221.

Methods of Fabrication

Devices of the invention may be fabricated using techniques well known in the art. The choice of fabrication technique will depend on the material used for the device and the size of the array. Exemplary materials for fabricating the devices of the invention include glass, silicon, steel, nickel, polymers, e.g., poly(methylmethacrylate) (PMMA), polycarbonate, polystyrene, polyethylene, polyolefins, silicones (e.g., poly(dimethylsiloxane)), polypropylene, cis-polyisoprene (rubber), poly(vinyl chloride) (PVC), poly(vinyl acetate) (PVAc), polychloroprene (neoprene), polytetrafluoroethylene (Teflon), poly(vinylidene chloride) (SaranA), and cyclic olefin polymer (COP) and cyclic olefin copolymer (COC), and combinations thereof. Other materials are known in the art. For example, deep Reactive Ion Etch (DRIE) is used to fabricate silicon-based devices with small gaps, small obstacles and large aspect ratios (ratio of obstacle height to lateral dimension). Thermoforming (embossing, injection molding) of plastic devices may also be used, e.g., when the smallest lateral feature is >20 microns and the aspect ratio of these features is ≤10. Additional methods include photolithography (e.g., stereolithography or x-ray photolithography), molding, embossing, silicon micromachining, wet or dry chemical etching, milling, diamond cutting, Lithographie Galvanoformung and Abformung (LIGA), and electroplating. For example, for glass, traditional silicon fabrication techniques of photolithography followed by wet (KOH) or dry etching (reactive ion etching with fluorine or other reactive gas) may be employed. Techniques such as laser nicromachining may be adopted for plastic materials with high photon absorption efficiency. This technique is suitable for lower throughput fabrication because of the serial nature of the process. For mass-produced plastic devices, thermoplastic injection molding, and compression molding may be suitable. Conventional thermoplastic injection molding used for mass-fabrication of compact discs (which preserves fidelity of features in sub-microns) may also be employed to fabricate the devices of the invention. For example, the device features are replicated on a glass master by conventional photolithography. The glass master is electroformed to yield a tough, thermal shock resistant, thermally conductive, hard mold. This mold serves as the master template for injection molding or compression molding the features into a plastic device. Depending on the plastic material used to fabricate the devices and the requirements on optical quality and throughput of the finished product, compression molding or injection molding may be chosen as the method of manufacture. Compression molding (also called hot embossing or relief imprinting) has the advantages of being compatible with high molecular weight polymers, which are excellent for small structures and may replicate high aspect ratio structures but has longer cycle times. Injection molding works well for low aspect ratio structures and is most suitable for low molecular weight polymers.

A device may be fabricated in one or more pieces that are then assembled. Layers of a device may be bonded together by clamps, adhesives, heat, anodic bonding, or reactions between surface groups (e.g., wafer bonding). Alternatively, a device with channels in more than one plane may be fabricated as a single piece, e.g., using stereolithography or other three-dimensional fabrication techniques.

To reduce non-specific adsorption of cells or compounds released by lysed cells onto the channel walls, one or more channel walls may be chemically modified to be non-adherent or repulsive. The walls may be coated with a thin film coating (e.g., a monolayer) of commercial non-stick reagents, such as those used to form hydrogels. Additional examples chemical species that may be used to modify the channel walls include oligoethylene glycols, fluorinated polymers, organosilanes, thiols, poly-ethylene glycol, hyaluronic acid, bovine serum albumin, poly-vinyl alcohol, mucin, poly-HEMA, methacrylated PEG, and agarose. Charged polymers may also be employed to repel oppositely charged species. The type of chemical species used for repulsion and the method of attachment to the channel walls will depend on the nature of the species being repelled and the nature of the walls and the species being attached. Such surface modification techniques are well known in the art. The walls may be functionalized before or after the device is assembled. The channel walls may also be coated in order to capture materials in the sample, e.g., membrane fragments or proteins.

Methods of Operation

Devices of the invention may be employed in any application where the production of a sample enriched in particles above or below a critical size is desired. A preferred use of the device is to produce samples enriched in CTCs or other rare cells. Once an enriched sample is produced, it may be collected for analysis or otherwise manipulated.

Figure 32:
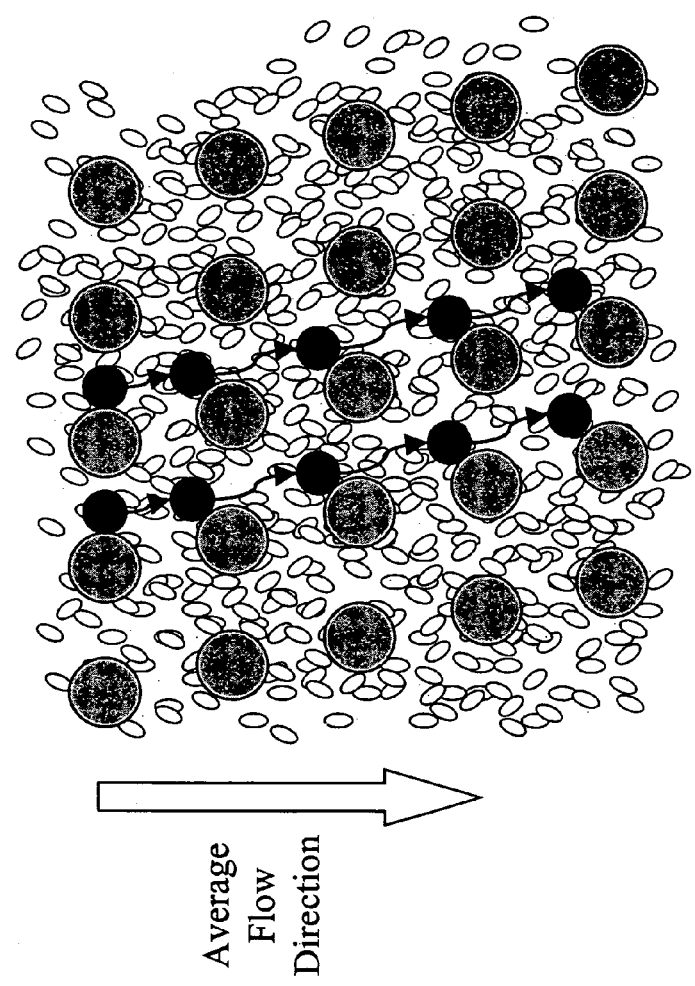
FIG. 32 is a schematic depiction of blood passing through a device.

Devices of the invention may be employed in concentrated samples, e.g., where particles are touching, hydrodynamically interacting with each other, or exerting an effect on the flow distribution around another particle. For example, the method may enrich CTCs from other cells in whole blood from a human donor. Human blood typically contains ~45% of cells by volume. Cells are in physical contact and/or coupled to each other hydrodynamically when they flow through the array. FIG. 32 shows schematically that cells are densely packed inside an array and could physically interact with each other.

Enrichment

In one embodiment, devices of the invention are employed to produce a sample enriched in particles of a desired hydrodynamic size. Applications of such enrichment include concentrating CTCs or other cells of interest, and size fractionization, e.g., size filtering (selecting cells in a particular size range). Devices may also be used to enrich components of cells, e.g., nuclei. Desirably, the methods of the invention retain at least 50%, 75%, 80%, 81%, 82%, 83%, 84%, 85%, 86%, 87%, 88%, 89%, 90%, 91%, 92%, 93%, 94%, 95%, 96%, 97%, 98%, or even 99% of the desired particles compared to the initial mixture, while potentially enriching the desired particles by a factor of at least 100, 1,000, 10,000, 100,000, 1,000,000, 10,000,000, or even 100,000,000 relative to one or more non-desired particles. Desirably, if a device produces any output sample in addition to the enriched sample, this additional output sample contains less than 50%, 25%, 20%, 19%, 18%, 17%, 16%, 15%, 14%, 13%, 12%, 11%, 10%, 9%, 8%, 7%, 6%, 5%, 4%, 3%, 2%, or even 1% of the desired particles compared to the initial mixture. The enrichment may also result in a dilution of the enriched particles compared to the original sample, although the concentration of the enriched particles relative to other particles in the sample has increased. Preferably, the dilution is at most 90%, e.g., at most 75%, 50%, 33%, 25%, 10%, or 1%.

In a preferred embodiment, the device produces a sample enriched in a rare particles, e.g., cells. In general, a rare particle is a particle that is present as less than 10% of a sample. Rare particles include, depending on the sample, rare cells, e.g., CTCs, epithelial cells, fetal cells, stem cells (e.g., undifferentiated), bone marrow cells, progenitor cells, foam cells, mesenchymal cells, endothelial cells, endometrial cells, trophoblasts, cancer cells, immune system cells (host or graft), connective tissue cells, bacteria, fungi, and pathogens (e.g., bacterial or protozoa). Rare particles also include viruses, as well as cellular components such as organelles (e.g., mitochondria and nuclei). Rare particles may be isolated from samples including bodily fluids, e.g., blood, or environmental sources, e.g., pathogens in water samples. Fetal red blood cells may be enriched from maternal peripheral blood, e.g., for the purpose of determining sex and identifying aneuploidies or genetic characteristics, e.g., mutations, in the developing fetus. CTCs, which are of epithelial type and origin, may also be enriched from peripheral blood for the purpose of diagnosis and monitoring therapeutic progress. Circulating endothelial cells may be similarly enriched from peripheral blood. Bodily fluids or environmental samples may also be screened for pathogens, e.g., for coliform bacteria, blood borne illnesses such as sepsis, or bacterial or viral meningitis. Rare cells also include cells from one organism present in another organism, e.g., an in cells from a transplanted organ.

In addition to enrichment of rare particles, devices of the invention may be employed for preparative applications. An exemplary preparative application includes generation of cell packs from blood. Devices of the invention may be configured to produce fractions enriched in platelets, red blood cells, and white cells. By using multiplexed devices or multistage devices, all three cellular fractions may be produced in parallel or in series from the same sample. In other embodiments, the device may be employed to separate nucleated from non-nucleated cells, e.g., from cord blood sources.

Using the devices of the invention is advantageous in situations where the particles being enriched are subject to damage or other degradation. As described herein, devices of the invention may be designed to enrich cells with a minnimum number of collisions between the cells and obstacles. This minimization reduces mechanical damage to cells and also prevents intracellular activation of cells caused by the collisions. This gentle handling of the cells preserves the limited number of rare cells in a sample, prevents rupture of cells leading to contamination or degradation by intracellular components, and prevents maturation or activation of cells, e.g., stem cells or platelets. In preferred embodiments, cells are enriched such that fewer than 30%, 10%, 5%, 1%, 0.1%, or even 0.01% are activated or mechanically lysed.

Figure 33C:
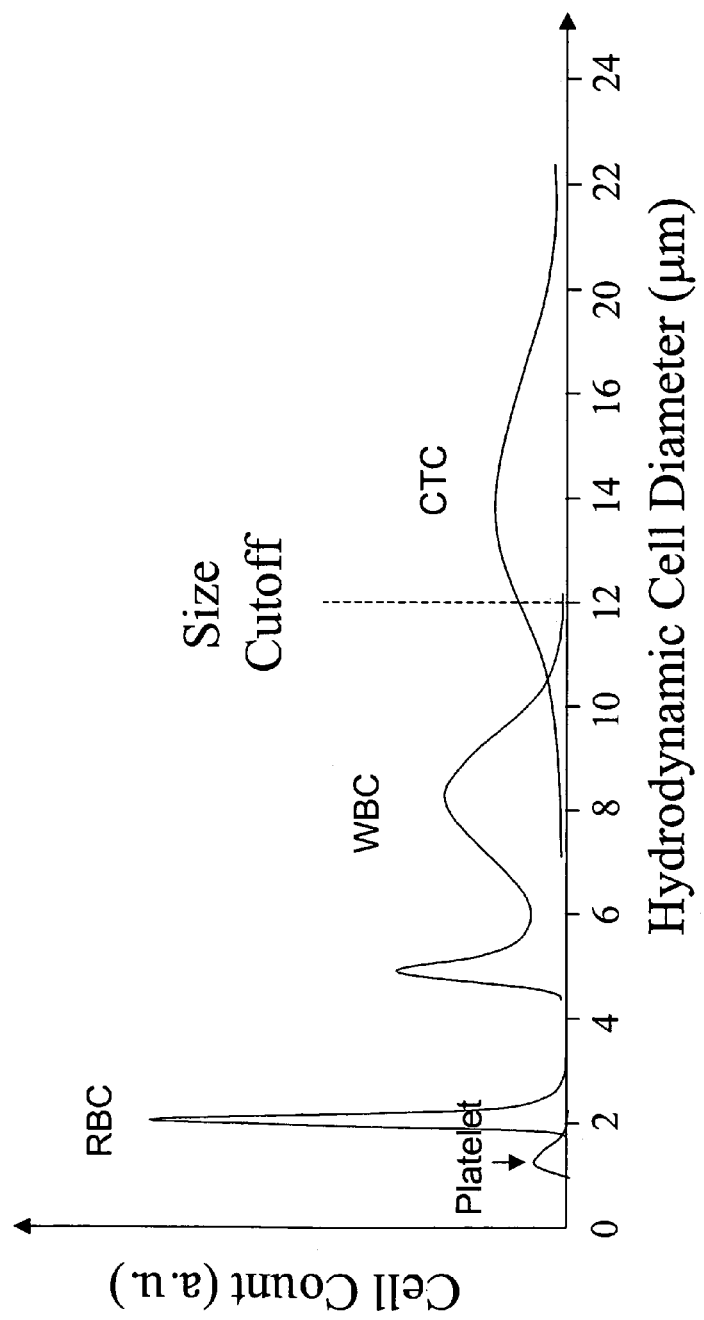
FIG. 33C is the graph of FIG. 33B, additionally showing a size cutoff that excludes most native blood cells.
Figure 33D:
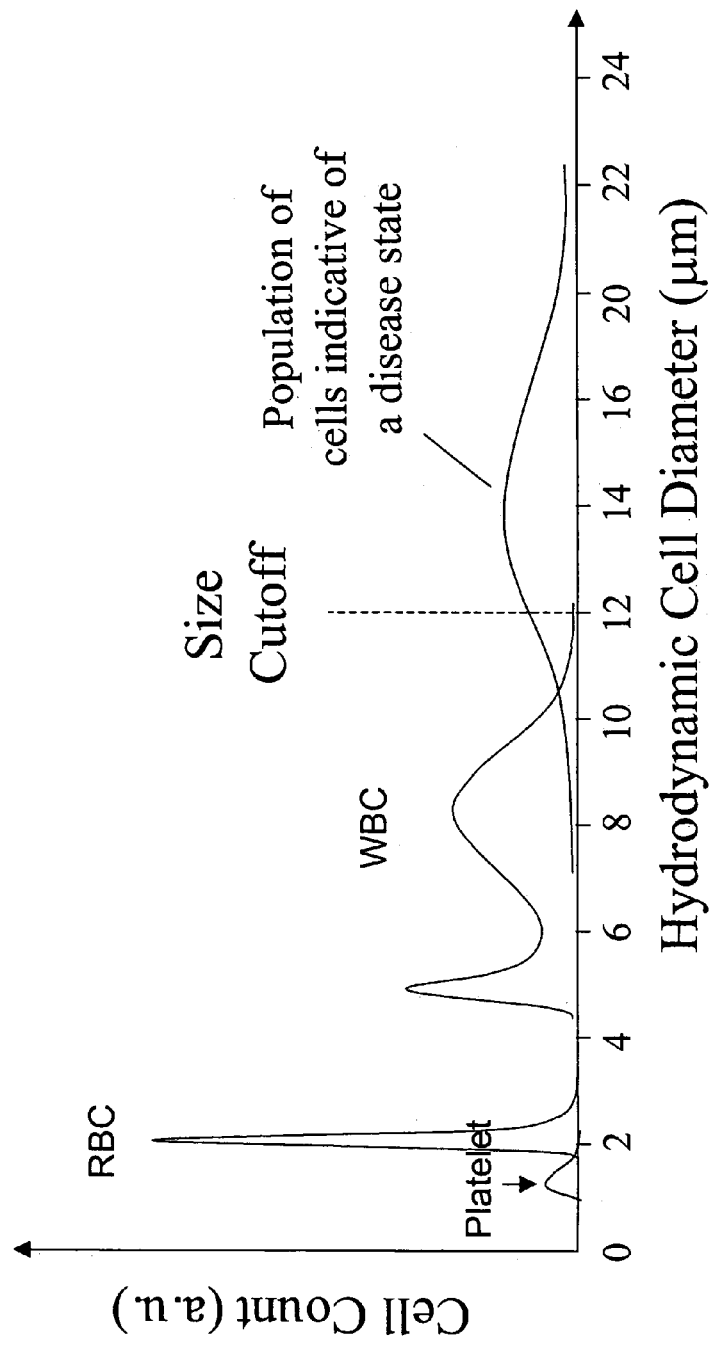
FIG. 33D is the graph of FIG. 33C, additionally showing a population of cells larger than the size cutoff and indicative of a disease state.

FIG. 33A shows a typical size distribution of cells in human peripheral blood. The white blood cells range from ~4 μm to ~12 μm, whereas the red blood cells are ~1.5-3 μm (short axis). FIG. 33B shows that CTCs are generally significantly larger than blood cells, with the majority of CTCs ranging from ~8 to ~22 μm. Thus, a size-based enrichment using a device of the invention, in which the size cutoff is chosen to be, e.g., 12 μm (FIG. 33C), would be effective in enriching CTCs from other blood cells. Any cell population with a similar distribution to CTCs may be similarly enriched from blood cells (FIG. 33D).

Figure 42A:
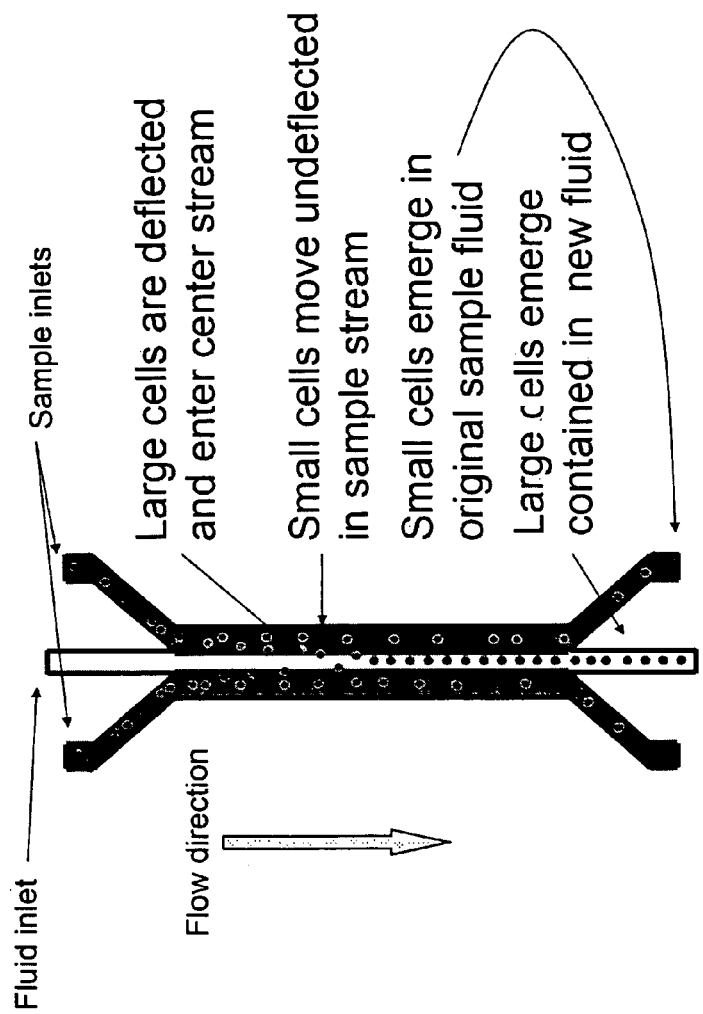
FIG. 42A is a schematic depiction of a device of the invention and its operation.

In an alternative embodiment, a cellular sample is added through a sample inlet of the device, and buffer medium is added through the fluid inlet (FIG. 42A). Cells below the critical size move through the device undeflected, emerging from the edge outlets in their original sample medium. Cells above the critical size, e.g., epithelial cells, in particular, CTCs, are deflected and emerge from the center outlet contained in the buffer medium added through the fluid inlet. Operation of the device thus produces samples enriched in cells above and below the critical size. Because epithelial cells are among the largest cells in the bloodstream, the size and geometry of the gaps of the device may be chosen so as to direct virtually all other cell types to the edge outlets, while producing a sample from the center outlet that is substantially enriched in epithelial cells after a single pass through the device.

Figure 42B:
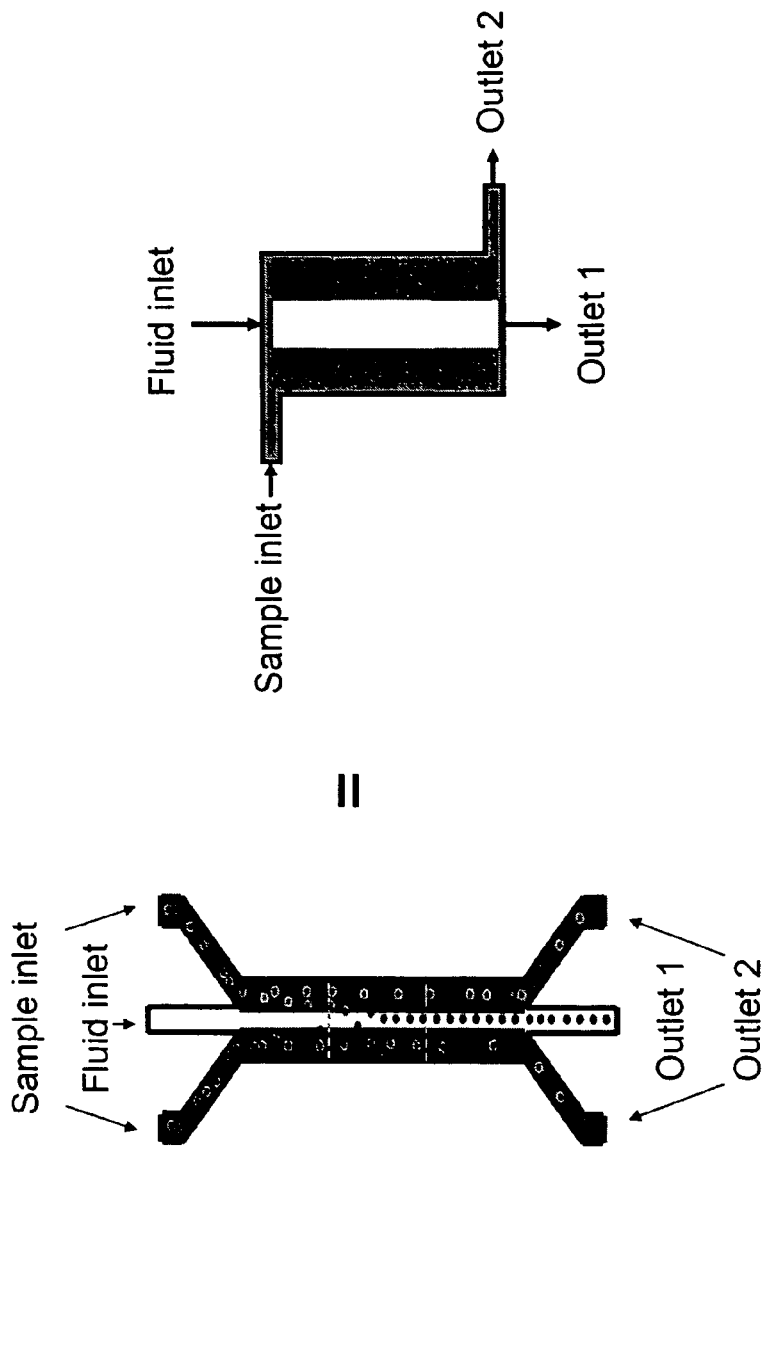
FIG. 42B is an illustration of the device of FIG. 42A and a further-schematized representation of this device.

A device of the invention need not be duplexed as shown in FIG. 42A in order to operate as described herein. The schematized representation shown in FIG. 42B may represent either a duplexed device or a single array.

Figure 44:
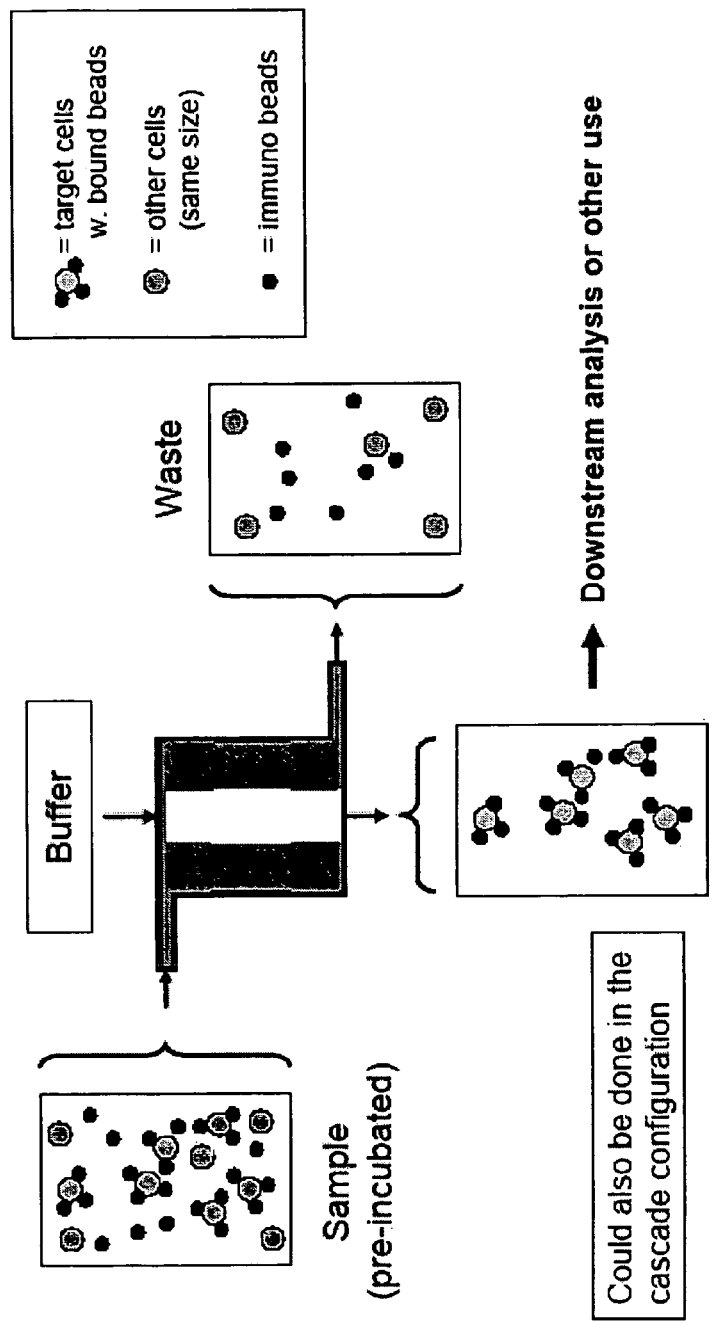
FIG. 44 is a schematic depiction of an enhanced method of size separation in which target cells are labeled with immunoaffinity beads.

Enrichment may be enhanced in numerous ways. For example, target cells may be labeled with immunoaffinity beads, thereby increasing their size (as depicted in FIG. 44). In the case of epithelial cells, e.g., CTCs, this may further increase their size and thus result in an even more efficient enrichment. Alternatively, the size of smaller cells may be increased to the extent that they become the largest objects in solution or occupy a unique size range in comparison to the other components of the cellular sample, or so that they copurify with other cells. The hydrodynamic size of a labeled target cell may be at least 10%, 100%, or even 1,000% greater than the hydrodynamic size of such a cell in the absence of label. Beads may be made of polystyrene, magnetic material, or any other material that may be adhered to cells. Desirably, such beads are neutrally buoyant so as not to disrupt the flow of labeled cells through the device of the invention.

Enrichment methods of the invention include devices that include obstacles that are capable of selectively capturing cells of interest, e.g., epithelial cells, e.g., CTCs.

The methods of the invention may also be used to deplete or remove an analyte from a cellular sample, for example, by producing a sample enriched in another analyte using the above-described methods. For example, a cellular sample may be depleted of cells having a hydrodynamic size less than or equal to 12 microns by enriching for cells having a hydrodynamic size greater than 12 microns. Any method of depletion or removal may be used in conjunction with the arrays and devices of the invention. In methods of the invention featuring depletion of removal of an analyte, sample processing may be continuous and may occur in vivo or ex vivo. Furthermore, in some embodiments, if the analyte to be depleted or removed is retained in a device of the invention, the analyte may be released from the device by applying a hypertonic solution to said device. The analyte may then be detected in the effluent from the device.

Alteration

In other embodiments, in addition to enrichment, CTCs or other cells of interest are contacted with an altering reagent that may chemically or physically alter the particle or the fluid in the suspension. Such applications include purification, buffer exchange, labeling (e.g., immunohistochemical, magnetic, and histochemical labeling, cell staining, and flow in-situ fluorescence hybridization (FISH)), cell fixation, cell stabilization, cell lysis, and cell activation.

Figure 34A:
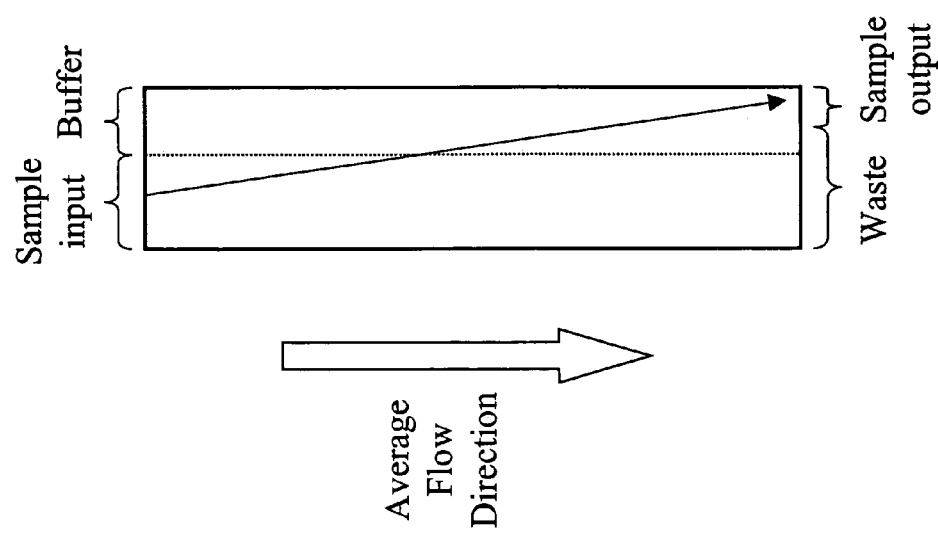
FIGS. 34A-34D are schematic depictions of moving a particle from a sample to a buffer in a single stage (A), three stage (B), duplex (C), or three stage duplex (D) device.
Figure 34B:
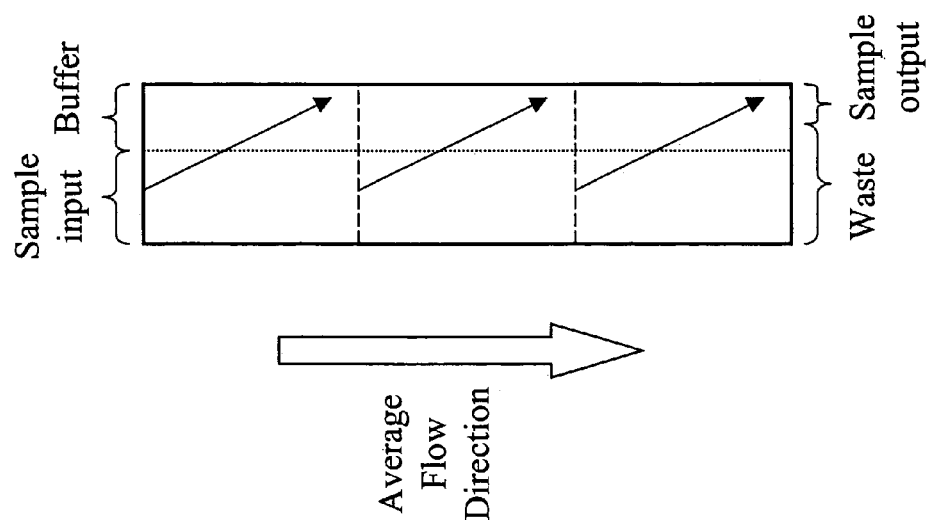
Figure 34C:
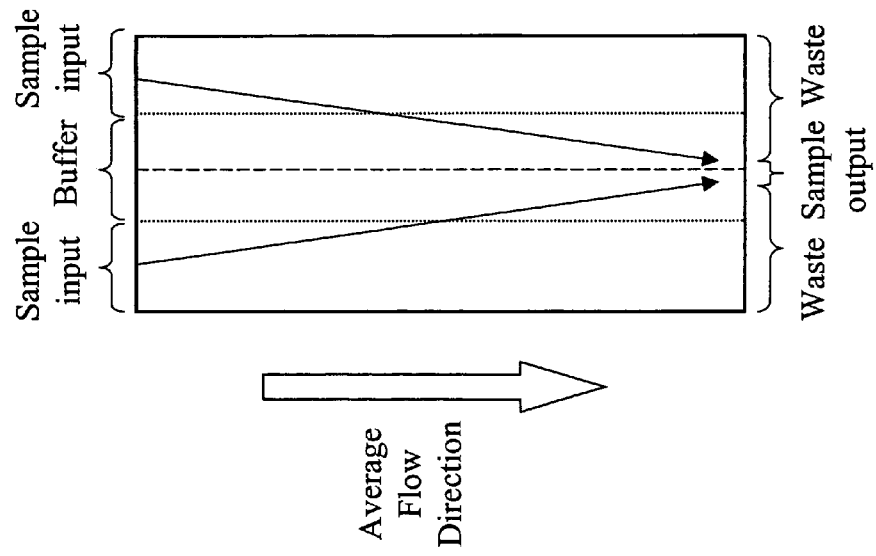
Figure 34D:
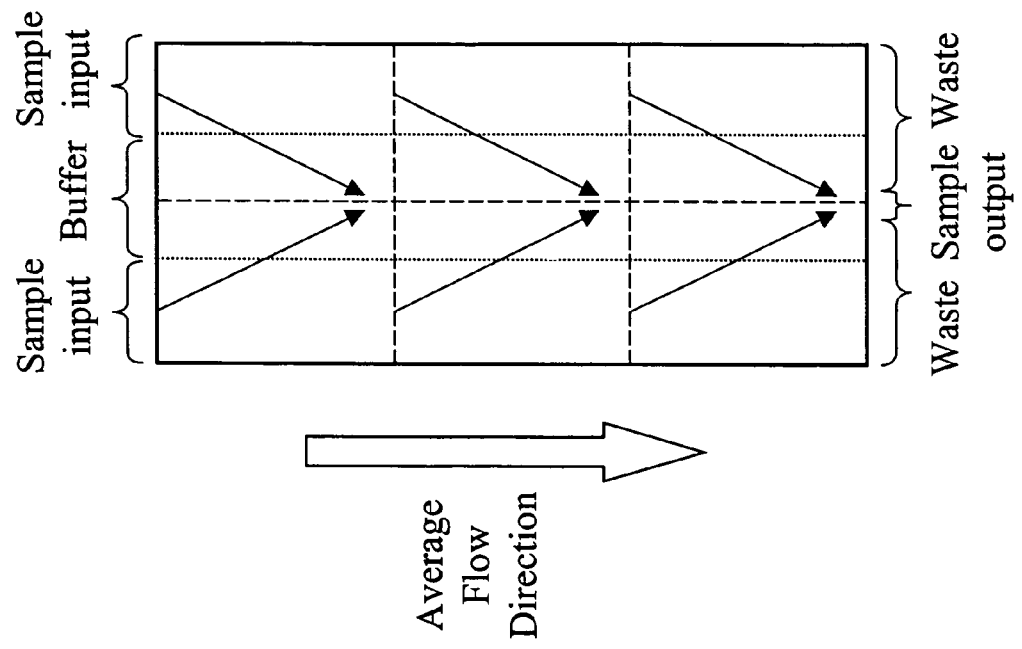

Such methods allow for the transfer of particles, e.g., CTCs, from a sample into a different liquid. FIG. 34A shows this effect schematically for a single stage device, FIG. 34B shows this effect for a multistage device, FIG. 34C shows this effect for a duplex array, and FIG. 34D shows this effect for a multistage duplex array. By using such methods, blood cells may be separated from plasma. Such transfers of particles from one liquid to another may be also employed to effect a series of alterations, e.g., Wright staining blood on-chip. Such a series may include reacting a particle with a first reagent and then transferring the particle to a wash buffer, and then another reagent.

Figure 35A:
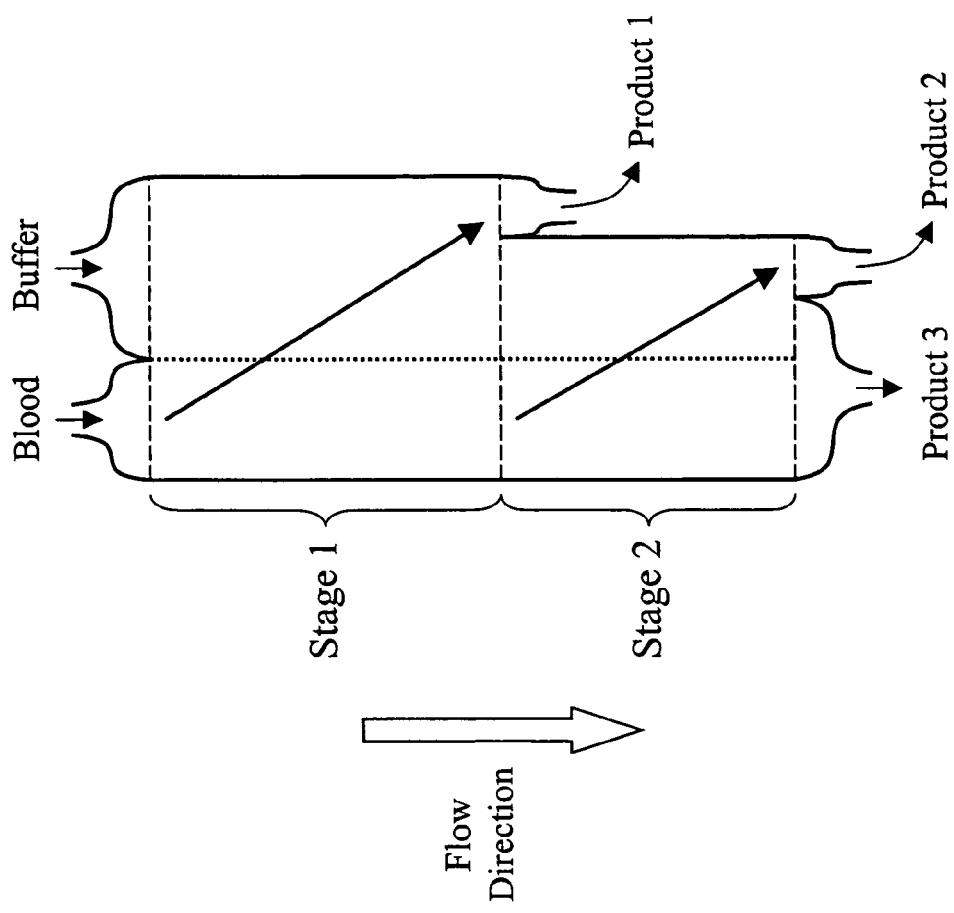
FIG. 35A is a schematic depiction of a two stage device employed to move a particle from blood to a buffer to produce three products.
Figure 35B:
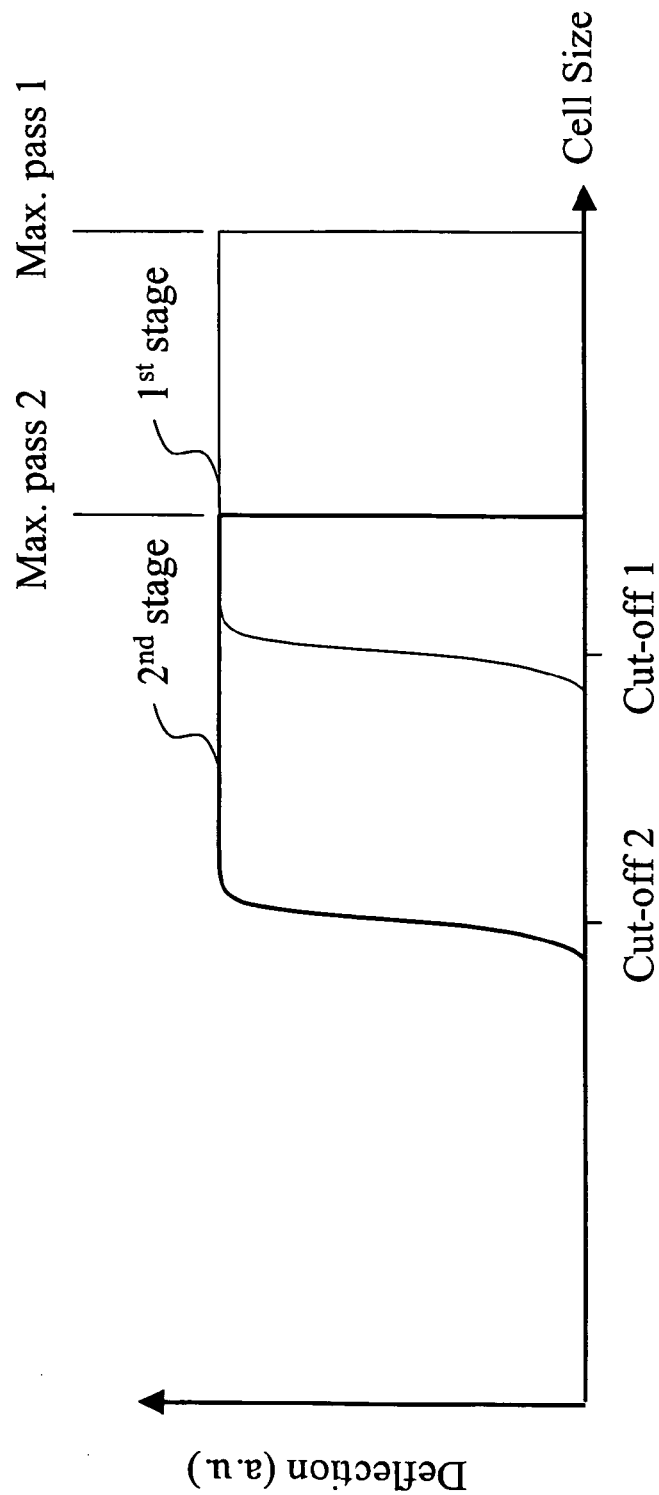
FIG. 35B is a schematic graph of the maximum size and cut off size of the two stages.
Figure 35C:
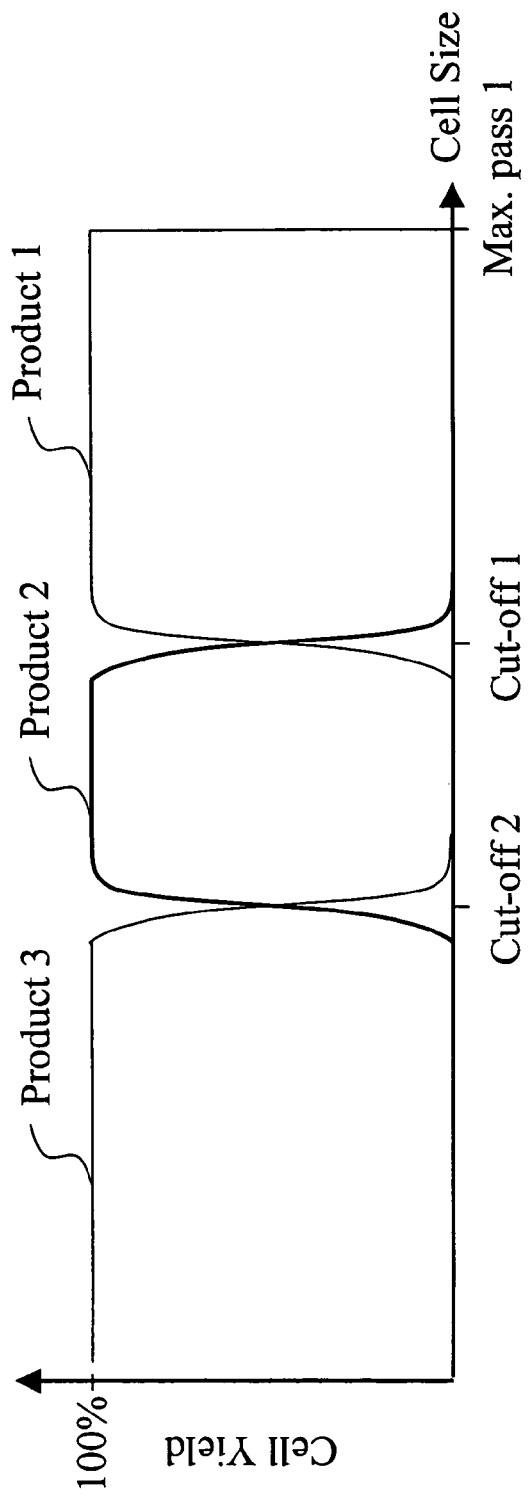
FIG. 35C is a schematic graph of the composition of the three products.

FIGS. 35A-35C illustrate a further example of alteration in a two stage device having two bypass channels. In this example, large blood particles are moved from blood to buffer and collected in stage 1, medium blood particles are moved from blood to buffer in stage 2, and small cells that are not moved from the blood in stage are collected also collected. FIG. 35B illustrates the size cut-off of the two stages, and FIG. 35C illustrates the size distribution of the three fractions collected.

Figure 36:
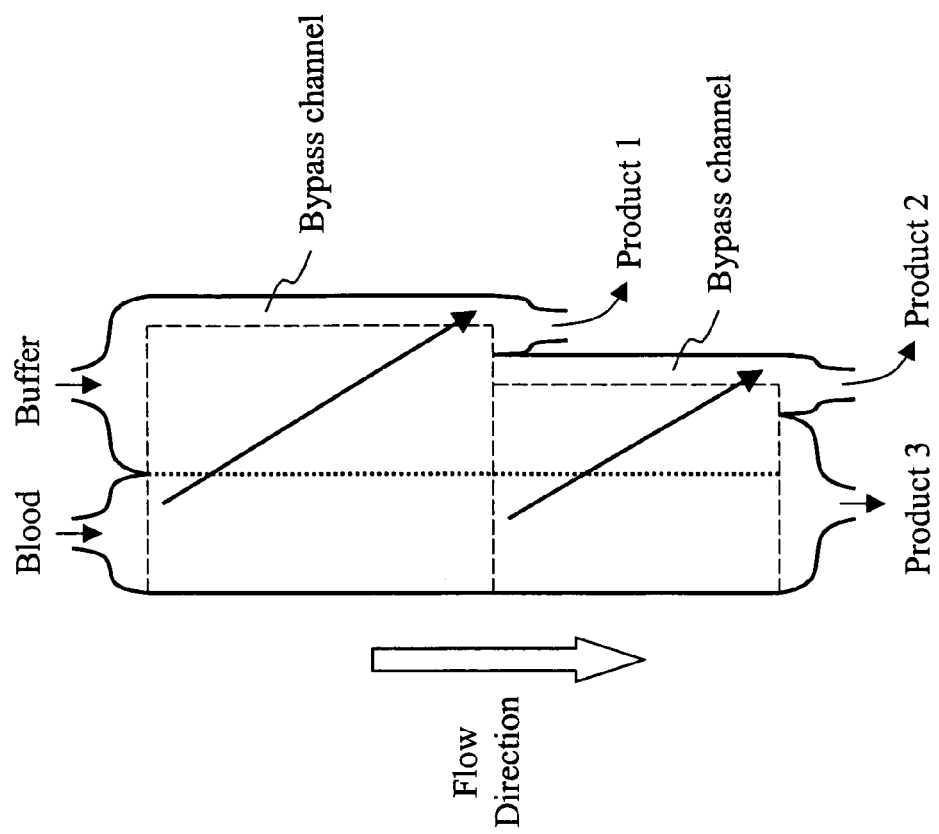
FIG. 36 is a schematic depiction of a two stage device for alteration, where each stage has a bypass channel.
Figure 37:
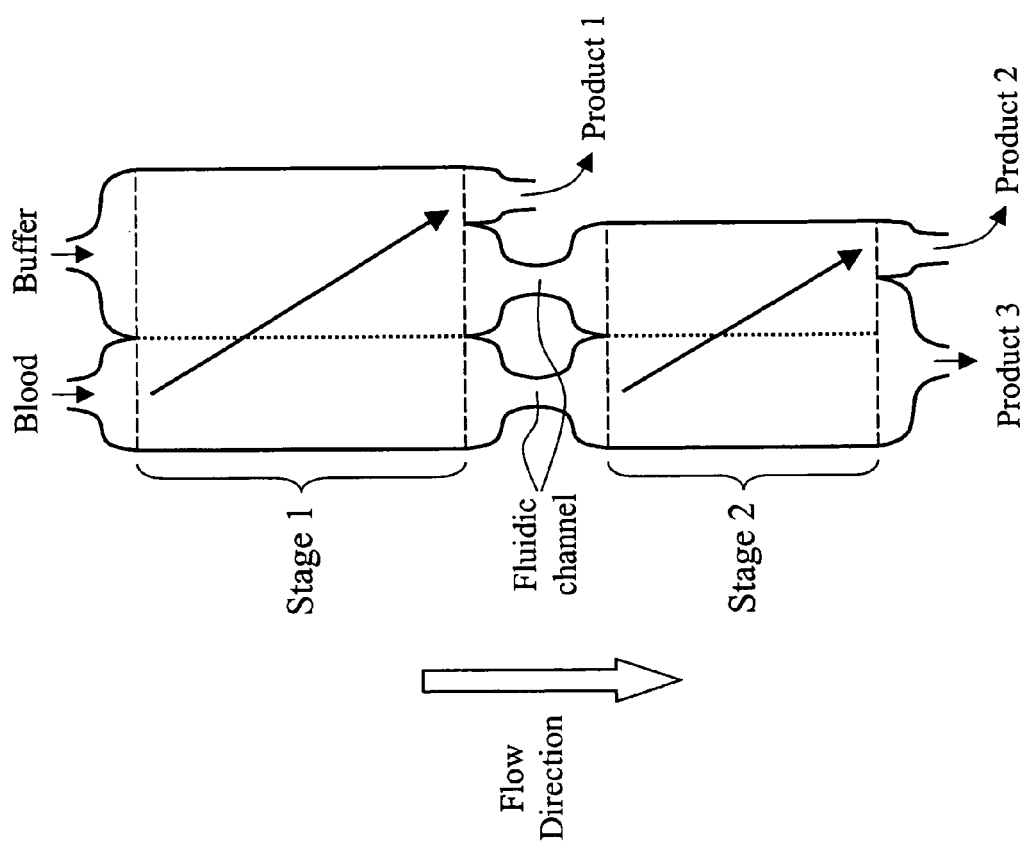
FIG. 37 is a schematic depiction of the use of fluidic channels to connect two stages in a device.
Figure 38:
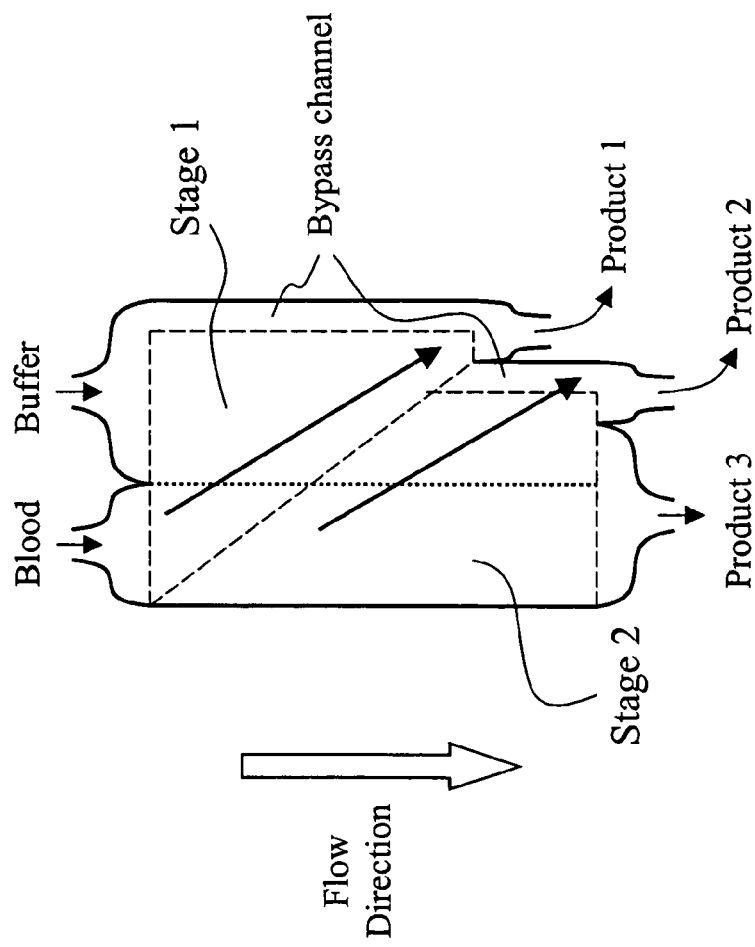
FIG. 38 is a schematic depiction of the use of fluidic channels to connect two stages in a device, wherein the two stages are configured as a small footprint array.
Figure 39A:
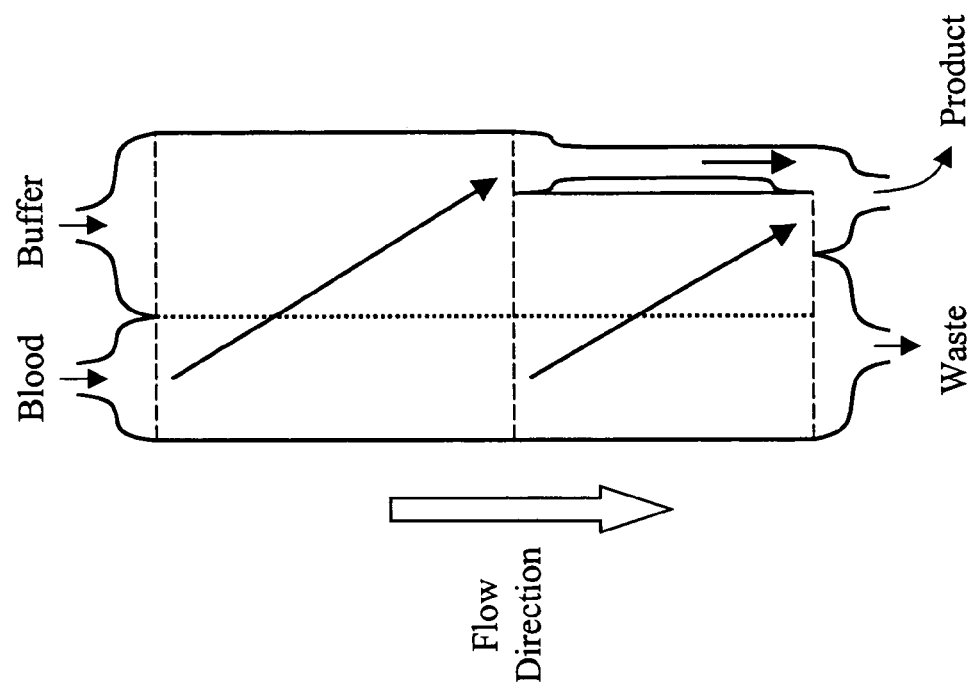
FIG. 39A is a schematic depiction of a two stage device having a bypass channel that accepts output from both stages.
Figure 39B:
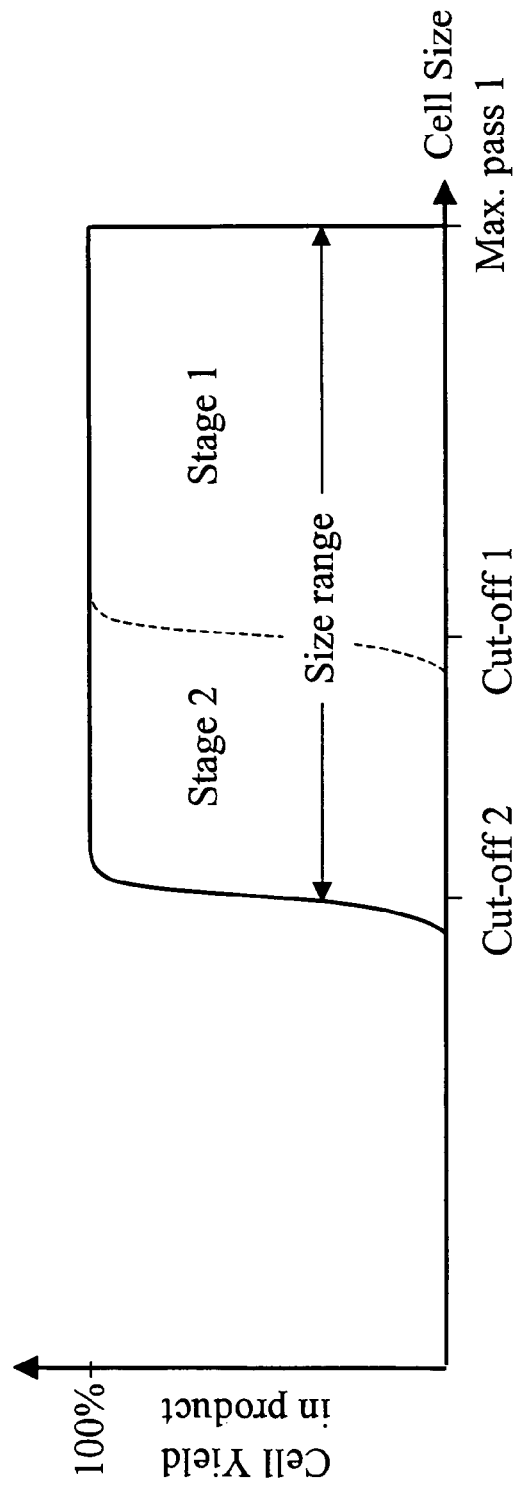
FIG. 39B is a schematic graph of the size range of product achievable with this device.
Figure 40:
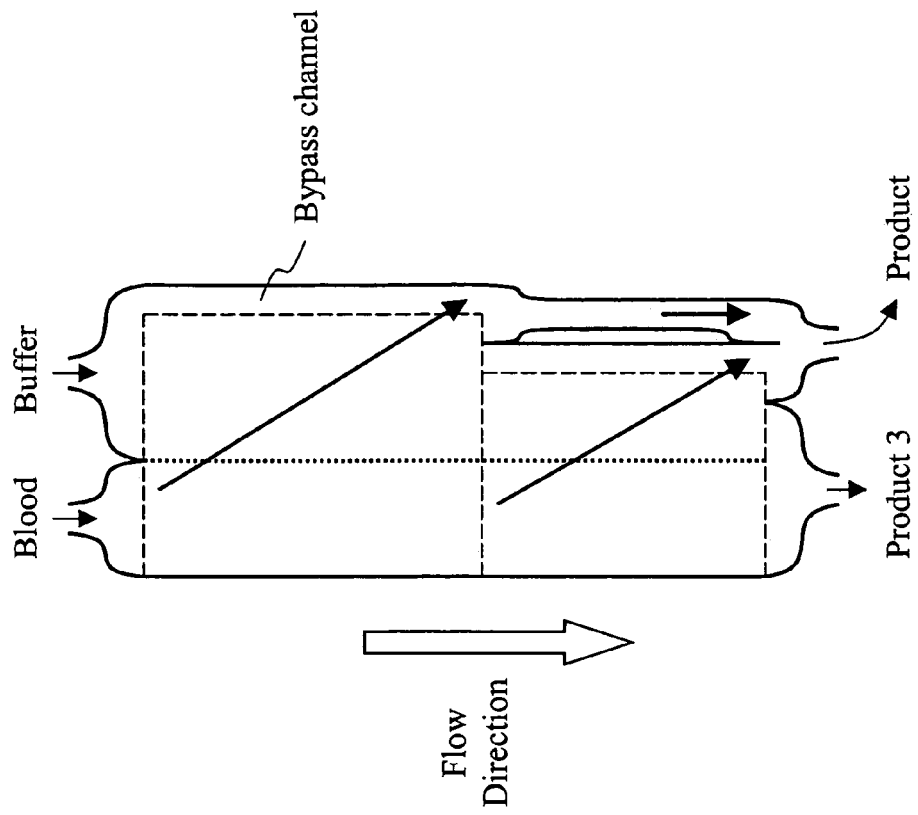
FIG. 40 is a schematic depiction of a two stage device for alteration having bypass channels that flank each stage and empty into the same outlet.

FIG. 36 illustrates an example of alteration in a two stage device having bypass channels that are disposed between the lateral edge of the array and the channel wall. FIG. 37 illustrates a device similar to that in FIG. 36, except that the two stages are connected by fluidic channels. FIG. 38 illustrates alteration in a device having two stages with a small footprint. FIGS. 39A-39B illustrate alteration in a device in which the output from the first and second stages is captured in a single channel. FIG. 40 illustrates another device for use in the methods of the invention.

Figure 41:
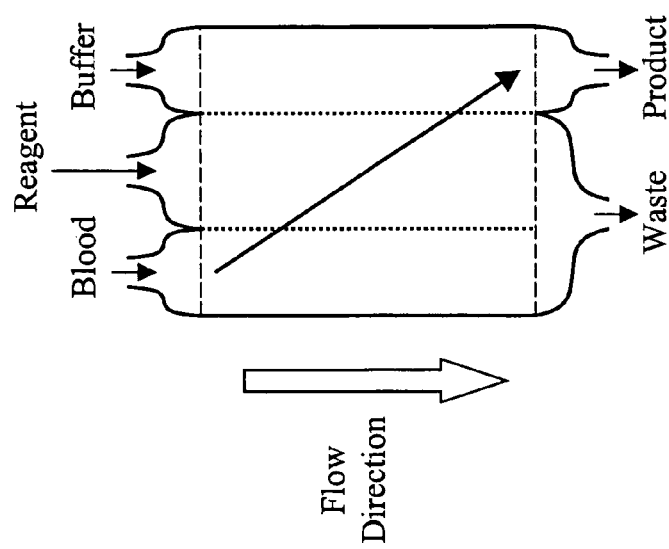
FIG. 41 is a schematic depiction of a device for the sequential movement and alteration of particles.

FIG. 41 illustrates the use of a device to perform multiple, sequential alterations on a particle. In this device a blood particles is moved from blood into a regent that reacts with the particle, and the reacted particle is then moved into a buffer, thereby removing the unreacted reagent or reaction byproducts. Additional steps may be added.

Enrichment and alteration may also be combined, e.g., where desired cells are contacted with a lysing reagent and cellular components, e.g., nuclei, are enriched based on size. In another example, particles may be contacted with particulate labels, e.g., magnetic beads, which bind to the particles. Unbound particulate labels may be removed based on size.

Separation of Free Labeling Reagent From Labeling Reagent Bound to Cells

Figure 45:
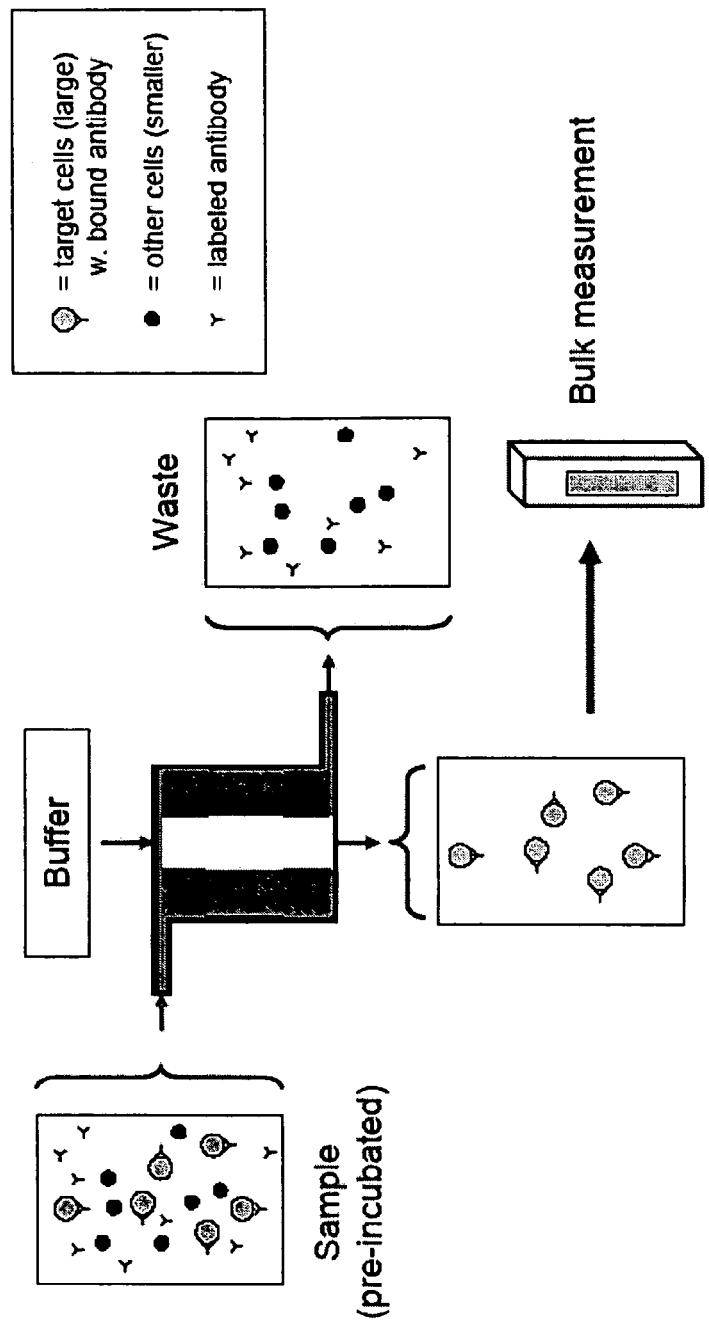
FIG. 45 is a schematic depiction of a method for performing size fractionation and for separating free labeling reagents, e.g., antibodies, from bound labeling reagents by using a device of the invention.

Devices of the invention may be employed in order to separate free labeling reagent from labeling reagent bound to CTCs or other cells. As shown in FIG. 45, a labeling reagent may be pre-incubated with a cellular sample prior to introduction to the device. Desirably, the labeling reagent specifically or preferentially binds the cell population of interest, e.g., epithelial cells such as CTCs. Exemplary labeling reagents include antibodies, quantum dots, phage, aptamers, fluorophore-containing molecules, enzymes capable of carrying out a detectable chemical reaction, or functionalized beads. Generally, the labeling reagent is smaller than the cell of interest, or the cell of interest bound to the bead; thus, when the cellular sample combined with the labeling reagent is introduced to the device, free labeling reagent moves through the device undeflected and emerges from the edge outlets, while bound labeling reagent emerges from the center outlet along with epithelial cells. Advantageously, this method simultaneously achieves size separation and separation of free labeling reagent from bound labeling reagent. Additionally, this method of separation facilitates downstream sample analysis without the need for a release step or destructive methods of analysis, as described below.

Figure 46:
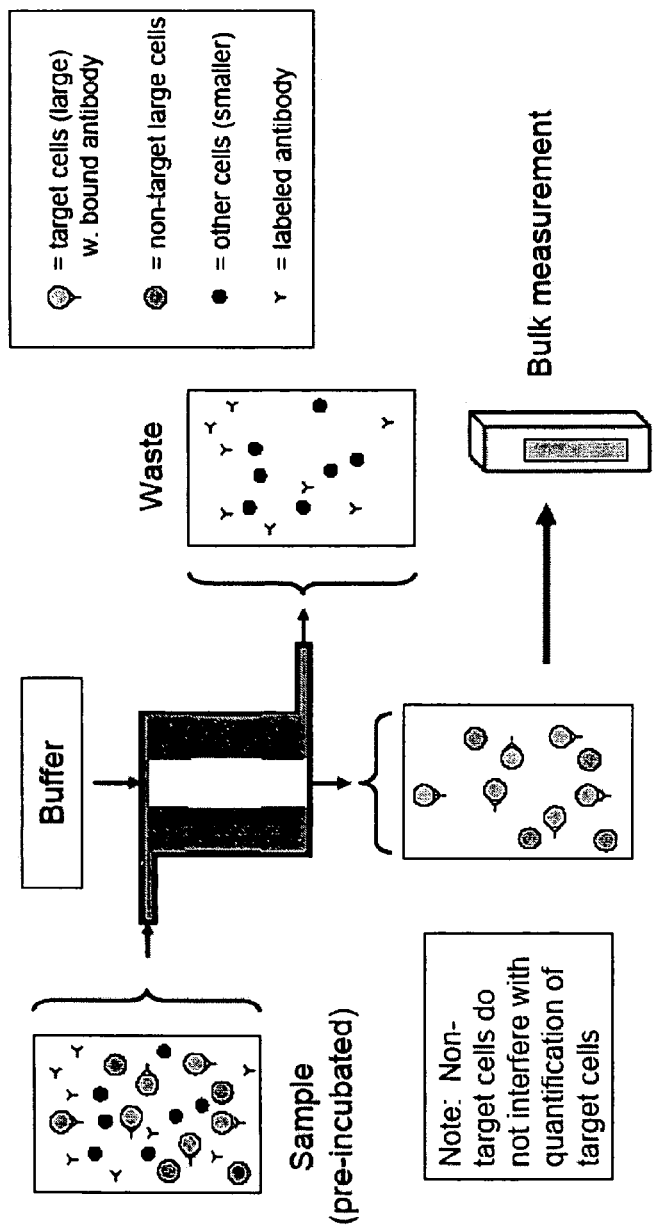
FIG. 46 is a schematic depiction of a method shown in FIG. 45. In this case, non-target cells may copurify with target cells, but these non-target cells do not interfere with quantification of target cells.

FIG. 46 shows a more general case, in which the enriched labeled sample contains a population of non-target cells that co-separate with the target cells due to similar size. The non-target cells do not interfere with downstream sample analysis that relies on detection of the bound labeling reagent, because this reagent binds selectively to the cells of interest.

Buffer Exchange

Devices of the invention may be employed for purposes of buffer exchange. To achieve this result, a protocol similar to that used for enrichment is followed: a cellular sample is added through a sample inlet of the device, and the desired final buffer medium is added through a fluid inlet. As described above, cells above the critical size are deflected and enter the buffer.

Concentration

Figure 47:
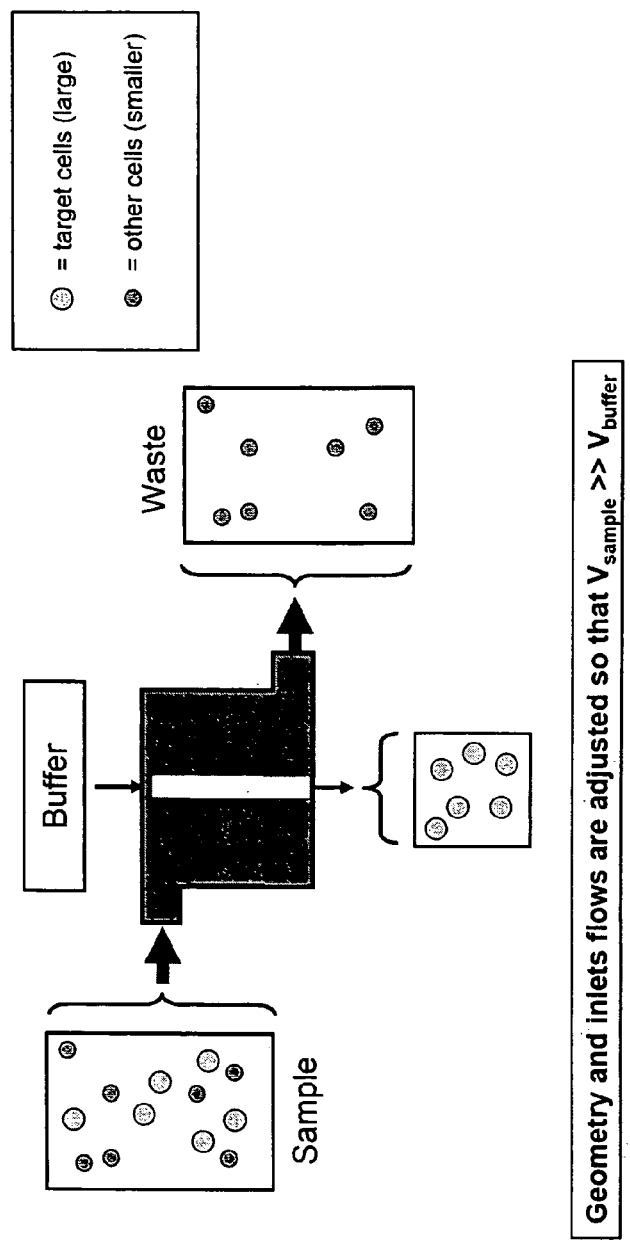
FIG. 47 is a schematic depiction of a method for enriching large cells from a mixture and producing a concentrated sample of these cells.

Devices of the invention may be employed in order to concentrate a cellular sample of interest, e.g., a sample containing CTCs. As shown in FIG. 47, a cellular sample is introduced to the sample inlet of the device. By reducing the volume of buffer introduced into the fluid inlet so that this volume is significantly smaller than the volume of the cellular sample, concentration of target cells in a smaller volume results. This concentration step may improve the results of any downstream analysis performed.

Cell Lysis

Figure 48:
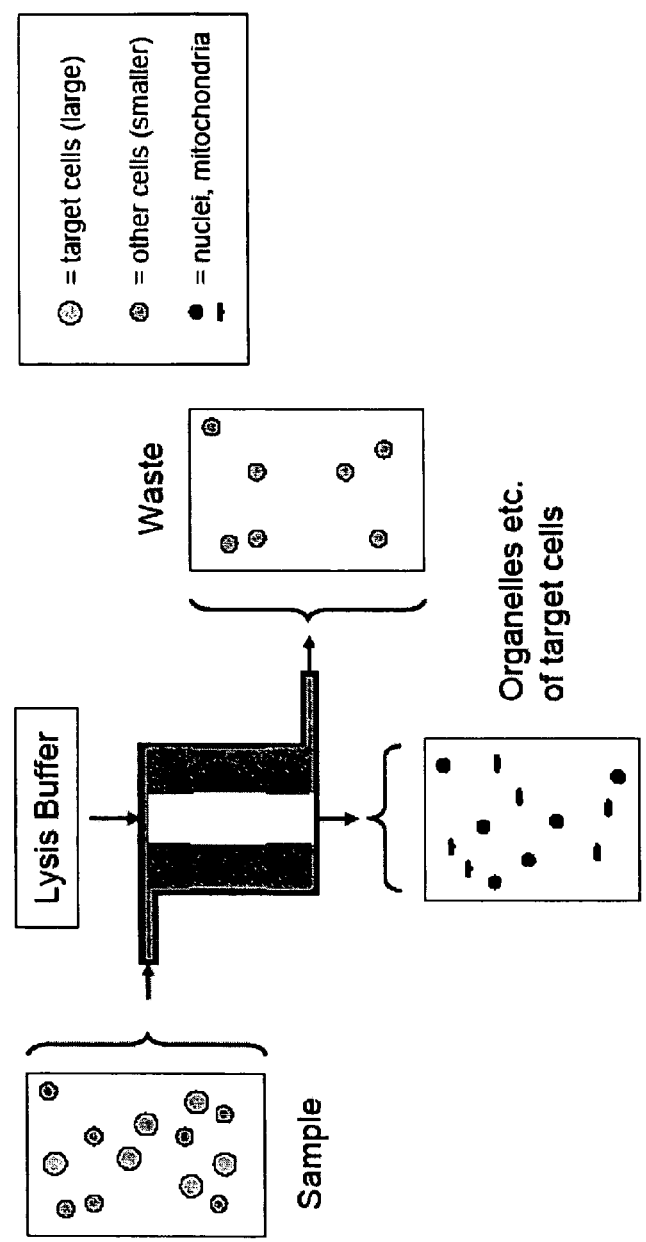
FIG. 48 is a schematic depiction of a method for lysing cells inside a device of the invention and separating whole cells from organelles and other cellular components.

Devices of the invention may be employed for purposes of cell lysis. To achieve this, a protocol similar to that used for enrichment is followed: a cellular sample is added through a sample inlet of the device (FIG. 48), and lysis buffer is added through the fluid inlet. As described above, cells above the critical size are deflected and enter the lysis buffer, leading to lysis of these cells. As a result, the sample emerging from the center outlet includes lysed cell components including organelles, while undeflected whole cells emerge from the other outlet. Thus, the device provides a method for selectively lysing target cells.

Multiple Stages

Figure 43A:
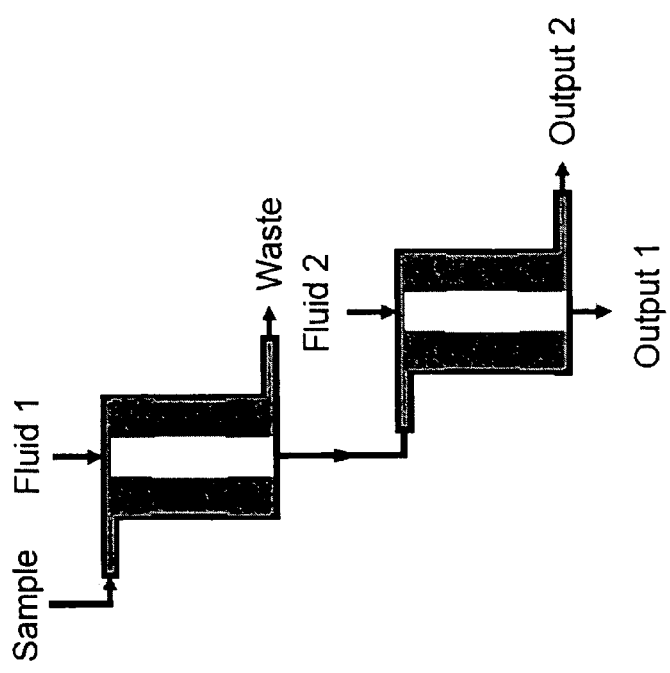
FIGS. 43A and 43B are schematic depictions of two distinct configurations for joining two devices together.

Devices of the invention may be joined together to provide multiple stages of enrichment and reaction. For example, FIG. 43A shows the "cascade" configuration, in which outlet 1 of one device is joined to a sample inlet of a second device. This allows for an initial enrichment step using the first device so that the sample introduced to the second device is already enriched for cells of interest. The two devices may have either identical or different critical sizes, depending on the intended application.

Figure 49:
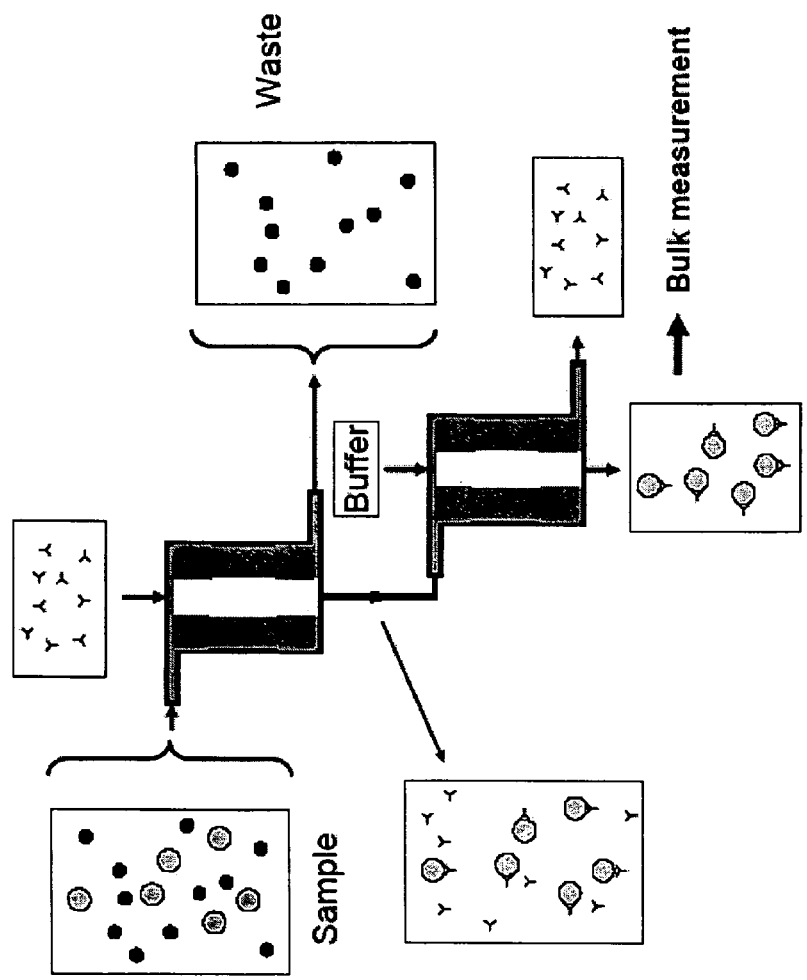
FIG. 49 is a schematic depiction of two devices arrayed in a cascade configuration and used for performing size fractionation and for separating free labeling reagent from bound labeling reagent by using a device of the invention.

In FIG. 49, an unlabeled cellular sample is introduced to the first device in the cascade via a sample inlet, and a buffer containing labeling reagent is introduced to the first device via the fluid inlet. Epithelial cells, e.g., CTCs, are deflected and emerge from the center outlet in the buffer containing labeling reagent. This enriched labeled sample is then introduced to the second device in the cascade via a sample inlet, while buffer is added to the second device via the fluid inlet. Further enrichment of target cells and separation of free labeling reagent is achieved, and the enriched sample may be further analyzed. Alternatively, labeling reagent may be added directly to the sample emerging from the center outlet of the first device before introduction to the second device. The use of a cascade configuration may allow for the use of a smaller quantity or a higher concentration of labeling reagent at less expense than the single-device configuration of FIG. 55; in addition, any nonspecific binding that may occur is significantly reduced by the presence of an initial enrichment step using the first device.

Figure 43B:
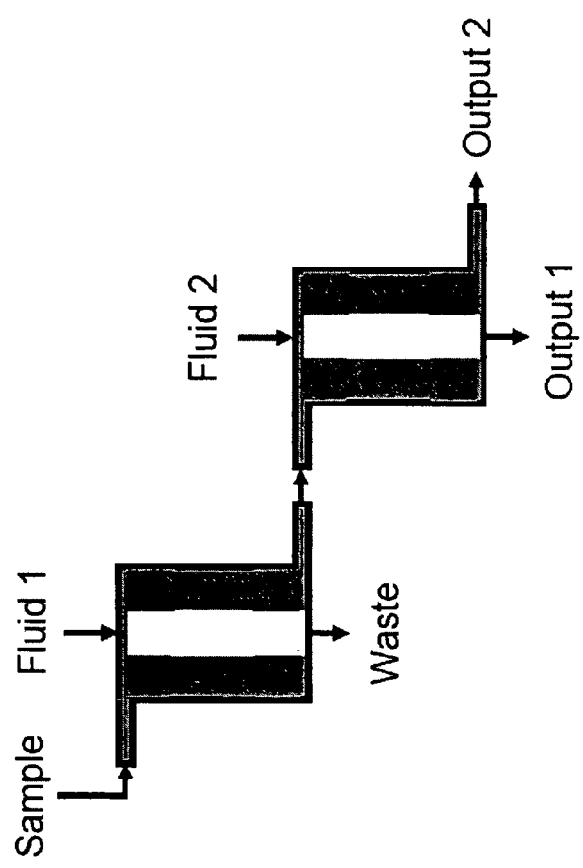

An alternative configuration of two or more device stages is the "bandpass" configuration. FIG. 43B shows this configuration, in which outlet 2 of one device is joined to a sample inlet of a second device. This allows for an initial enrichment step using the first device so that the sample introduced to the second device contains cells that remained undeflected within the first device. This method may be useful when the cells of interest are not the largest cells in the sample; in this instance, the first stage may be used to reduce the number of large non-target cells by deflecting them to the center outlet. As in the cascade configuration, the two devices may have either identical or different critical sizes, depending on the intended application. For example, different critical sizes are appropriate for an application requiring the enrichment of epithelial cells, e.g., CTCs, in comparison with an application requiring the enrichment of smaller endothelial cells.

Figure 51:
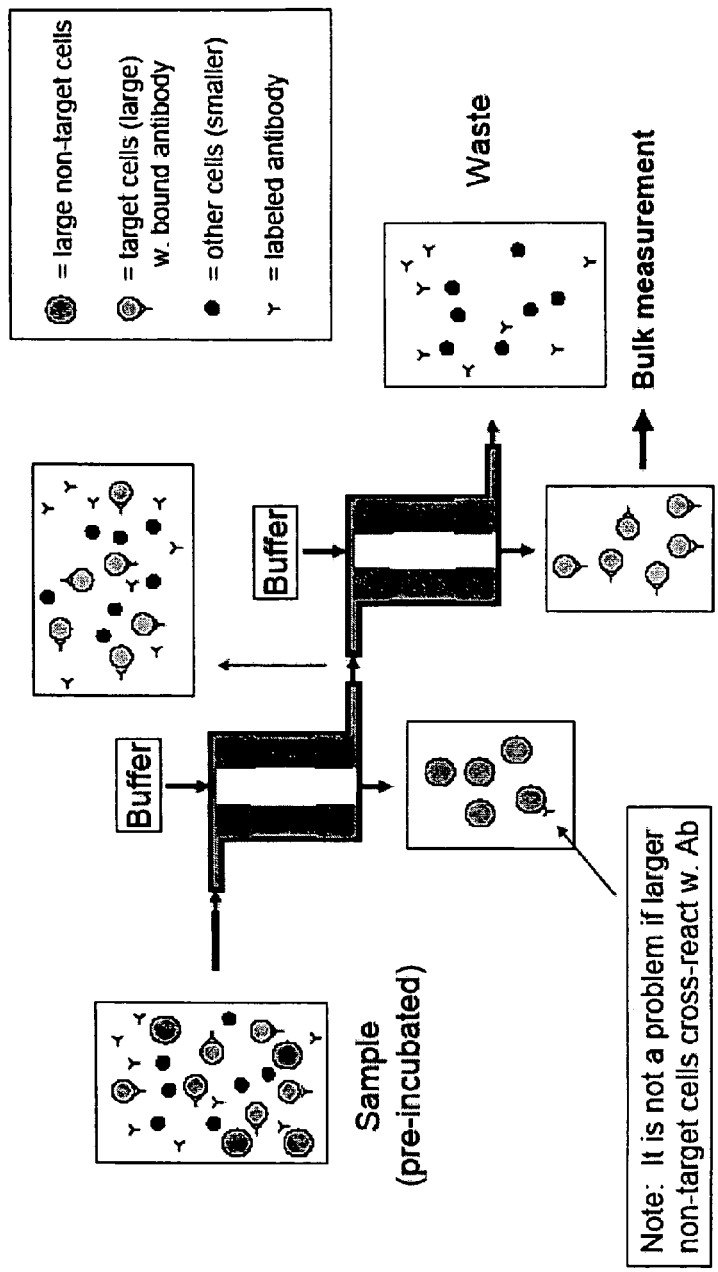
FIG. 51 is a schematic depiction of two devices arrayed in a bandpass configuration.

In FIG. 51, a cellular sample pre-incubated with labeling reagent is introduced to a sample inlet of the first device of the bandpass configuration, and a buffer is introduced to the first device via the fluid inlet. The first device is disposed in such a manner that large, non-target cells are deflected and emerge from the center outlet, while a mixture of target cells, small non-target cells, and labeling reagent emerge from outlet 2 of the first device. This mixture is then introduced to the second device via a sample inlet, while buffer is added to the second device via the fluid inlet. Enrichment of target cells and separation of free labeling reagent is achieved, and the enriched sample may be further analyzed. Non-specific binding of labeling reagent to the deflected cells in the first stage is acceptable in this method, as the deflected cells and any bound labeling reagent are removed from the system.

In any of the multiple device configurations described above, the devices and the connections joining them may be integrated into a single device. For example, a single cascade device including two or more stages is possible, as is a single bandpass device including two or more stages.

Downstream Analysis

A useful step for many diagnostic assays is the removal of free labeling reagent from the sample to be analyzed. As described above, devices of the invention are able to separate free labeling reagent from labeling reagent bound to cells, e.g., CTCs. It is then possible to perform a bulk measurement of the labeled sample without significant levels of background interference from free labeling reagent. For example, fluorescent antibodies selective for a particular epithelial cell marker such as EpCAM may be used. The fluorescent moiety may include Cy dyes, Alexa dyes, or other fluorophore-containing molecules. The resulting labeled sample is then analyzed by measuring the fluorescence of the resulting sample of labeled enriched cells using a fluorometer. Alternatively, a chromophore-containing label may be used in conjunction with a spectrometer, e.g., a UV or visible spectrometer. The measurements obtained may be used to quantify the number of target cells or all cells in the sample. Alternatively, the ratio of two cells types in the sample, e.g., the ratio of cancer cells to endothelial cells, may be determined. This ratio may be a ratio of the number of each type of cell, or alternatively it may be a ratio of any measured characteristic of each type of cell.

Any method of identifying cells, e.g., cells that have a cell surface marker associated with cancer, e.g., Ber-Ep4, CD34+, EpCAM, E-Cadherin, Mucin-1, Cytokeratin 8, EGFR, and leukocyte associated receptor (LAR), may be used. For example, an enriched sample of CTCs may be contacted with a device that includes a surface with one or more binding moieties that selectively bind one or more cells of the enriched sample. The binding moieties may include a polypeptide, e.g., an antibody or fragment thereof, e.g., monoclonal. For example, such a monoclonal antibody could be specific for EpCAM, e.g., anti-human EpCAM/TROP1 (catalog #AF960, R&D Systems).

Many other methods of measurement and labeling reagents are useful in the methods of the invention. Any imaging technique, e.g., hyperspectral imaging, may be used. Labeling antibodies, e.g., antibodies selective for any cancer marker, e.g., those listed in Table 1, may possess covalently bound enzymes that cleave a substrate, altering its absorbance at a given wavelength; the extent of cleavage is then quantified with a spectrometer. Colorimetric or luminescent readouts are possible, depending on the substrate used. Advantageously, the use of an enzyme label allows for significant amplification of the measured signal, lowering the threshold of detectability.

Quantum dots, e.g., Qdots® from QuantumDot Corp., may also be utilized as a labeling reagent that is covalently bound to a targeting antibody. Qdots are resistant to photobleaching and may be used in conjunction with two-photon excitation measurements.

Other possible labeling reagents useful in the methods of the invention are phage. Phage display is a technology in which binding peptides are displayed by engineered phage strains having strong binding affinities for a target protein, e.g., those found on the surface of cells of interest. The peptide sequence corresponding to a given phage is encoded in that phage's nucleic acid, e.g., DNA or RNA. Thus, phage are useful labeling reagents in that they are small relative to epithelial cells such as CTCs and thus may be easily separated, and they additionally carry nucleic acid that may be analyzed and quantified using PCR or similar techniques, enabling a quantitative determination of the number of cells present in an enriched bound sample.

Figure 50:
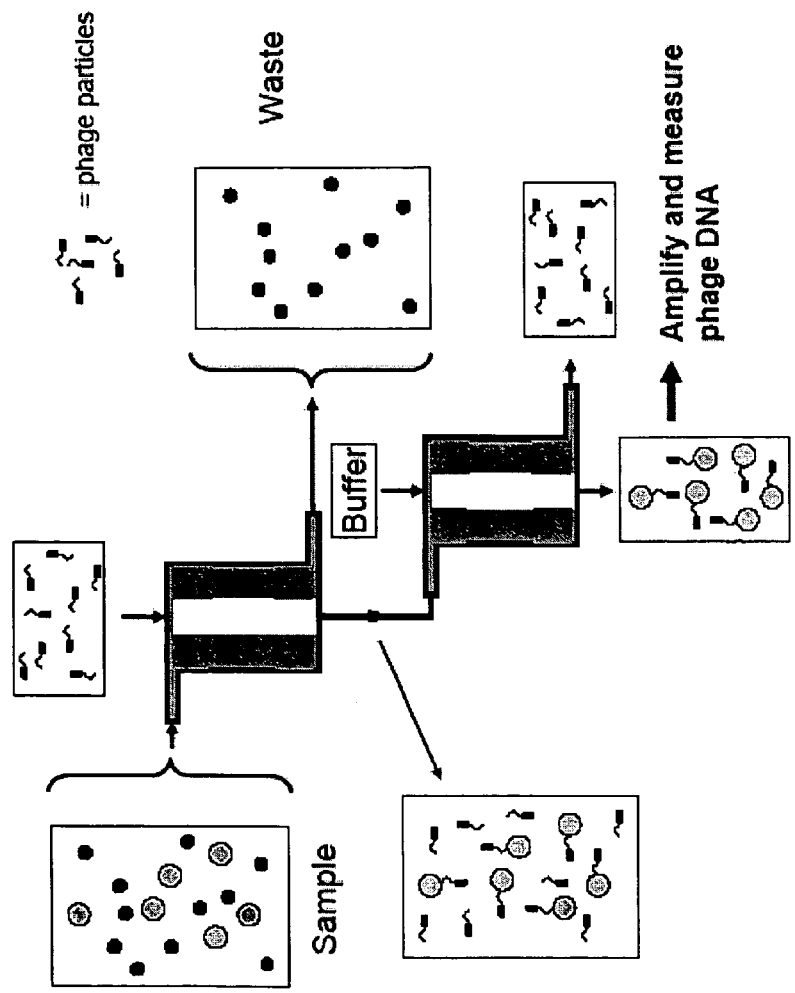
FIG. 50 is a schematic depiction of two devices arrayed in a cascade configuration and used for performing size fractionation and for separating free labeling reagent from bound labeling reagent by using a device of the invention. In this figure, phage is utilized for binding and detection rather than antibodies.

FIG. 50 depicts the use of phage as a labeling reagent in which two device stages are arrayed in a cascade configuration. The method depicted in FIG. 50 fits the general description of FIG. 49, with the exception of the labeling reagent employed.

Desirably, downstream analysis results in an accurate determination of the number of target cells in the sample being analyzed. In order to produce accurate quantitative results, the surface antigen being targeted on the cells of interest typically has known or predictable expression levels, and the binding of the labeling reagent should also proceed in a predictable manner, free from interfering substances. Thus, methods of the invention that result in highly enriched cellular samples prior to introduction of labeling reagent are particularly useful. In addition, labeling reagents that allow for amplification of the signal produced are preferred, because of the low incidence of target cells, such as epithelial cells, e.g., CTCs, in the bloodstream. Reagents that allow for signal amplification include enzymes and phage. Other labeling reagents that do not allow for convenient amplification but nevertheless produce a strong signal, such as quantum dots, are also desirable.

It is not necessary to include a labeling reagent in the methods of the invention. For example, one method includes the steps of introducing a cellular sample, e.g., a sample of peripheral blood, into a device of the invention. For example, the device enriches cells having a hydrodynamic size greater than 12 microns, 14 microns, 16 microns, 18 microns, or even 20 microns from smaller cells in the sample. Alternatively, the device may enrich cells having a hydrodynamic size greater than or equal to 6 microns and less than or equal to 12 microns, e.g., cells having a hydrodynamic size greater than or equal to 8 microns and less than or equal to 10 microns, from other cells. The device may also enrich cells having a hydrodynamic size greater than or equal to 5 microns and less than or equal to 10 microns from cells having a hydrodynamic size greater than 10 microns; alternatively, It may enrich cells having a hydrodynamic size greater than or equal to 4 microns and less than or equal to 8 microns from cells having a hydrodynamic size greater than 8 microns. Each of these subsets of cells may then be collected and analyzed, e.g., by detecting the presence of a particular cell type, e.g., a rare cell, e.g., an epithelial cell or progenitor endothelial cell, in one of the samples thus collected. Because of the enrichment that this method generally achieves, the concentration of rare cells may be higher in a recovered sample than in the starting cellular sample, allowing for rare cell detection by a variety of means. In one embodiment, the cellular sample is applied to an inlet of the device; a second reagent, e.g., a buffer, e.g., a buffer containing BSA, a lysis reagent, a nucleic acid amplification reagent, an osmolarity regulating reagent, a labeling reagent, a preservative, or a fixing reagent, is optionally applied to a second inlet; and two output samples flow out of two outlets of the device. For example, application of a cellular sample containing cancer cells to an inlet of the device could result in one output sample that is enriched in such cells, while the other sample is depleted in these cells or even completely devoid of them. Any of the second reagents listed above may be employed in any of the devices and methods of the invention, e.g., those in which the device contains a second inlet.

In embodiments in which two cell types are directed in different directions, the first cell type being the cell type of interest, the second cell type may be any other cell type. For example, the second cell type may include white blood cells or red blood cells, e.g., enucleated red blood cells.

The methods of the invention need not employ either magnetic particles or interaction with an antibody or fragment thereof in order to enrich cells of interest, e.g., cancer cells, from a cellular sample. Any method based on cell size, shape, or deformability may be used in order to enrich cells of interest; subsequently, cell detection or any other downstream applications, e.g., those described herein, may be performed.

The methods of the invention allow for enrichment, quantification, and molecular biology analysis of the same set of cells. The gentle treatment of the cells in the devices of the invention, coupled with the described methods of bulk measurement, maintain the integrity of the cells so that further analysis may be performed if desired. For example, techniques that destroy the integrity of the cells may be performed subsequent to bulk measurement; such techniques include DNA or RNA analysis, proteome analysis, or metabolome analysis. For example, the total amount of DNA or RNA in a sample may be determined; alternatively, the presence of a particular sequence or mutation, e.g., a deletion, in DNA or RNA may be detected, e.g., a mutation in a gene encoding a polypeptide listed in Table 1. Furthermore, mitochondrial DNA, telomerase, or nuclear matrix proteins in the sample may be analyzed (for mitochondrial mutations in cancer, see, e.g., Parrella et al., Cancer Res. 61:7623-7626 (2001), Jones et al., Cancer Res. 61:1299-1304 (2001), and Fliss et al., Science 287:2017-2019 (2000); for telomerase, see, e.g., Soria et al., Clin. Cancer Res. 5:971-975 (1999)). For example, the sample may be analyzed to determine whether any mitochondrial abnormalities (see, e.g., Carew et al., Mol. Cancer 1:9 (2002), and Wallace, Science 283:1482-1488 (1999)) or perinuclear compartments are present. One useful method for analyzing DNA is PCR, in which the cells are lysed and levels of particular DNA sequences are amplified. Such techniques are particularly useful when the number of target cells isolated is very low. In-cell PCR may be employed; in addition, gene expression analysis (see, e.g., Giordano et al., Am. J. Pathol. 159:1231-1238 (2001), and Buckhaults et al., Cancer Res. 63:4144-4149 (2003)) or fluorescence in-situ hybridization may be used, e.g., to determine the tissue or tissues of origin of the cells being analyzed. A variety of cellular characteristics may be measured using any of the above techniques, such as protein phosphorylation, protein glycosylation, DNA methylation (see, e.g., Das et al., J. Clin. Oncol. 22:4632-4642 (2004)), microRNA levels (see, e.g., He et al., Nature 435:828-833 (2005), Lu et al., Nature 435:834-838 (2005), O'Donnell et al., Nature 435:839-843 (2005), and Calin et al., N. Engl. J. Med. 353:1793-1801 (2005)), cell morphology or other structural characteristics, e.g., pleomorphisms, adhesion, migration, binding, division, level of gene expression, and presence of a somatic mutation. This analysis may be performed on any number of cells, including a single cell of interest, e.g., a cancer cell. In addition, the size distribution of cells may be analyzed. Desirably, downstream analysis, e.g., detection, is performed on more than one sample, preferably from the same subject.

Quantification of Cells

Cells found in blood are of various types and span a range of sizes. Using the methods of the invention, it is possible to distinguish, size, and count blood cell populations, e.g., CTCs. For example, a Coulter counter may be used. FIG. 33A shows a typical size distribution for a normal blood sample. Under some conditions, e.g., the presence of a tumor in the body that is exfoliating tumor cells, cells that are not native to blood may appear in the peripheral circulation. The ability to isolate and count large cells, or other desired cells, that may appear in the blood provides powerful opportunities for diagnosing disease states.

Desirably, a Coulter counter, or other cell detector, is fluidically coupled to an outlet of a device of the invention, and a cellular sample is introduced to the device of the invention. Cells flowing through the outlet fluidically coupled to the Coulter counter then pass through the Coulter aperture, which includes two electrodes separated by an opening through which the cells pass, and which measures the volume displaced as each cell passes through the opening. Preferably, the Coulter counter determines the number of cells of cell volume greater than 500 fL in the enriched sample. Alternatively, the Coulter counter preferably determines the number of cells of diameter greater than 14 µm in the enriched sample. The Coulter counter, or other cell detector, may also be an integral part of a device of the invention rather than constituting a separate device. The counter may utilize any cellular characteristic, e.g., impedance, light absorption, light scattering, or capacitance.

In general, any means of generating a cell count is useful in the methods of the invention. Such means include optical, such as scattering, absorption, or fluorescence means. Alternatively, non-aperture electrical means, such as determining capacitance, are useful.

Combination with Other Enrichment Techniques

Enrichment and alteration methods employing devices of the invention may be combined with other particulate sample manipulation techniques. In particular, further enrichment or purification of CTCs or other particles may be desirable. Further enrichment may occur by any technique, including affinity enrichment. Suitable affinity enrichment techniques include contacting particles of interest with affinity agents bound to channel walls or an array of obstacles. Such affinity agents may be selective for any cell type, e.g., cancer cells. This includes using a device of the invention in which antibodies specific for target cells are immobilized within the device. This allows for binding and enrichment of target cells within the device; subsequently the target cells are eluted using a higher flow rate, competing ligands, or another method.

Diagnosis

As described herein, epithelial cells exfoliated from solid tumors have been found in the circulation of patients with cancers of the breast, colon, liver, ovary, prostate, and lung. In general, the presence of CTCs after therapy has been associated with tumor progression and spread, poor response to therapy, relapse of disease, and/or decreased survival over a period of several years. Therefore, enumeration of CTCs offers a means to stratify patients for baseline characteristics that predict initial risk and subsequent risk based upon response to therapy.

The devices and methods of the invention may be used, e.g., to evaluate cancer patients and those at risk for cancer. In any of the methods of diagnosis described herein, either the presence or the absence of an indicator of cancer, e.g., a cancer cell, or of any other disorder, may be used to generate a diagnosis. In one example, a blood sample is drawn from the patient and introduced to a device of the invention with a critical size chosen appropriately to enrich epithelial cells, e.g., CTCs, from other blood cells. Using a method of the invention, the number of epithelial cells in the blood sample is determined. For example, the cells may be labeled with an antibody that binds to EpCAM, and the antibody may have a covalently bound fluorescent label. A bulk measurement may then be made of the enriched sample produced by the device, and from this measurement, the number of epithelial cells present in the initial blood sample may be determined. Microscopic techniques may be used to visually quantify the cells in order to correlate the bulk measurement with the corresponding number of labeled cells in the blood sample.

Besides epithelial tumor cells, there are other cell types that are involved in metastatic tumor formation. Studies have provided evidence for the involvement of hematopoietic bone marrow progenitor cells and endothelial progenitor cells in metastasis (see, e.g., Kaplan et al., Nature 438:820-827 (2005), and Brugger et al., Blood 83:636-640 (1994)). The number of cells of a second cell type, e.g., hematopoietic bone marrow progenitor cells, e.g., progenitor endothelial cells, may be determined, and the ratio of epithelial tumor cells to the number of the second cell type may be calculated. Such ratios are of diagnostic value in selecting the appropriate therapy and in monitoring the efficacy of treatment.

Cells involved in metastatic tumor formation may be detected using any methods known in the art. For example, antibodies specific for particular cell surface markers may be used. Useful endothelial cell surface markers include CD105, CD106, CD144, and CD146; useful tumor endothelial cell surface markers include TEM1, TEM5, and TEM8 (see, e.g., Carson-Walter et al., Cancer Res. 61:6649-6655 (2001)); and useful mesenchymal cell surface markers include CD133. Antibodies to these or other markers may be obtained from, e.g., Chemicon, Abcam, and R&D Systems.

By making a series of measurements, optionally made at regular intervals such as one day, two days, three days, one week, two weeks, one month, two months, three months, six months, or one year, one may track the level of epithelial cells present in a patient's bloodstream as a function of time. In the case of existing cancer patients, this provides a useful indication of the progression of the disease and assists medical practitioners in making appropriate therapeutic choices based on the increase, decrease, or lack of change in epithelial cells, e.g., CTCs, in the patient's bloodstream. For those at risk of cancer, a sudden increase in the number of cells detected may provide an early warning that the patient has developed a tumor. This early diagnosis, coupled with subsequent therapeutic intervention, is likely to result in an improved patient outcome in comparison to an absence of diagnostic information.

Diagnostic methods include making bulk measurements of labeled epithelial cells, e.g., CTCs, isolated from blood, as well as techniques that destroy the integrity of the cells. For example, PCR may be performed on a sample in which the number of target cells isolated is very low; by using primers specific for particular cancer markers, information may be gained about the type of tumor from which the analyzed cells originated. Additionally, RNA analysis, proteome analysis, or metabolome analysis may be performed as a means of diagnosing the type or types of cancer present in the patient.

One important diagnostic indicator for lung cancer and other cancers is the presence or absence of certain mutations in EGFR (see, e.g., International Publication WO 2005/094357). EGFR consists of an extracellular ligand-binding domain, a transmembrane portion, and an intracellular tyrosine kinase (TK) domain. The normal physiologic role of EGFR is to bind ErbB ligands, including epidermal growth factor (EGF), at the extracellular binding site to trigger a cascade of downstream intracellular signals leading to cell proliferation, survival, motility and other related activities. Many non-small cell lung tumors with EGFR mutations respond to small molecule EGFR inhibitors, such as gefitinib (Iressa; AstraZeneca), but often eventually acquire secondary mutations that make them drug resistant. Using the devices and method of the invention, one may monitor patients taking such drugs by taking frequent samples of blood and determining the number of epithelial cells, e.g., CTCs, in each sample as a function of time. This provides information as to the course of the disease. For example, a decreasing number of circulating epithelial cells over time suggests a decrease in the severity of the disease and the size of the tumor or tumors. Immediately following quantification of epithelial cells, these cells may be analyzed by PCR to determine what mutations may be present in the EFGR gene expressed in the epithelial cells. Certain mutations, such as those clustered around the ATP-binding pocket of the EGFR TK domain, are known to make the cancer cells susceptible to gefitinib inhibition. Thus, the presence of these mutations supports a diagnosis of cancer that is likely to respond to treatment using gefitinib. However, many patients who respond to gefitinib eventually develop a second mutation, often a methionine-tothreonine substitution at position 790 in exon 20 of the TK domain, which renders them resistant to gefitinib. By using the devices and method of the invention, one may test for this mutation as well, providing further diagnostic information about the course of the disease and the likelihood that it will respond to gefitinib or similar compounds. Since many EGFR mutations, including all EGFR mutations in NSC lung cancer reported to date that are known to confer sensitivity or resistance to gefitinib, lie within the coding regions of exons 18 to 21, this region of the EGFR gene may be emphasized in the development of assays for the presence of mutations (see Examples 4-6).

The methods of the invention described above are not limited to epithelial cells and cancer, but rather may be used to diagnose any condition. Exemplary conditions that may be diagnosed using the methods of the invention are hematological conditions, inflammatory conditions, ischemic conditions, neoplastic conditions, infections, traumas, endometriosis, and kidney failure (see, e.g., Takahashi et al., Nature Med. 5:434-438 (1999), Healy et al., Hum. Reprod. Update 4:736-740 (1998), and Gill et al., Circ. Res. 88:167-174 (2001)). Neoplastic conditions include acute lymphoblastic leukemia, acute or chronic lymphocyctic or granulocytic tumor, acute myeloid leukemia, acute promyelocytic leukemia, adenocarcinoma, adenoma, adrenal cancer, basal cell carcinoma, bone cancer, brain cancer, breast cancer, bronchi cancer, cervical dysplasia, chronic myelogenous leukemia, colon cancer, epidermoid carcinoma, Ewing's sarcoma, gallbladder cancer, gallstone tumor, giant cell tumor, glioblastoma multiforma, hairy-cell tumor, head cancer, hyperplasia, hyperplastic corneal nerve tumor, in situ carcinoma, intestinal ganglion-euroma, islet cell tumor, Kaposi's sarcoma, kidney cancer, larynx cancer, leiomyomater tumor, liver cancer, lung cancer, lymphomas, malignant carcinoid, malignant hypercalcemia, malignant melanomas, marfanoid habitus tumor, medullary carcinoma, metastatic skin carcinoma, mucosal neuromas, mycosis fungoide, myelodysplastic syndrome, myeloma, neck cancer, neural tissue cancer, neuroblastoma, osteogenic sarcoma, osteosarcoma, ovarian tumor, pancreas cancer, parathyroid cancer, pheochromocytoma, polycythemia Vera, primary brain tumor, prostate cancer, rectum cancer, renal cell tumor, retinoblastoma, rhabdomyosarcoma, seminoma, skin cancer, small-cell lung tumor, soft tissue sarcoma, squamous cell carcinoma, stomach cancer, thyroid cancer, topical skin lesion, veticulum cell sarcoma, and Wilm's tumor. In one embodiment, neoplastic cells associated with thyroid cancer are not detected. A cellular sample taken from a patient, e.g., a sample of less than 50 mL, 40 mL, 30 mL, 20 mL, or even 10 mL, may be processed through a device of the invention in order to produce a sample enriched in any cell of interest, e.g., a rare cell. Detection of this cell in the enriched sample may then enable one skilled in the art to diagnose the presence or absence of a particular condition in the patient. Furthermore, determination of ratios of numbers of cells, e.g., cancer cells to endothelial cells, in the sample may be used to generate a diagnosis. Alternatively, detection of cancer biomarkers, e.g., any of those listed in Table 1, or a nucleic acid associated with cancer, e.g., a nucleic acid enoding any marker listed in Table 1, may result in the diagnosis of a cancer or another condition. For example, analysis of the expression level or pattern of such a polypeptide or nucleic acid, e.g., cell surface markers, genomic DNA, mRNA, or microRNA, may result in a diagnosis.

Cell detection may be combined with other information, e.g., imaging studies of the patient, in order to diagnose a patient. For example, computed axial tomography, positron emission tomography, or magnetic resonance imaging may be used.

A diagnosis may also be made using a cell pattern associated with a particular condition. For example, by comparing the size distribution of cells in an enriched sample, e.g., a sample containing cells having a hydrodynamic size greater than 12 microns, with a size distribution associated with a condition, e.g., cancer, a diagnosis may be made based on this comparison. A cell pattern for comparison may be generated by any method. For example, an association study may be performed in which cellular samples from a plurality of control subjects (e.g., 50) and a plurality of case subjects (e.g., 50) having a condition of interest are processed, e.g., by enriching cells having a hydrodynamic size greater than 12 microns, the results samples are analyzed, and the results of the analysis are compared. To perform such a study, it may be useful to analyze RNA levels, e.g., mRNA or microRNA levels, in the enriched cells. Alternatively, it is useful to count the number of cells enriched in each case, or to determine a cellular size distribution, e.g., by using a microscope, a cell counter, or a microarray device. The presence of particular cell types, e.g., rare cells, may also be identified.

Once a drug treatment is administered to a patient, it is possible to determine the efficacy of the drug treatment using the methods of the invention. For example, a cellular sample taken from the patient before the drug treatment, as well as one or more cellular samples taken from the patient concurrently with or subsequent to the drug treatment, may be processed using the methods of the invention. By comparing the results of the analysis of each processed sample, one may determine the efficacy of the drug treatment. For example, an enrichment device may be used to enrich cells having a hydrodynamic size greater than 12 microns, or cells having a hydrodynamic size greater than or equal to 6 microns and less than or equal to 12 microns, from other cells. Any other detection or analysis described above may be performed, e.g., identification of the presence or quantity of specific cell types.

Methods of Using Sample Mobilization Devices

A sample mobilization device of the invention may be used to enrich CTCs or other cells from a sample. In one embodiment, a cellular sample is placed in a sample mobilization device, e.g., a device that includes a receptacle, a lid with a functionalized surface, and a sample mobilizer. The receptacle containing the sample is then covered with the lid, the sample mobilizer is employed to mobilize the sample, and the lid is removed. Such a device may be used to enrich a CTC or other cell of interest.

Any type of sample mobilization, e.g., centrifugation, may be applied. Any centrifugal field that is known in the art may be applied, e.g., a centrifugal field between 100 g and 100,000 g. For example, the centrifugal field may be between 1,000 g and 10,000 g. The application of this field results in a centrifugal force on the sample. Additional forces may also be applied, e.g., a force opposite to the centrifugal force; furthermore, forces may be applied repeatedly and in alternation, with an optional time interval between applications of each force.

General Considerations

Samples may be employed in the methods described herein with or without purification, e.g., stabilization and removal of certain components. Some sample may be diluted or concentrated prior to introduction into the device.

In one embodiment, reagents are added to the sample, to selectively or nonselectively increase the hydrodynamic size of the particles within the sample. This modified sample is then pumped through an obstacle array. Because the particles are swollen and have an increased hydrodynamic size, it will be possible to use obstacle arrays with larger and more easily manufactured gap sizes. In a preferred embodiment, the steps of swelling and size-based enrichment are performed in an integrated fashion on a device. Suitable reagents include any hypotonic solution, e.g., deionized water, 2% sugar solution, or neat non-aqueous solvents. Other reagents include beads, e.g., magnetic or polymer, that bind selectively (e.g., through antibodies or avidin-biotin) or non-selectively.

In another embodiment, reagents are added to the sample to selectively or nonselectively decrease the hydrodynamic size of the particles within the sample. Nonuniform decrease in particles in a sample will increase the difference in hydrodynamic size between particles. For example, nucleated cells are separated from enucleated cells by hypertonically shrinking the cells. The enucleated cells may shrink to a very small particle, while the nucleated cells cannot shrink below the size of the nucleus. Exemplary shrinking reagents include hypertonic solutions.

In an alternative embodiment, affinity functionalized beads and other appropriate beads are used to increase the volume of particles of interest relative to the other particles present in a sample, thereby allowing for the operation of a obstacle array with a larger and more easily manufactured gap size.

Fluids may be driven through a device either actively or passively. Fluids may be pumped using electric field, a centrifugal field, pressure-driven fluid flow, an electro-osmotic flow, and capillary action. In preferred embodiments, the average direction of the field will be parallel to the walls of the channel that contains the array.

Sample Preparation

Samples may be employed in the methods described herein with or without manipulation, e.g., stabilization and removal of certain components. In one embodiment, the sample is enriched in CTCs or other cells of interest prior to introduction to a device of the invention. Methods for enriching cell populations are known in the art, e.g., affinity mechanisms, agglutination, and size, shape, and deformability based enrichments. Exemplary methods for enriching a sample in a cell of interest are found in U.S. Pat. Nos. 5,837,115 and 5,641,628, International Publications WO 2004/029221 and WO 2004/113877, and U.S. Application Publication 2004/0144651.

EXAMPLES

Example 1

Figure 52:
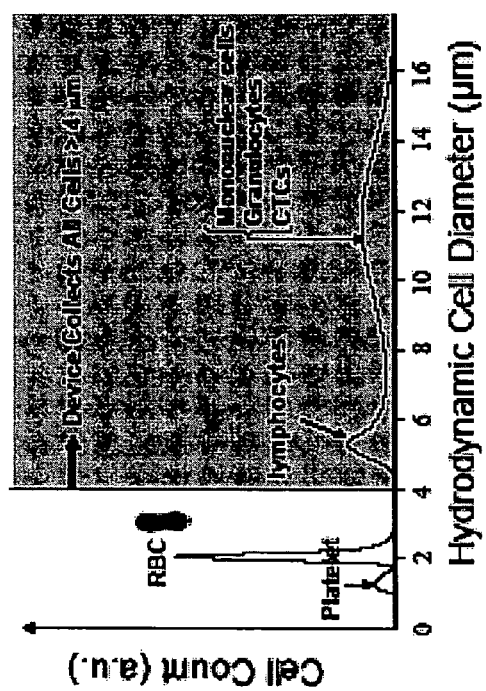
FIG. 52 is a graph of cell count versus hydrodynamic size for a microfluidic separation of normal whole blood.
Figure 53:
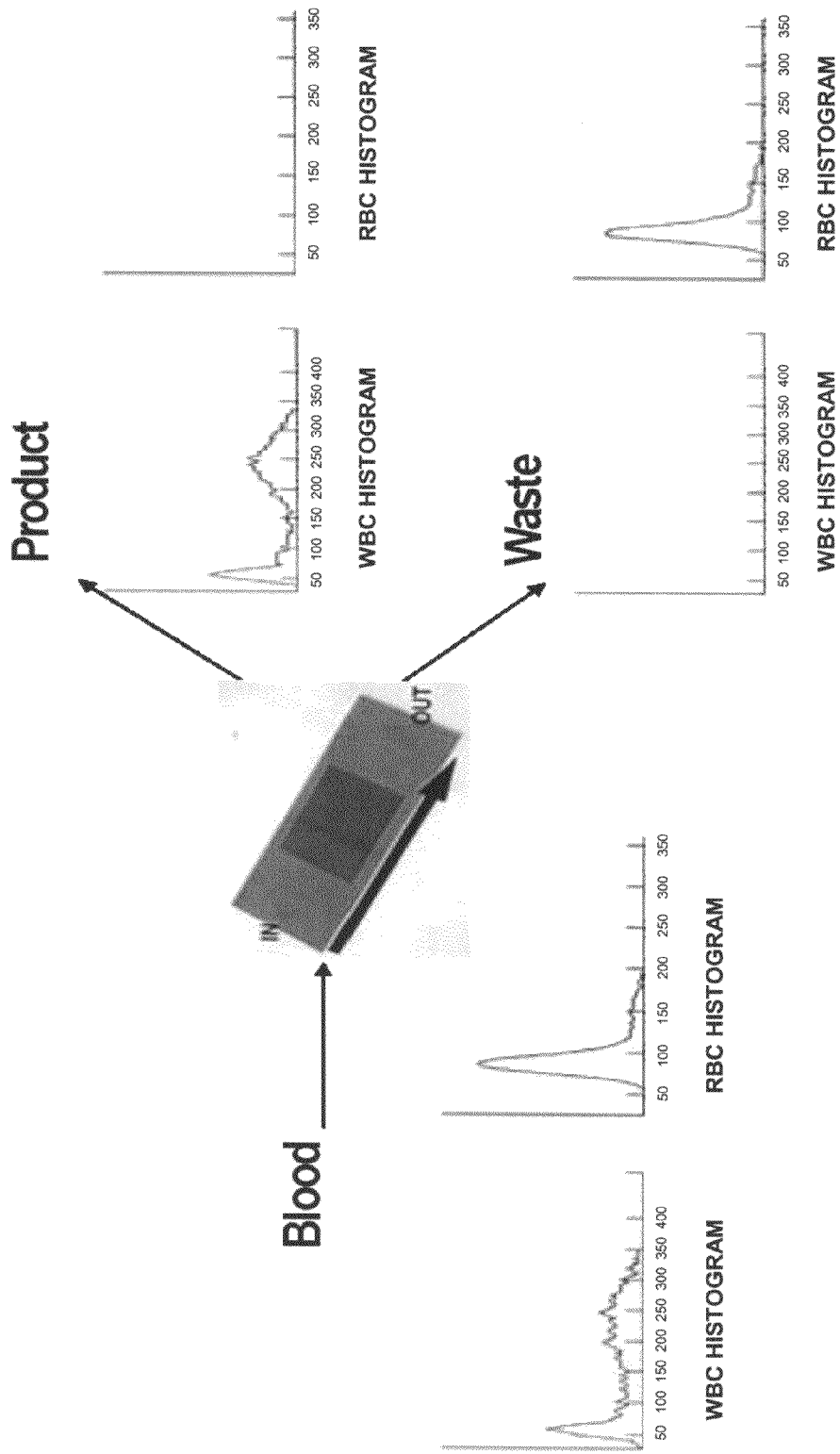
FIG. 53 is a set of histograms from input, product, and waste samples generated with a Coulter "$A^C$-T diff" clinical blood analyzer. The x-axis depicts cell volume in femtomoles.
Figure 54:
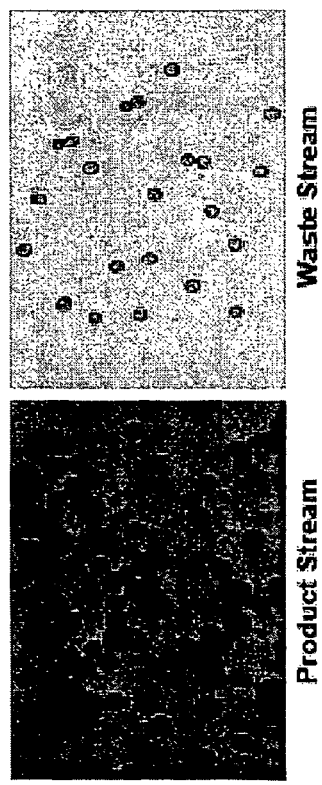
FIG. 54 is a pair of representative micrographs from product and waste streams of fetal blood processed with a cell enrichment module, showing clear separation of nucleated cells and red blood cells.

Microfluidic devices of the invention were designed by computer-aided design (CAD) and microfabricated by photolithography. A two-step process was developed in which a blood sample is first debulked to remove the large population of small cells, and then the rare target epithelial cells target cells are recovered by immunoaffinity capture. The devices were defined by photolithography and etched into a silicon substrate based on the CAD-generated design. The cell enrichment module, which is approximately the size of a standard microscope slide, contains 14 parallel sample processing sections and associated sample handling channels that connect to common sample and buffer inlets and product and waste outlets. Each section contains an array of microfabricated obstacles that is optimized to enrich the target cell type by hydrodynamic size via displacement of the larger cells into the product stream. In this example, the microchip was designed to separate red blood cells (RBCs) and platelets from the larger leukocytes and CTCs. Enriched populations of target cells were recovered from whole blood passed through the device. Performance of the cell enrichment microchip was evaluated by separating RBCs and platelets from white blood cells (WBCs) in normal whole blood (FIG. 52). In cancer patients, CTCs are found in the larger WBC fraction. Blood was minimally diluted (30%), and a 6 ml sample was processed at a flow rate of up to 6 ml/hr. The product and waste stream were evaluated in a Coulter Model "A$^C$-T diff" clinical blood analyzer, which automatically distinguishes, sizes, and counts different blood cell populations. The enrichment chip achieved separation of RBCs from WBCs, in which the WBC fraction had >99% retention of nucleated cells, >99% depletion of RBCs, and >97% depletion of platelets. Representative histograms of these cell fractions are shown in FIG. 53. Routine cytology confirmed the high degree of enrichment of the WBC and RBC fractions (FIG. 54).

Next, epithelial cells were recovered by affinity capture in a microfluidic module that is functionalized with immobilized antibody. A capture module with a single chamber containing a regular array of antibody-coated microfabricated obstacles was designed. These obstacles are disposed to maximize cell capture by increasing the capture area approximately four-fold, and by slowing the flow of cells under laminar flow adjacent to the obstacles to increase the contact time between the cells and the immobilized antibody. The capture modules may be operated under conditions of relatively high flow rate but low shear to protect cells against damage. The surface of the capture module was functionalized by sequential treatment with 10% silane, 0.5% gluteraldehyde, and avidin, followed by biotinylated anti-EpCAM. Active sites were blocked with 3% bovine serum albumin in PBS, quenched with dilute Tris HCl, and stabilized with dilute L-histidine. Modules were washed in PBS after each stage and finally dried and stored at room temperature. Capture performance was measured with the human advanced lung cancer cell line NCI-H1650 (ATCC Number CRL-5883). This cell line has a heterozygous 15 bp in-frame deletion in exon 19 of EGFR that renders it susceptible to gefitinib. Cells from confluent cultures were harvested with trypsin, stained with the vital dye Cell Tracker Orange (CMRA reagent, Molecular Probes, Eugene, Oreg.), resuspended in fresh whole blood, and fractionated in the microfluidic chip at various flow rates. In these initial feasibility experiments, cell suspensions were processed directly in the capture modules without prior fractionation in the cell enrichment module to debulk the red blood cells; hence, the sample stream contained normal blood red cells and leukocytes as well as tumor cells. After the cells were processed in the capture module, the device was washed with buffer at a higher flow rate (3 ml/hr) to remove the nonspecifically bound cells. The adhesive top was removed and the adherent cells were fixed on the chip with paraformaldehyde and observed by fluorescence microscopy. Cell recovery was calculated from hemacytometer counts; representative capture results are shown in Table 2. Initial yields in reconstitution studies with unfractionated blood were greater than 60% with less than 5% of non-specific binding.

TABLE 2

| Run number | Avg. flow rate | Length of run | No. cells processed | No. cells captured | Yield |
|---|---|---|---|---|---|
| 1 | 3.0 | 1 hr | 150,000 | 38,012 | 25% |
| 2 | 1.5 | 2 hr | 150,000 | 30,000/ml | 60% |
| 3 | 1.08 | 2 hr | 108,000 | 68,661 | 64% |
| 4 | 1.21 | 2 hr | 121,000 | 75,491 | 62% |

Figure 55:
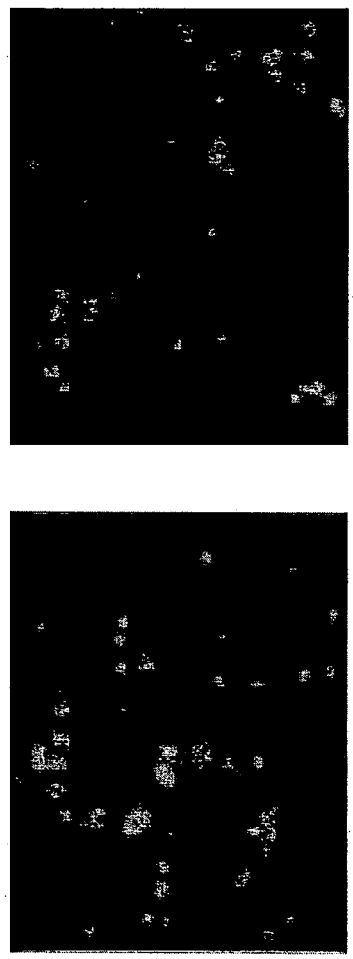
FIG. 55 is a pair of images showing cells fixed on a cell enrichment module with paraformaldehyde and observed by fluorescence microscopy. Target cells are bound to the obstacles and floor of the capture module.

Next, NCI-H1650 cells that were spiked into whole blood and recovered by size fractionation and affinity capture as described above were successfully analyzed in situ. In a trial run to distinguish epithelial cells from leukocytes, 0.5 ml of a stock solution of fluorescein-labeled CD45 pan-leukocyte monoclonal antibody were passed into the capture module and incubated at room temperature for 30 minutes. The module was washed with buffer to remove unbound antibody, and the cells were fixed on the chip with 1% paraformaldehyde and observed by fluorescence microscopy. As shown in FIG. 55, the epithelial cells were bound to the obstacles and floor of the capture module. Background staining of the flow passages with CD45 pan-leukocyte antibody is visible, as are several stained leukocytes, apparently because of a low level of non-specific capture.

Example 2

Device Embodiments

Figure 57A:
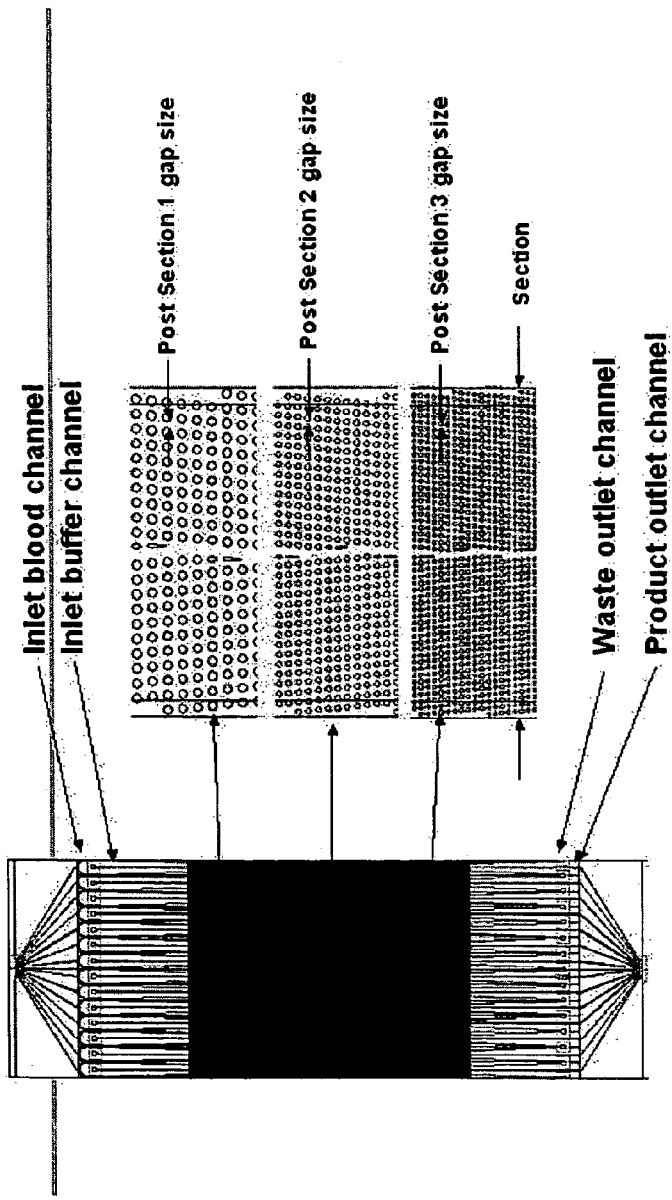
FIG. 57A is a design for a preferred embodiment of the invention.

A design for preferred device embodiments of the invention is shown in FIG. 57A, and parameters corresponding to three preferred device embodiments associated with this design are shown in FIG. 57B. These embodiments are particularly useful for enrich epithelial cells from blood.

Example 3

Determining Counts for Non-epithelial Cell Types

Using the methods of the invention, one may make a diagnosis based on counting cell types other than CTCs or other epithelial cells. A diagnosis of the absence, presence, or progression of cancer may be based on the number of cells in a cellular sample that are larger than a particular cutoff size. For example, cells with a hydrodynamic size of 14 microns or larger may be selected. This cutoff size would eliminate most leukocytes. The nature of these cells may then be determined by downstream molecular or cytological analysis.

Cell types other than epithelial cells that would be useful to analyze include endothelial cells, endothelial progenitor cells, endometrial cells, or trophoblasts indicative of a disease state. Furthermore, determining separate counts for epithelial cells, e.g., cancer cells, and other cell types, e.g., endothelial cells, followed by a determination of the ratios between the number of epithelial cells and the number of other cell types, may provide useful diagnostic information.

A device of the invention may be configured to isolate targeted subpopulations of cells such as those described above, as shown in FIGS. 33A-D. A size cutoff may be selected such that most native blood cells, including red blood cells, white blood cells, and platelets, flow to waste, while non-native cells, which could include endothelial cells, endothelial progenitor cells, endometrial cells, or trophoblasts, are collected in an enriched sample. This enriched sample may be further analyzed.

Figure 56:
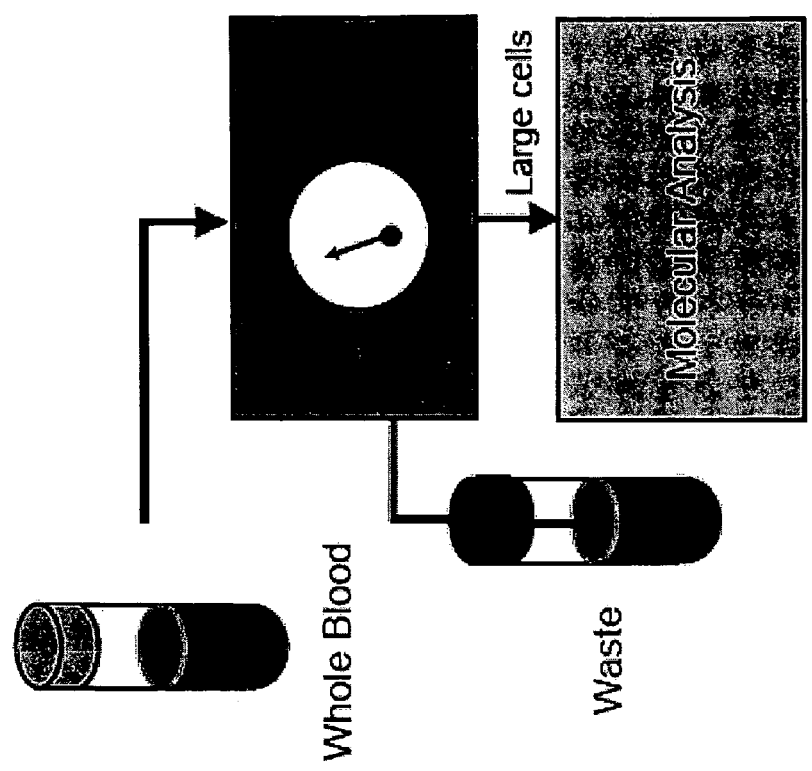
FIG. 56 is a schematic depiction of a method of the invention. This method features isolating and counting large cells within a cellular sample, wherein the count is indicative of a patient's disease state, and subsequently further analyzing the large cell subpopulation.

Using a device of the invention, therefore, it is possible to isolate a subpopulation of cells from blood or other bodily fluids based on size, which conveniently allows for the elimination of a large proportion of native blood cells when large cell types are targeted. As shown schematically in FIG. 56, a device of the invention may include counting means to determine the number of cells in the enriched sample, or the number of cells of a particular type, e.g., cancer cells, within the enriched sample, and further analysis of the cells in the enriched sample may provide additional information that is useful for diagnostic or other purposes.

Example 4

Method for Detection of EGFR Mutations

Figure 58:
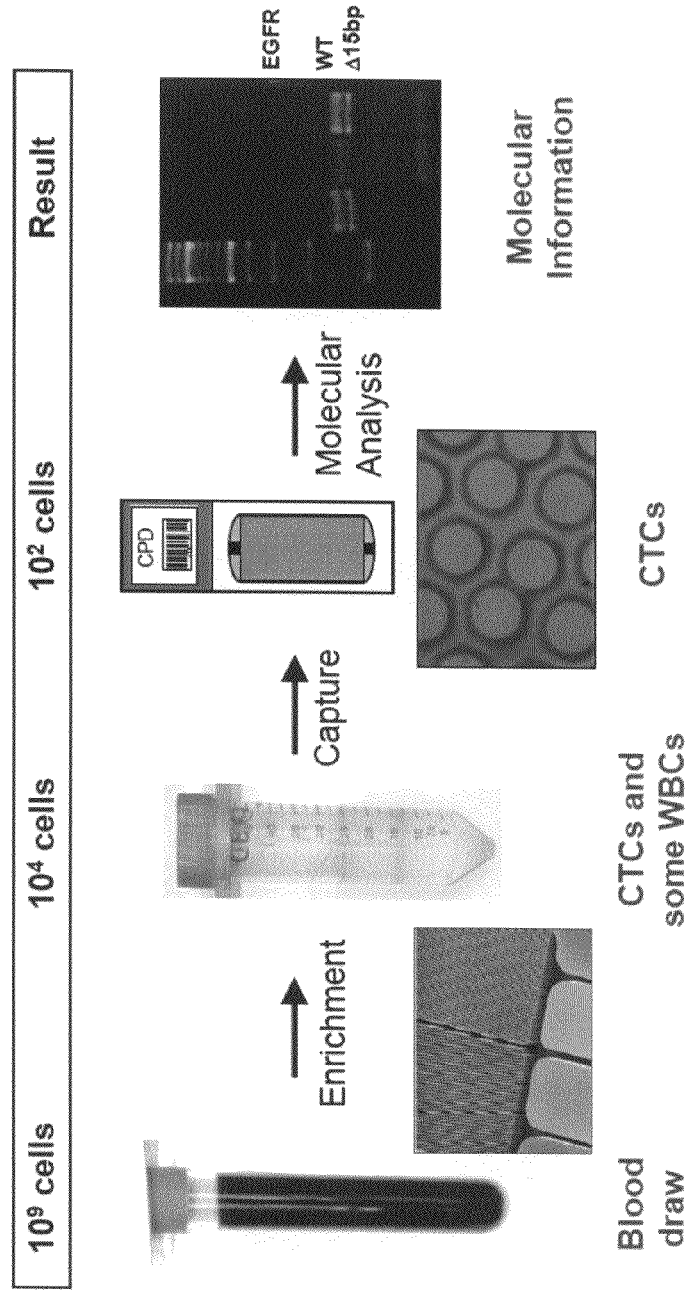
FIG. 58 is a schematic depiction of a method of detecting epidermal growth factor receptor (EGFR) mutations in CTCs in blood.

A blood sample from a cancer patient is processed and analyzed using the devices and methods of the invention, e.g., those of Example 1, resulting in an enriched sample of epithelial cells containing CTCs. This sample is then analyzed to identify potential EGFR mutations. The method permits both identification of known, clinically relevant EGFR mutations as well as discovery of novel mutations. An overview of this process is shown in FIG. 58.

Below is an outline of the strategy for detection and confirmation of EGFR mutations:
1) Sequence CTC EGFR mRNA
 a) Purify CTCs from blood sample;
 b) Purify total RNA from CTCs;
 c) Convert RNA to cDNA using reverse transcriptase;
 d) Use resultant cDNA to perform first and second PCR reactions for generating sequencing templates; and
 e) Purify the nested PCR amplicon and use as a sequencing template to sequence EGFR exons 18-21.
2) Confirm RNA sequence using CTC genomic DNA
 a) Purify CTCs from blood sample;
 b) Purify genomic DNA (gDNA) from CTCs;
 c) Amplify exons 18, 19, 20, and/or 21 via PCR reactions; and
 d) Use the resulting PCR amplicon(s) in real-time quantitative allele-specific PCR reactions in order to confirm the sequence of mutations discovered via RNA sequencing.

Figure 59:
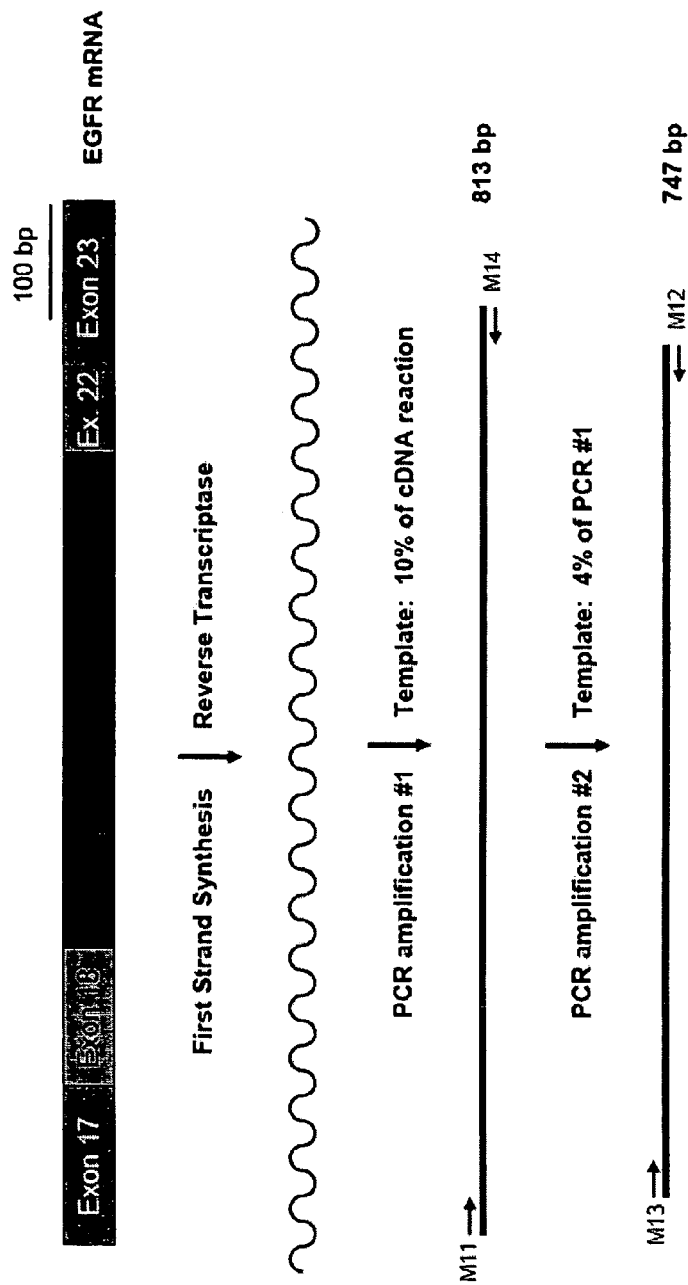
FIG. 59 is a schematic depiction of a process for generating EGFR sequencing templates. EGFR mRNA is reverse transcribed to make cDNA; next, two PCR amplifications are performed sequentially.

Further details for each step outlined above are as follows.
1) Sequence CTC EGFR mRNA
 a) Purify CTCs from blood sample. CTCs are isolated using any of the size-based enrichment and/or affinity purification devices of the invention.
 b) Purify total RNA from CTCs. Total RNA is then purified from isolated CTC populations using, e.g., the Qiagen Micro RNeasy kit, or a similar total RNA purification protocol from another manufacturer; alternatively, standard RNA purification protocols such as guanidium isothiocyanate homogenization followed by phenol/chloroform extraction and ethanol precipitation may be used. One such method is described in "Molecular Cloning—A Laboratory Manual, Second Edition" (1989) by J. Sambrook, E. F. Fritch and T. Maniatis, p. 7.24.
 c) Convert RNA to cDNA using reverse transcriptase. cDNA reactions are carried out based on the protocols of the supplier of reverse transcriptase. Typically, the amount of input RNA into the cDNA reactions is in the range of 10 picograms (pg) to 2 micrograms (µg) total RNA. First-strand DNA synthesis is carried out by hybridizing random 7mer DNA primers, or oligo-dT primers, or gene-specific primers, to RNA templates at 65° C. followed by snap-chilling on ice cDNA synthesis is initiated by the addition of iScript Reverse Transcriptase (BioRad) or SuperScript Reverse Transcriptase (Invitrogen) or a reverse transcriptase from another commercial vendor along with the appropriate enzyme reaction buffer. For iScript, reverse transcriptase reactions are carried out at 42° C. for 30-45 minutes, followed by enzyme inactivation for 5 minutes at 85° C. cDNA is stored at −20° C. until use or used immediately in PCR reactions. Typically, cDNA reactions are carried out in a final volume of 20 µl, and 10% (2 µl) of the resultant cDNA is used in subsequent PCR reactions.
 d) Use resultant cDNA to perform first and second PCR reactions for generating sequencing templates. cDNA from the reverse transcriptase reactions is mixed with DNA primers specific for the region of interest (FIG. 59). See Table 3 for sets of primers that may be used for amplification of exons 18-21. In Table 3, primer set M13(+)/M12(−) is internal to primer set M11(+)/M14(−). Thus primers M13(+) and M12(−) may be used in the nested round of amplification, if primers M11(+) and M14(−) were used in the first round of expansion. Similarly, primer set M11(+)/M14(−) is internal to primer set M15(+)/M16(−), and primer set M23(+)/M24(−) is internal to primer set M21(+)/M22(−). Hot Start PCR reactions are performed using Qiagen Hot-Star Taq Polymerase kit, or Applied Biosystems HotStart TaqMan polymerase, or, other Hot Start thermostable polymerase, or without a hot start using Promega GoTaq Green Taq Polymerase master mix, TaqMan DNA polymerase, or other thermostable DNA polymerase. Typically, reaction volumes are 50 µl, nucleotide triphosphates are present at a final concentration of 200 µM for each nucleotide, $MgCl_2$ is present at a final concentration of 1-4 mM, and oligo primers are at a final concentration of 0.5 µM. Hot start protocols begin with a 10-15 minute incubation at 95° C., followed by 40 cycles of 94° C. for one minute (denaturation), 52° C. for one minute (annealing), and 72° C. for one minute (extension). A 10 minute terminal extension at 72° C. is performed before samples are stored at 4° C. until they are either used as template in the second (nested) round of PCRs, or purified using QiaQuick Spin Columns (Qiagen) prior to sequencing. If a hot-start protocol is not used, the initial incubation at 95° C. is omitted. If a PCR product is to be used in a second round of PCRs, 2 µl (4%) of the initial PCR product is used as template in the second round reactions, and the identical reagent concentrations and cycling parameters are used.

TABLE 3

Primer Sets for expanding EGFR mRNA around Exons 18-21

| Name | SEQ ID NO | Sequence (5' to 3') | cDNA Coordinates | Amplicon Size |
|---|---|---|---|---|
| NXK-M11(+) | 1 | TTGCTGCTGGTGGT GGC | (+) 1966-1982 | 813 |
| NXK-M14(−) | 2 | CAGGGATTCCGTCA TATGGC | (−) 2778-2759 | |
| NXK-M13(+) | 3 | GATCGGCCTCTTCA TGCG | (+) 1989-2006 | 747 |
| NXK M12(−) | 4 | GATCCAAAGGTCAT CAACTCCC | (−) 2735-2714 | |
| NXK-M15(+) | 5 | GCTGTCCAACGAAT GGGC | (+) 1904-1921 | 894 |
| NXK-M16(−) | 6 | GGCGTTCTCCTTTC TCCAGG | (−) 2797-2778 | |
| NXK-M21(+) | 7 | ATGCACTGGGCCAG GTCTT | (+) 1881-1899 | 944 |
| NXK-M22(−) | 8 | CGATGGTACATATG GGTGGCT | (−) 2824-2804 | |
| NXK-M23(+) | 9 | AGGCTGTCCAACGA ATGGG | (+) 1902-1920 | 904 |
| NXK-M24(−) | 10 | CTGAGGGAGGCGTT CTCCT | (−) 2805-2787 | | e) Purify the nested PCR amplicon and use as a sequencing template to sequence EGFR exons 18-21. Sequencing is performed by ABI automated fluorescent sequencing machines and fluorescence-labeled DNA sequencing ladders generated via Sanger-style sequencing reactions using fluorescent dideoxynucleotide mixtures. PCR products are purified using Qiagen QuickSpin columns, the Agencourt AMPure PCR Purification System, or PCR product purification kits obtained from other vendors. After PCR products are purified, the nucleotide concentration and purity is determined with a Nanodrop 7000 spectrophotometer, and the PCR product concentration is brought to a concentration of 25 ng/µl. As a quality control measure, only PCR products that have a UV-light absorbance ratio ($A_{260}/A_{280}$) greater than 1.8 are used for sequencing. Sequencing primers are brought to a concentration of 3.2 pmol/µl.

2) Confirm RNA sequence using CTC genomic DNA a) Purify CTCs from blood sample. As above, CTCs are isolated using any of the size-based enrichment and/or affinity purification devices of the invention.

b) Purify genomic DNA (gDNA) from CTCs. Genomic DNA is purified using the Qiagen DNeasy Mini kit, the Invitrogen ChargeSwitch gDNA kit, or another commercial kit, or via the following protocol:

1. Cell pellets are either lysed fresh or stored at −80° C. and are thawed immediately before lysis.
2. Add 500 µl 50 mM Tris pH 7.9/100 mM EDTA/0.5% SDS (TES buffer).
3. Add 12.5 µl Proteinase K (IBI5406, 20 mg/ml), generating a final [ProtK]=0.5 mg/ml.
4. Incubate at 55° C. overnight in rotating incubator.
5. Add 20 µl of RNase cocktail (500 U/ml RNase A+20,000 U/ml RNase T1, Ambion #2288) and incubate four hours at 37° C.
6. Extract with Phenol (Kodak, Tris pH 8 equilibrated), shake to mix, spin 5 min. in tabletop centrifuge.
7. Transfer aqueous phase to fresh tube.
8. Extract with Phenol/Chloroform/Isoamyl alcohol (EMD, 25:24:1 ratio, Tris pH 8 equilibrated), shake to mix, spin five minutes in tabletop centrifuge.
9. Add 50 µl 3M NaOAc pH=6.
10. Add 500 µl EtOH.
11. Shake to mix. Strings of precipitated DNA may be visible. If anticipated DNA concentration is very low, add carrier nucleotide (usually yeast tRNA).
12. Spin one minute at max speed in tabletop centrifuge.
13. Remove supernatant.
14. Add 500 µl 70% EtOH, Room Temperature (RT)
15. Shake to mix.
16. Spin one minute at max speed in tabletop centrifuge.
17. Air dry 10-20 minutes before adding TE.
18. Resuspend in 400 µl TE. Incubate at 65° C. for 10 minutes, then leave at RT overnight before quantitation on Nanodrop.

c) Amplify exons 18, 19, 20, and/or 21 via PCR reactions. Hot start nested PCR amplification is carried out as described above in step 1d, except that there is no nested round of amplification. The initial PCR step may be stopped during the log phase in order to minimize possible loss of allele-specific information during amplification. The primer sets used for expansion of EGFR exons 18-21 are listed in Table 4 (see also Paez et al., Science 304:1497-1500 (Supplementary Material) (2004)).

TABLE 4

Primer sets for expanding EGFR genomic DNA

| Name | SEQ ID NO | Sequence (5' to 3') | Exon | Amplicon Size |
|---|---|---|---|---|
| NXK-ex18.1(+) | 11 | TCAGAGCCTGTGTTTCTACCAA | 18 | 534 |
| NXK-ex18.2(−) | 12 | TGGTCTCACAGGACCACTGATT | 18 | |
| NXK-ex18.3(+) | 13 | TCCAAATGAGCTGGCAAGTG | 18 | 397 |

TABLE 4-continued

Primer sets for expanding EGFR genomic DNA

Figure 60:
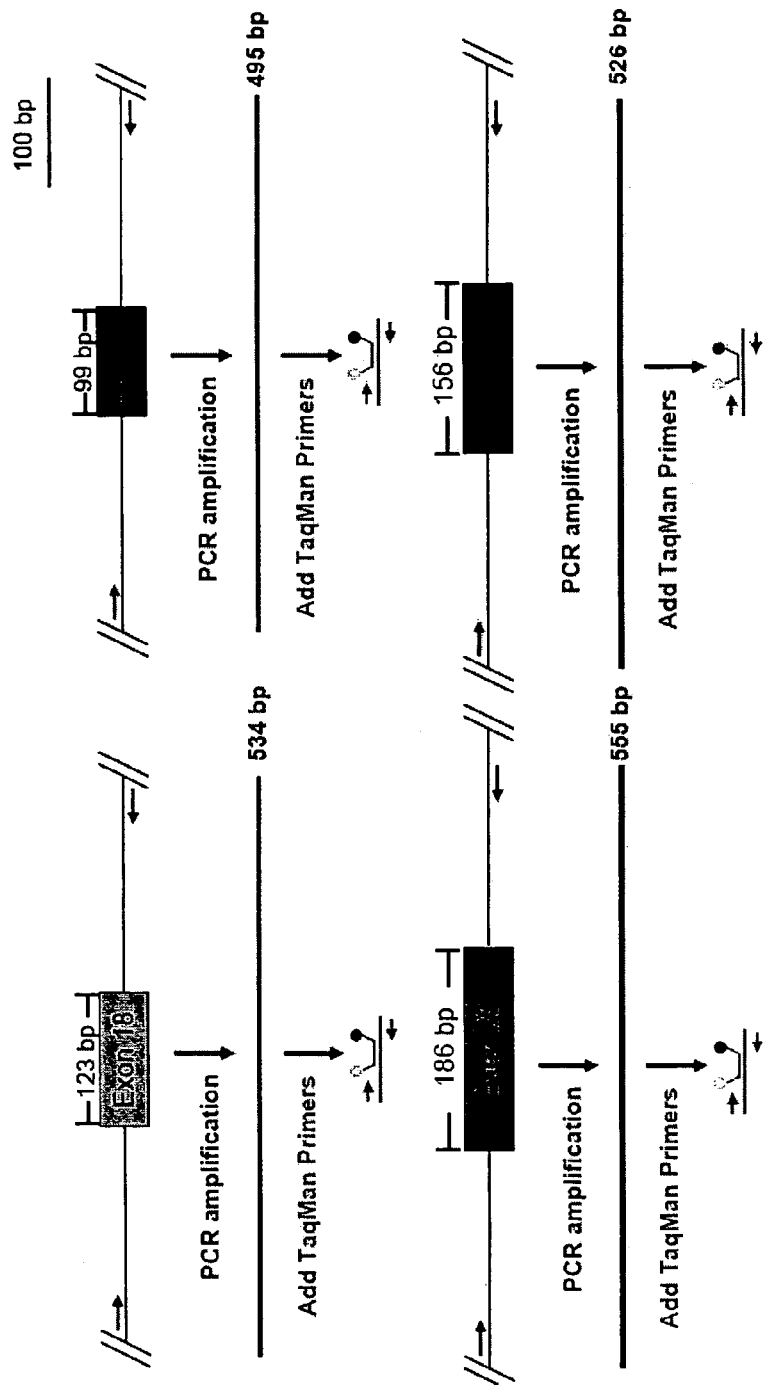
FIG. 60 is a schematic depiction of an allele-specific TaqMan 5' Nuclease Real Time PCR assay used to amplify EGFR subregions specific to particular mutations of interest.

| Name | SEQ ID NO | Sequence (5' to 3') | Exon | Amplicon Size |
|---|---|---|---|---|
| NXK-ex18.4(-) | 14 | TCCCAAACACTCAGTGAAACAAA | 18 | |
| NXK-ex19.1(+) | 15 | AAATAATCAGTGTGATTCGTGGAG | 19 | 495 |
| NXK-ex19.2(-) | 16 | GAGGCCAGTGCTGTCTCTAAGG | 19 | |
| NXK-ex19.3(+) | 17 | GTGCATCGCTGGTAACATCC | 19 | 298 |
| NXK-ex19.4(-) | 18 | TGTGGAGATGAGCAGGGTCT | 19 | |
| NXK-ex20.1(+) | 19 | ACTTCACAGCCCTGCGTAAAC | 20 | 555 |
| NXK-ex20.2(-) | 20 | ATGGGACAGGCACTGATTTGT | 20 | |
| NXK-ex20.3(+) | 21 | ATCGCATTCATGCGTCTTCA | 20 | 379 |
| NXK-ex20.4(-) | 22 | ATCCCCATGGCAAACTCTTG | 20 | |
| NXK-ex21.1(+) | 23 | GCAGCGGGTTACATCTTCTTTC | 21 | 526 |
| NXK-ex21.2(-) | 24 | CAGCTCTGGCTCACACTACCAG | 21 | |
| NXK-ex21.3(+) | 25 | GCAGCGGGTTACATCTTCTTTC | 21 | 349 |
| NXK-ex21.4(-) | 26 | CATCCTCCCCTGCATGTGT | 21 | | d) Use the resulting PCR amplicon(s) in real-time quantitative allele-specific PCR reactions in order to confirm the sequence of mutations discovered via RNA sequencing. An aliquot of the PCR amplicons is used as template in a multiplexed allele-specific quantitative PCR reaction using TaqMan PCR 5' Nuclease assays with an Applied Biosystems model 7500 Real Time PCR machine (FIG. 60). This round of PCR amplifies subregions of the initial PCR product specific to each mutation of interest. Given the very high sensitivity of Real Time PCR, it is possible to obtain complete information on the mutation status of the EGFR gene even if as few as 10 CTCs are isolated. Real Time PCR provides quantification of allelic sequences over 8 logs of input DNA concentrations; thus, even heterozygous mutations in impure populations are easily detected using this method.

Probe and primer sets are designed for all known mutations that affect gefitinib responsiveness in NSCLC patients, including over 40 such somatic mutations, including point mutations, deletions, and insertions, that have been reported in the medical literature. For illustrative purposes, examples of primer and probe sets for five of the point mutations are listed in Table 5. In general, oligonucleotides may be designed using the primer optimization software program Primer Express (Applied Biosystems), with hybridization conditions optimized to distinguish the wild type EGFR DNA sequence from mutant alleles. EGFR genomic DNA amplified from lung cancer cell lines that are known to carry EGFR mutations, such as H358 (wild type), H1650 (15-bp deletion, Δ2235-2249), and H1975 (two point mutations, 2369 C→T, 2573 T→G), is used to optimize the allele-specific Real Time PCR reactions. Using the TaqMan 5' nuclease assay, allele-specific labeled probes specific for wild type sequence or for known EGFR mutations are developed. The oligonucleotides are designed to have melting temperatures that easily distinguish a match from a mismatch, and the Real Time PCR conditions are optimized to distinguish wild type and mutant alleles. All Real Time PCR reactions are carried out in triplicate.

Initially, labeled probes containing wild type sequence are multiplexed in the same reaction with a single mutant probe. Expressing the results as a ratio of one mutant allele sequence versus wild type sequence may identify samples containing or lacking a given mutation. After conditions are optimized for a given probe set, it is then possible to multiplex probes for all of the mutant alleles within a given exon within the same Real Time PCR assay, increasing the ease of use of this analytical tool in clinical settings.

Figure 61:
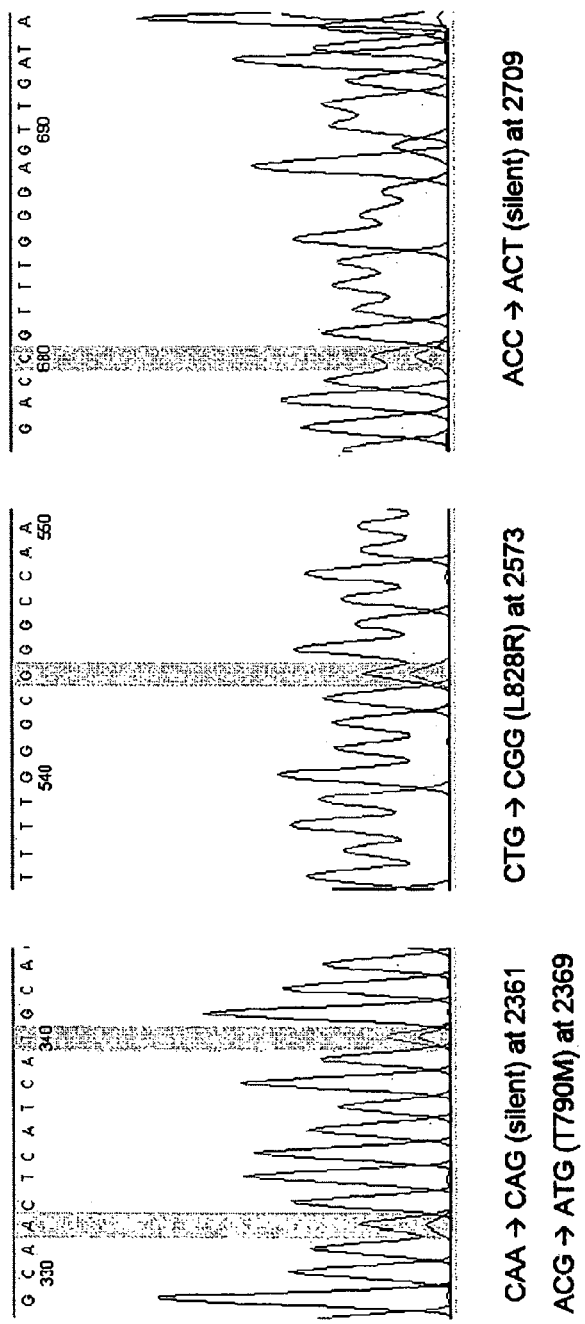
FIG. 61 is a set of sequencing charts showing the detection of several EGFR mutations (shaded regions) above the background level of fluorescence.

A unique probe is designed for each wild type allele and mutant allele sequence. Wild-type sequences are marked with the fluorescent dye VIC at the 5' end, and mutant sequences with the fluorophore FAM. A fluorescence quencher and Minor Groove Binding moiety are attached to the 3' ends of the probes. ROX is used as a passive reference dye for normalization purposes. A standard curve is generated for wild type sequences and is used for relative quantitation. Precise quantitation of mutant signal is not required, as the input cell population is of unknown, and varying, purity. The assay is set up as described by ABI product literature, and the presence of a mutation is confirmed when the signal from a mutant allele probe rises above the background level of fluorescence (FIG. 61), and this threshold cycle gives the relative frequency of the mutant allele in the input sample.

TABLE 5

Probes and Primers for Allele-Specific qPCR

| Name | SEQ ID NO | Sequence (5' to 3', mutated position in bold) | cDNA Coordinates | Description | Mutation |
|---|---|---|---|---|---|
| NXK-M01 | 27 | CCGCAGCATGTCAAGATCAC | (+) 2542-2561 | (+) primer | L858R |
| NXK-M02 | 28 | TCCTTCTGCATGGTATTCTTTCTCT | (-) 2619-2595 | (-) primer | |
| Pwt-L858R | 29 | VIC-TTTGGGCTGGCCAA-MGB | (+) 2566-2579 | WT allele probe | |

TABLE 5-continued

Probes and Primers for Allele-Specific qPCR

| Name | SEQ ID NO | Sequence (5' to 3', mutated position in bold) | cDNA Coordinates | Description | Mutation |
|---|---|---|---|---|---|
| Pmut-L858R | 30 | FAM-TTTTGGGCGGGCCA-MGB | (+) 2566-2579 | Mutant allele probe | |
| NXK-M03 | 31 | ATGGCCAGCGTGGACAA | (+) 2296-2312 | (+) primer | T790M |
| NXK-M04 | 32 | AGCAGGTACTGGGAGCCAATATT | (-) 2444-2422 | (-) primer | |
| Pwt-T790M | 33 | VIC-ATGAGCTGCGTGATGA-MGB | (-) 2378-2363 | WT allele probe | |
| Pmut-T790M | 34 | FAM-ATGAGCTGCATGATGA-MGB | (-) 2378-2363 | Mutant allele probe | |
| NXK-M05 | 35 | GCCTCTTACACCCAGTGGAGAA | (+) 2070-2091 | (+) primer | G719S,C |
| NXK-M06 | 36 | TTCTGGGATCCAGAGTCCCTTA | (-) 2202-2181 | (-) primer | |
| Pwt-G719SC | 37 | VIC-ACCGGAGCCCAGCA-MGB | (-) 2163-2150 | WT allele probe | |
| Pmut-G719S | 38 | FAM-ACCGGAGCTCAGCA-MGB | (-) 2163-2150 | Mutant allele probe | |
| Pmut-G719C | 39 | FAM-ACCGGAGCACAGCA-MGB | (-) 2163-2150 | Mutant allele probe | |
| NXK-M09 | 40 | TCGCAAAGGGCATGAACTACT | (+) 2462-2482 | (+) primer | H835L |
| NXK-M10 | 41 | ATCTTGACATGCTGCGGTGTT | (-) 2558-2538 | (-) primer | |
| Pwt-H835L | 42 | VIC-TTGGTGCACCGCGA-MGB | (+) 2498-2511 | WT allele probe | |
| Pmut-H835L | 43 | FAM-TGGTGCTCCGCGAC-MGB | (+) 2498-2511 | Mutant allele probe | |

Example 5

Absence of EGFR Expression in Leukocytes

The protocol of Example 4 would be most useful if EGFR were expressed in target cancer cells but not in background leukocytes. To test whether EGFR mRNA is present in leukocytes, several PCR experiments were performed. Four sets of primers, shown in Table 6, were designed to amplify four corresponding genes:

1) BCKDK (branched-chain a-ketoacid dehydrogenase complex kinase)—a "housekeeping" gene expressed in all types of cells, a positive control for both leukocytes and tumor cells;

2) CD45—specifically expressed in leukocytes, a positive control for leukocytes and a negative control for tumor cells;

3) EpCAM—specifically expressed in epithelial cells, a negative control for leukocytes and a positive control for tumor cells; and 4) EGFR—the target mRNA to be examined.

TABLE 6

| Name | SEQ ID NO | Sequence (5' to 3') | Description | Amplicon Size |
|---|---|---|---|---|
| BCKD_1 | 44 | AGTCAGGACCCATGCACGG | BCKDK (+) primer | 273 |
| BCKD_2 | 45 | ACCCAAGATGCAGCAGTGTG | BCKDK (-) primer | |
| CD_1 | 46 | GATGTCCTCCTTGTTCTACTC | CD45 (+) primer | 263 |
| CD_2 | 47 | TACAGGGAATAATCGAGCATGC | CD45 (-) primer | |
| EpCAM_1 | 48 | GAAGGGAAATAGCAAATGGACA | EpCAM (+) primer | 222 |
| EpCAM_2 | 49 | CGATGGAGTCCAAGTTCTGG | EpCAM (-) primer | |
| EGFR_1 | 50 | AGCACTTACAGCTCTGGCCA | EGFR (+) primer | 371 |

TABLE 6-continued

| Name | SEQ ID NO | Sequence (5' to 3') | Description | Amplicon Size |
|---|---|---|---|---|
| EGFR_2 | 51 | GACTGAACATAACTGTAGG CTG | EGFR (-) primer | |

Figure 62A:
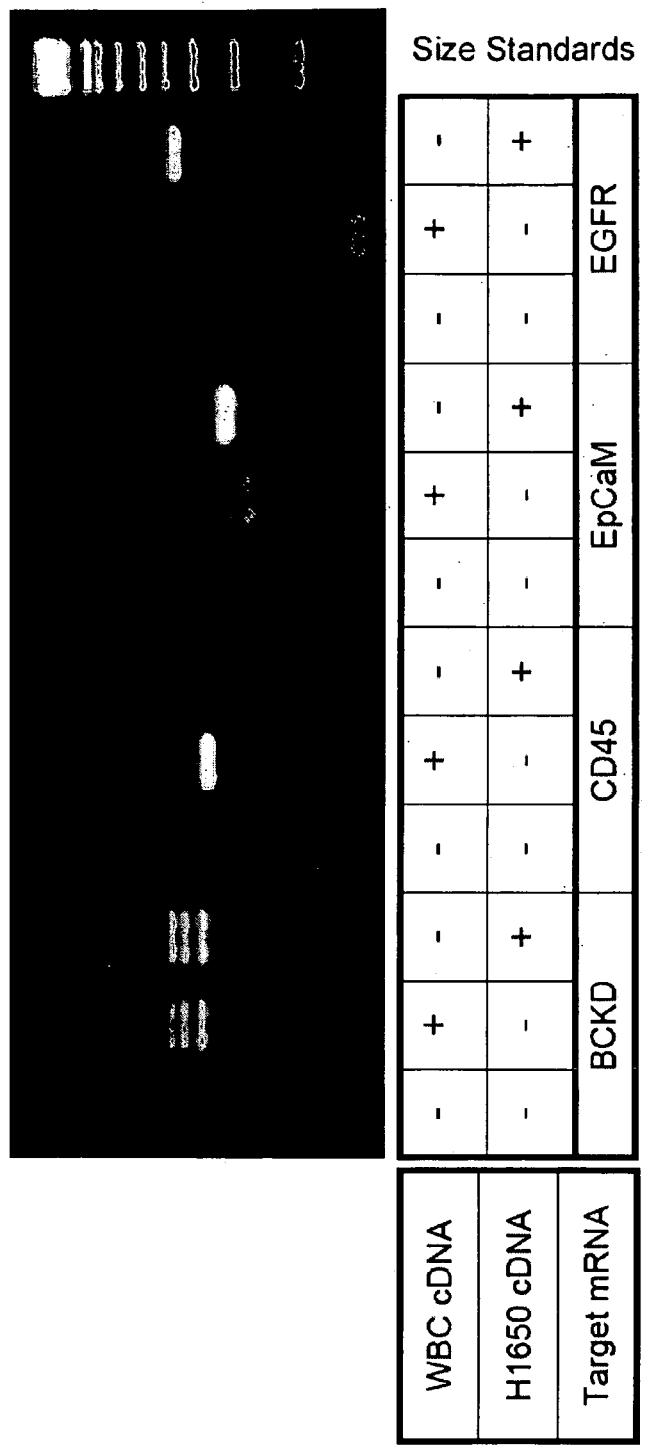
FIG. 62A is an image of an agarose gel showing that EpCAM and EGFR are expressed in tumor cells but not in leukocytes. BCKDK is expressed in both types of cells, while CD45 is expressed only in leukocytes.
Figure 62B:
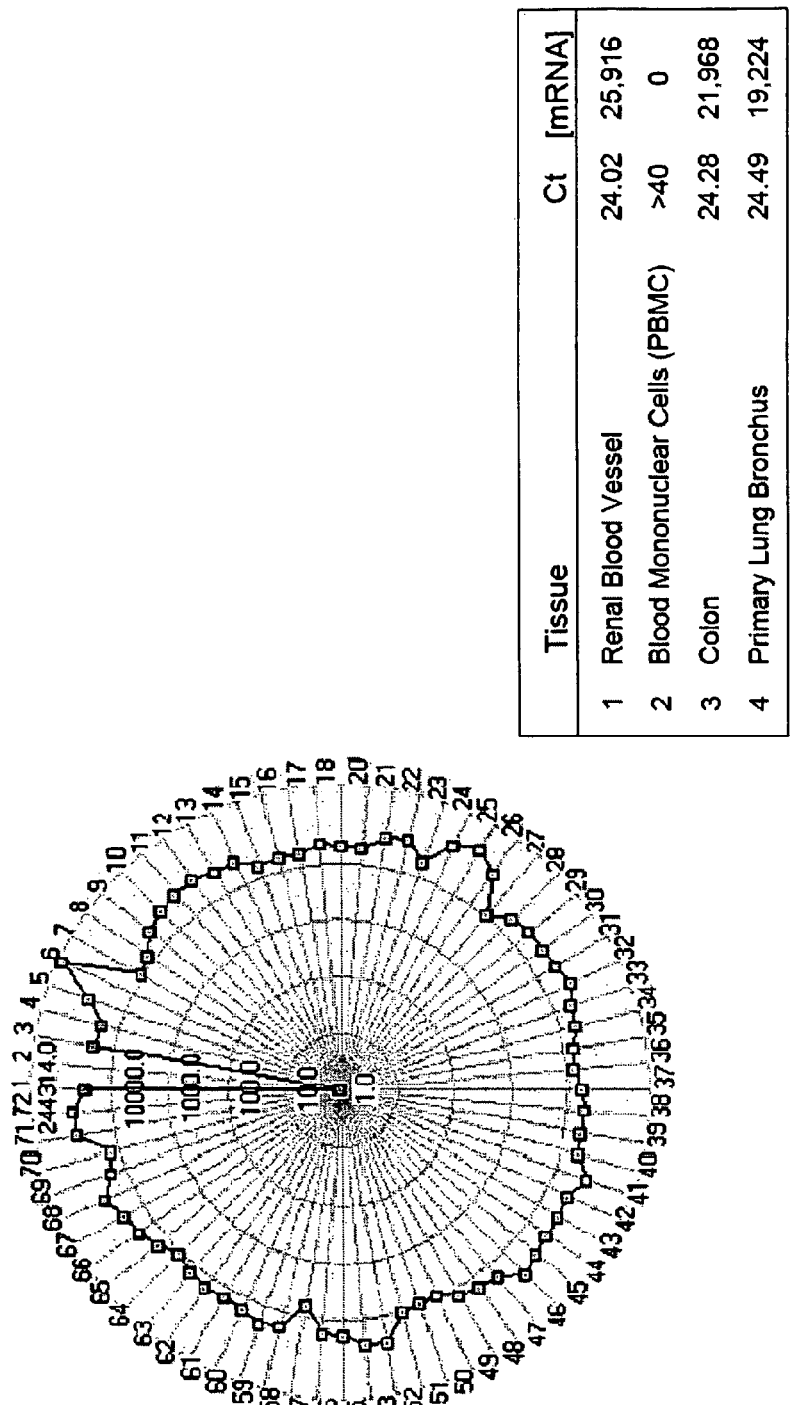
FIG. 62B is a graph and table showing a Pharmagene XpressWay™ profile of EGFR mRNA expression. Expression levels are profiled in 72 tissues via quantitative RT-PCR, and >10,000 copies per cell are detected in almost every tissue profiled except for blood. The table shows quantitation of mRNA for tissues #1-4 from the graph.

Total RNAs of approximately 9×10$^6$ leukocytes isolated using a cell enrichment device of the invention (cutoff size 4 µm) and 5×10$^6$ H1650 cells were isolated by using RNeasy mini kit (Qiagen). Two micrograms of total RNAs from leukocytes and H1650 cells were reverse transcribed to obtain first strand cDNAs using 100 pmol random hexamer (Roche) and 200 U Superscript II (Invitrogen) in a 20 µl reaction. The subsequent PCR was carried out using 0.5 µl of the first strand cDNA reaction and 10 pmol of forward and reverse primers in total 25 µl of mixture. The PCR was run for 40 cycles of 95° C. for 20 seconds, 56° C. for 20 seconds, and 70° C. for 30 seconds. The amplified products were separated on a 1% agarose gel. As shown in FIG. 62A, BCKDK was found to be expressed in both leukocytes and H1650 cells; CD45 was expressed only in leukocytes; and both EpCAM and EGFR were expressed only in H1650 cells. These results, which are fully consistent with the profile of EGFR expression shown in FIG. 62B, confirmed that EGFR is a particularly useful target for assaying mixtures of cells that include both leukocytes and cancer cells, because only the cancer cells will be expected to produce a signal.

Example 6

Figure 63:
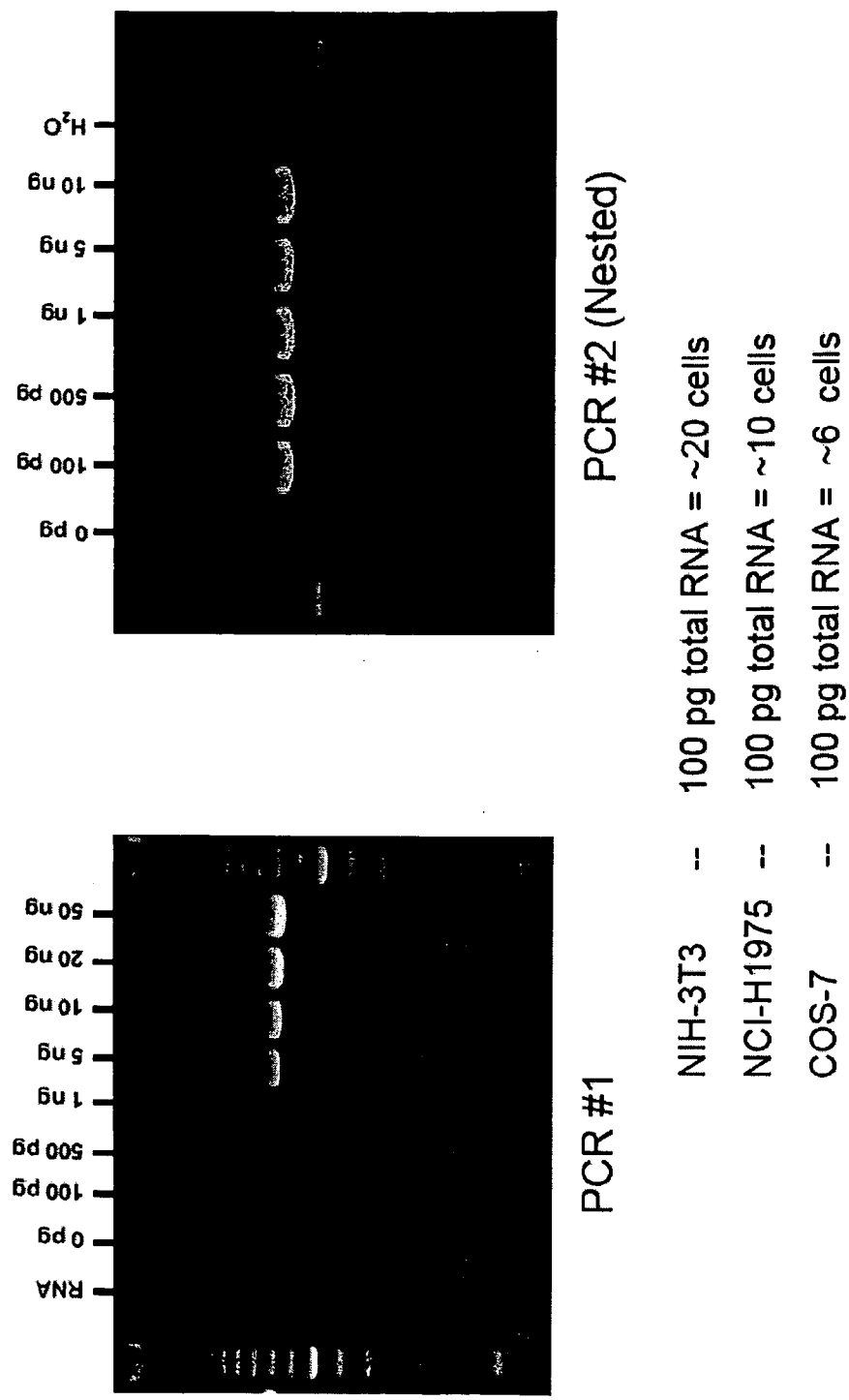
FIG. 63 is a pair of images of agarose gels showing the results of a two sets of PCR assays. In the first set (left), PCR is performed on EGFR input RNA at various concentrations. In the second set of assays, samples from the first set of PCR reactions are amplified with nested primers.

EGFR Assay with Low Quantities of Target RNA or High Quantities of Background RNA In order to determine the sensitivity of the assay described in Example 4, various quantities of input NSCLC cell line total RNA were tested, ranging from 100 pg to 50 ng. The results of the first and second EGFR PCR reactions (step 1$d$, Example 4) are shown in FIG. 63. The first PCR reaction was shown to be sufficiently sensitive to detect 1 ng of input RNA, while the second round increased the sensitivity to 100 pg or less of input RNA. This corresponds to 7-10 cells, demonstrating that even extremely dilute samples may generate detectable signals using this assay.

Figure 64A:
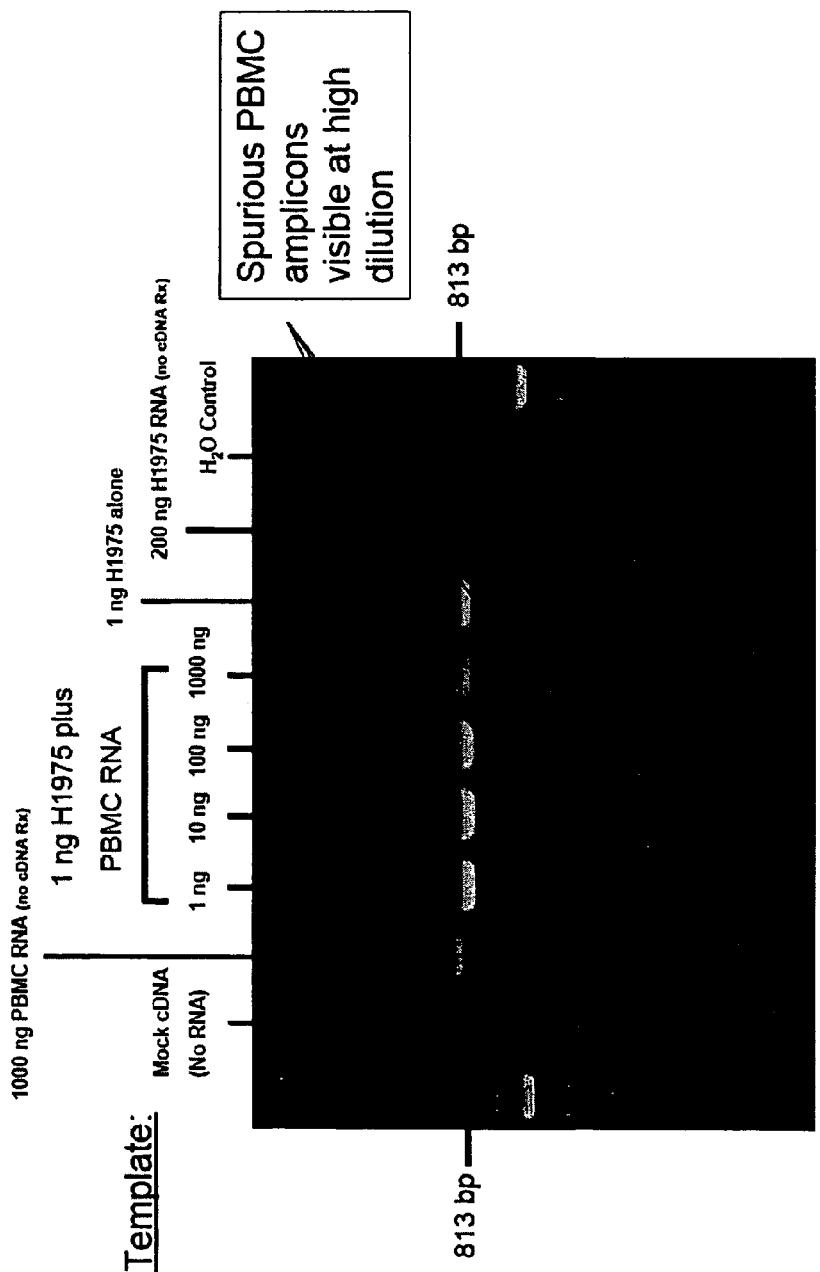
FIG. 64A is an image of an agarose gel showing the results of a set of PCR assays in which NCI-H1975 RNA is mixed with various quantities of peripheral blood mononuclear cell (PBMC) RNA and reverse transcribed prior to PCR. Spurious amplification bands are seen at the highest dilution.
Figure 64B:
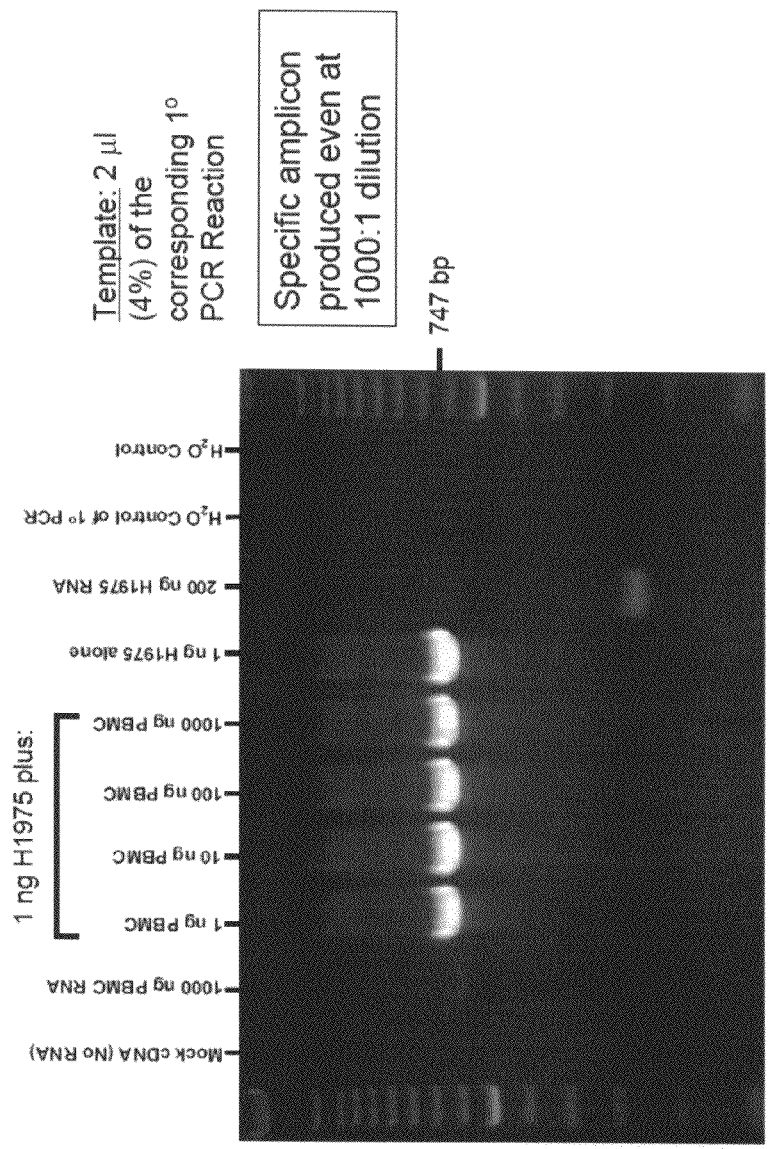
FIG. 64B is an image of an agarose gel showing the results of a set of PCR assays in which the samples shown in FIG. 64A are further amplified using nested primers. No spurious amplification bands are produced, even at the highest dilution.

Next, samples containing 1 ng of NCI-H1975 RNA were mixed with varying quantities of peripheral blood mononuclear cell (PBMC) RNA ranging from 1 ng to 1 µg and used in PCR reactions as before. As shown in FIG. 64A, the first set of PCR reactions demonstrated that, while amplification occurred in all cases, spurious bands appeared at the highest contamination level. However, as shown in FIG. 64B, after the second, nested set of PCR reactions, the desired specific amplicon was produced without spurious bands even at the highest contamination level. Therefore, this example demonstrates that the EGFR PCR assays described herein are effective even when the target RNA occupies a tiny fraction of the total RNA in the sample being tested.

Table 7 lists the RNA yield in a variety of cells and shows that the yield per cell is widely variable, depending on the cell type. This information is useful in order to estimate the amount of target and background RNA in a sample based on cell counts. For example, 1 ng of NCI-H1975 RNA corresponds to approximately 100 cells, while 1 µg of PBMC RNA corresponds to approximately 10$^6$ cells. Thus, the highest contamination level in the above-described experiment, 1,000:1 of PBMC RNA to NCL-H1975 RNA, actually corresponds to a 10,000:1 ratio of PBMCs to NCL-H1975 cells. Thus, these data indicate that EGFR may be sequenced from as few as 100 CTCs contaminated by as many as 10$^6$ leukocytes.

TABLE 7

RNA Yield versus Cell Type

| Cells | Count | RNA Yield | [RNA]/Cell |
|---|---|---|---|
| NCI-H1975 | 2 × 10$^6$ | 26.9 µg | 13.5 pg |
| NCI-H1650 | 2 × 10$^6$ | 26.1 µg | 13.0 pg |
| H358 | 2 × 10$^6$ | 26.0 µg | 13.0 pg |
| HT29 | 2 × 10$^6$ | 21.4 µg | 10.7 pg |
| MCF7 | 2 × 10$^6$ | 25.4 µg | 12.7 pg |
| PBMC #1 | 19 × 10$^6$ | 10.2 µg | 0.5 pg |
| PBMC #2 | 16.5 × 10$^6$ | 18.4 µg | 1.1 pg |

Figure 57C:
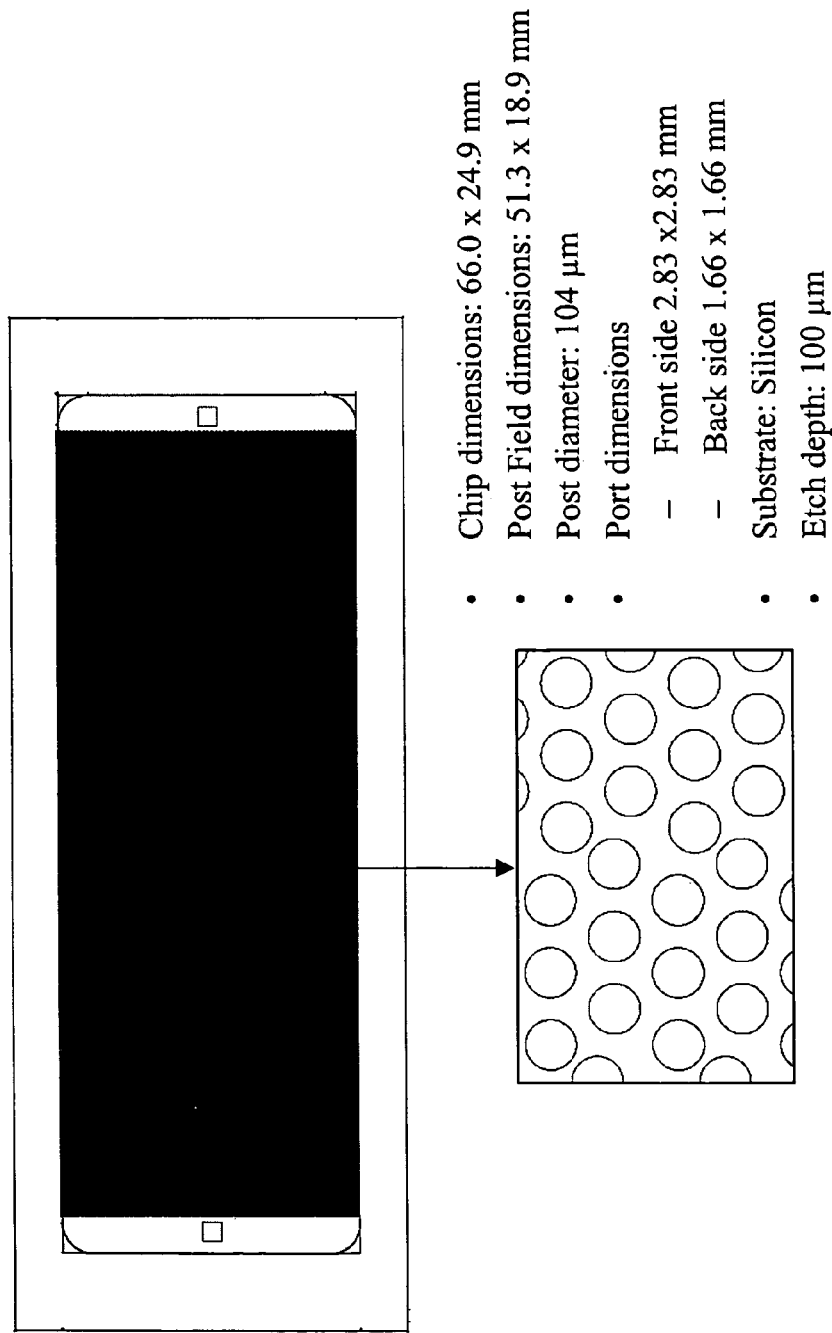
FIG. 57C is a mask design of a chip of the invention.
Figure 65:
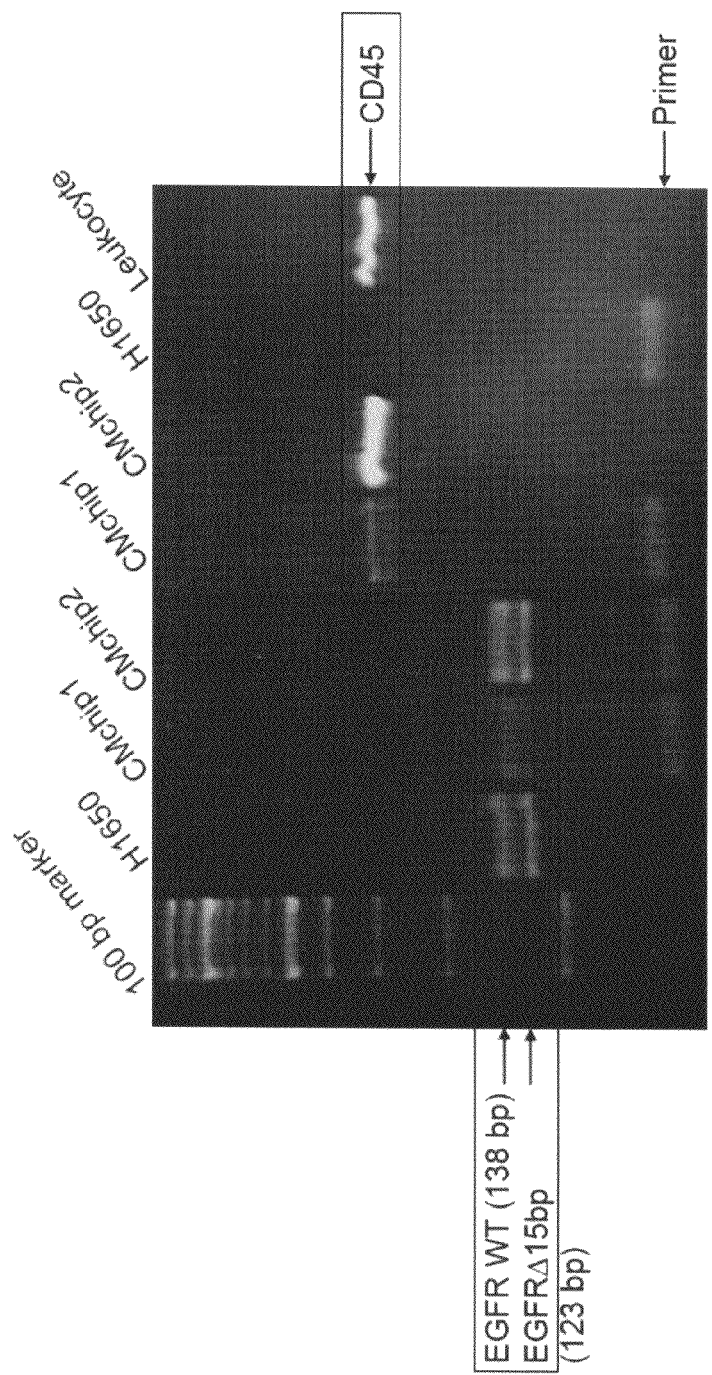
FIG. 65 is an image of an agarose gel showing the results of a set of PCR assays. In the associated experiment, whole blood spiked with H1650 cells was run on two devices of the invention, and cDNA was synthesized from the resulting enriched samples. PCR using EGFR and CD45 primers was performed. Both wild type (138 bp) and mutant (123 bp) EGFR bands are visible in the lanes showing EGFR-amplifications.

Next, whole blood spiked with 1,000 cells/ml of Cell Tracker (Invitrogen)-labeled H1650 cells was run through the capture module chip of FIG. 57C. To avoid inefficiency in RNA extraction from fixed samples, the captured H1650 cells were immediately counted after running and subsequently lysed for RNA extraction without formaldehyde fixation. Approximately 800 captured H1650 cells and >10,000 contaminated leukocytes were lysed on the chip with 0.5 ml of 4M guanidine thiocyanate solution. The lysate was extracted with 0.5 ml of phenol/chloroform and precipitated with 1 ml of ethanol in the presence of 10 µg of yeast tRNA as carrier. The precipitated RNAs were DNase I-treated for 30 minutes and then extracted with phenol/chloroform and precipitated with ethanol prior to first strand cDNA synthesis and subsequent PCR amplification. These steps were repeated with a second blood sample and a second chip. The cDNA synthesized from chip1 and chip2 RNAs along with H1650 and leukocyte cDNAs were PCR amplified using two sets of primers, CD45_1 and CD45_2 (Table 6) as well as EGFR_5 (forward primer, 5'-GTTCGGCACGGTG-TATAAGG-3') (SEQ ID NO: 52) and EGFR_6 (reverse primer, 5'-CTGGCCATCACGTAGGCTTC-3') (SEQ ID NO: 53). EGFR_5 and EGFR_6 produce a 138 bp wild type amplified fragment and a 123 bp mutant amplified fragment in H1650 cells. The PCR products were separated on a 2.5% agarose gel. As shown in FIG. 65, EGFR wild type and mutant amplified fragments were readily detected, despite the high leukocyte background, demonstrating that the EGFR assay is robust and does not require a highly purified sample.

Example 7

Protocol for Processing a Blood Sample Through an Enrichment Module Coupled to a Capture Module Using a sample of healthy blood spiked with tumor cells, a device of the invention containing an enrichment module coupled to a capture module was tested for the ability to enrich and capture tumor cells from blood.

To prepare the blood sample, a human non-small-cell lung cancer line, NCI-H1650 from ATCC) was stained with cell tracker orange (CMRA from Molecular Probes) and then spiked into fresh blood from a healthy patient (Research Blood Component). The spike level was 1,000 cells/ml. The spiked blood was diluted to a ratio of 2:1 (blood to buffer, 1% BSA in PBS). Both leukocytes and tumor cells were labeled with nuclear staining dye, Hoechst 33342; labeling the tumor cells with an additional stain, cell tracker orange, helped to distinguish tumor cells from leukocytes.

Next, the enrichment module manifold, chip, and tubing were set up, and the enrichment module chip was primed with degassed buffer. The spiked blood sample was run through the enrichment module at a pressure of 2.4 psi, and the flow rate of product was 6.91 ml/hr.

Prior to running the product through the capture module, the product was characterized. Taking into account the dilution factor in the product, the number of leukocytes per ml of equivalent whole blood was $7.02 \times 10^5$. The removal efficiency of leukocytes was 90%. The yield of tumor cells was 89.5%, and the purity of the tumor cells was 0.14%.

The product from the enrichment module was then run through the capture module, which contained anti-EpCAM-coated obstacles. The tumor cells expressing epithelial cell adhesion molecule were captured on the obstacles. The flow rate was 2.12 ml/hr, and the running time was one hour. The device was then washed with buffer at a higher flow rate, 3 ml/hr, to remove the nonspecifically-bound cells. The yield was 74%. The purity was not determined.

The results of these experiments are summarized in Table 8.

TABLE 8

| | Yield of enrichment module (%) | Number of leukocytes/ml of whole blood | Tumor cell purity (%) | Yield of capture module (%) | Number of leukocytes/ml of whole blood | Tumor cell purity (%) | Combined yield (%) |
|---|---|---|---|---|---|---|---|
| Enrichment module (V1) - capture module | 89 | $7.02 \times 10^5$ | 0.14 | 74 (2.12 ml/hr) | Not measured | N/A | 66 |

Example 8

Cell Capture Using Staggered Arrays

Figure 66A:
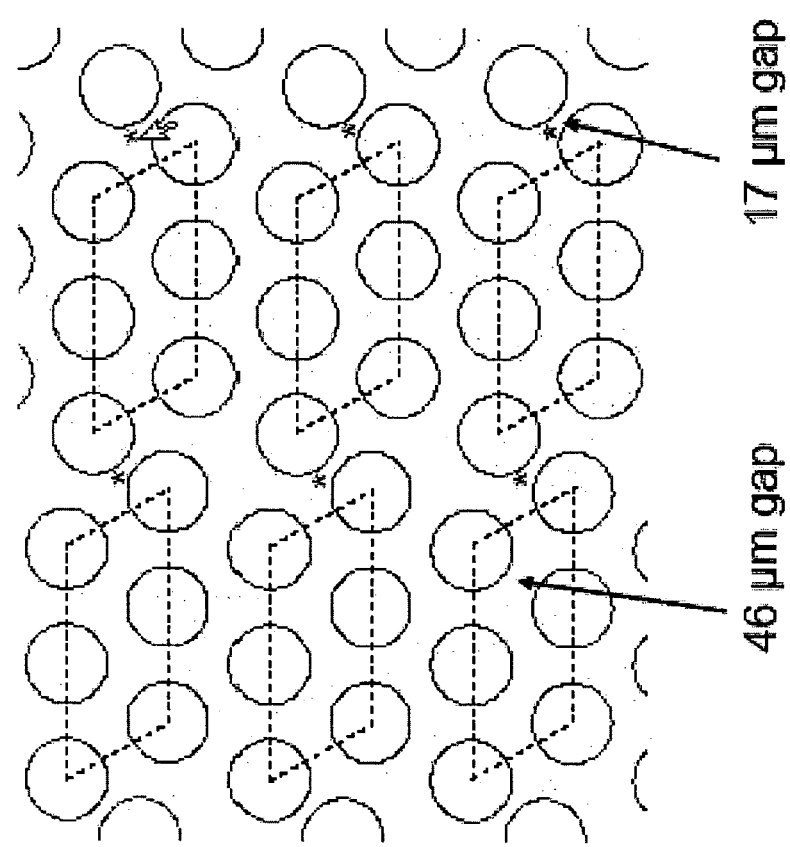
FIG. 66A is a schematic depiction of an array of the invention containing staggered subarrays.

In one embodiment of the invention, CTCs or other cells larger than a chosen cutoff size may be captured using a device that includes obstacles arranged in an array of subarrays. The subarrays are arrayed over the field with a slight stagger, or uneven spacing, initially designed in order to introduce variation in the flow lines and encourage the interaction of cells with the obstacles. One effect of this arrangement is that each subarray gives rise to a region in which the flow path is narrowed, as shown in FIG. 66A. In the array shown in the figure, the regular gap between obstacles is 46 µm, while the narrowed gap is 17 µm. The array and subarrays may be varied in order to result in any desirable gap sizes, as well as any desired density of narrowed gaps in relation to regular gaps.

Such a staggered array is particularly useful for preferential capture of CTCs in a blood sample, since CTCs tend to be larger than most other blood cells. CTCs or other large cells may be captured within the array without the need for a functionalized surface containing antibodies or other binding moieties, since cell capture is based on array geometry. Fabrication of such a device is therefore simplified.

Figure 66B:
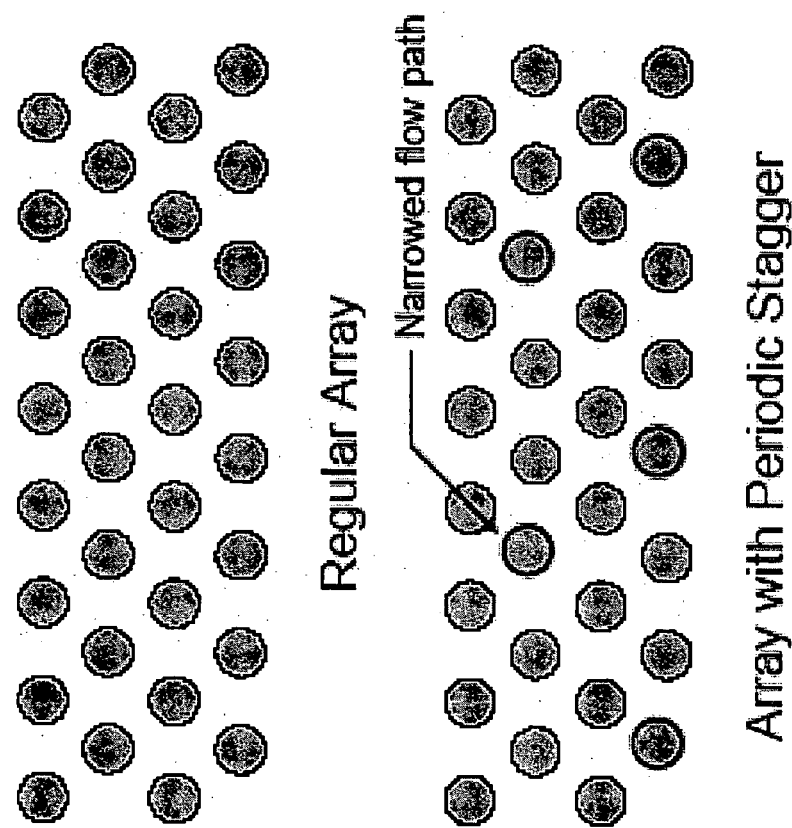
FIG. 66B is a schematic depiction contrasting a regular array with a staggered array.
Figure 66C:
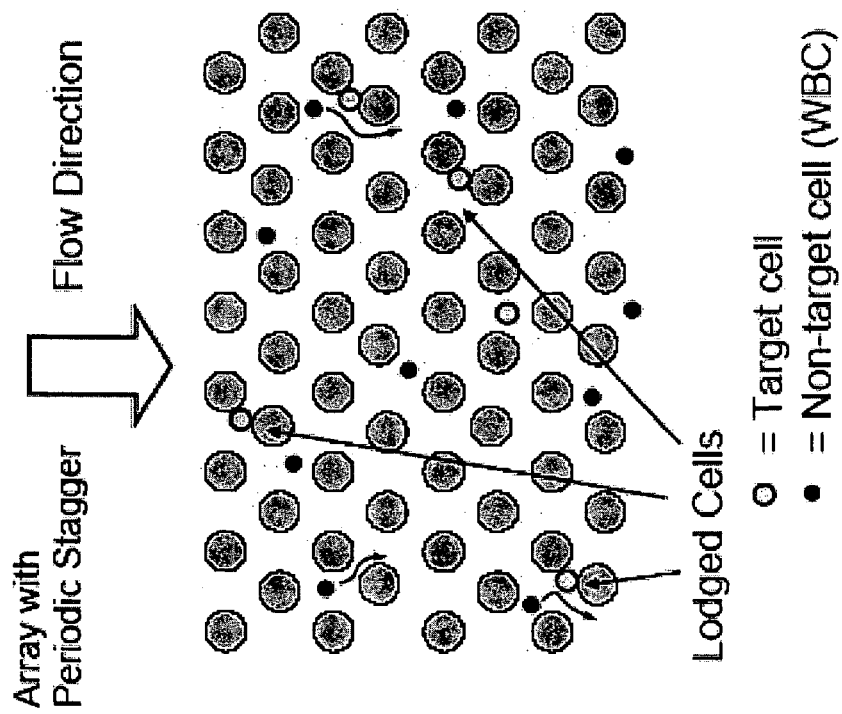
FIG. 66C is a schematic depiction showing the flow and capture of cells in a staggered array.

A staggered array of the invention is shown in FIG. 66B. Narrowed flow paths are dispersed regularly throughout the device, and these paths may be sized to capture cells of a given hydrodynamic size or larger, while allowing cells smaller than this cutoff size to flow through the array without being retained. If a large cell is lodged in a narrow flow path, thereby blocking it, smaller cells are still able to flow around via the unblocked larger flow paths, as shown in FIG. 66C. This design avoids the problem of clogging that may occur in a uniform array.

Desirably, the device is configured such that CTCs or other cells of interest are statistically likely to encounter and be trapped in the areas of narrowed gaps. Devices may be optimized for particular applications by varying the density of the restricted flow paths to alter the probability of capture of target cells.

Figure 66D:
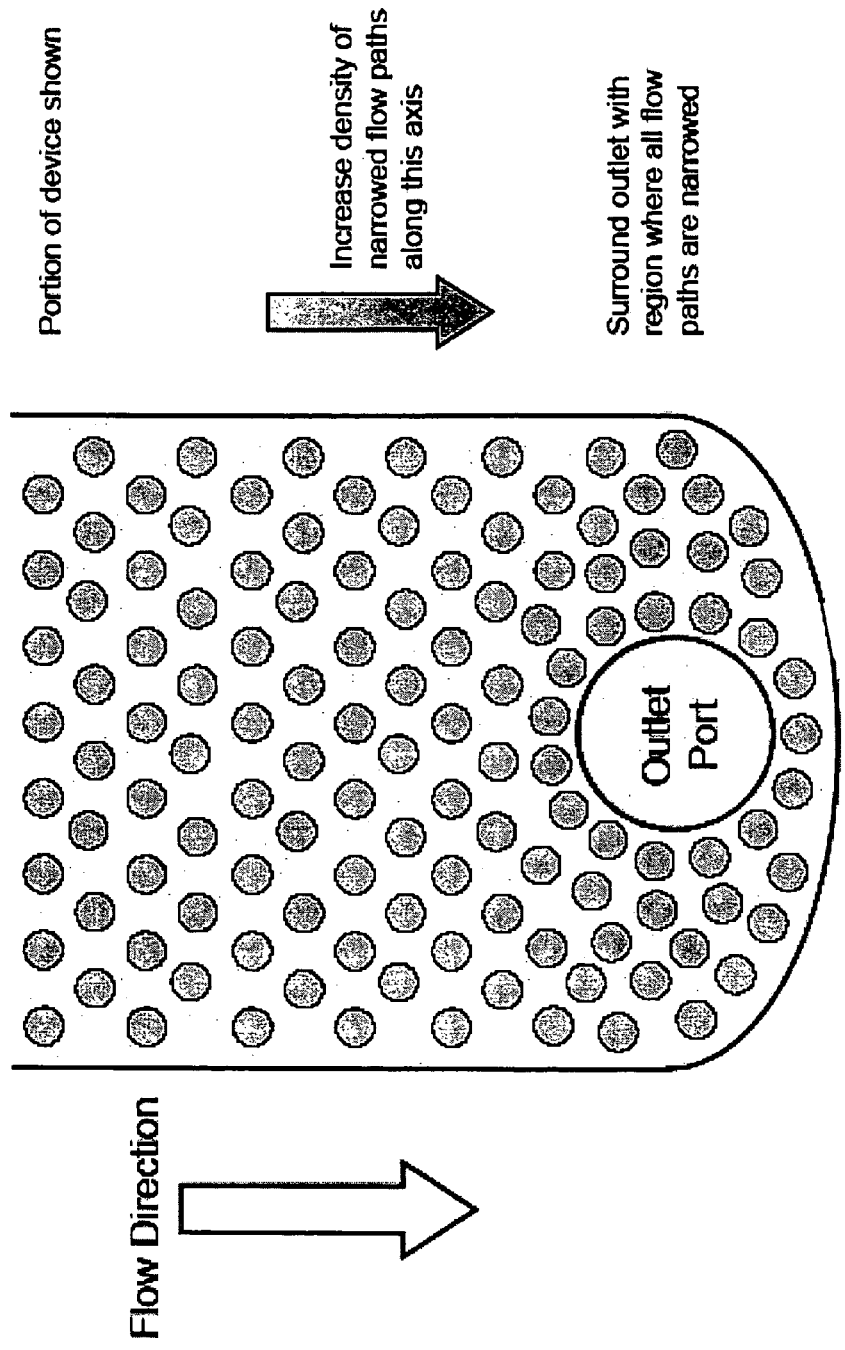
FIG. 66D is a schematic depiction showing a device containing an outlet port surrounded by a region of narrowed flow paths.

In one configuration, a larger percentage of flow paths near the device outlet may be designed to be narrow (FIG. 66D), thereby allowing for capture of any large cells that were not captured elsewhere in the array. Unless all available narrow gaps are occupied by target cells, clogging is still avoided in this configuration.

Figure 66E:
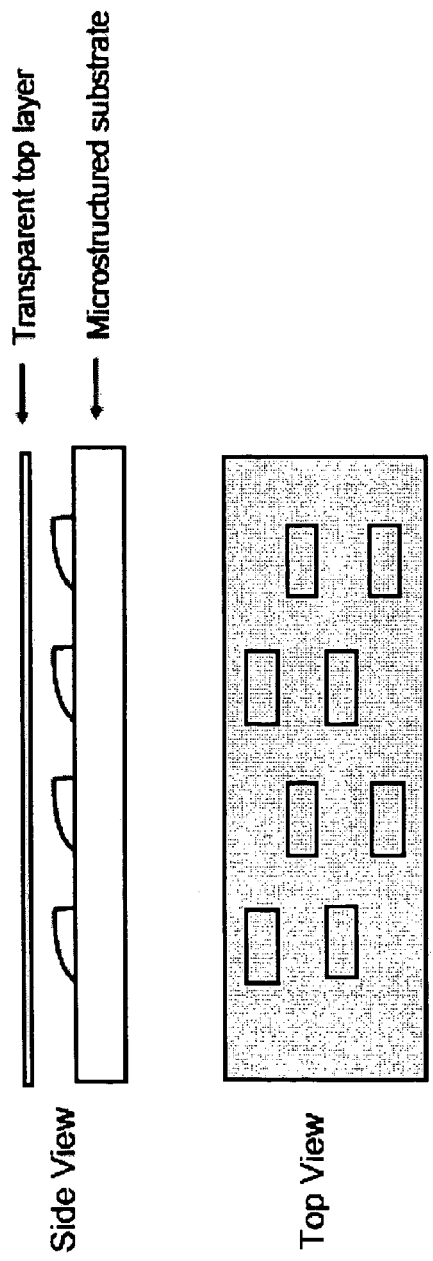
FIG. 66E is a schematic depiction of a device that is structured in the depth dimension to create narrowed flow paths.
Figure 66F:
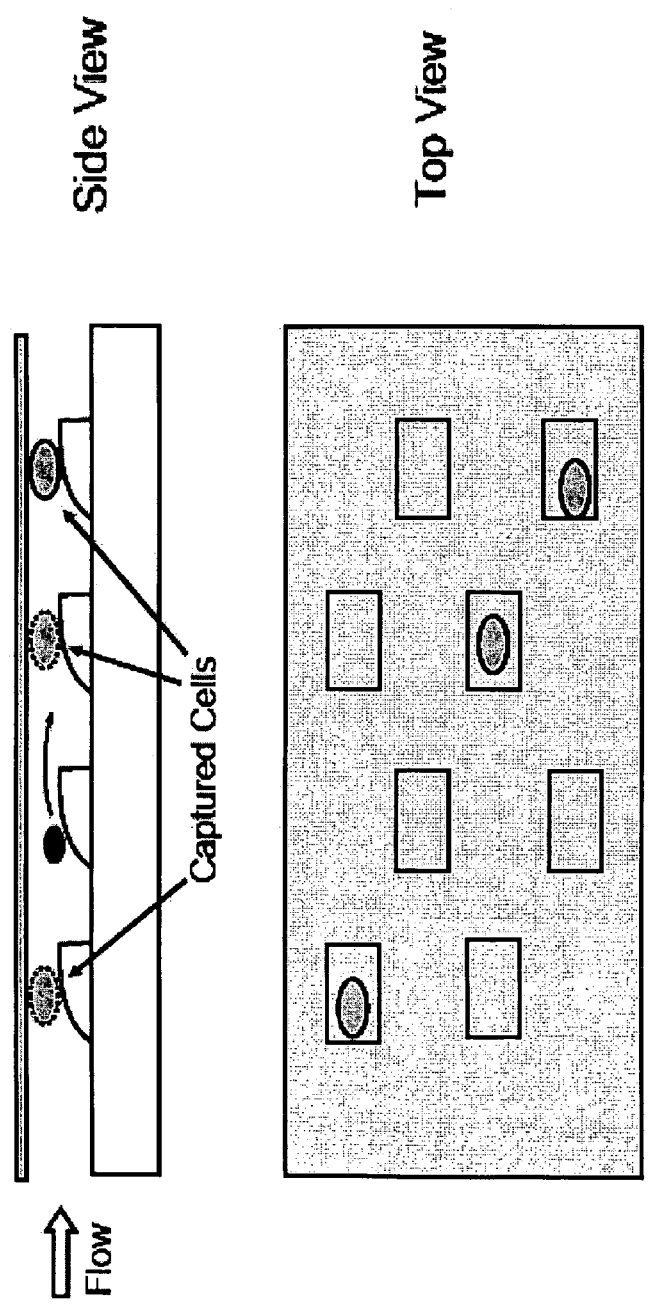
FIG. 66F is a schematic depiction of the device of FIG. 66E, showing captured cells.

Some devices of the invention have a relatively large depth dimension in order to accommodate high throughput of sample, whereas in other embodiments, the depth dimension is much smaller, with the result that captured cells are largely found in one focal plane and are easier to view under a microscope. In the device shown in FIG. 66E, the depth dimension is structured to create narrowed flow paths, resulting in capture of cells in a single focal plane (FIG. 66F). The captured cells are directly below the transparent window for simplified viewing. Fabrication of such devices may be achieved readily by a variety of means, e.g., injection molding or hot embossing of polymer substrates.

Once captured, cells may be released, e.g., by treatment with a hypotonic solution that causes the cells to shrink and be released from the device. Upon release and collection, cells may be returned to their original osmolarity and subjected to further analysis, e.g, molecular analysis. Alternatively, analysis may be conducted within the device without releasing the cells.

Example 9

Cell Capture of H1650 Cells Using Staggered Arrays

Figure 66G:
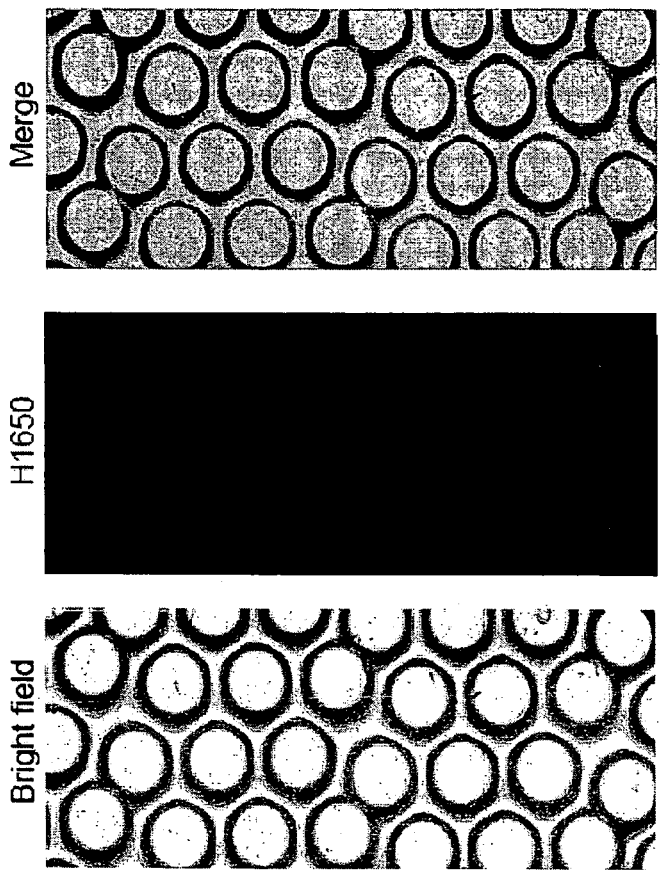
FIG. 66G is a set of microscope views showing stained H1650 cells captured in the narrow flow regions of a device of the invention.

A capture module chip (FIG. 57C) was used to process a sample of H1650 lung cancer cells. Parameters of the capture module are as follows: the chip dimensions are 66.0×24.9 mm; the obstacle field dimensions are 51.3×18.9 mm; the obstacle diameter is 104 µm; the port dimensions are 2.83×2.83 mm on the front side and 1.66×1.66 mm on the back side; the substrate is silicon; and the etch depth is 100 µm. The H1650 lung cancer cells were spiked at 10,000 cells/ml into buffy coat and run at 1.6 ml/hour (FIG. 66G). An estimated 12,700 H1650 cells passed through the device. The device contained approximately 7,230 capture locations in the active area. The yield of H1650 cells following the experiment was 16%, indicating that a substantial portion of available capture locations was occupied by H1650 cells.

Example 10

Size Distribution of Cancer Cells

Figure 67A:
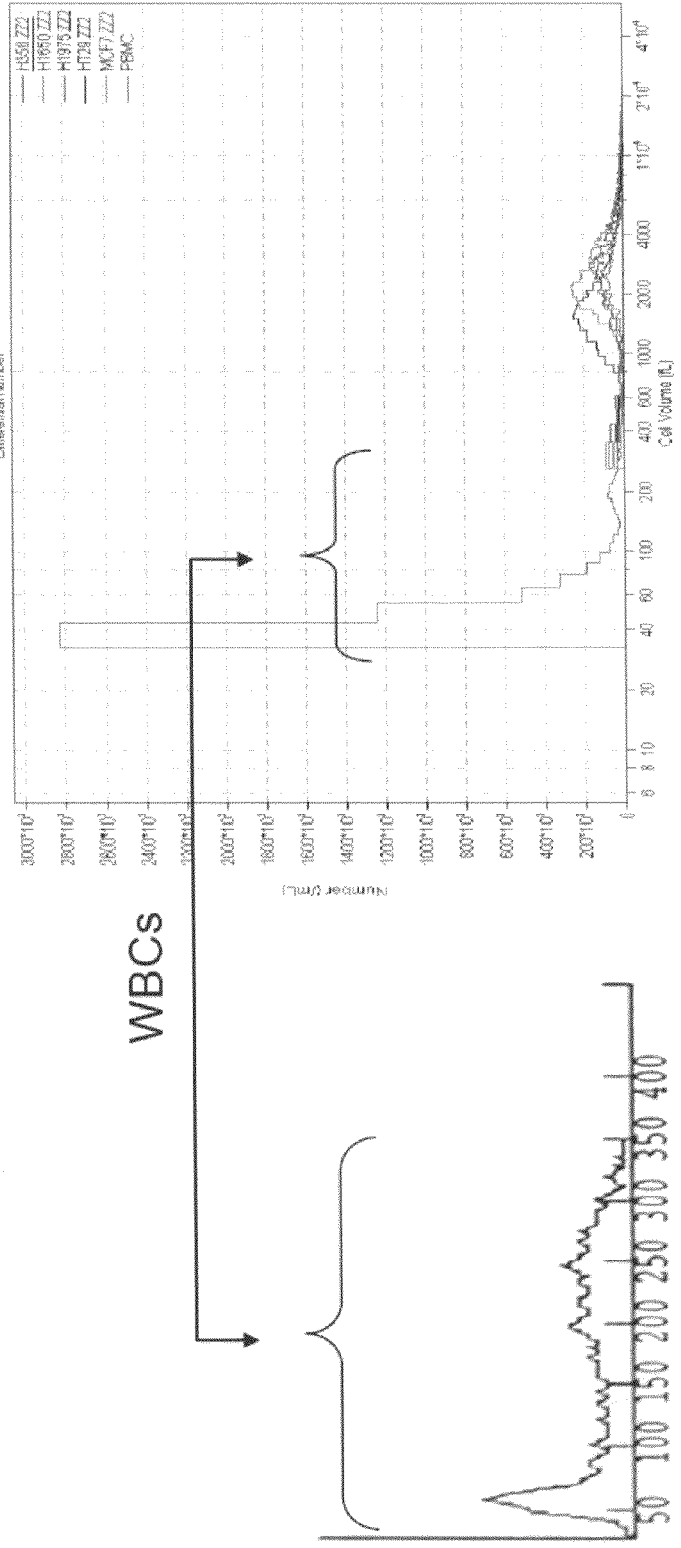
FIG. 67A is a chart and inset showing the size distribution of several cellular samples, including white blood cells and various cancer cell lines, as measured by a Beckman Coulter Z2 counting device. The main chart uses a logarithmic scale for the volume axis, while the inset uses a linear scale to better represent the distribution of white blood cells.
Figure 67B:
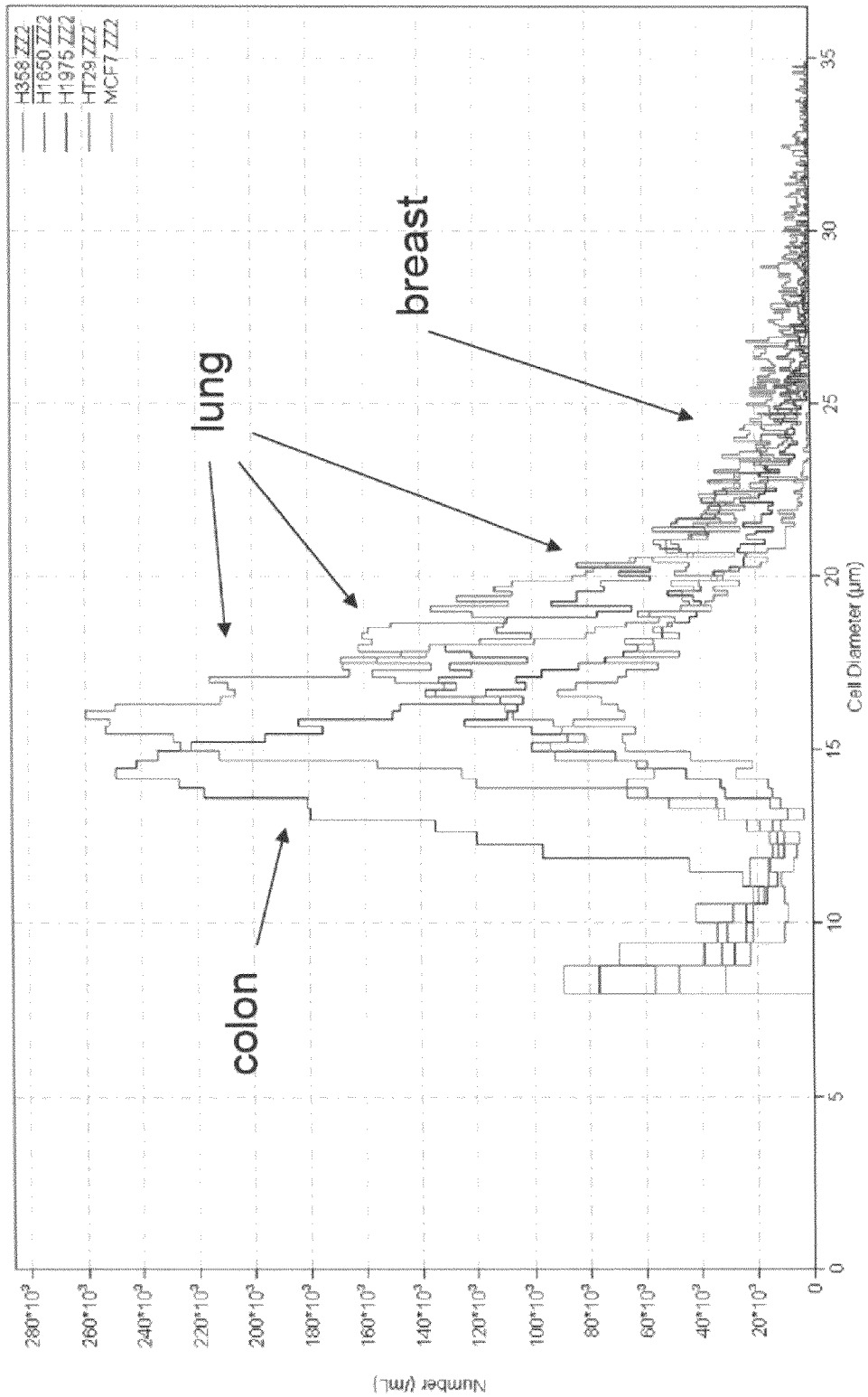
FIG. 67B is a chart showing the size distribution of several cancer cell lines.
Figure 67C:
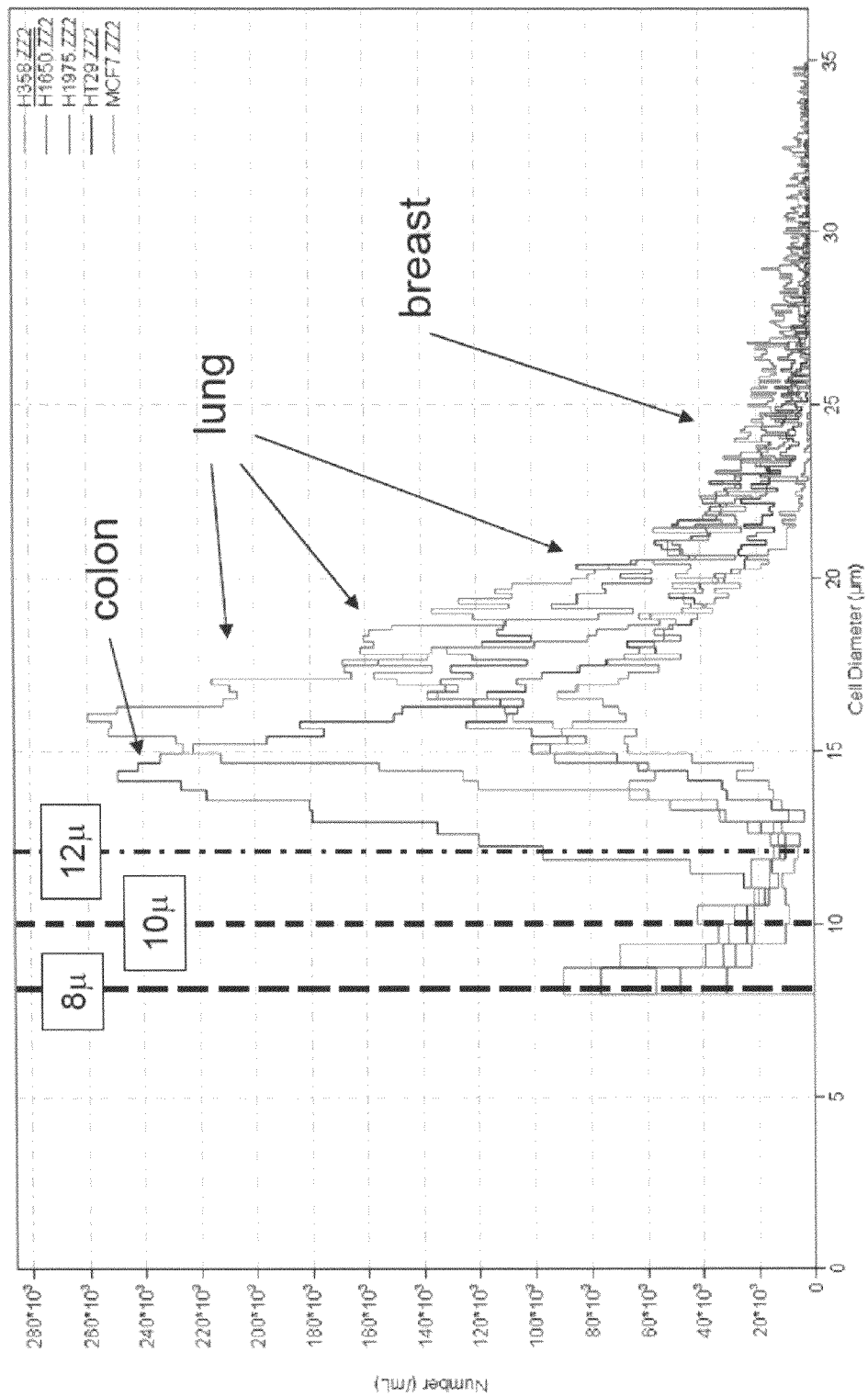
FIG. 67C is the chart of FIG. 67B, further showing three exemplary size cutoffs.

In order to determine the size distribution of cancer cells, several cancer cell lines were passed through a Beckman Coulter Model Z2 counting device (FIG. 67A). Cell lines that were tested in this experiment included H358, H1650, H1975, HT29, and MCF7 cells, which include colon, lung, and breast cancer cells. As FIG. 67A shows, each of these cell lines consists of cells that are larger than most white blood cells. The size distributions of each cancer cell line are similar to each other and are well-separated from the distribution of white blood cells shown. A closeup of the size distribution of the cancer cells (FIG. 67B) reveals a generally Gaussian distribution of cells in each case, with only a small minority of cells below 8, 10, or even 12 µm in size (FIG. 67C). These data offer strong support for the principle of enrichment of CTCs from other blood cells based on size.

Example 11

Capture Device Using a Microscope Slide

Figure 68A:
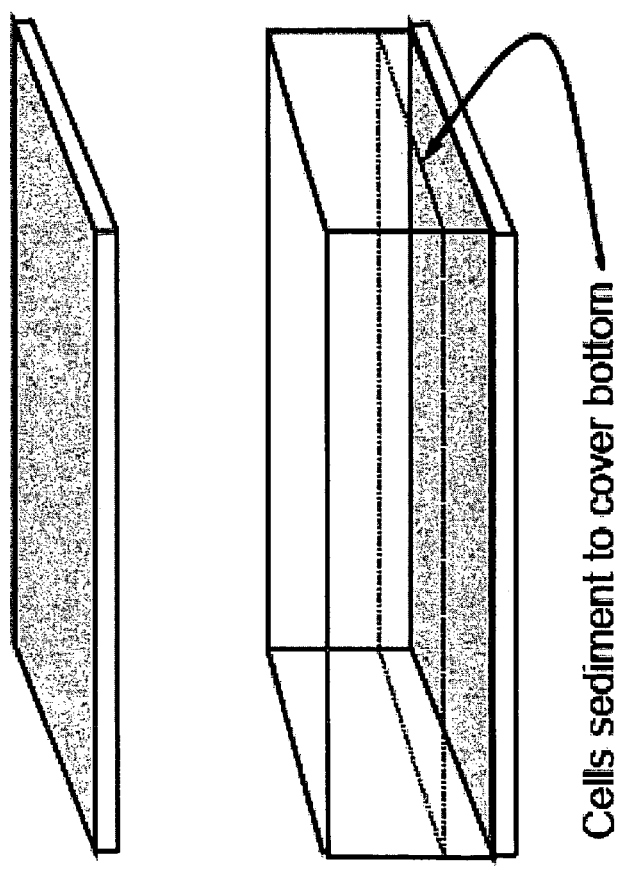
FIG. 68A is a schematic depiction of a capture device of the invention that features a functionalized microscope slide on the bottom of a sample chamber.

The invention encompasses a variety of cell capture devices and methods. In one embodiment, a capture device of the invention utilizes a functionalized surface, e.g., a glass microscope slide, as shown in FIG. 68A. The slide may be functionalized with an antibody or other capture moiety specific for the cell type of interest, e.g., CTCs, using standard chemistries. The device includes a sample fluid chamber, which may have, for example, a capacity of 10 ml or greater, with the functionalized slide on the bottom of the chamber. Any fluid, e.g., blood or a blood fraction, may be placed within the chamber for processing.

Figure 68B:
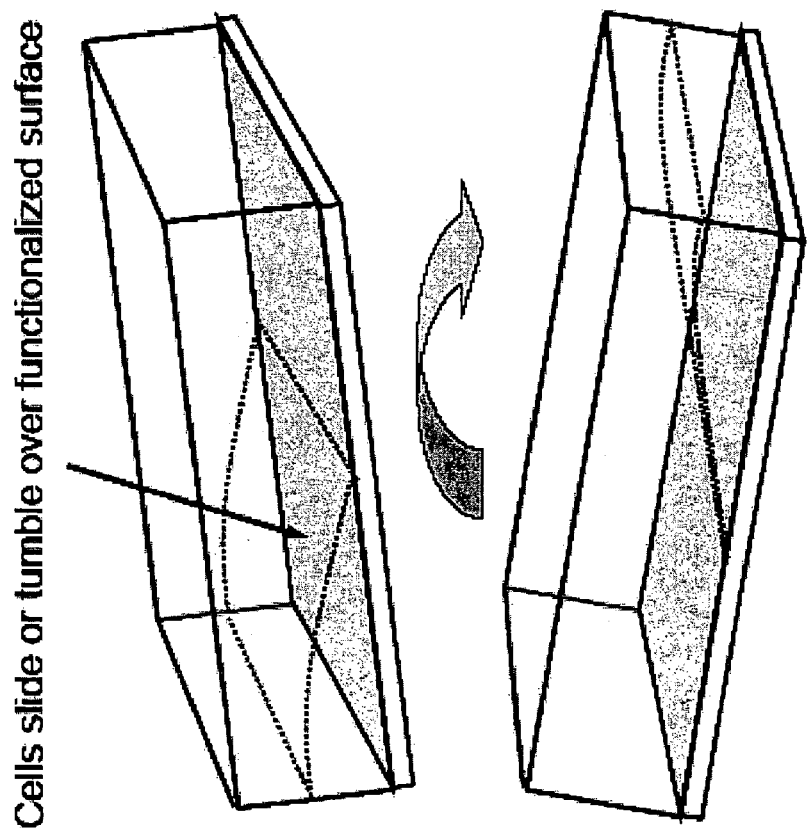
FIG. 68B is a schematic depiction of a method of rocking cells in the capture device in order to keep the cells tumbling and prevent sedimentation.
Figure 68C:
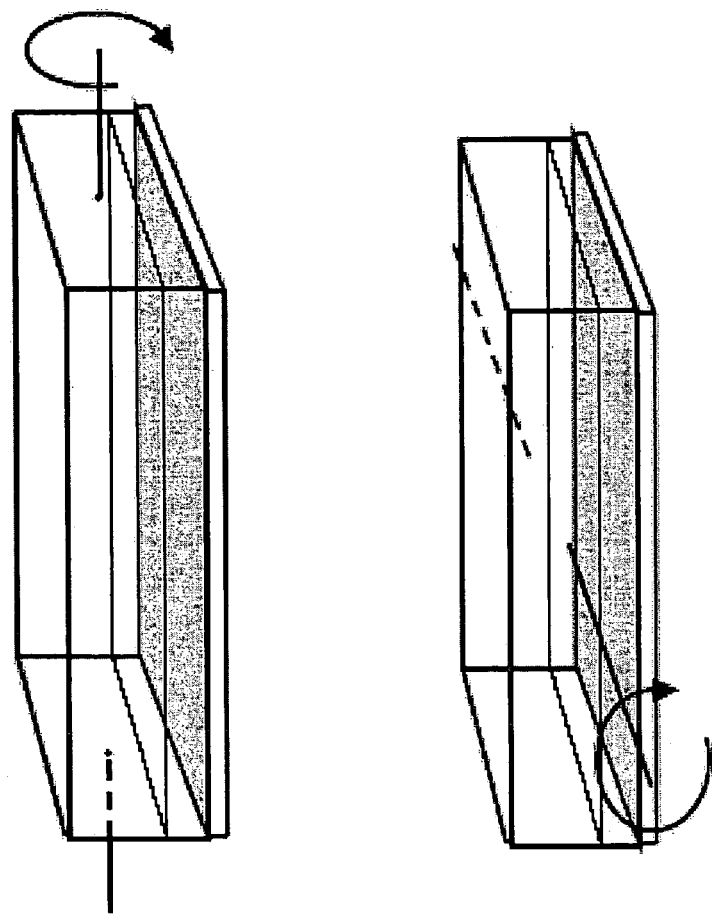
FIG. 68C is a schematic depiction of a method of rotating the capture device as an alternative to rocking.

Cells within the fluid sample sediment to the bottom of the chamber via gravity, or optionally centrifugation (see Example 12), or application of other forces, and are bound by the functionalized surface. In order to keep the remaining cells tumbling, the chamber may be rocked (FIG. 68B) or rotated (FIG. 68C). Subsequently, the chamber may be washed and removed, and the slide is then available for staining, visualization, and/or other subsequent analysis.

Several advantages of such a device and method are evident. For example, the flat capture surface allows for easy visualization of captured cells. Furthermore, the uniform cell capture on the flat surface simplifies cell quantification. In addition, the residence time for cells contacting the surface is long in comparison to other methods, improving capture efficiency and allowing for the total duration of the experiment to be shortened. This duration may also be shortened in view of the fact that there is no limiting flow rate. Because the cells are not flowing through a device, they are also not subjected to flow-induced shear.

Other advantages include the fact that, in the configuration described here, surface area is generally not a limiting factor in the capture of rare cells. Furthermore, it is particularly straightforward to analyze captured cells using a light microscope or other visualization techniques, allowing for the analysis of morphology, organelle characteristics, or other cellular characteristics.

The capture device may be coupled to other devices for processing cellular samples or other fluid samples, and it is compatible with microcapture technologies.

Figure 68D:
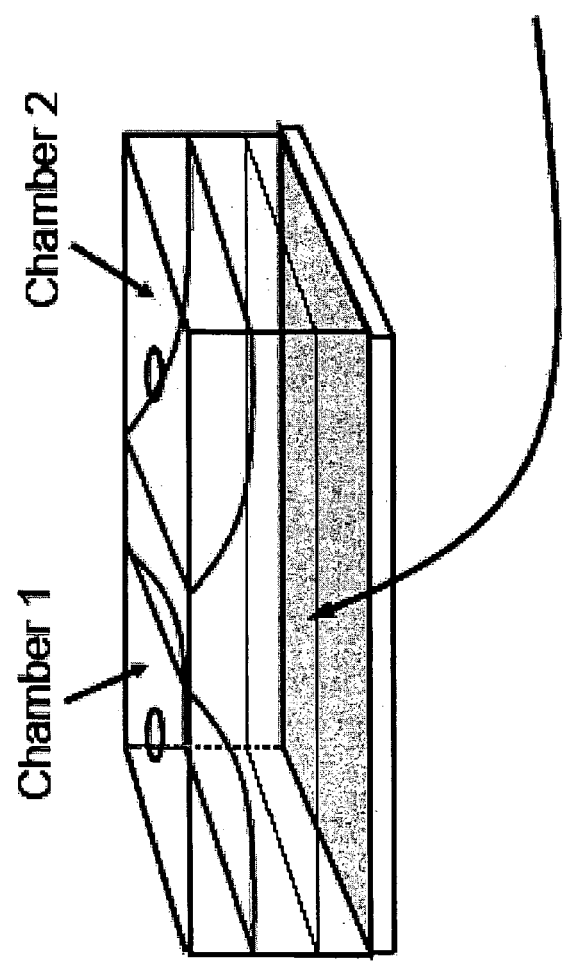
FIG. 68D is a schematic depiction of a capture device that includes two additional fluid chambers, which may be alternately filled and emptied in order to cause fluid motion inside the main chamber of the device.

In one variation, shown in FIG. 68D, two additional fluid chambers are present in the device. The fluid chambers, which may be filled with air, are alternately filled and emptied in order to cause fluid motion inside the main chamber of the device. The air chambers have a flexible wall separating them, and may be filled and emptied using any mechanism. The device mobilizes the cellular sample or other fluid sample, keeping sedimented cells tumbling and preventing the blockage of capture sites on the functionalized surface.

Figure 68E:
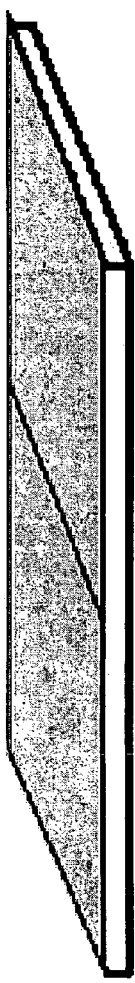
FIG. 68E is a schematic depiction of a microscope slide with multiple, spatially patterned capture functionalities on the surface.

The capture surface of any of the above devices may be microstructured, e.g., with low relief, including micro-posts, micro-fins, and/or micro-corrugation. The functionalized surface may be, e.g., a microfabricated silicon chip surface or a plastic surface. This approach provides, for example, multiple, spatially patterned capture functionalities on the surface for differential capture, quantification, and/or targeting of multiple cell populations (FIG. 68E).

Example 12

Centrifugal Capture Device Using a Microscope Slide

Prior to using a capture device of the invention, it is advantageous to perform microfluidics-based cell enrichment with a cell enrichment device of the invention. For example, by applying a first enrichment step to a blood sample, most erythrocytes, leukocytes, and platelets are removed. In one set of experiments, when blood samples were processed using cell enrichment devices of the invention having a cutoff of 8 µm, 10 µm, and 12 µm, erythrocytes and platelets were removed completely in each case, and the leukocyte concentration was reduced to $1.25 \times 10^5$ cells/ml, 2,900 cells/ml, and 111 cells/ml, respectively. Thus, a large portion of the contaminating cells in a blood sample or other cellular sample may be removed prior to a capture step, helping to avoid nonspecific sedimentation on a functionalized surface. However, the resulting enriched sample may be highly diluted, thereby increasing the processing time necessary to capture cells of interest, e.g., CTCs.

Figure 69A:
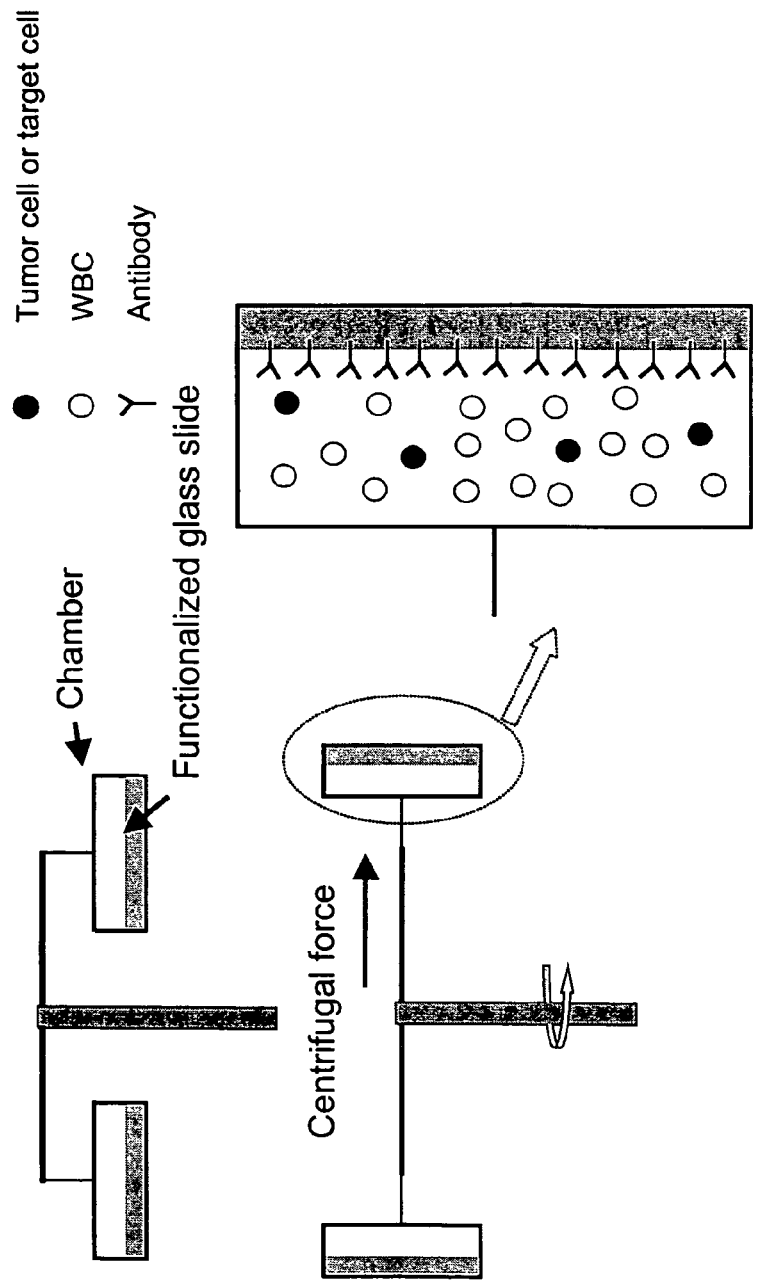
FIG. 69A is a schematic depiction of a centrifugation device of the invention, shown both at rest and in operation.
Figure 69B:
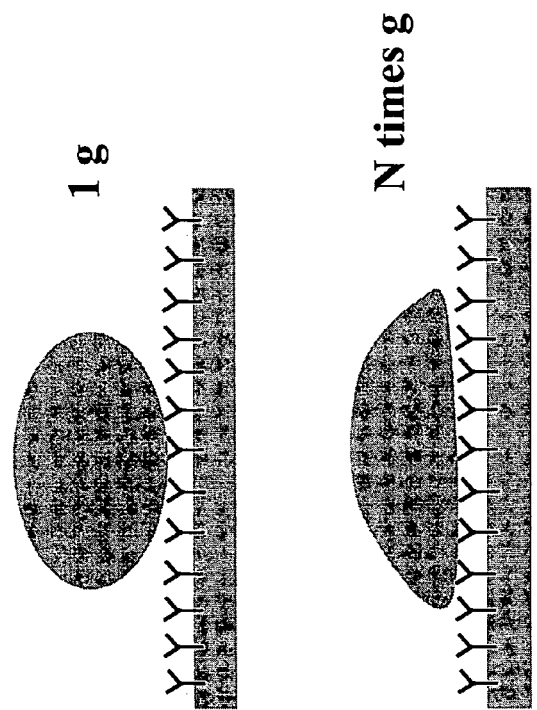
FIG. 69B is a schematic depiction of a cell binding to a functionalized surface in a gravitational field (top) and a centrifugal field (bottom).

To decrease the time required to process a sample, the device described in Example 11 may be used in combination with a centrifuge (FIG. 69A). In this method, cells of interest, e.g., CTCs, are flattened against the functionalized slide (FIG. 69B) when the sample is exposed to a high centrifugal field of N×g, where, for example, N is a large number, e.g., 1,000 or greater. This centrifugal method substantially increases the contact location and area between CTCs and binding moieties, e.g., antibodies.

Cell sedimentation velocity may be estimated by the equation:

$$u = \frac{a d_{cell}^2 (\rho_{cell} - \rho_{plasma})}{18 \mu_{plasma}}$$

where u represents velocity, d represents cell diameter, ρ represents density, µ represents viscosity, and a represents acceleration, i.e., gravitational or centrifugal field. The parameter a may be expressed as N×g, where N equals 1 in the case of gravity, and N generally equals a large number, e.g., 1,000 or greater, in the case of centrifugation. When N equals 1, i.e., in the presence of gravity alone, it takes approximately one hour for a 14 µm diameter cell to settle in a 2 cm high liquid level chamber; however, with a centrifugal field of N×g, sedimentation time is reduced by a factor of N, thereby significantly reducing the time required to perform the experiment.

Figure 69C:
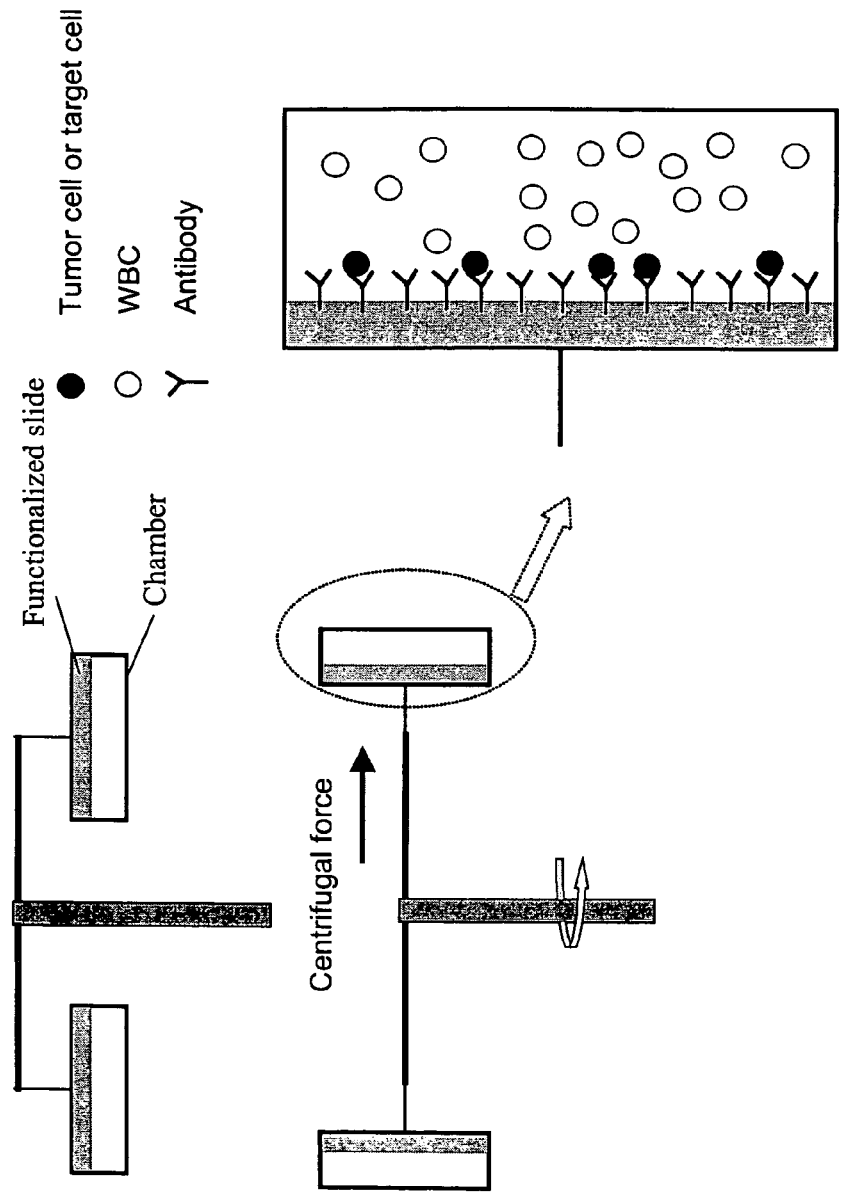
FIG. 69C is a schematic depiction of the device of FIG. 69A in which the chambers are inverted during the spin.
Figure 69D:
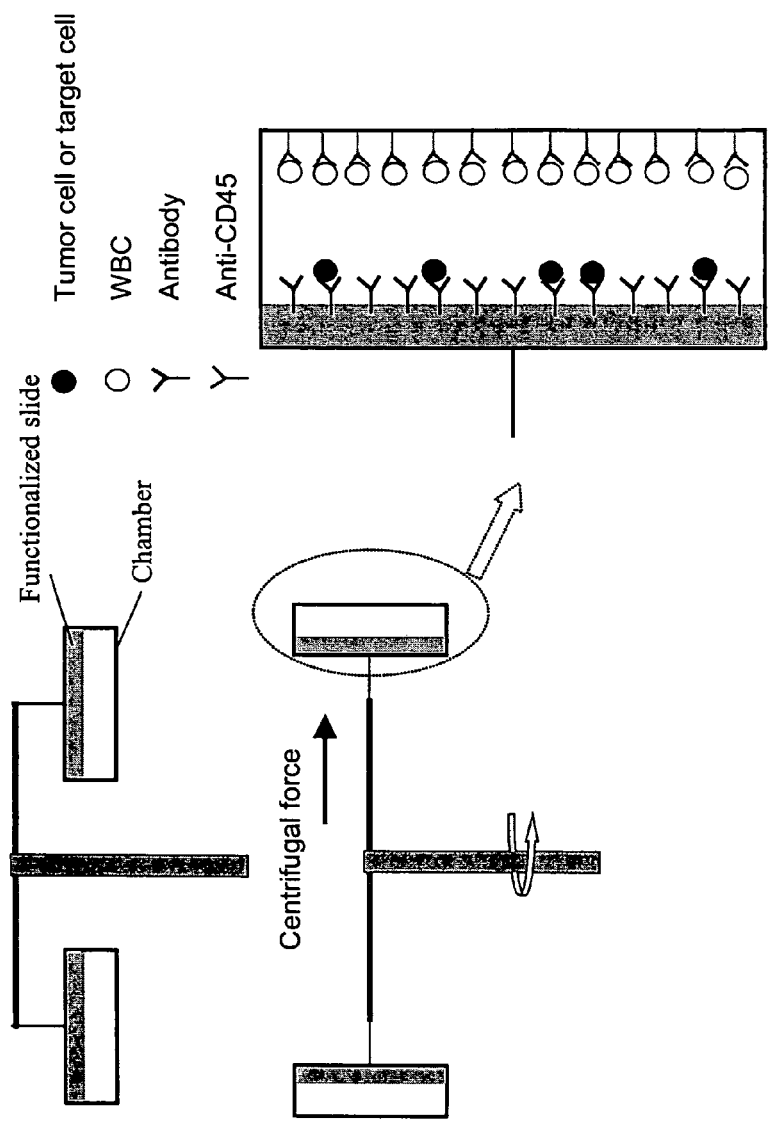
FIG. 69D is a schematic depiction of the device of FIG. 69C, further showing a second functionalized surface for the capture of contaminating cells.
Figure 69E:
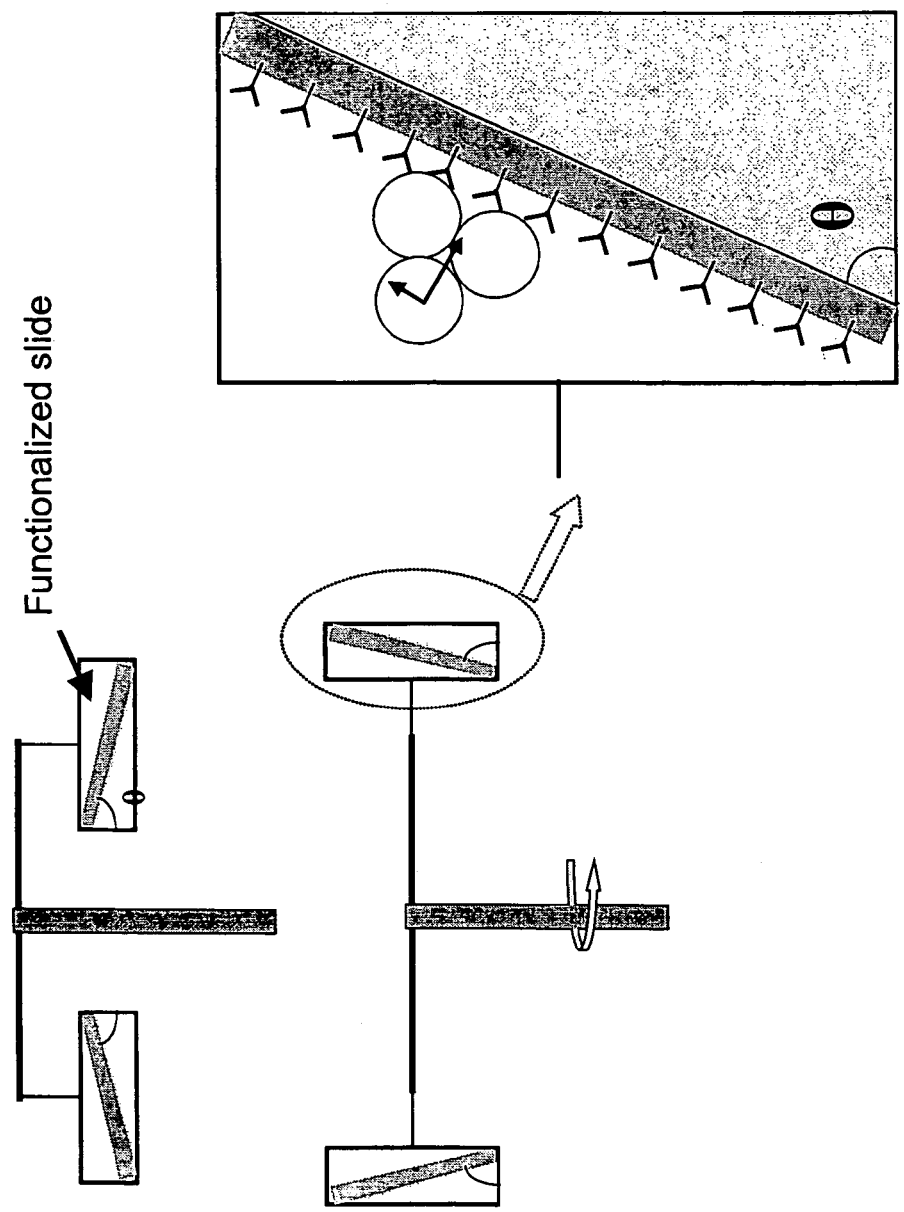
FIG. 69E is a schematic depiction of a centrifugal device in which the functionalized slide is inclined at an angle during the spin.

Following capture of CTCs, leukocytes or other contaminating cells that are bound nonspecifically to the functionalized surface may be removed by inverting the chamber and subjecting it once again to a high centrifugal force (FIG. 69C). This step greatly reduces the number of contaminating cells that remain attached to the functionalized surface. In one embodiment, antibodies specific for contaminating cells such as leukocytes may be coupled to a functionalized surface opposite the surface that is used to capture the cells of interest (FIG. 69D), thereby capturing the contaminating cells and further minimizing contamination of the captured cells of interest. In another variation, the functionalized surface used to capture cells of interest may be inclined at an angle, resulting in a centrifugal force component that drives cell rolling along the planar surface, in addition to the perpendicular component of the centrifugal force (FIG. 69E). The component of the centrifugal force that drives cell rolling helps to spread clusters of cells and increases the efficiency of cell capture.

Figure 69F:
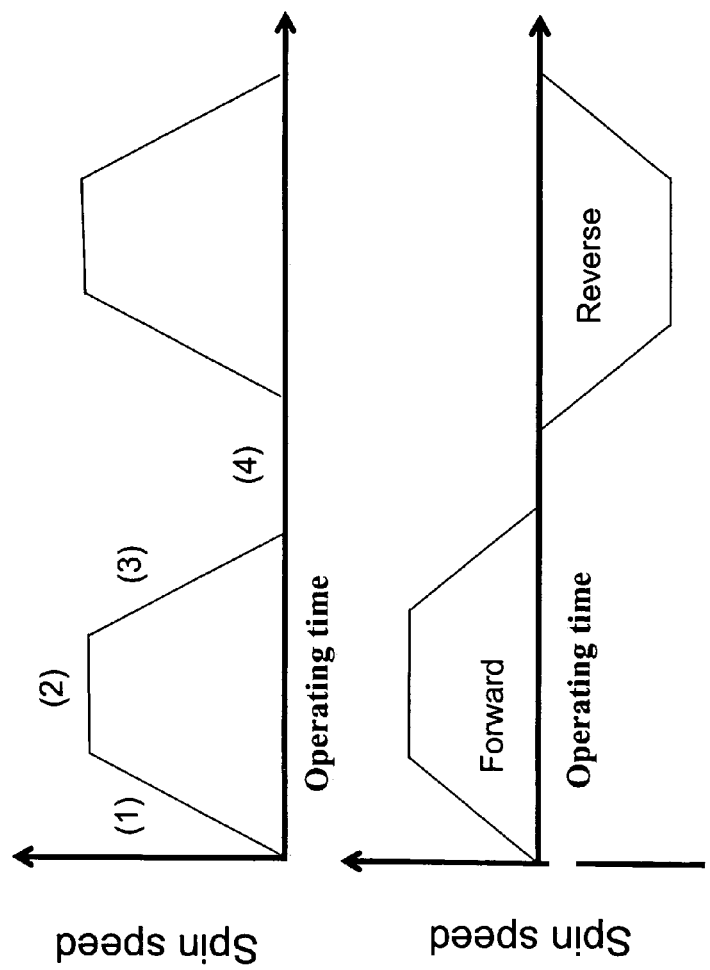
FIG. 69F is a pair of charts showing spin speed versus operating time, including periods that may be optimized: "spin up" (1), "spin time" (2), "spin down" (3), and rest time (4).

The applied centrifugal field may be optimized in a number of ways (FIG. 69F). For example, each period of centrifugation may be modified, including the "spin up" phase (period between starting centrifugation and attaining the desired rotational speed), "spin time" (period of centrifugation at desired rotational speed), "spin down" (period between beginning to slow centrifugation and coming to a stop), and "rest time" (period between spins). In each case, the duration, rotational speed, and/or rotational acceleration may be optimized to suit the application. This includes spinning the chamber in both the forward and reverse directions, as described above.

Figure 69G:
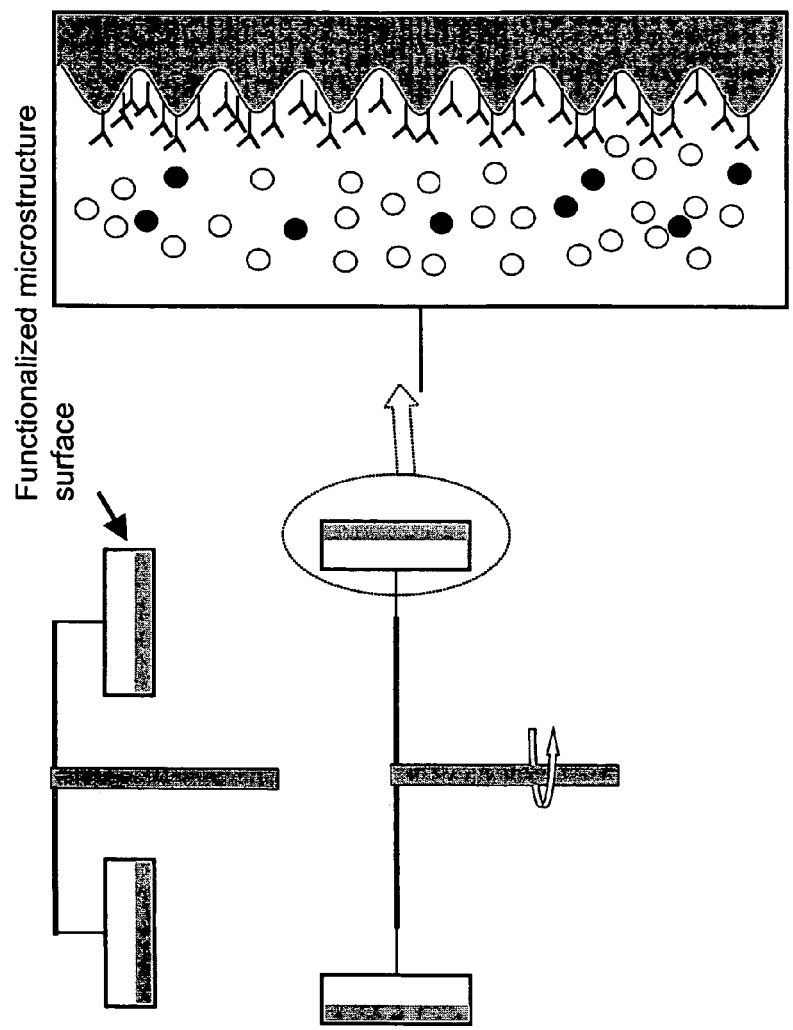
FIG. 69G is a schematic depiction of a centrifugal device that includes a functionalized microstructure surface.

To improve capture efficiency, the functionalized surface may be micro-structured (FIG. 69G), as in Example 11.

Example 13

Capture Device

Figure 70A:
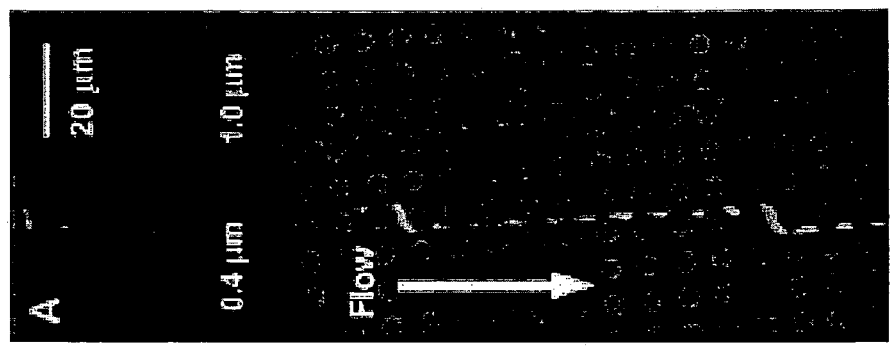
FIG. 70A is an image of an enrichment device showing the flow paths of a small cell (left) and a large cell (right). The small cell may be seen to have very little interaction with the obstacles and flows essentially in the average flow direction, while the large cell contacts each obstacle along its path and is directed laterally through the array.

In the enrichment devices of the invention that include obstacles (FIG. 70A, and described above), large cells generally have numerous interactions with the obstacles, while small cells are able to flow through the device with minimal contact with the obstacles. A capture device that includes antibodies or other binding moieties attached to the surfaces of arrayed obstacles may be designed using similar principles, and combines both size and affinity selectivity.

Figure 70B:
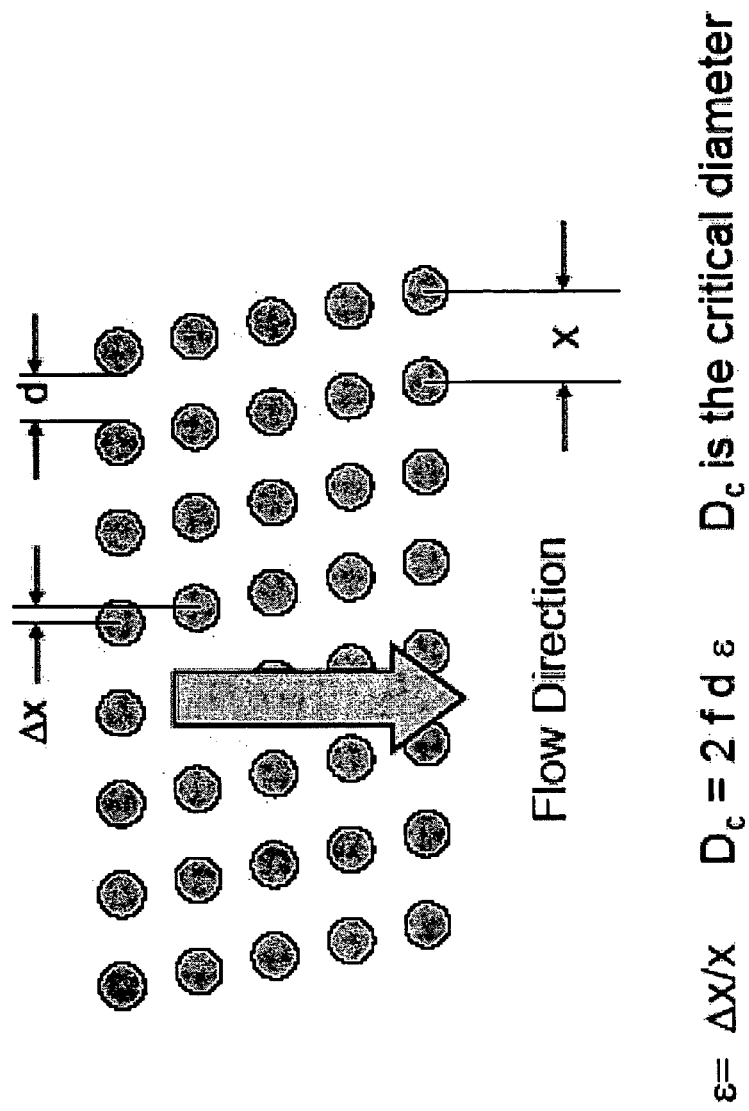
FIG. 70B is a schematic depiction of a device of the invention containing a regular array of obstacles.

In a regular array of obstacles, the critical diameter depends on a number of parameters, including the gap size and the distance between obstacles (obstacle offset), as shown in FIG. 70B. As described above, cells that are larger than the critical diameter are deflected, while cells that are smaller than this parameter move in the average flow direction. Thus, based on the size of the cell type of interest, e.g., a particular type of CTC, the critical diameter may be optimized. This may be achieved, for example, by selecting an appropriate gap size and offset. The optimized device may provide efficient capture with very low contamination.

In one instance, the obstacle density may be varied throughout the device. For example, obstacles may be arrayed at a lower density near the sample inlet of the device, or order to prevent clogging, while the density may be increased near the device outlet, in order to maximize capture.

Figure 70C:
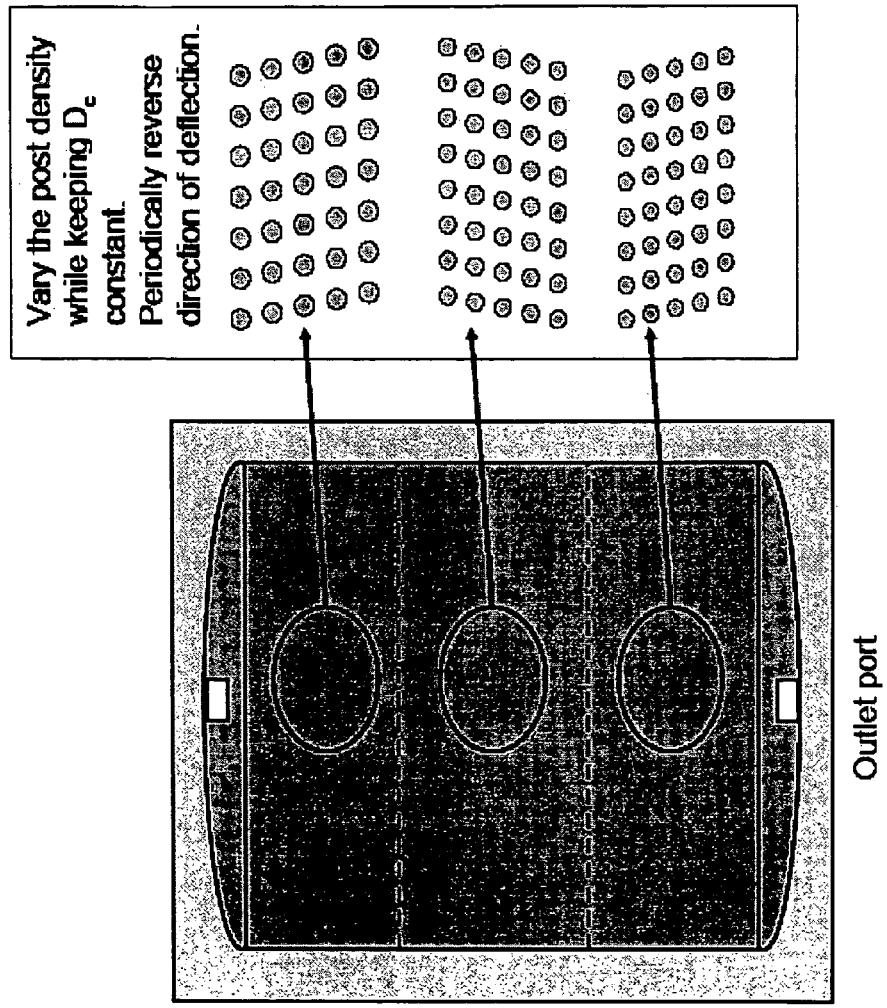
FIG. 70C is a schematic depiction of a device of the invention that includes multiple arrays in which the direction of deflection, the gap size, and/or the distance between obstacles is varied throughout the device, while the critical size is kept constant.

It is possible to vary the arrangement of obstacles while keeping the critical size constant. Thus, devices of the invention may include variable obstacle arrays in which the direction of deflection, the gap size, and/or the distance between obstacles is varied throughout the device, in order to increase flow rate, decrease clogging, or achieve other design goals (FIG. 70C).

In some devices, both target cells, e.g., CTCs, and contaminating cells, e.g., leukocytes, bind to the floor of the device. For example, this may occur in devices that include a functionalized silicon substrate containing obstacles, as all exposed surfaces of the silicon substrate are typically functionalized with antibody or other binding moiety. Thus, capture devices may be operated in an inverted orientation, such that any cells that sediment come into contact with a non-functionalized surface and do not bind. This may result in reduced clogging and may generally improve device performance.

The capture device described in this example, or other capture devices of the invention, may also include nonfunctionalized areas that may be used for enrichment or other purposes.

Other Embodiments

All publications, patents, and patent applications mentioned in the above specification are hereby incorporated by reference. Various modifications and variations of the described method and system of the invention will be apparent to those skilled in the art without departing from the scope and spirit of the invention. Although the invention has been described in connection with specific embodiments, it should be understood that the invention as claimed should not be unduly limited to such specific embodiments. Indeed, various modifications of the described modes for carrying out the invention that are obvious to those skilled in the art are intended to be within the scope of the invention.

Other embodiments are in the claims.

What is claimed is:

1. A two-dimensional array of obstacles in a microfluidic device comprising:
a first subarray of obstacles comprising a first gap between at least two obstacles in said first subarray, wherein said first subarray comprises a plurality of rows of obstacles, wherein said obstacles of each successive row are offset by 50%; and
a second subarray of obstacles comprising a second gap between at least two obstacles in said second subarray, wherein said second subarray comprises a plurality of rows of obstacles, wherein said obstacles of each successive row of obstacles of said second subarray are offset by 50%,
and wherein said two-dimensional array comprises an interface between said first subarray and said second subarray, said interface comprising at least one restricted gap smaller than both said first gap and said second gap, wherein said obstacles of said first and second subarray protrude from a substrate and wherein said obstacles of said first subarray do not extend into said second subarray.

2. The array of claim 1, wherein said substrate comprises plastic.

3. The array of claim 1, wherein said array comprises a microfluidic gap.

4. The array of claim 1, wherein said obstacles in said subarrays are staggered.

5. The array of claim 4, further comprising a multiplicity of subarrays wherein said obstacles in adjacent subarrays are staggered periodically or uniformly.

6. The array of claim 1, wherein each of said subarrays has between 6 and 20 obstacles.

7. The array of claim 1, wherein said first gap is at least 40 microns.

8. The array of claim 1, wherein a diameter of said obstacles is between 25 and 200 microns.

9. The array of claim 1, wherein said restricted gap is less than 60 microns.

10. The array of claim 1, wherein said array is coupled to one or more binding moieties that selectively bind one or more cells.

11. The array of claim 10, wherein said one or more binding moieties comprise an antibody that selectively binds one or more epithelial cells, cancer cells, bone marrow cells, fetal cells, progenitor cells, stem cells, foam cells, mesenchymal cells, immune system cells, endothelial cells, endometrial cells, connective tissue cells, trophoblasts, bacteria, fungi, or pathogens.

12. The array of claim 1, wherein said array is coupled to one or more binding moieties that selectively bind one or more cell surface cancer markers.

13. The array of claim 12, wherein said one or more cell surface markers are selected from the group consisting of EpCAM, E-Cadherin, Mucin-1, Cytokeratin 8, EGFR, and leukocyte associated receptor (LAR).

14. The array of claim 1, wherein said array of obstacles is coupled to a transparent cover.

15. The array of claim 1 wherein a spacing of said array is designed to encourage interaction of cells with said obstacles.

16. The array of claim 1, wherein said second gap is at least 40 microns.

17. The array of claim 1, wherein said restricted gap is at most 20 microns.

18. The array of claim 1, wherein said first gap and said second gap are the same size.

19. The array of claim 1, wherein said obstacles protrude approximately perpendicularly from said substrate.

20. The array of claim 1, wherein said obstacles of said first subarray, said second subarray, or both are round.

21. The array of claim 1, wherein said obstacles of said first and second subarray are substantially uniform in size.

* * * * *

SEQUENCE LISTING

<160> NUMBER OF SEQ ID NOS: 53

<210> SEQ ID NO 1
<211> LENGTH: 17
<212> TYPE: DNA
<213> ORGANISM: artificial sequence
<220> FEATURE:
<223> OTHER INFORMATION: synthetic

<400> SEQUENCE: 1
ttgctgctgg tggtggc                                                  17

<210> SEQ ID NO 2
<211> LENGTH: 20
<212> TYPE: DNA
<213> ORGANISM: artificial sequence

```
<220> FEATURE:
<223> OTHER INFORMATION: synthetic

<400> SEQUENCE: 2
cagggattcc gtcatatggc                                              20

<210> SEQ ID NO 3
<211> LENGTH: 18
<212> TYPE: DNA
<213> ORGANISM: artificial sequence
<220> FEATURE:
<223> OTHER INFORMATION: synthetic

<400> SEQUENCE: 3
gatcggcctc ttcatgcg                                                18

<210> SEQ ID NO 4
<211> LENGTH: 22
<212> TYPE: DNA
<213> ORGANISM: artificial sequence
<220> FEATURE:
<223> OTHER INFORMATION: synthetic

<400> SEQUENCE: 4
gatccaaagg tcatcaactc cc                                           22

<210> SEQ ID NO 5
<211> LENGTH: 18
<212> TYPE: DNA
<213> ORGANISM: artificial sequence
<220> FEATURE:
<223> OTHER INFORMATION: synthetic

<400> SEQUENCE: 5
gctgtccaac gaatgggc                                                18

<210> SEQ ID NO 6
<211> LENGTH: 20
<212> TYPE: DNA
<213> ORGANISM: artificial sequence
<220> FEATURE:
<223> OTHER INFORMATION: synthetic

<400> SEQUENCE: 6
ggcgttctcc tttctccagg                                              20

<210> SEQ ID NO 7
<211> LENGTH: 19
<212> TYPE: DNA
<213> ORGANISM: artificial sequence
<220> FEATURE:
<223> OTHER INFORMATION: synthetic

<400> SEQUENCE: 7
atgcactggg ccaggtctt                                               19

<210> SEQ ID NO 8
<211> LENGTH: 21
<212> TYPE: DNA
<213> ORGANISM: artificial sequence
<220> FEATURE:
<223> OTHER INFORMATION: synthetic

<400> SEQUENCE: 8
cgatggtaca tatgggtggc t                                            21
```

```
<210> SEQ ID NO 9
<211> LENGTH: 19
<212> TYPE: DNA
<213> ORGANISM: artificial sequence
<220> FEATURE:
<223> OTHER INFORMATION: synthetic

<400> SEQUENCE: 9
aggctgtcca acgaatggg                                              19

<210> SEQ ID NO 10
<211> LENGTH: 19
<212> TYPE: DNA
<213> ORGANISM: artificial sequence
<220> FEATURE:
<223> OTHER INFORMATION: synthetic

<400> SEQUENCE: 10
ctgagggagg cgttctcct                                              19

<210> SEQ ID NO 11
<211> LENGTH: 22
<212> TYPE: DNA
<213> ORGANISM: artificial sequence
<220> FEATURE:
<223> OTHER INFORMATION: synthetic

<400> SEQUENCE: 11
tcagagcctg tgtttctacc aa                                          22

<210> SEQ ID NO 12
<211> LENGTH: 22
<212> TYPE: DNA
<213> ORGANISM: artificial sequence
<220> FEATURE:
<223> OTHER INFORMATION: synthetic

<400> SEQUENCE: 12
tggtctcaca ggaccactga tt                                          22

<210> SEQ ID NO 13
<211> LENGTH: 20
<212> TYPE: DNA
<213> ORGANISM: artificial sequence
<220> FEATURE:
<223> OTHER INFORMATION: synthetic

<400> SEQUENCE: 13
tccaaatgag ctggcaagtg                                             20

<210> SEQ ID NO 14
<211> LENGTH: 23
<212> TYPE: DNA
<213> ORGANISM: artificial sequence
<220> FEATURE:
<223> OTHER INFORMATION: synthetic

<400> SEQUENCE: 14
tcccaaacac tcagtgaaac aaa                                         23

<210> SEQ ID NO 15
<211> LENGTH: 24
<212> TYPE: DNA
<213> ORGANISM: artificial sequence
<220> FEATURE:
<223> OTHER INFORMATION: synthetic
```

<400> SEQUENCE: 15
aaataatcag tgtgattcgt ggag                                    24

<210> SEQ ID NO 16
<211> LENGTH: 22
<212> TYPE: DNA
<213> ORGANISM: artificial sequence
<220> FEATURE:
<223> OTHER INFORMATION: synthetic

<400> SEQUENCE: 16
gaggccagtg ctgtctctaa gg                                      22

<210> SEQ ID NO 17
<211> LENGTH: 20
<212> TYPE: DNA
<213> ORGANISM: artificial sequence
<220> FEATURE:
<223> OTHER INFORMATION: synthetic

<400> SEQUENCE: 17
gtgcatcgct ggtaacatcc                                         20

<210> SEQ ID NO 18
<211> LENGTH: 20
<212> TYPE: DNA
<213> ORGANISM: artificial sequence
<220> FEATURE:
<223> OTHER INFORMATION: synthetic

<400> SEQUENCE: 18
tgtggagatg agcagggtct                                         20

<210> SEQ ID NO 19
<211> LENGTH: 21
<212> TYPE: DNA
<213> ORGANISM: artificial sequence
<220> FEATURE:
<223> OTHER INFORMATION: synthetic

<400> SEQUENCE: 19
acttcacagc cctgcgtaaa c                                       21

<210> SEQ ID NO 20
<211> LENGTH: 21
<212> TYPE: DNA
<213> ORGANISM: artificial sequence
<220> FEATURE:
<223> OTHER INFORMATION: synthetic

<400> SEQUENCE: 20
atgggacagg cactgatttg t                                       21

<210> SEQ ID NO 21
<211> LENGTH: 20
<212> TYPE: DNA
<213> ORGANISM: artificial sequence
<220> FEATURE:
<223> OTHER INFORMATION: synthetic

<400> SEQUENCE: 21
atcgcattca tgcgtcttca                                         20

```
<210> SEQ ID NO 22
<211> LENGTH: 20
<212> TYPE: DNA
<213> ORGANISM: artificial sequence
<220> FEATURE:
<223> OTHER INFORMATION: synthetic

<400> SEQUENCE: 22
atccccatgg caaactcttg                                               20

<210> SEQ ID NO 23
<211> LENGTH: 22
<212> TYPE: DNA
<213> ORGANISM: artificial sequence
<220> FEATURE:
<223> OTHER INFORMATION: synthetic

<400> SEQUENCE: 23
gcagcgggtt acatcttctt tc                                            22

<210> SEQ ID NO 24
<211> LENGTH: 22
<212> TYPE: DNA
<213> ORGANISM: artificial sequence
<220> FEATURE:
<223> OTHER INFORMATION: synthetic

<400> SEQUENCE: 24
cagctctggc tcacactacc ag                                            22

<210> SEQ ID NO 25
<211> LENGTH: 22
<212> TYPE: DNA
<213> ORGANISM: artificial sequence
<220> FEATURE:
<223> OTHER INFORMATION: synthetic

<400> SEQUENCE: 25
gcagcgggtt acatcttctt tc                                            22

<210> SEQ ID NO 26
<211> LENGTH: 19
<212> TYPE: DNA
<213> ORGANISM: artificial sequence
<220> FEATURE:
<223> OTHER INFORMATION: synthetic

<400> SEQUENCE: 26
catcctcccc tgcatgtgt                                                19

<210> SEQ ID NO 27
<211> LENGTH: 20
<212> TYPE: DNA
<213> ORGANISM: artificial sequence
<220> FEATURE:
<223> OTHER INFORMATION: synthetic

<400> SEQUENCE: 27
ccgcagcatg tcaagatcac                                               20

<210> SEQ ID NO 28
<211> LENGTH: 25
<212> TYPE: DNA
<213> ORGANISM: artificial sequence
<220> FEATURE:
<223> OTHER INFORMATION: synthetic
```

```
<400> SEQUENCE: 28
tccttctgca tggtattctt tctct                                         25

<210> SEQ ID NO 29
<211> LENGTH: 14
<212> TYPE: DNA
<213> ORGANISM: artificial sequence
<220> FEATURE:
<223> OTHER INFORMATION: synthetic

<400> SEQUENCE: 29
tttgggctgg ccaa                                                     14

<210> SEQ ID NO 30
<211> LENGTH: 14
<212> TYPE: DNA
<213> ORGANISM: artificial sequence
<220> FEATURE:
<223> OTHER INFORMATION: synthetic

<400> SEQUENCE: 30
ttttgggcgg gcca                                                     14

<210> SEQ ID NO 31
<211> LENGTH: 17
<212> TYPE: DNA
<213> ORGANISM: artificial sequence
<220> FEATURE:
<223> OTHER INFORMATION: synthetic

<400> SEQUENCE: 31
atggccagcg tggacaa                                                  17

<210> SEQ ID NO 32
<211> LENGTH: 23
<212> TYPE: DNA
<213> ORGANISM: artificial sequence
<220> FEATURE:
<223> OTHER INFORMATION: synthetic

<400> SEQUENCE: 32
agcaggtact gggagccaat att                                           23

<210> SEQ ID NO 33
<211> LENGTH: 16
<212> TYPE: DNA
<213> ORGANISM: artificial sequence
<220> FEATURE:
<223> OTHER INFORMATION: synthetic

<400> SEQUENCE: 33
atgagctgcg tgatga                                                   16

<210> SEQ ID NO 34
<211> LENGTH: 16
<212> TYPE: DNA
<213> ORGANISM: artificial sequence
<220> FEATURE:
<223> OTHER INFORMATION: synthetic

<400> SEQUENCE: 34
atgagctgca tgatga                                                   16
```

-continued

```
<210> SEQ ID NO 35
<211> LENGTH: 22
<212> TYPE: DNA
<213> ORGANISM: artificial sequence
<220> FEATURE:
<223> OTHER INFORMATION: synthetic

<400> SEQUENCE: 35
gcctcttaca cccagtggag aa                                              22

<210> SEQ ID NO 36
<211> LENGTH: 22
<212> TYPE: DNA
<213> ORGANISM: artificial sequence
<220> FEATURE:
<223> OTHER INFORMATION: synthetic

<400> SEQUENCE: 36
ttctgggatc cagagtccct ta                                              22

<210> SEQ ID NO 37
<211> LENGTH: 14
<212> TYPE: DNA
<213> ORGANISM: artificial sequence
<220> FEATURE:
<223> OTHER INFORMATION: synthetic

<400> SEQUENCE: 37
accggagccc agca                                                       14

<210> SEQ ID NO 38
<211> LENGTH: 14
<212> TYPE: DNA
<213> ORGANISM: artificial sequence
<220> FEATURE:
<223> OTHER INFORMATION: synthetic

<400> SEQUENCE: 38
accggagctc agca                                                       14

<210> SEQ ID NO 39
<211> LENGTH: 14
<212> TYPE: DNA
<213> ORGANISM: artificial sequence
<220> FEATURE:
<223> OTHER INFORMATION: synthetic

<400> SEQUENCE: 39
accggagcac agca                                                       14

<210> SEQ ID NO 40
<211> LENGTH: 21
<212> TYPE: DNA
<213> ORGANISM: artificial sequence
<220> FEATURE:
<223> OTHER INFORMATION: synthetic

<400> SEQUENCE: 40
tcgcaaaggg catgaactac t                                               21

<210> SEQ ID NO 41
<211> LENGTH: 21
<212> TYPE: DNA
<213> ORGANISM: artificial sequence
<220> FEATURE:
<223> OTHER INFORMATION: synthetic
```

```
<400> SEQUENCE: 41
atcttgacat gctgcggtgt t                                           21

<210> SEQ ID NO 42
<211> LENGTH: 14
<212> TYPE: DNA
<213> ORGANISM: artificial sequence
<220> FEATURE:
<223> OTHER INFORMATION: synthetic

<400> SEQUENCE: 42
ttggtgcacc gcga                                                   14

<210> SEQ ID NO 43
<211> LENGTH: 14
<212> TYPE: DNA
<213> ORGANISM: artificial sequence
<220> FEATURE:
<223> OTHER INFORMATION: synthetic

<400> SEQUENCE: 43
tggtgctccg cgac                                                   14

<210> SEQ ID NO 44
<211> LENGTH: 19
<212> TYPE: DNA
<213> ORGANISM: artificial sequence
<220> FEATURE:
<223> OTHER INFORMATION: synthetic

<400> SEQUENCE: 44
agtcaggacc catgcacgg                                              19

<210> SEQ ID NO 45
<211> LENGTH: 20
<212> TYPE: DNA
<213> ORGANISM: artificial sequence
<220> FEATURE:
<223> OTHER INFORMATION: synthetic

<400> SEQUENCE: 45
acccaagatg cagcagtgtg                                             20

<210> SEQ ID NO 46
<211> LENGTH: 21
<212> TYPE: DNA
<213> ORGANISM: artificial sequence
<220> FEATURE:
<223> OTHER INFORMATION: synthetic

<400> SEQUENCE: 46
gatgtcctcc ttgttctact c                                           21

<210> SEQ ID NO 47
<211> LENGTH: 22
<212> TYPE: DNA
<213> ORGANISM: artificial sequence
<220> FEATURE:
<223> OTHER INFORMATION: synthetic

<400> SEQUENCE: 47
tacagggaat aatcgagcat gc                                          22
```

-continued

```
<210> SEQ ID NO 48
<211> LENGTH: 22
<212> TYPE: DNA
<213> ORGANISM: artificial sequence
<220> FEATURE:
<223> OTHER INFORMATION: synthetic

<400> SEQUENCE: 48
gaagggaaat agcaaatgga ca                                              22

<210> SEQ ID NO 49
<211> LENGTH: 20
<212> TYPE: DNA
<213> ORGANISM: artificial sequence
<220> FEATURE:
<223> OTHER INFORMATION: synthetic

<400> SEQUENCE: 49
cgatggagtc caagttctgg                                                 20

<210> SEQ ID NO 50
<211> LENGTH: 20
<212> TYPE: DNA
<213> ORGANISM: artificial sequence
<220> FEATURE:
<223> OTHER INFORMATION: synthetic

<400> SEQUENCE: 50
agcacttaca gctctggcca                                                 20

<210> SEQ ID NO 51
<211> LENGTH: 22
<212> TYPE: DNA
<213> ORGANISM: artificial sequence
<220> FEATURE:
<223> OTHER INFORMATION: synthetic

<400> SEQUENCE: 51
gactgaacat aactgtaggc tg                                              22

<210> SEQ ID NO 52
<211> LENGTH: 20
<212> TYPE: DNA
<213> ORGANISM: artificial sequence
<220> FEATURE:
<223> OTHER INFORMATION: synthetic

<400> SEQUENCE: 52
gttcggcacg gtgtataagg                                                 20

<210> SEQ ID NO 53
<211> LENGTH: 20
<212> TYPE: DNA
<213> ORGANISM: artificial sequence
<220> FEATURE:
<223> OTHER INFORMATION: synthetic

<400> SEQUENCE: 53
ctggccatca cgtaggcttc                                                 20
```